US012606833B2

(12) United States Patent　　(10) Patent No.:　US 12,606,833 B2

Koirala　　(45) Date of Patent:　Apr. 21, 2026

(54) MODIFIED MINI-NUCLEOSOME CORE PROTEINS AND USE IN NUCLEIC ACID DELIVERY

(71) Applicant: Adarsha Koirala, Framingham, MA (US)

(72) Inventor: Adarsha Koirala, Framingham, MA (US)

(73) Assignee: Adarsha Koirala, Framingham, MA (US)

( * ) Notice: Subject to any disclaimer, the term of this patent is extended or adjusted under 35 U.S.C. 154(b) by 748 days.

(21) Appl. No.: 17/918,469

(22) PCT Filed: Apr. 12, 2021

(86) PCT No.: PCT/US2021/026917

§ 371 (c)(1),
(2) Date: Oct. 12, 2022

(87) PCT Pub. No.: WO2021/211467

PCT Pub. Date: Oct. 21, 2021

(65) Prior Publication Data

US 2023/0203507 A1　　Jun. 29, 2023

Related U.S. Application Data

(60) Provisional application No. 63/009,124, filed on Apr. 13, 2020.

(51) Int. Cl.

| | |
|---|---|
| *C12N 15/62* | (2006.01) |
| *A61K 48/00* | (2006.01) |
| *C12N 15/87* | (2006.01) |
| *A61K 38/00* | (2006.01) |

(52) U.S. Cl.

CPC .......... *C12N 15/62* (2013.01); *A61K 48/0025* (2013.01); *A61K 48/005* (2013.01); *C12N 15/87* (2013.01); *A61K 38/00* (2013.01); *C07K 2319/033* (2013.01); *C07K 2319/09* (2013.01); *C07K 2319/35* (2013.01); *C07K 2319/80* (2013.01)

(58) Field of Classification Search

None

See application file for complete search history.

(56) References Cited

U.S. PATENT DOCUMENTS

| | | | |
|---|---|---|---|
| 5,166,320 A | 11/1992 | Wu et al. |
| 5,670,347 A | 9/1997 | Gopal |
| 5,844,107 A | 12/1998 | Hanson et al. |
| 6,506,890 B1 | 1/2003 | Cooper et al. |
| 9,102,759 B2 | 8/2015 | Pieczykolan et al. |
| 9,486,540 B2 | 11/2016 | Harmon et al. |
| 2003/0040496 A1 | 2/2003 | Chandler et al. |
| 2003/0181658 A1 | 9/2003 | Madison et al. |
| 2004/0192609 A1 | 9/2004 | Farzan et al. |
| 2005/0048606 A1 | 3/2005 | Wang et al. |
| 2006/0018911 A1 | 1/2006 | Ault-Riche et al. |
| 2006/0182736 A1 | 8/2006 | Kim et al. |
| 2006/0258603 A1 | 11/2006 | Ivics et al. |
| 2009/0018098 A1 | 1/2009 | Varshavsky |
| 2009/0155853 A1 | 6/2009 | Nabel et al. |
| 2010/0203627 A1 | 8/2010 | Cooper et al. |
| 2011/0035819 A1 | 2/2011 | Cooper et al. |
| 2014/0134232 A1 | 5/2014 | Boulikas |
| 2014/0287426 A1 | 9/2014 | Arnold et al. |
| 2017/0037426 A1* | 2/2017 | Alexandrov ....... C12N 15/8271 |
| 2017/0057997 A1 | 3/2017 | Choi et al. |
| 2017/0258933 A1 | 9/2017 | Pellois |
| 2017/0283467 A1 | 10/2017 | Hernandez-Garcia et al. |
| 2018/0161447 A1 | 6/2018 | Watson et al. |
| 2018/0258429 A1 | 9/2018 | Sætrom et al. |
| 2024/0336664 A1 | 10/2024 | Koirala et al. |

FOREIGN PATENT DOCUMENTS

| | | |
|---|---|---|
| EP | 1031626 A1 | 8/2000 |
| JP | 4521519 B2 | 8/2010 |
| WO | WO-96/40958 A1 | 12/1996 |
| WO | WO-96/41606 A2 | 12/1996 |
| WO | WO-97/030731 A2 | 8/1997 |
| WO | WO-98/046274 A2 | 10/1998 |
| WO | WO-99/19502 A1 | 4/1999 |

(Continued)

OTHER PUBLICATIONS

Wagstaff et al (FASEB (2008)1-11) (Year: 2008).*

Anderson et al., "Transcytosis of NgCAM in epithelial cells reflects differential signal recognition on the endocytic and secretory pathways," J Cell Biol, 170(4): 595-605 (2005).

Arap et al., "Cancer treatment by targeted drug delivery to tumor vasculature in a mouse model," Science, 279(5349): 377-80 (1998).

Asch et al., "Thrombospondin sequence motif (CSVTCG) is responsible for CD36 binding," Biochem Biophys Res Commun, 182(3):1208-17 (1992), Abstract Only.

Asokan et al., "Adeno-associated virus type 2 contains an integrin alpha5betal binding domain essential for viral cell entry," J Virol., 80(18): 8961-8969 (2006).

(Continued)

*Primary Examiner* — James D Schultz

*Assistant Examiner* — Andrea Lynne Morris Spencer

(74) *Attorney, Agent, or Firm* — Foley Hoag LLP; David E. Shore

(57) ABSTRACT

The present disclosure provides compositions and methods relating to modified mini-nucleosome core proteins and/or delivery of nucleic acids. In particular, the present disclosure includes, among other things, non-viral proteinaceous vehicles for delivery of nucleic acids. In various embodiments, non-viral proteinaceous vehicles provided herein include (a) a nucleic acid binding domain; (b) a targeting domain; (c) a nucleic acid release domain; and, optionally, (d) further domains including, e.g., one or more of a stability domain, an oligomerization domain, and/or a linker domain. In various embodiments, the proteinaceous vehicles include one or more modified residues.

4 Claims, 35 Drawing Sheets

Specification includes a Sequence Listing.

(56) References Cited

FOREIGN PATENT DOCUMENTS

| | | |
|---|---|---|
| WO | WO-2008/137066 A1 | 11/2008 |
| WO | WO-2008/153927 A2 | 12/2008 |
| WO | WO-2009/104001 A2 | 8/2009 |
| WO | WO-2011/017313 A1 | 2/2011 |
| WO | WO-2018/112278 A1 | 6/2018 |
| WO | WO-2019/210005 A1 | 10/2019 |
| WO | WO-2020/097235 A1 | 5/2020 |
| WO | WO-2021/211467 A1 | 10/2021 |
| WO | WO-2023/014879 A2 | 2/2023 |

OTHER PUBLICATIONS

Barua et al., "Challenges associated with Penetration of Nanoparticles across Cell and Tissue Barriers: A Review of Current Status and Future Prospects," Nano today, 9(2):223-243 (2014).

Beitia Ortiz de Zarate et al., "Contribution of endocytic motifs in the cytoplasmic tail of herpes simplex virus type 1 glycoprotein B to virus replication and cell-cell fusion," J Virol, 81(24): 13889-13903 (2007).

Bottomley, "Structures of protein domains that create or recognize histone modifications," EMBO Rep, 5(5): 464-9 (2004).

Brand, "The Popeye Domain Containing Genes and Their Function as cAMP Effector Proteins in Striated Muscle," J Cardiovasc Dev Dis, 5(1):18 (2018).

Buning et al., "Receptor targeting of adeno-associated virus vectors," Gene Ther, 10(14):1142-51 (2003).

Caberoy et al., "Tubby and tubby-like protein 1 are new MerTK ligands for phagocytosis," EMBO J, 29(23):3898-910 (2010).

Cardin et al., "Molecular modeling of protein-glycosaminoglycan interactions," Arteriosclerosis, 9(1):21-32 (1989).

Chan et al., "Enhancement of Polylysine-Mediated Transferrinfection by Nuclear Localization Sequences: Polylysine Does Not Function as a Nuclear Localization Sequence," Human Gene Therapy, 10(10)(1999).

Chen et al., "Role of Peptide Hydrophobicity in the Mechanism of Action of A-Helical Antimicrobial Peptides," Antimicrobial Agents and Chemotherapy, 51(4):1398-1406, (2007).

Chinnapen et al., "Rafting with cholera toxin: endocytosis and trafficking from plasma membrane to ER," FEMS Microbiol Lett., 266(2):129-37 (2007).

Dahlin-Huppe et al., "Mutational analysis of the L1 neuronal cell adhesion molecule identifies membrane-proximal amino acids of the cytoplasmic domain that are required for cytoskeletal anchorage," Mol Cell Neurosci., 9(2):144-56 (1997).

Database UniProt, "B2R4R0 • B2R4R0_HUMAN," 2008, pp. 1-6, https://www.uniprot.org/uniprotkb/B2R4R0/entry [date of retrieval: Dec. 24, 2024].

Database UniProt, Accession No. A0A1A8YRB7 "Uncharacterized protein from Plasmodium ovale wallikeri.", Oct. 5, 2016.

Di Paolo et al., "Fiber shaft-chimeric adenovirus vectors lacking the KKTK motif efficiently infect liver cells in vivo," J Virol., 81(22):12249-59 (2007).

Dramsi et al., "Covalent attachment of proteins to peptidoglycan," FEMS Microbiol Rev, 32(2):307-20 (2008).

D'Souza et al., "Arginyl-glycyl-aspartic acid (RGD): a cell adhesion motif," Trends Biochem Sci., 16(7):246-50, (1991).

Feuz et al., "Small-angle neutron scattering of PLL grafted PEG molecular brushes," Eur. Phys. J. E 23:237-245 (2007), Abstract Only.

Fitzpatrick et al., "Influence of Pre-existing Anti-capsid Neutralizing and Binding Antibodies on AAV Vector Transduction," Molecular Therapy, Methods and Clinical Development, 9: 119129, (2018).

Graf et al., "Identification of the major epithelial-cell attachment site (yigsr) in the b 1-chain of Laminin," J. Invest. Dermatol., 88, 491, (1987), Abstract Only.

Guerra-Crespo et al., "Polyethylenimine improves the transfection efficiency of primary cultures of post-mitotic rat fetal hypothalamic neurons," J Neurosci Methods, 127(2):179-92, (2003).

Hergeth et al., "The H1 linker histones: multifunctional proteins beyond the nucleosomal core particle", EMBO Reports, vol. 16, No. 11, Nov. 1, 2015, pp. 1439-1453.

Hinderer et al., "Severe Toxicity in Nonhuman Primates and Piglets Following High-Dose Intravenous Administration of an Adeno-Associated Virus Vector Expressing Human SMN," Human Gene Therapy, 29(3):285-298, (2018).

Hong et al., "Studies of he DNA Binding Properties of Histone H4 Amino Terminus," The Journal of Biological Chemistry, 268(1):305-314 (1993).

Hunter et al., "Primary sequence of a motor neuron-selective adhesive site in the synaptic basal lamina protein S-laminin," Cell, 59(5):905-13 (1989).

Iida et al., "A role of chondroitin sulfate glycosaminoglycan binding site in alpha4beta1 integrin-mediated melanoma cell adhesion," J Biol Chem, 273(10):5955-62 (1998).

Inabe et al., "The YXXL sequences of a transmembrane protein of bovine leukemia virus are required for viral entry and incorporation of viral envelope protein into virions," J Virol., 73(2):1293-301 (1999).

International Search Report and Written Opinion for International Application No. PCT/US22/39413, mailed Feb. 2, 2023.

International Search Report and Written Opinion for PCT/US19/60119 dated Feb. 20, 2020.

Jans et al., "Cyclin-dependent kinase site-regulated signal-dependent nuclear localization of the SW15 yeast transcription factor in mammalian cells," J Biol Chem, 270(29):17064-7, (1995).

Jean et al., "Unmasking a hyaluronan-binding site of the BX(7)B type in the H3 heavy chain of the inter-alpha-inhibitor family," Eur J Biochem, 268(3):544-53 (2001).

Johnson et al., "The Leu-Arg-Glu (LRE) adhesion motif in protein of the neuromuscular junction with special reference to proteins of the carboxylesterase/cholinesterase family," Comparative Biochemistry and Physiology, Part D (2013): 231-243.

Kalthoff et al., "Unusual structural organization of the endocytic proteins AP180 and epsin 1," J Biol Chem, 277(10):8209-16 (2002).

Kirchhausen, "Adaptors for clathrin-mediated traffic," Annu Rev Cell Dev. 15:705-732, (1999).

Knight et al., "The collagen-binding A-domains of integrins alpha(1)beta(1) and alpha(2)beta(1) recognize the same specific amino acid sequence, GFOGER, in native (triple-helical) collagens," J Biol Chem, 275(1):35-40 (2000).

Konstan et al., "Compacted DNA Nanoparticles Administered to the Nasal Mucosa of Cystic Fibrosis Subjects Are Safe and Demonstrate Partial to Complete Cystic Fibrosis Transmembrane Regulator Reconstitution," Human Gene Therapy. 15:1255-1269, (2004).

Korolev et al., "Cation-induced polyelectrolytepolyelectrolyte attraction in solutions of DNA and nucleosome core particles", Advances in Colliod and Interface Science, Elsevier, NL, vol. 158, No. 1-2, Jul. 12, 2010, pp. 32-47.

Kouzi-Koliakos et al., "Mapping of three major heparin-binding sites on laminin and identification of a novel heparin-binding site on the B1 chain," J Biol Chem, 264(30):17971-8 (1989).

Kusakawa et al., "Functional interaction of hepatitis C Virus NS5B with Nucleolin GAR domain," J Biochem, 141(6):917-27 (2007).

Lai et al., "Evidence for the failure of adeno-associated virus serotype 5 to package a viral genome A.2 kb," Mol Ther 18(1): 75-79, (2010).

Leung et al., "ENPD—A Database of Eukaryotic Nucleic Acid Binding Proteins: Linking Gene Regulations to Proteins," Nucleic Acids Research 47 (2019): D322-D329.

Li et al., "Developing Covalent Protein Drugs via Proximity-Enabled Reactive Therapeutics", 2020, Cell 182, pp. 85-97.

Liu et al., "Nanoparticles of Compacted DNA Transfect Postmitotic Cells," The Journal of Biological Chemistry. 278(35):32578-32586, (2003).

Maginnis et al., "Beta1 integrin mediates internalization of mammalian reovirus," J Virol, 80(6):2760-70 (2006).

Martin et al., "Peptide-guided Gene Delivery", The AAPS Journal 2007; 9 (1) Article 3, pp. E18-E29.

Mishra et al., "HIV TAT forms pores in membranes by inducing saddle-splay curvature: potential role of bidentate hydrogen bonding," Angew. Chem., Int. Ed. 47(16):2986-2989, (2008).

(56) References Cited

OTHER PUBLICATIONS

Najjar et al., "Delivery of proteins, peptides or cell-impermeable small molecules into live cells by incubation with the endosomolytic reagent of dfTAT," J Vis Exp. (103):53175, 9 pages, (2015).

Nastasie et al.,"Enhancing Histone-Mediated Gene Delivery Through Increased Nuclear Targeting." The Journal Of Gene Medicine, 2011, vol. 13, pp. 442-443.

Pandey et al., "Functional roles of short sequence motifs in the endocytosis of membrane receptors," Frontiers in Bioscience 14:5339-5360, (2009).

Park et al., "Regulation of amyloid precursor protein processing by its KFERQ motif," BMB Rep, 49(6):337-42 (2016).

Partial European Search Report for EP Application No. 19881972.4 dated Oct. 11, 2022.

Pentikainen et al., ""RKKH" peptides from the snake venom metalloproteinase of Bothrops jararaca bind near the metal ion-dependent adhesion site of the human integrin alpha(2) l-domain," J Biol Chem, 274(44):31493-505 (1999).

Redrejo-Rodriguez et al., "Functional eukaryotic nuclear localization signals are widespread in terminal proteins of bacteriophages," PNAS, 109(45):18482-18487, (2012).

Reszka et al., "Identification of amino acid sequences in the integrin beta 1 cytoplasmic domain implicated in cytoskeletal association," J Cell Biol, 117(6):1321-30 (1992).

Rothbard et al., "Adaptive translocation: the role of hydrogen bonding and membrane potential in the uptake of guanidinium-rich transporters into cells," Adv. Drug Deliv. Rev. 57(4):495-504, (2005), Abstract Only.

Saleh et al., "Improved Tat-mediated plasmid DNA transfer by fusion to LK15 peptide", Journal of Controlled Release, Jan. 11, 2010, vol. 143, No. 2, pp. 233-242.

Smith, "Adeno-associated virus integration: virus versus vector," Gene Ther., 15:817-822, (2008).

Sunyach et al., "The mechanism of internalization of glycosylphosphatidylinositol-anchored prion protein," The EMBO Journal 22(14):3591-3601, (2003).

Supplementary European Search Report for EP Application No. 19881972.4 dated Feb. 27, 2023.

Supplementary Partial European Search Report for EP Application No. 21788559.9 dated Sep. 18, 2024.

Tashiro et al., "A synthetic peptide containing the IKVAVA sequence form the A chain of Laminin mediates cell attachment, migration, and neurite growth," J. Biol Chem. 264(27):1617416182, (1989).

Templeton et al., "Optimization of Non-Viral Gene Therapeutics Using Bilamellar Invaginated Vesicles," J Genet Syndr Gene Ther., S5(0):002, (2012).

Tervo et al., "A Designer AAV Variant Permits Efficient Retrograde Access to Projection Neurons," Neuron, 92(2):372-382 (2016).

Th'ng et al., "H1 family histones in the nucleus. Control of binding and localization by the C-terminal domain," J Biol Chem., 280(30):27809-14 (2005).

Tian et al., "FurinDB: A Database of 20-Residue Furin Cleavage Site Motifs, Substrates and their Associated Drugs," International Journal of Molecular Sciences, 12(2):1060-1065, (2011).

Ton-That et al., "Assembly of pili on the surface of Corynebacterium diphtheriae," Mol Microbiol., 50(4):1429-38 (2003).

Torrent et al., "The CPC clip motif: a conserved structural signature for heparin-binding proteins," PLoS One, 7(8):e42692 (2012).

Vandevondele et al., "RGD-Grafted Poly-L-lysine-graft (polyethylene glycol) copolymers block non-specific protein adsorption while promoting cell adhesion," Biotechnology and Bioengineering, 82(7):784-790, (2003).

Wilke et al., "Efficacy of a peptide-based gene delivery system depends on mitotic activity," Gene Ther. 3:1133-1142 (1996), Abstract Only.

Wischjnow et al., "Renal Targeting: Peptide-Based Drug Delivery to Proximal Tubule Cells," Bioconjug Chem, 27(4):1050-7 (2016), Abstract Only.

Wodrich et al., "A Capsid- Encoded PPxY-Motif Facilitates Adenovirus Entry," PLoS Pathog 6(3):e1000808, (2010).

Work et al., "Development of efficient viral vectors selective for vascular smooth muscle cells," Mol Ther, 9(2):198-208 (2004).

Work et al., "Vascular bed-targeted in vivo gene delivery using tropism-modified adeno-associated viruses," Mol Ther, 13(4):683-93 (2006).

Wu et al., "Tryptophan- and dileucine-based endocytosis signals in the neonatal Fc receptor," J Biol Chem., 276(7):5240-7, (2000).

Yan et al., "Advances in Importin Beta1-Mediated Nuclear Transport of Viral Proteins in the Replication of Viruses," Chinese Journal of Cell Biology 2017, 39(8): 1091-1098.

Yu et al., "A muscle-targeting peptide displayed on AAV2 improves muscle tropism on systemic delivery," Gene Ther, 16(8):953-62 (2009).

Zabner et al., "Cellular and molecular barriers to gene transfer by a cationic lipid," J. Biol. Chem. 270(32):18997-19007, (1995).

Zheng et al., "PAT1, a microtubule-interacting protein, recognizes the basolateral sorting signal of amyloid precursor protein," Proc Natl Acad Sci USA, 95(25):14745-50 (1998).

International Search Report for PCT/US21/26917, 4 pages (mailed Aug. 5, 2021).

Written Opinion for PCT/US21/26917, 9 pages (mailed Aug. 5, 2021).

* cited by examiner

Fig. 4

Mini-nucleosome

Control-uninjected

RPE
ONL
INL
GCL

A    Retinal section    B

C    IS/OS facing upward    D
Retina wholemount

Figure 20 : N-Glycosylation

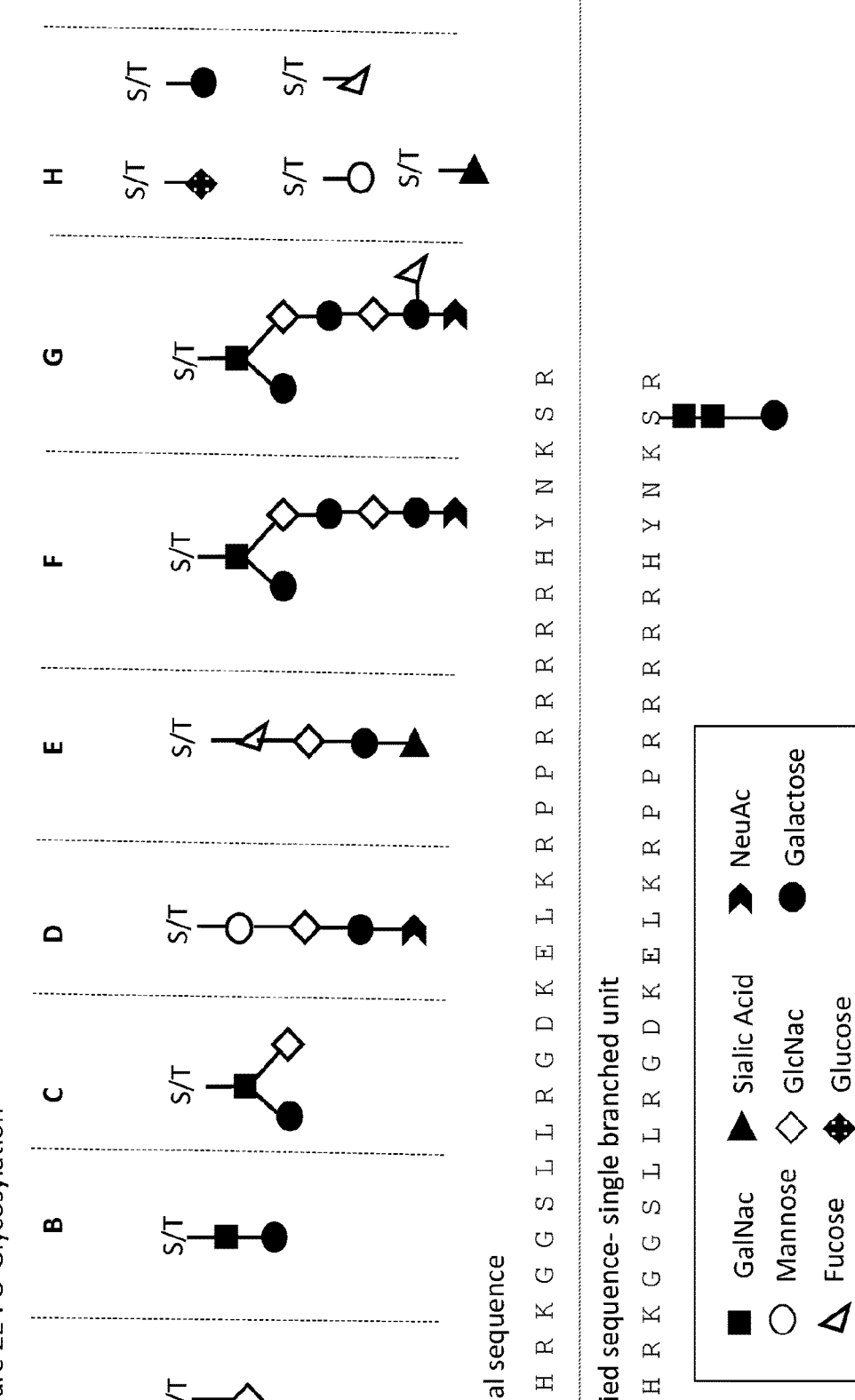
Figure 22 : O-Glycosylation

Figure 23:
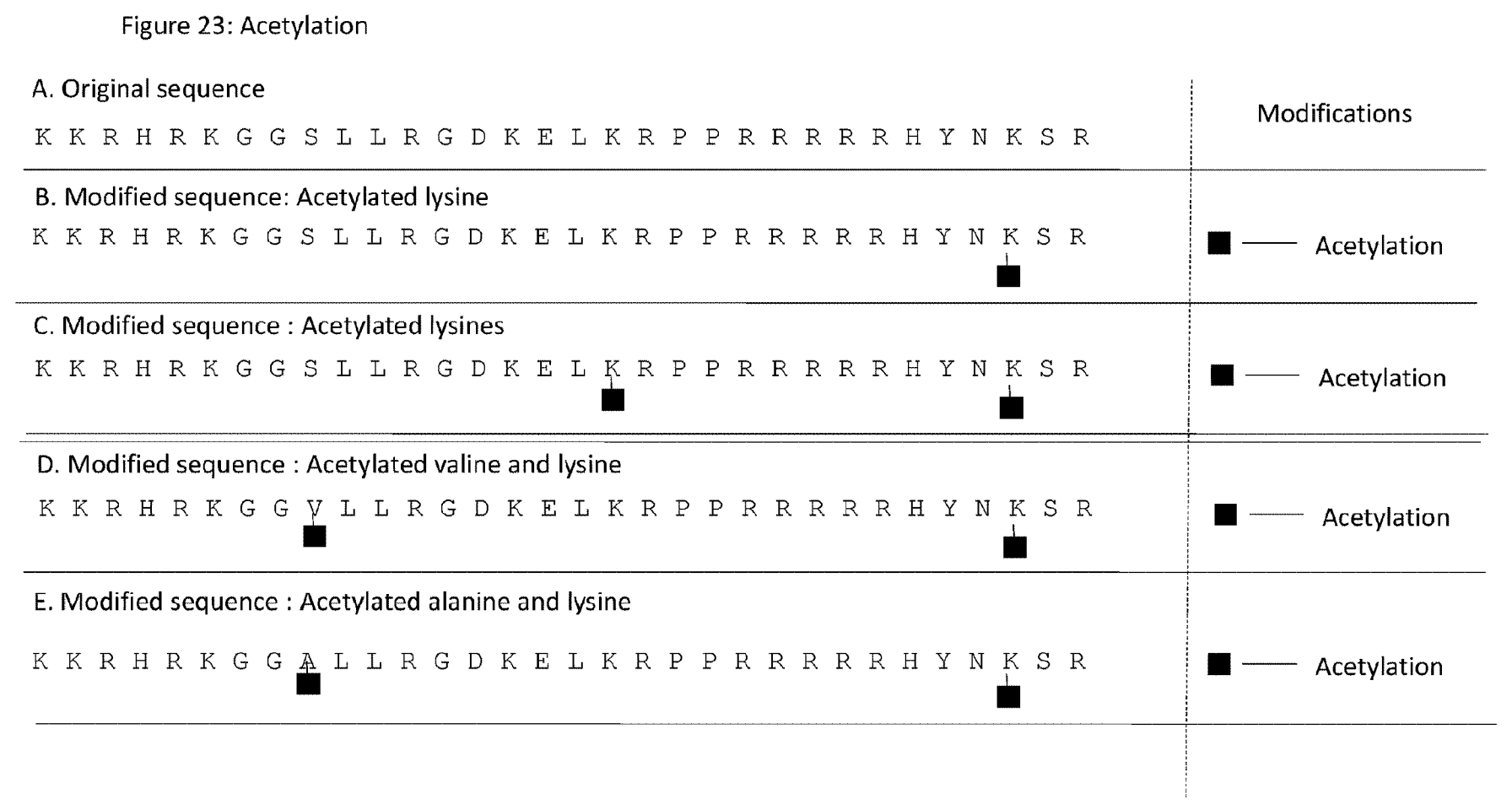

Figure 23: Acetylation

A. Original sequence

K K R H R K G G S L L R G D K E L K R P P R R R H Y N K S R

B. Modified sequence: Acetylated lysine

K K R H R K G G S L L R G D K E L K R P P R R R H Y N K S R          ■——— Acetylation          Modifications C. Modified sequence : Acetylated lysines K K R H R K G G S L L R G D K E L K R P P R R R H Y N K S R          ■——— Acetylation D. Modified sequence : Acetylated valine and lysine K K R H R K G G Y L L R G D K E L K R P P R R R H Y N K S R          ■——— Acetylation E. Modified sequence : Acetylated alanine and lysine K K R H R K G G A L L R G D K E L K R P P R R R H Y N K S R          ■——— Acetylation $$CH_3—CO—HN—CH_2—CH_2—CH_2—CH_2—CH—CO—$$
$$NH—$$

Figure 5: Acetyl-lysine

Figure 24: Acetylation

Figure 25:
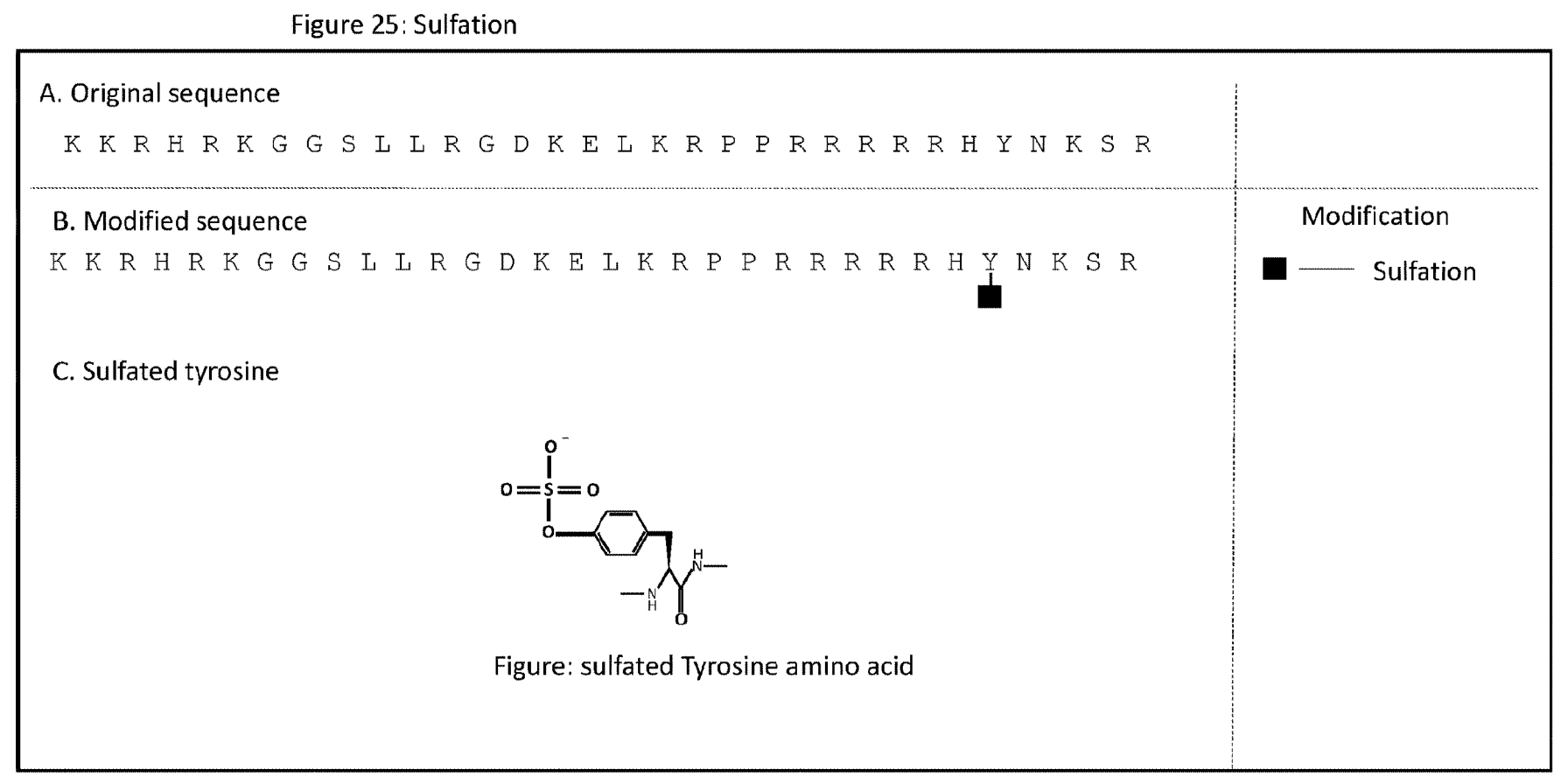

Figure 25: Sulfation

A. Original sequence

K K R H R K G G S L L R G D K E L K R P P P R R R R H Y N K S R

B. Modified sequence

K K R H R K G G S L L R G D K E L K R P P P R R R R H Y N K S R

Modification
■ ——— Sulfation

C. Sulfated tyrosine

Figure: sulfated Tyrosine amino acid

Figure 26:
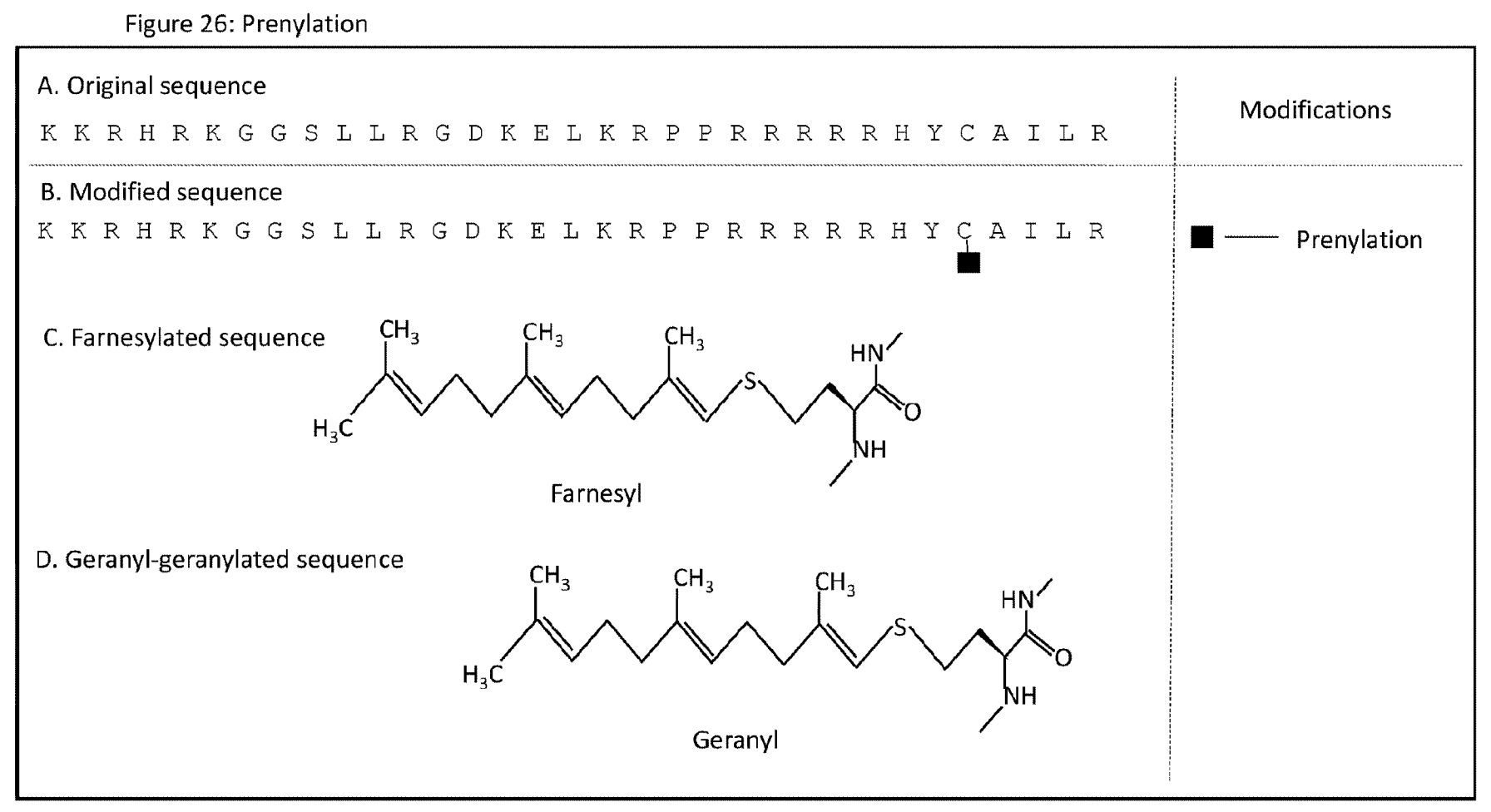

Figure 26: Prenylation

A. Original sequence

K K H R K G G S L L R G D K E L K R P P R R R H Y C A I L R

B. Modified sequence

K K H R K G G S L L R G D K E L K R P P R R R H Y C A I L R

C. Farnesylated sequence

Farnesyl

D. Geranyl-geranylated sequence

Geranyl

Modifications

■ ——— Prenylation

Figure 27:
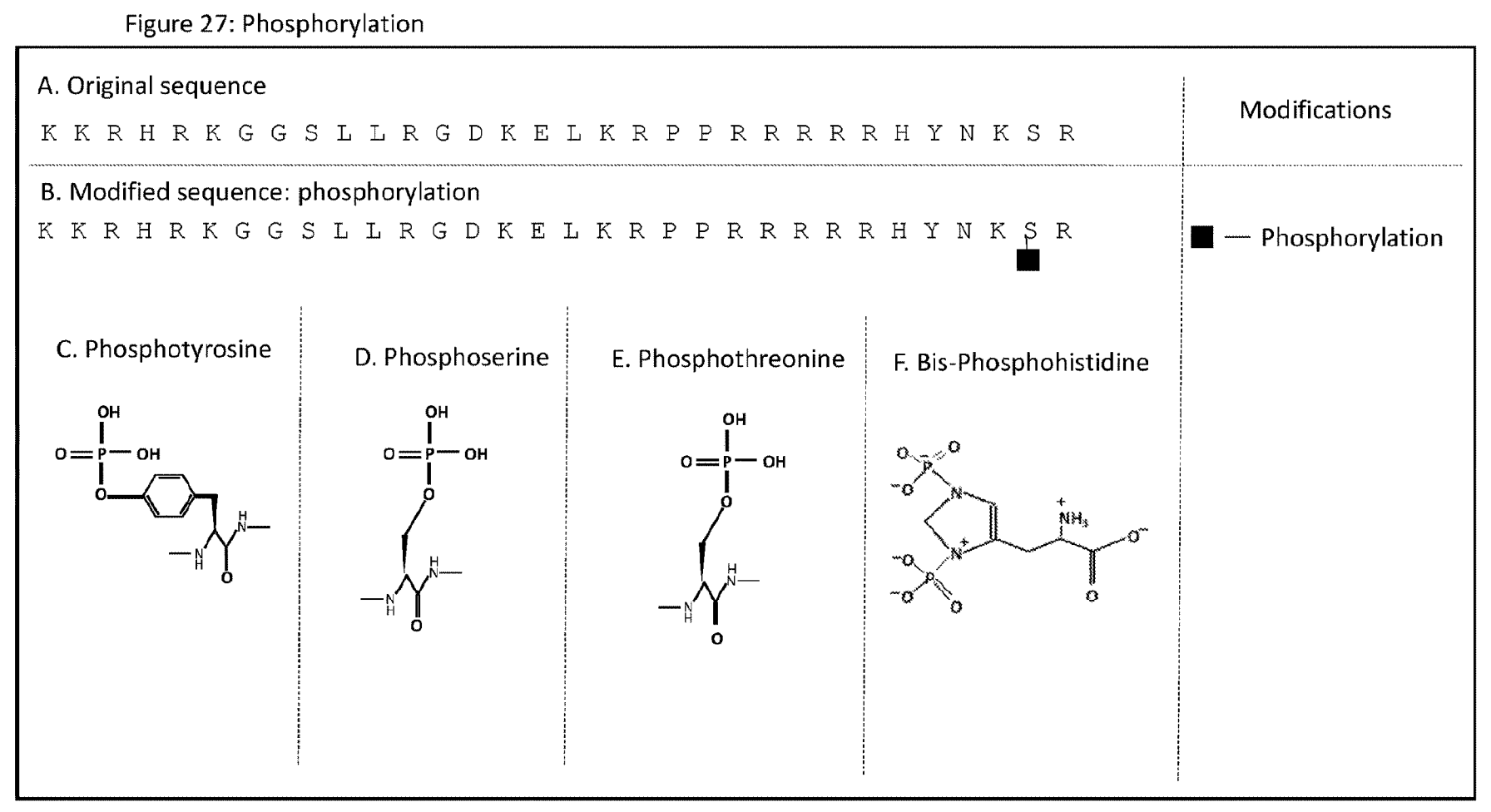

Figure 27: Phosphorylation

A. Original sequence

K K R H R K G G S L L R G D K E L K R P P P R R R H Y N K S R

B. Modified sequence: phosphorylation

K K R H R K G G S L L R G D K E L K R P P P R R R H Y N K S R

Modifications

■ —— Phosphorylation

C. Phosphotyrosine

D. Phosphoserine

E. Phosphothreonine

F. Bis-Phosphohistidine

Figure 28:
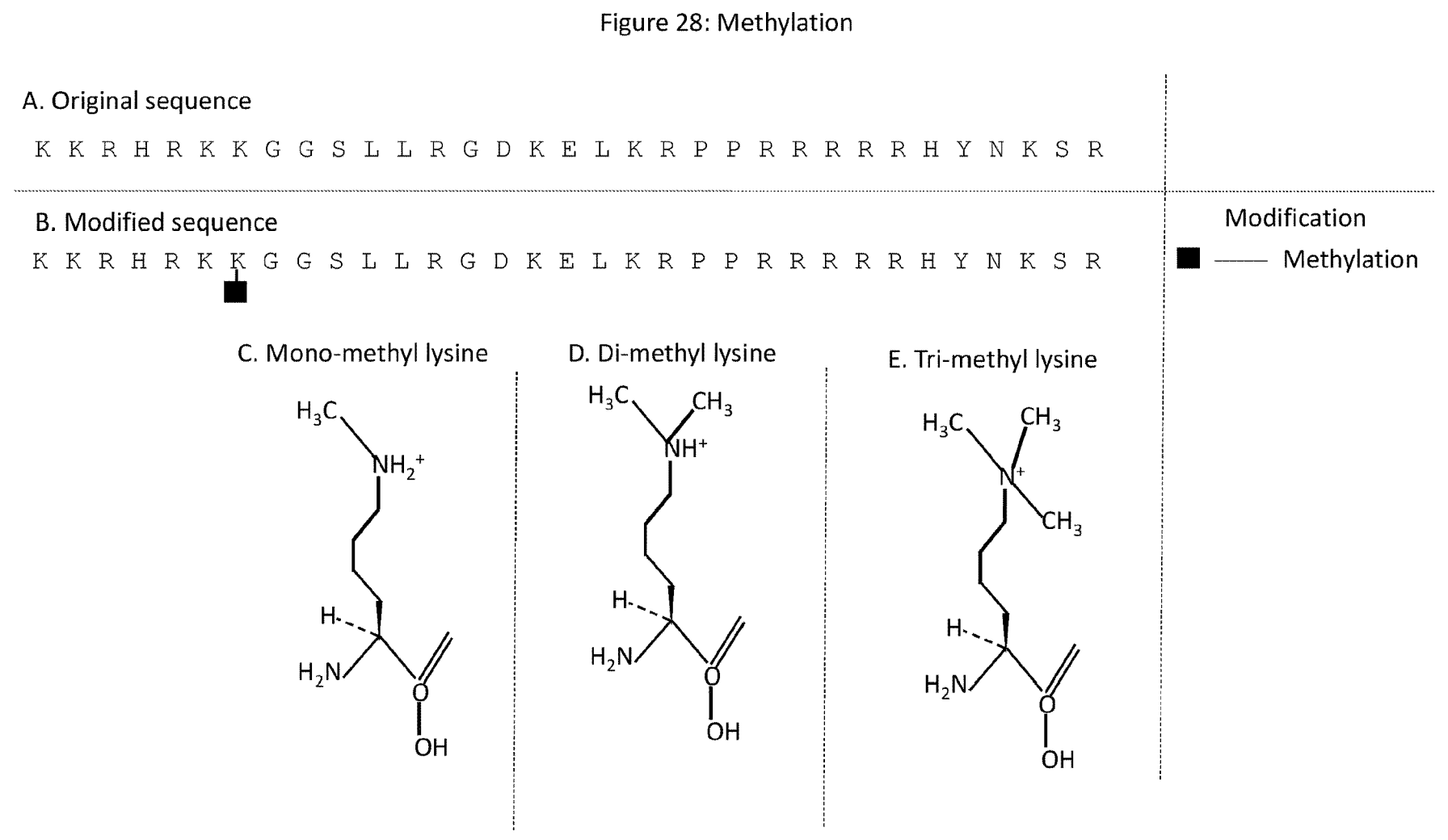

Figure 28: Methylation

Modification

■ ——— Methylation

A. Original sequence

K K H R R K K G G S L L R G D K E L K R P P R R R H Y N K S R

B. Modified sequence

K K H R R K K G G S L L R G D K E L K R P P R R R H Y N K S R ■

C. Mono-methyl lysine

D. Di-methyl lysine

E. Tri-methyl lysine

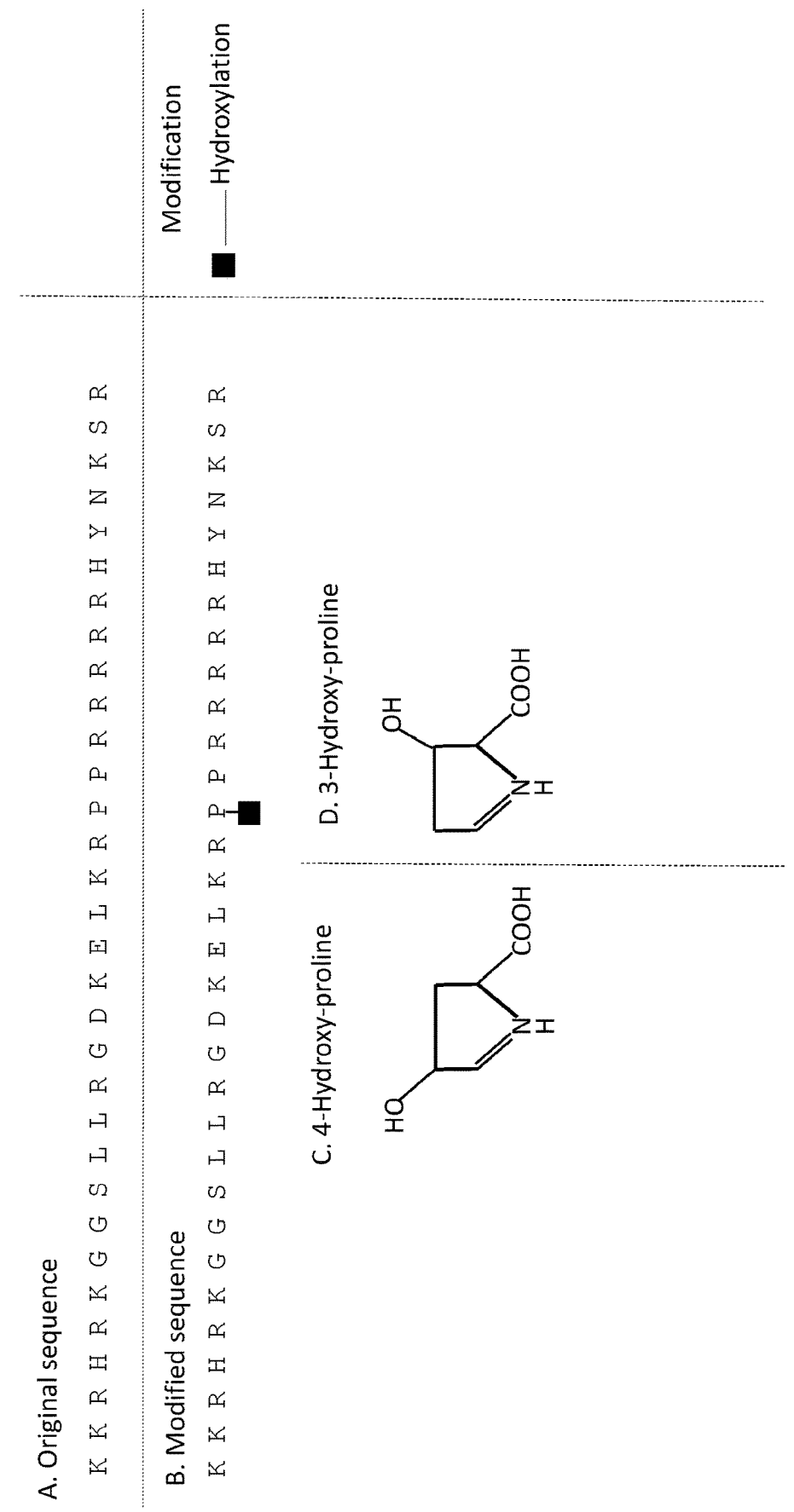
Figure 29: Hydroxylation

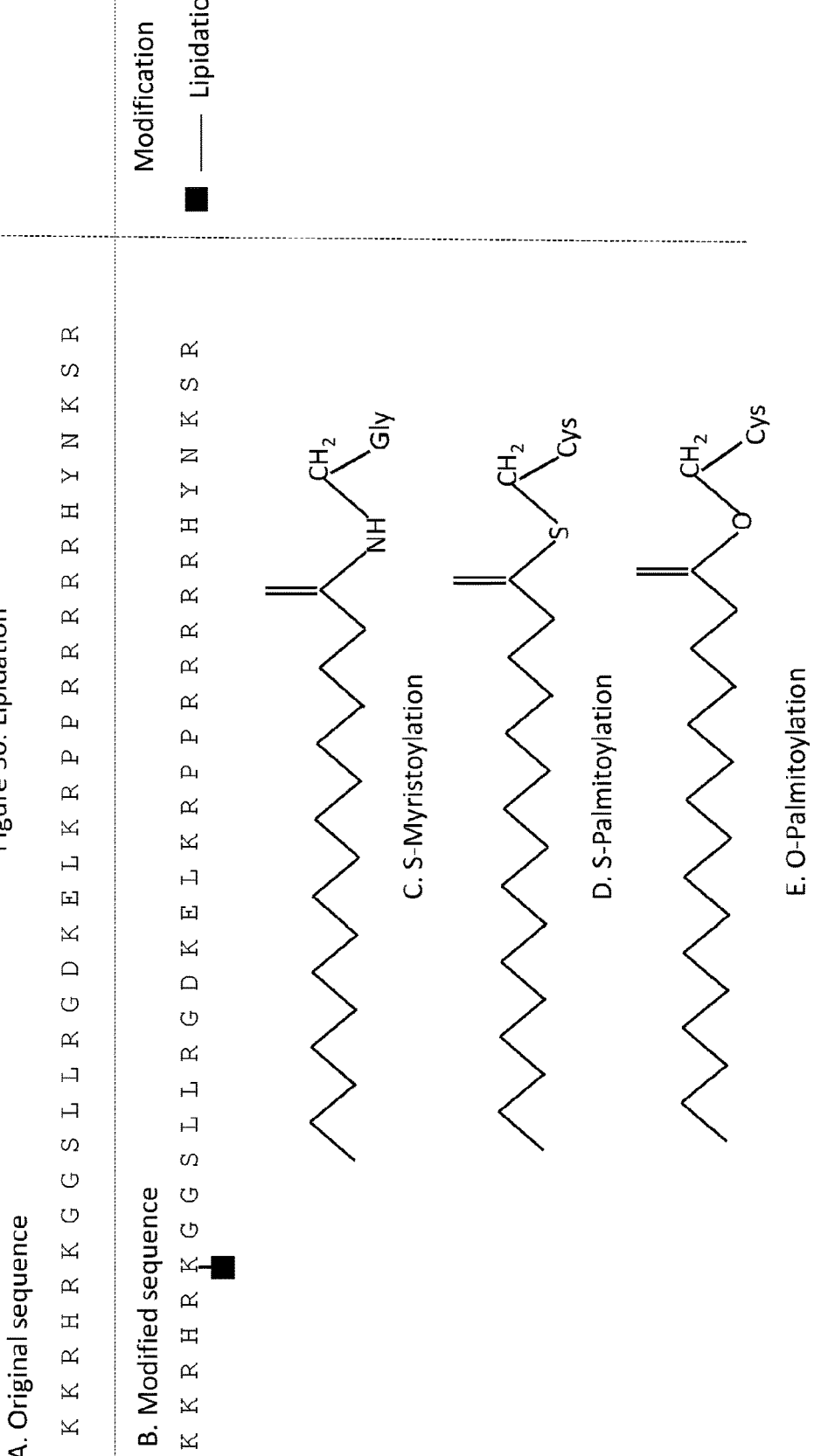
Figure 30: Lipidation

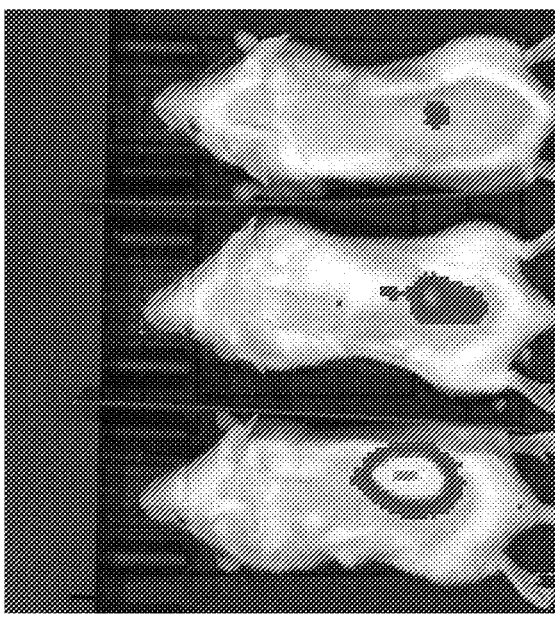
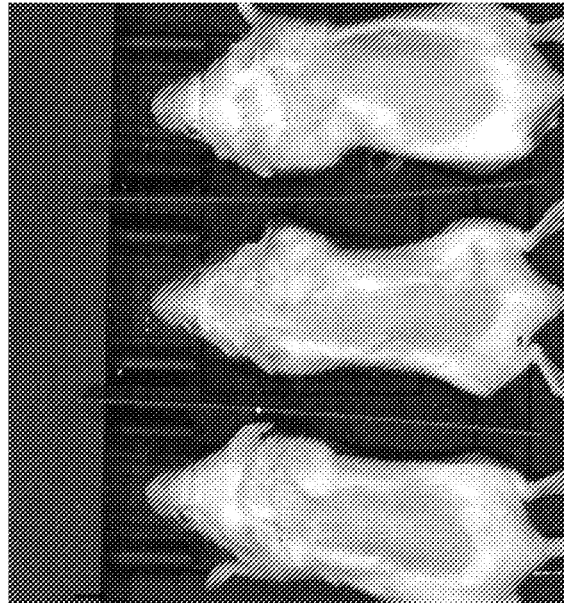
Fig. 32

```
                        SEQUENCE LISTING

<160> NUMBER OF SEQ ID NOS: 477

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Arg His Arg Lys
1               5

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 2

Arg Arg Arg
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Arg Arg
1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Arg Arg Arg Arg
1               5

<210> SEQ ID NO 5
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg
1

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Leu Ala Arg Arg
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Lys Ala Lys Ala Ala Ala Lys Pro Lys Lys
1               5                   10

<210> SEQ ID NO 8
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Lys Asp Gly Lys Lys Arg Lys Arg
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Lys Lys Leu Lys
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Lys Arg Ile Arg Lys
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Lys Lys Ser Lys
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Lys Pro Lys Lys
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Arg His Arg Arg
```

-continued

```
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg His Arg Arg Arg
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Arg Arg His Arg
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Arg Thr Val Arg Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Arg Gln Arg Asn Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Val Cys Ala Cys Pro Gly Arg
1               5

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 19

Lys Lys Lys
1

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Glu Met Gly Leu Gly Lys Thr
1               5

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Arg Glu
1

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

His Leu Ser Gln His Leu Asn
1               5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Thr Gln Lys
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Phe Lys Trp
1

<210> SEQ ID NO 25

-continued

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Val Tyr
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Arg Arg Lys
1

<210> SEQ ID NO 27
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Phe Phe
1

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Pro Arg Gly Arg Pro Arg Lys His Thr Val Thr Ser
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Gly Arg Glu Glu Arg Gln
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30
```

```
Asn Thr Gln Ile His
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Trp Asn Asn Lys Thr Pro His
1               5

<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Pro His
1

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Val Asn Arg Trp Ser
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(4)
<223> OTHER INFORMATION: Arg, Lys, or His
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (7)..(7)
<223> OTHER INFORMATION: Arg, Lys, or His
<220> FEATURE:
<221> NAME/KEY: MOD_RES
<222> LOCATION: (8)..(8)
<223> OTHER INFORMATION: Any amino acid

<400> SEQUENCE: 34

Xaa Xaa Xaa Xaa Xaa Xaa Xaa Xaa
1               5
```

-continued

```
<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Arg Lys Lys Ala Ala Lys Ala
1               5

<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Arg Arg
1

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Arg Arg
1

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Glu Pro Ser Arg Pro Phe Pro Val Asp
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

His Arg Arg Thr Arg Lys Ala Pro Lys Arg Ile Arg Leu Pro His Ile
1               5                   10                  15

Arg

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 40

Lys Arg Thr Gly Gln Tyr Lys Leu Gly Ser Lys Thr Gly Pro Gly Gln
1               5                   10                  15

Lys

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Lys Thr Lys
1

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Leu Arg Ser Gln Leu Val Lys Lys
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Arg Arg Cys Gly Gln Lys Lys Lys
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, Lys, or His
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (9)..(9)
<223> OTHER INFORMATION: Arg, Lys, or His

<400> SEQUENCE: 44

Xaa Xaa Xaa Xaa Xaa Xaa Xaa Xaa Xaa
1               5

<210> SEQ ID NO 45

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ile Gln Asn Leu Leu Lys Ile Thr Asn Leu Arg Ile Lys Phe Val
1               5                   10                  15

Lys

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Lys Glu Lys Asp Ile Met Lys Lys Thr Ile
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

His Gly Ser Arg Phe Thr Phe His Arg Gly Ser Met
1               5                   10

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Arg Pro His
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Val Ala Arg
1

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 50

His Phe Asn Pro Arg
1               5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Gly Thr Glu
1

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Lys Gln Phe Gly Ala Glu Cys
1               5

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Arg Pro Arg Pro Gly Thr Gly Pro Gly Arg Arg Pro Arg Pro Arg
1               5                   10                  15

Pro Arg Pro

<210> SEQ ID NO 54
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Gly Glu
1

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Gly Asp
1

<210> SEQ ID NO 56
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Gly Asp Ser
1

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Thr Val Val Asn Pro Lys Tyr Glu Gly Lys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Arg Met Ser Gln Ile Lys Arg Leu Leu Ser
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Arg His Arg Ala Arg Ser
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline

<400> SEQUENCE: 60

Gly Phe Pro Gly Glu Arg
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
        peptide

<400> SEQUENCE: 61

Leu Phe Asp Leu Met
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Gly Arg Glu Glu Arg Gln
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ser Thr Glu Lys Arg Gly
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Pro Asn Thr Gly
1               5

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Phe
<220> FEATURE:
<221> NAME/KEY: MOD_RES
<222> LOCATION: (2)..(2)
<223> OTHER INFORMATION: Ser or Gln
<220> FEATURE:
<221> NAME/KEY: MOD_RES
<222> LOCATION: (3)..(3)
<223> OTHER INFORMATION: Pro or Val
<220> FEATURE:
<221> NAME/KEY: MOD_RES
<222> LOCATION: (4)..(4)
<223> OTHER INFORMATION: Glu or Thr
<220> FEATURE:
<221> NAME/KEY: MOD_RES
<222> LOCATION: (1)..(4)
<223> OTHER INFORMATION: This sequence may encompass "DSPE" or "FQVT"

<400> SEQUENCE: 65
```

Xaa Xaa Xaa Xaa
1

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ser Thr Glu Lys Arg Gly
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Gln Gly Leu Ile Asp
1               5

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Lys Lys His
1

<210> SEQ ID NO 69
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Tyr Pro Lys
1

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Asn Gln Tyr Thr
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Trp Asn Tyr Lys
1               5

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Pro Gln Ser Val Lys Phe Lys Ser Pro Asp Gln Ile
1               5                   10

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Val Gly Glu Asn Trp Trp Tyr
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Thr Leu Gln Ala His His Asp Arg
1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Glu Ser Pro Phe Ser Gly Ser Ser Arg
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Glu Glu Ile Gln Glu Arg Met Arg
1               5

```
<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Asp Ser Ser Ser Phe His His Gln
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Lys Gln Phe Gly Ala Glu Cys
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Lys Arg Ala Leu His Asn Ala Glu Cys
1               5

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Lys Gln Lys Ile Lys His Val Val Lys Leu Lys
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Leu Arg Cys Gln Leu Ala Lys Lys Lys
1               5                   10

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 82

Phe Xaa Asp Xaa Phe
1               5

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Pro Pro Ser Tyr
1

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Phe Glu Asp Asn Phe Val Pro
1               5

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Tyr Ile Arg Val
1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Tyr Ala Asp Trp
1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87
```

-continued

```
Tyr Thr Gln Val
1

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Lys Lys Arg Pro Lys Pro
1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Ser Asp Asp Glu
1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Arg Ala Ser Ser
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 91

Tyr Xaa Xaa Leu Tyr Xaa Xaa Leu
1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92
```

-continued

```
Leu Pro Leu Thr Gly
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Leu Ala Phe Thr Gly
1               5

<210> SEQ ID NO 94
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu
1

<210> SEQ ID NO 95
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ile
1

<210> SEQ ID NO 96
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Ile
1

<210> SEQ ID NO 97
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Leu
1

<210> SEQ ID NO 98
<211> LENGTH: 2
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 98

Leu Leu
1

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Arg Arg His Pro Lys Lys
1               5

<210> SEQ ID NO 100
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu Pro Ser
1

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu Pro Asn Leu Pro Glu Glu
1               5

<210> SEQ ID NO 102
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Asp
1

<210> SEQ ID NO 103
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asn Phe Arg
1
```

```
<210> SEQ ID NO 104
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Tyr Trp Val
1

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ala Ile Cys Lys Arg Ile Pro Asn Lys Lys Pro Gly Lys Arg Thr
1               5                   10                  15

<210> SEQ ID NO 106
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Val Ala Arg
1

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Cys Pro Cys Arg
1               5

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ala Asn Val Lys His Leu Lys Ile Leu Asn
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109
```

```
Val Ala Arg Leu Lys Asn Asn Asn Arg Gln Val
1               5                   10

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Val Arg Lys Lys Pro
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Val Arg Lys Lys Pro Lys Leu Lys
1               5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ile Ser Arg Arg Leu Ile
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Leu Thr Lys Arg Ser Arg Gln
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asn Arg Lys Ile Ser Val Gln Arg Leu
1               5

<210> SEQ ID NO 115
<211> LENGTH: 7
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 115

Tyr Tyr Lys Gln Arg Leu Ile
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Lys Lys Tyr Lys Leu Lys
1               5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Lys Lys Arg Lys Leu Glu
1               5

<210> SEQ ID NO 118
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Arg Ser Lys
1

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

His Arg Lys Arg Lys Arg
1               5

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asn Lys Arg Lys Arg Lys
1               5
```

-continued

```
<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Glu Lys Ser Lys Lys Lys
1               5

<210> SEQ ID NO 122
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Lys Ser Lys
1

<210> SEQ ID NO 123
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Lys Arg Val Lys
1

<210> SEQ ID NO 124
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Lys Arg Lys
1

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Leu Gln Gln Thr Pro Leu His Leu Ala Val Ile
1               5                   10

<210> SEQ ID NO 126
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 126

Arg Arg Pro Arg
1

<210> SEQ ID NO 127
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Pro Arg Pro Arg
1

<210> SEQ ID NO 128
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Pro Pro Pro
1

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Arg Lys Lys Arg Lys Gly Lys
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Pro Ala Ala Lys Arg Val Lys Leu Asp
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Leu Lys Ile Lys Arg Pro Val Lys
1               5

<210> SEQ ID NO 132
<211> LENGTH: 7
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 132

Pro Lys Lys Lys Arg Lys Val
1               5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Arg Lys Arg Gln Lys
1               5

<210> SEQ ID NO 134
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Lys Arg Pro Arg
1

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Lys Arg Arg Arg Pro
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys Lys Gly Arg Arg Asn Arg Phe Lys
1               5

<210> SEQ ID NO 137
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg His Arg Asp Arg Leu Asn Thr Glu Leu Asp Arg Leu Ala Ser Leu
1               5                   10                  15
```

-continued

```
Leu Pro Phe Pro Gln Asp Val Ile Asn Lys Leu Asp Lys
            20                  25
```

```
<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys Arg Gly Arg Lys Pro
1               5
```

```
<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Lys Lys Arg Ala Gly Arg Arg Ile Phe Lys Glu Thr Arg
1               5                   10
```

```
<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Ser Ser Leu Asn Ile Ala
1               5
```

```
<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ser Lys Thr Phe Asn Thr His Pro Gln Ser Thr Pro
1               5                   10
```

```
<210> SEQ ID NO 142
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Tyr Lys Gln Cys His Lys Lys Gly Gly His Cys Phe Pro Lys Glu Lys
1               5                   10                  15
```

```
<210> SEQ ID NO 143
<211> LENGTH: 18
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 143

Leu Gly Lys Met Asp Cys Arg Trp Lys Trp Lys Cys Cys Lys Lys Gly
1               5                   10                  15

Ser Gly

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

His Gly Ser Arg Phe Thr Phe His Arg Gly Ser Met
1               5                   10

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Lys Lys Glu Glu Glu Lys Lys Glu Glu Glu Lys Lys Glu Glu Glu
1               5                   10                  15

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Leu Ile Phe His Lys Glu Gln
1               5

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Lys Phe Asn Lys Pro Phe Val Phe Leu Ile
1               5                   10

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Pro Glu His Ser Ser Thr
```

```
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Glu Tyr His His Tyr Asn Lys
1               5

<210> SEQ ID NO 150
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Gly Arg
1

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Glu Lys Gly Glu Pro
1               5

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Lys Thr Lys Lys Lys
1               5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Lys Ala Leu Lys Lys Lys
1               5

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued

```
               peptide

<400> SEQUENCE: 154

Lys Gly Lys Lys Lys
1               5

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Cys Ser Val Thr Cys Gly
1               5

<210> SEQ ID NO 156
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Leu Arg Glu
1

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Tyr Lys Tyr Asn Leu Asn Gly Arg Glu Ser
1               5                   10

<210> SEQ ID NO 158
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Tyr Arg Ser Leu
1

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Lys Gly Gly Lys Lys Lys Lys Lys Lys
1               5                   10

<210> SEQ ID NO 160
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Lys Lys Lys Gln Tyr Thr Ser Ile His His Gly
1               5                   10

<210> SEQ ID NO 161
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Lys Asp Glu Leu
1

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Leu Ala Asp Gln Asp Tyr Thr Lys Thr Ala
1               5                   10

<210> SEQ ID NO 163
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Asp Asn Asn
1

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Ala Val Thr Thr Val Val Asn
1               5

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165
```

```
Gly Arg Lys Lys Arg Arg Gln Arg Arg Arg Pro Gln
1               5                   10

<210> SEQ ID NO 166
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Lys Arg His
1

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Lys Ser Val Lys Lys Arg Ser Val Ser Glu Ile Gln
1               5                   10

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asn Arg Arg Lys Lys Arg Ala Leu
1               5

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Lys Phe Glu Arg Gln
1               5

<210> SEQ ID NO 170
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Val Arg Gly Pro
1

<210> SEQ ID NO 171
<211> LENGTH: 4
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 171

Asn Lys Asp Ser
1

<210> SEQ ID NO 172
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Asn Asn Arg
1

<210> SEQ ID NO 173
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

His Leu
1

<210> SEQ ID NO 174
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Arg Ile
1

<210> SEQ ID NO 175
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Glu Thr
1

<210> SEQ ID NO 176
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Gln
1
```

```
<210> SEQ ID NO 177
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Arg Ser
1

<210> SEQ ID NO 178
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Arg Asp
1

<210> SEQ ID NO 179
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Arg Asn
1

<210> SEQ ID NO 180
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Cys
1

<210> SEQ ID NO 181
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Arg Gly
1

<210> SEQ ID NO 182
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182
```

-continued

Arg Leu
1

<210> SEQ ID NO 183
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Asp Ala
1

<210> SEQ ID NO 184
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Ala
1

<210> SEQ ID NO 185
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Ser
1

<210> SEQ ID NO 186
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Leu Thr
1

<210> SEQ ID NO 187
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Phe Ser
1

<210> SEQ ID NO 188
<211> LENGTH: 2
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 188

Gly Leu
1

<210> SEQ ID NO 189
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ser Ala
1

<210> SEQ ID NO 190
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Pro
1

<210> SEQ ID NO 191
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Thr
1

<210> SEQ ID NO 192
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Cys
1

<210> SEQ ID NO 193
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Arg Gln
1
```

-continued

```
<210> SEQ ID NO 194
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Leu Ser
1

<210> SEQ ID NO 195
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

His Ala
1

<210> SEQ ID NO 196
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Phe Val
1

<210> SEQ ID NO 197
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln His
1

<210> SEQ ID NO 198
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Glu Ala
1

<210> SEQ ID NO 199
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 199

Ala Leu
1

<210> SEQ ID NO 200
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Tyr
1

<210> SEQ ID NO 201
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Tyr Leu
1

<210> SEQ ID NO 202
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Phe
1

<210> SEQ ID NO 203
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Pro Ser
1

<210> SEQ ID NO 204
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Arg Glu
1

<210> SEQ ID NO 205
<211> LENGTH: 2
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 205

Asp Pro
1

<210> SEQ ID NO 206
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Pro Ile
1

<210> SEQ ID NO 207
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gln Ser
1

<210> SEQ ID NO 208
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asn Asp
1

<210> SEQ ID NO 209
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Tyr Thr Arg Phe
1

<210> SEQ ID NO 210
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Asp Ala Tyr
1
```

```
<210> SEQ ID NO 211
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Leu Leu Glu Glu
1

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Arg Lys Lys Arg Arg Gln Arg Arg Arg
1               5

<210> SEQ ID NO 213
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Tyr Lys Ser Leu
1

<210> SEQ ID NO 214
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Tyr Glu Asn Phe
1

<210> SEQ ID NO 215
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Phe Gln Asp Leu
1

<210> SEQ ID NO 216
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 216

Tyr Ile Gly Ser Arg
1               5

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ile Lys Val Ala Val
1               5

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Glu Phe Ala Lys Phe Glu
1               5

<210> SEQ ID NO 219
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Leu Leu Glu Glu Glu Gln Leu Arg Gly Leu Gly Phe Arg Gln Thr Arg
1               5                   10                  15

Gly Tyr Lys Ser Leu
            20

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Leu Ile Arg Glu Arg Thr Glu
1               5

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Leu Val Glu Glu Arg Thr Gln
1               5
```

-continued

```
<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ile Ile Thr Phe Thr Lys
1               5

<210> SEQ ID NO 223
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ile Leu Phe Asn Lys
1               5

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Pro Ile Arg Thr Leu Ser Lys
1               5

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Tyr Gly Asn Ser Pro Leu His Arg Phe Lys
1               5                   10

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Phe Phe Gln Lys Asp Arg
1               5

<210> SEQ ID NO 227
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 227

Lys Ser Arg Pro
1

<210> SEQ ID NO 228
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Tyr Val Met
1

<210> SEQ ID NO 229
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Tyr Met Lys Met
1

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Arg Ser Ser Ser Phe Gly
1               5

<210> SEQ ID NO 231
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Leu Lys Ile Arg Gly Arg Glu Arg
1               5

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Leu Lys Ile Arg Gly Arg Lys Arg
1               5

<210> SEQ ID NO 233
<211> LENGTH: 9
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 233

His Val Ile Phe Lys Lys Val Ser Arg
1               5

<210> SEQ ID NO 234
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Arg Gly Pro Arg Val
1               5

<210> SEQ ID NO 235
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Arg Ala Asn Val Lys His Leu Lys
1               5

<210> SEQ ID NO 236
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Tyr Pro Lys Ala Gly
1               5

<210> SEQ ID NO 237
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Tyr Pro Arg Thr Gly
1               5

<210> SEQ ID NO 238
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Leu
1
```

```
<210> SEQ ID NO 239
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Leu Leu
1

<210> SEQ ID NO 240
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Ser Ser
1

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Ser Ser Gly Ser Ser
1               5

<210> SEQ ID NO 242
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Gly Ser
1

<210> SEQ ID NO 243
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ser Ser Ser
1

<210> SEQ ID NO 244
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 244

Ser Ser Ser Ser Ser Ser
1               5

<210> SEQ ID NO 245
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gly Gly Ser Gly Gly
1               5

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Gly Ser Gly Gly Gly Gly Gly
1               5

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Gly Ser Gly Gly His Met Gly Ser Gly Gly
1               5                   10

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Glu Ala Ala Ala Lys Ala
1               5

<210> SEQ ID NO 249
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Pro
1

<210> SEQ ID NO 250
<211> LENGTH: 2

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Lys Pro
1

<210> SEQ ID NO 251
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Glu Pro
1

<210> SEQ ID NO 252
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Thr
1

<210> SEQ ID NO 253
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ala Ala Gly Ala Ala Thr Ala Ala
1               5

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gly Ser Gly Ser Gly Ser Gly Ser
1               5

<210> SEQ ID NO 255
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gly Gly Ser Ser Gly
```

-continued

```
1               5

<210> SEQ ID NO 256
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Pro Pro
1

<210> SEQ ID NO 257
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Trp Trp
1

<210> SEQ ID NO 258
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Met His
1

<210> SEQ ID NO 259
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gln Pro
1

<210> SEQ ID NO 260
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Pro Leu
1

<210> SEQ ID NO 261
<211> LENGTH: 2
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 261

Cys Met
1

<210> SEQ ID NO 262
<211> LENGTH: 2
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 262

Arg Met
1

<210> SEQ ID NO 263
<211> LENGTH: 2
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 263

Arg Lys
1

<210> SEQ ID NO 264
<211> LENGTH: 2
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 264

Gln Arg
1

<210> SEQ ID NO 265
<211> LENGTH: 2
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 265

His Arg
1

<210> SEQ ID NO 266
<211> LENGTH: 2
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 266

Phe Trp
1

<210> SEQ ID NO 267
```

-continued

```
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Pro Trp
1

<210> SEQ ID NO 268
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

His Arg
1

<210> SEQ ID NO 269
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Asp His
1

<210> SEQ ID NO 270
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gln Ser
1

<210> SEQ ID NO 271
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Trp Gly
1

<210> SEQ ID NO 272
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272
```

Gly Met
1

<210> SEQ ID NO 273
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Lys Pro
1

<210> SEQ ID NO 274
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Leu Phe
1

<210> SEQ ID NO 275
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Tyr Gln
1

<210> SEQ ID NO 276
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Arg Ile
1

<210> SEQ ID NO 277
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Phe Tyr
1

<210> SEQ ID NO 278
<211> LENGTH: 2
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 278

Phe Asn
1

<210> SEQ ID NO 279
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Thr Ala
1

<210> SEQ ID NO 280
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

His Tyr
1

<210> SEQ ID NO 281
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gln Val
1

<210> SEQ ID NO 282
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Asp Trp
1

<210> SEQ ID NO 283
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ala Trp
1
```

-continued

```
<210> SEQ ID NO 284
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Tyr Ile
1

<210> SEQ ID NO 285
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

His Thr
1

<210> SEQ ID NO 286
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Cys His
1

<210> SEQ ID NO 287
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

His Pro
1

<210> SEQ ID NO 288
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Thr Ala
1

<210> SEQ ID NO 289
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289
```

Glu Met
1

<210> SEQ ID NO 290
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Lys His
1

<210> SEQ ID NO 291
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Met Leu
1

<210> SEQ ID NO 292
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ala Gln
1

<210> SEQ ID NO 293
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Tyr Leu
1

<210> SEQ ID NO 294
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Phe Ile
1

<210> SEQ ID NO 295
<211> LENGTH: 2
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 295

Lys Tyr
1

<210> SEQ ID NO 296
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Trp Arg
1

<210> SEQ ID NO 297
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Leu Ala
1

<210> SEQ ID NO 298
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Phe Ser
1

<210> SEQ ID NO 299
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ala Arg
1

<210> SEQ ID NO 300
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Phe Asn
1
```

```
<210> SEQ ID NO 301
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Glu Thr
1

<210> SEQ ID NO 302
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Leu Trp
1

<210> SEQ ID NO 303
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Asn Glu
1

<210> SEQ ID NO 304
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Leu His
1

<210> SEQ ID NO 305
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Met His
1

<210> SEQ ID NO 306
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 306

Phe Tyr
1

<210> SEQ ID NO 307
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Pro His
1

<210> SEQ ID NO 308
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Tyr Glu
1

<210> SEQ ID NO 309
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

His Lys
1

<210> SEQ ID NO 310
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Pro Trp
1

<210> SEQ ID NO 311
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

His Phe
1

<210> SEQ ID NO 312
<211> LENGTH: 2
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 312

Ile Met
1

<210> SEQ ID NO 313
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Asp His
1

<210> SEQ ID NO 314
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Val His
1

<210> SEQ ID NO 315
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asp Arg
1

<210> SEQ ID NO 316
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Arg Ile
1

<210> SEQ ID NO 317
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Ser
1

```
<210> SEQ ID NO 318
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Phe Cys
1

<210> SEQ ID NO 319
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gly Met
1

<210> SEQ ID NO 320
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

His Arg
1

<210> SEQ ID NO 321
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

His Asn
1

<210> SEQ ID NO 322
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Glu Cys
1

<210> SEQ ID NO 323
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 323

Val Thr
1

<210> SEQ ID NO 324
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Thr His
1

<210> SEQ ID NO 325
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Cys Arg
1

<210> SEQ ID NO 326
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Phe Gln
1

<210> SEQ ID NO 327
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Glu Val
1

<210> SEQ ID NO 328
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Lys Thr
1

<210> SEQ ID NO 329
<211> LENGTH: 2

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Thr Asp
1

<210> SEQ ID NO 330
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ser Phe
1

<210> SEQ ID NO 331
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ser Thr
1

<210> SEQ ID NO 332
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Gln Val
1

<210> SEQ ID NO 333
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Tyr Lys
1

<210> SEQ ID NO 334
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Asn Gln
```

-continued

1

<210> SEQ ID NO 335
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gln Lys
1

<210> SEQ ID NO 336
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Lys Arg His Arg Lys Leu Arg Glu Lys Arg His Arg Lys Leu Arg Arg
1               5                   10                  15

Arg Arg Arg Leu Lys Arg His Arg Lys Lys Arg His Arg Lys Leu Arg
            20                  25                  30

Glu Lys

<210> SEQ ID NO 337
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Lys Arg His Arg Lys Gly Ser Ser Leu Arg Glu Lys Arg His Arg Lys
1               5                   10                  15

Leu Arg Arg Arg Arg Arg Leu Lys Arg His Arg Lys Lys Arg His Arg
            20                  25                  30

Lys Leu Arg Glu Gly Gly Ser Lys
        35                  40

<210> SEQ ID NO 338
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Lys Arg His Arg Lys Arg Glu Gly Ser Ser Leu Arg Glu Lys Arg His
1               5                   10                  15

Arg Lys Asn Asp Leu Arg Arg Arg Arg Arg Leu Lys Arg His Arg Lys
            20                  25                  30

Lys Arg His Arg Lys Leu Arg Glu Gly Gly Ser Lys
        35                  40

<210> SEQ ID NO 339
<211> LENGTH: 44
<212> TYPE: PRT

-continued

<213> ORGANISM: Artificial Sequence
<220> FEATURE:
<223> OTHER INFORMATION: Description of Artificial Sequence: Synthetic
      polypeptide

<400> SEQUENCE: 339

Lys Lys Pro Lys Lys Arg Glu Gly Ser Ser Leu Arg Glu Lys Arg His
1               5                   10                  15

Arg Lys Asn Asp Leu Arg Arg Arg Arg Arg Leu Lys Arg His Arg Lys
            20                  25                  30

Lys Arg His Arg Lys Leu Arg Glu Gly Gly Ser Lys
        35                  40

<210> SEQ ID NO 340
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Arg Arg Leu Ala Arg Arg Gly Ser Ser Leu Arg Glu Lys Arg His Arg
1               5                   10                  15

Lys Leu Arg Arg Arg Arg Arg Leu Lys Lys Pro Lys Lys Arg His
            20                  25                  30

Arg Lys Leu Arg Glu Gly Gly Ser Lys
        35                  40

<210> SEQ ID NO 341
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Lys Arg His Arg Lys Leu Arg Glu Lys Arg His Arg Lys Leu Arg Glu
1               5                   10                  15

Lys Arg His Arg Lys Leu Lys Arg His Arg Lys Lys Arg His Arg Lys
            20                  25                  30

Leu Arg Glu Lys
        35

<210> SEQ ID NO 342
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Lys Arg His Arg Lys Arg Ile Leu Arg Glu Lys Arg His Arg Lys Leu
1               5                   10                  15

Arg Glu Ala Arg Lys Arg His Arg Lys Leu Lys Arg His Arg Lys Lys
            20                  25                  30

Arg His Arg Lys Leu Arg Glu Lys
        35                  40

<210> SEQ ID NO 343
<211> LENGTH: 35

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Lys Arg His Arg Lys Lys Gly Lys Lys Lys Lys Gly Glu Lys Gly Lys
1               5                   10                  15

Lys Lys Leu Lys Gly Lys Lys Lys Leu Arg Arg Arg Arg Arg Arg Arg
            20                  25                  30

Gln Arg Arg
        35

<210> SEQ ID NO 344
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Lys Arg His Arg Lys Ala Pro Ala Pro Lys Gly Lys Lys Lys Lys Gly
1               5                   10                  15

Glu Lys Gly Lys Lys Lys Leu Lys Gly Lys Lys Lys Leu Lys Pro Lys
            20                  25                  30

Pro Arg Arg Arg Arg Arg Arg Arg Gln Arg Arg
        35                  40

<210> SEQ ID NO 345
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Lys Arg His Arg Lys Gly Gly Ser Gly Gly Lys Gly Lys Lys Lys Lys
1               5                   10                  15

Gly Glu Lys Gly Lys Lys Lys Leu Lys Gly Lys Lys Lys Leu Ala Arg
            20                  25                  30

Arg Arg Arg Arg Arg Arg Gln Arg Arg
        35                  40

<210> SEQ ID NO 346
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Lys Arg His Arg Lys Leu Arg Glu Lys Arg His Arg Lys Arg Arg Arg
1               5                   10                  15

Arg Arg Arg Arg Lys Arg His Arg Lys Leu Arg Glu Lys Arg Arg Gln
            20                  25                  30

Arg Arg

<210> SEQ ID NO 347
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Lys Arg His Arg Lys Lys Arg His Arg Lys Lys Arg Val Lys Lys Lys
1               5                   10                  15

Arg His Arg Lys Arg Arg Arg Arg Arg Asp Ser Leu Leu
            20                  25                  30

<210> SEQ ID NO 348
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Lys Arg His Arg Lys Lys Arg His Arg Lys Tyr Gln Lys Arg Val Lys
1               5                   10                  15

Lys Lys Arg His Arg Lys Ser Ser Ser Arg Arg Arg Arg Arg Asp
            20                  25                  30

Ser Leu Leu
        35

<210> SEQ ID NO 349
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Lys Arg His Arg Lys Lys Lys Glu Glu Glu Lys Lys Glu Glu Glu Lys
1               5                   10                  15

Lys Glu Glu Glu Lys Arg Arg Arg Arg Arg Arg Arg Gln Arg Arg Arg
            20                  25                  30

<210> SEQ ID NO 350
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Lys Arg His Arg Lys Trp Arg Lys Lys Glu Glu Glu Lys Lys Glu Glu
1               5                   10                  15

Glu Lys Lys Glu Glu Glu Lys Arg Ile Arg Arg Arg Arg Arg Arg Arg
            20                  25                  30

Gln Arg Arg Arg
        35

<210> SEQ ID NO 351
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 351

Lys Arg His Arg Lys Arg Gly Asp Lys Arg His Arg Lys Arg Arg Arg
1               5                   10                  15

Arg Arg Lys Arg His Arg Lys Thr Pro His Lys Lys Lys
            20                  25

<210> SEQ ID NO 352
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Lys Arg His Arg Lys Phe Ile Arg Gly Asp Lys Arg His Arg Lys Arg
1               5                   10                  15

Arg Arg Arg Arg Lys Arg His Arg Lys Leu Ala Thr Pro His Lys Lys
            20                  25                  30

Lys

<210> SEQ ID NO 353
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Lys Arg His Arg Lys Arg Gly Asp Lys Arg His Arg Lys Arg Arg Arg
1               5                   10                  15

Arg Arg Lys Arg His Arg Lys Gly Ser Ser Arg Asn Thr Pro His Gln
            20                  25                  30

Lys Lys Lys Lys
        35

<210> SEQ ID NO 354
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Lys Arg His Arg Lys Arg Gly Asp Lys Arg His Arg Lys Leu Lys Arg
1               5                   10                  15

His Arg Lys Arg Arg Arg Arg Lys Arg His Arg Lys Thr Pro His Lys
            20                  25                  30

Lys

<210> SEQ ID NO 355
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Lys Arg His Arg Lys Arg Gly Asp Lys Arg His Arg Lys Lys Arg His

-continued

```
1              5                    10                  15

Arg Lys Lys Arg His Arg Lys Arg Gly Asp Lys Lys Thr Lys
           20                  25                  30
```

<210> SEQ ID NO 356
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

```
Lys Arg His Arg Lys Arg Gly Asp Lys Lys Arg Lys Lys Lys Lys Arg
1               5                    10                  15

Gly Asp Lys Lys Arg Arg Arg Arg Arg Lys Lys Lys Pro Pro Ser Tyr
           20                  25                  30
```

<210> SEQ ID NO 357
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

```
Lys Arg His Arg Lys Arg Lys Arg Lys Arg Lys Arg Arg Arg Arg Arg
1               5                    10                  15

Lys Lys Lys Arg Ala Ser Ser Leu Asn Ile Ala Lys Arg Arg Arg Arg
           20                  25                  30
```

<210> SEQ ID NO 358
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

```
Lys Arg Lys Lys Arg Lys Gly Lys Arg Leu Lys Arg Arg Arg Glu Lys
1               5                    10                  15

Arg His Arg Lys Arg Ala Ser Ser Leu Asn Ile Ala Lys Lys Lys Lys
           20                  25                  30
```

<210> SEQ ID NO 359
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

```
Lys Arg Lys Lys Arg Arg Leu Lys Arg Lys Arg Lys Arg Arg Arg Arg
1               5                    10                  15

Arg Glu Lys Arg His Arg Lys Arg Arg Arg Gln Arg Arg Arg Lys Lys
           20                  25                  30
```

<210> SEQ ID NO 360
<211> LENGTH: 31
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 360

Lys Arg Lys Lys Arg Arg Lys Arg Lys Arg Arg Arg Arg Lys Arg
1               5               10              15

His Arg Lys Leu Arg Glu Arg Lys Arg Leu Arg Glu Lys Lys
            20              25              30

<210> SEQ ID NO 361
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Lys Arg Lys Asn Gly Arg Lys Arg Lys Arg Lys Lys Arg His Arg Lys
1               5               10              15

Lys Lys Lys Arg Arg Arg Arg Lys Arg His Arg Lys Asn Gly Arg Lys
            20              25              30

Lys Lys

<210> SEQ ID NO 362
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Lys Arg His Arg Lys Trp Arg His Arg Ala Arg Ser Lys Arg His Arg
1               5               10              15

Lys Lys Lys Lys Lys Lys Arg Lys Lys Arg Lys Gly Lys
            20              25

<210> SEQ ID NO 363
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Lys Arg His Arg Lys Arg Gly Asp Lys Arg His Arg Lys Lys Lys Lys
1               5               10              15

Asn Arg Arg Lys Lys Arg Ala Leu Arg Lys Lys Arg Lys Gly Lys
            20              25              30

<210> SEQ ID NO 364
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Lys Lys Arg Lys Arg Gly Gly Lys Thr Lys Lys Lys Ala Lys Lys Ala
1               5               10              15

Leu Lys Lys Lys Lys Lys Gly Lys Lys Lys Lys Arg Arg Arg Arg Lys

-continued

```
                20              25              30

Lys Ala Ala Pro Lys Lys
        35

<210> SEQ ID NO 365
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Lys Lys Lys Ala Tyr Pro Lys Ala Leu Lys Lys Pro Lys Lys Lys Lys
1               5                   10                  15

Lys Ala Tyr Pro Lys Ala Leu Lys Arg Arg Arg Arg Arg Lys Asn Arg
                20              25              30

Arg Lys Lys Arg Ala Leu Lys Arg His Arg Lys
        35              40

<210> SEQ ID NO 366
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Lys Thr Arg Ser Lys Lys Lys Lys Lys Arg Gly Asp Lys Lys Lys Lys
1               5                   10                  15

Asn Arg Arg Lys Lys Arg Ala Leu Asn Thr Gln Ile His Lys Lys Lys
                20              25              30

Lys Lys Ala Ala Pro Lys Lys
        35

<210> SEQ ID NO 367
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Lys Gly Lys Lys Lys Lys Gly Glu Lys Gly Lys Lys Lys Leu Lys Gly
1               5                   10                  15

Lys Lys Lys Leu Arg Arg Arg Arg Arg Ser Pro Lys Lys Arg Arg Gln
                20              25              30

Arg Arg

<210> SEQ ID NO 368
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Lys Arg His Arg Lys Leu Arg Glu Lys Arg His Arg Lys Leu Arg Arg
1               5                   10                  15

Arg Arg Arg Leu Lys Arg His Arg Lys Lys Arg His Arg Lys Leu Arg
```

-continued

```
              20                25                30

Glu Lys

<210> SEQ ID NO 369
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Lys Arg His Arg Lys Leu Arg Glu Lys Arg His Arg Lys Leu Arg Glu
1               5                   10                  15

Lys Arg His Arg Lys Leu Lys Arg His Arg Lys Arg His Arg Lys
              20                  25                  30

Leu Arg Glu Lys
          35

<210> SEQ ID NO 370
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Lys Arg His Arg Lys Lys Gly Lys Lys Lys Lys Gly Glu Lys Gly Lys
1               5                   10                  15

Lys Lys Leu Lys Gly Lys Lys Lys Leu Arg Arg Arg Arg Arg Arg
              20                  25                  30

Gln Arg Arg
          35

<210> SEQ ID NO 371
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Lys Arg His Arg Lys Leu Arg Glu Lys Arg His Arg Lys Arg Arg Arg
1               5                   10                  15

Arg Arg Arg Arg Lys Arg His Arg Lys Leu Arg Glu Lys Arg Arg Gln
              20                  25                  30

Arg Arg

<210> SEQ ID NO 372
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Lys Arg His Arg Lys Lys Arg His Arg Lys Lys Arg Val Lys Lys Lys
1               5                   10                  15

Arg His Arg Lys Arg Arg Arg Arg Arg Arg Asp Ser Leu Leu
              20                  25                  30
```

```
<210> SEQ ID NO 373
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Lys Arg His Arg Lys Lys Lys Glu Glu Glu Lys Lys Glu Glu Glu Lys
1               5                   10                  15

Lys Glu Glu Glu Lys Arg Arg Arg Arg Arg Arg Arg Gln Arg Arg Arg
            20                  25                  30

<210> SEQ ID NO 374
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Lys Arg His Arg Lys Gln Ser Lys Lys Glu Glu Glu Lys Lys Glu Glu
1               5                   10                  15

Glu Lys Lys Glu Glu Glu Lys Asn Gln Arg Arg Arg Arg Arg Arg Arg
            20                  25                  30

Gln Arg Arg Arg
        35

<210> SEQ ID NO 375
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Lys Arg His Arg Lys Arg Gly Asp Lys Arg His Arg Lys Arg Arg Arg
1               5                   10                  15

Arg Arg Lys Arg His Arg Lys Thr Pro His Lys Lys Lys
            20                  25

<210> SEQ ID NO 376
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Lys Arg His Arg Lys Arg Gly Asp Lys Arg His Arg Lys Leu Lys Arg
1               5                   10                  15

His Arg Lys Arg Arg Arg Arg Lys Arg His Arg Lys Thr Pro His Lys
            20                  25                  30

Lys

<210> SEQ ID NO 377
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 377

Lys Arg His Arg Lys Arg Gly Asp Lys Arg His Arg Lys Lys Arg His
1               5                   10                  15

Arg Lys Lys Arg His Arg Lys Arg Gly Asp Lys Lys Thr Lys
            20                  25                  30

<210> SEQ ID NO 378
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Lys Arg His Arg Lys Arg Gly Asp Lys Lys Arg Lys Lys Lys Lys Arg
1               5                   10                  15

Gly Asp Lys Lys Arg Arg Arg Arg Lys Lys Lys Pro Pro Ser Tyr
            20                  25                  30

<210> SEQ ID NO 379
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Lys Arg His Arg Lys Gly Gly Ser Arg Gly Asp Lys Lys Arg Lys Lys
1               5                   10                  15

Lys Lys Arg Gly Asp Ser Ser Ser Lys Lys Arg Arg Arg Arg Arg Lys
            20                  25                  30

Lys Lys Pro Pro Ser Tyr
        35

<210> SEQ ID NO 380
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Lys Arg His Arg Lys Arg Lys Arg Lys Arg Lys Arg Arg Arg Arg Arg
1               5                   10                  15

Lys Lys Lys Arg Ala Ser Ser Leu Asn Ile Ala Lys Arg Arg Arg Arg
            20                  25                  30

<210> SEQ ID NO 381
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Lys Arg Lys Lys Arg Lys Gly Lys Arg Leu Lys Arg Arg Arg Glu Lys
1               5                   10                  15
```

```
Arg His Arg Lys Arg Ala Ser Ser Leu Asn Ile Ala Lys Lys Lys Lys
            20                  25                  30

<210> SEQ ID NO 382
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

Lys Arg Lys Lys Arg Arg Leu Lys Arg Lys Arg Lys Arg Arg Arg Arg
1               5                   10                  15

Arg Glu Lys Arg His Arg Lys Arg Arg Arg Gln Arg Arg Arg Lys Lys
            20                  25                  30

<210> SEQ ID NO 383
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 383

Lys Arg Lys Lys Arg Arg Lys Arg Lys Arg Arg Arg Arg Arg Lys Arg
1               5                   10                  15

His Arg Lys Leu Arg Glu Arg Lys Arg Arg Leu Arg Glu Lys Lys
            20                  25                  30

<210> SEQ ID NO 384
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

Lys Arg Lys Asn Gly Arg Lys Arg Lys Arg Lys Lys Arg His Arg Lys
1               5                   10                  15

Lys Lys Lys Arg Arg Arg Arg Lys Arg His Arg Lys Asn Gly Arg Lys
            20                  25                  30

Lys Lys

<210> SEQ ID NO 385
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Lys Arg Lys Trp Arg Asn Gly Arg Lys Arg Lys Arg Gln Lys Arg His
1               5                   10                  15

Arg Lys Lys Lys Lys Arg Ala Arg Arg Arg Lys Arg His Arg Lys
            20                  25                  30

Asn Gly Arg Lys His Lys Lys Lys
        35                  40

<210> SEQ ID NO 386
```

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Lys Arg His Arg Lys Trp Arg His Arg Ala Arg Ser Lys Arg His Arg
1               5                   10                  15

Lys Lys Lys Pro Lys Lys Arg Lys Lys Arg Lys Gly Lys
            20                  25

<210> SEQ ID NO 387
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

Lys Arg His Arg Lys Pro Lys Pro Arg Ile Trp Arg His Arg Ala Arg
1               5                   10                  15

Ser Arg Asp Lys Arg His Arg Lys Lys Lys Pro Lys Lys Arg Lys Lys
            20                  25                  30

Arg Lys Gly Lys
        35

<210> SEQ ID NO 388
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Lys Lys Lys Arg Lys Leu Arg Gly Asp Leu Lys Arg Lys Gly Ser Ser
1               5                   10                  15

Tyr Gln Pro Leu Ala Pro Ala Pro Lys Lys Lys Arg Lys Arg Gly Asp
            20                  25                  30

Lys Arg Lys Leu Phe Tyr Gln Pro Leu
        35                  40

<210> SEQ ID NO 389
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (20)..(21)
<223> OTHER INFORMATION: Residues at these positions can be separated by
      a linker of unknown length
<220> FEATURE:
<221> NAME/KEY: NON_CONS
<222> LOCATION: (28)..(29)
<223> OTHER INFORMATION: Residues at these positions can be separated by
      a linker of unknown length
<220> FEATURE:
<223> OTHER INFORMATION: See specification as filed for detailed
      description of substitutions and preferred embodiments

<400> SEQUENCE: 389
```

```
Lys Lys Lys Arg His Arg Lys Arg Lys Arg Lys Arg Lys Arg Arg Arg
1               5                   10                  15

Arg Lys Lys Lys Ala Ser Ser Leu Asn Ile Ala Lys Arg Arg Arg Arg
                20              25                  30

<210> SEQ ID NO 390
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (5)..(6)
<223> OTHER INFORMATION: Residues at these positions can be separated by
      a linker of unknown length
<220> FEATURE:
<221> NAME/KEY: NON_CONS
<222> LOCATION: (8)..(9)
<223> OTHER INFORMATION: Residues at these positions can be separated by
      a linker of unknown length
<220> FEATURE:
<221> NAME/KEY: NON_CONS
<222> LOCATION: (30)..(31)
<223> OTHER INFORMATION: Residues at these positions can be separated by
      a linker of unknown length
<220> FEATURE:
<221> NAME/KEY: NON_CONS
<222> LOCATION: (33)..(34)
<223> OTHER INFORMATION: Residues at these positions can be separated by
      a linker of unknown length
<220> FEATURE:
<223> OTHER INFORMATION: See specification as filed for detailed
      description of substitutions and preferred embodiments

<400> SEQUENCE: 390

Lys Lys Lys Arg Lys Asn Gly Arg Lys Arg Lys Arg Lys Lys Arg His
1               5                   10                  15

Arg Lys Lys Lys Lys Arg Arg Arg Arg Lys Arg His Arg Lys Asn Gly
                20              25                  30

Arg Lys Lys Lys
          35

<210> SEQ ID NO 391
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (11)..(12)
<223> OTHER INFORMATION: Residues at these positions can be separated by
      a linker of unknown length
<220> FEATURE:
<221> NAME/KEY: NON_CONS
<222> LOCATION: (14)..(15)
<223> OTHER INFORMATION: Residues at these positions can be separated by
      a linker of unknown length
<220> FEATURE:
<221> NAME/KEY: NON_CONS
<222> LOCATION: (18)..(19)
<223> OTHER INFORMATION: Residues at these positions can be separated by
      a linker of unknown length
<220> FEATURE:
<221> NAME/KEY: NON_CONS
<222> LOCATION: (23)..(24)
<223> OTHER INFORMATION: Residues at these positions can be separated by
      a linker of unknown length
<220> FEATURE:
<221> NAME/KEY: NON_CONS
```

-continued

```
<222> LOCATION: (28)..(29)
<223> OTHER INFORMATION: Residues at these positions can be separated by
      a linker of unknown length
<220> FEATURE:
<221> NAME/KEY: NON_CONS
<222> LOCATION: (31)..(32)
<223> OTHER INFORMATION: Residues at these positions can be separated by
      a linker of unknown length
<220> FEATURE:
<223> OTHER INFORMATION: See specification as filed for detailed
      description of substitutions and preferred embodiments

<400> SEQUENCE: 391

Lys Lys Lys Arg His Arg Lys Lys Lys Lys Lys Arg Gly Asp Lys Lys
1               5                   10                  15

Lys Lys Asn Thr Gln Ile His Arg Arg Arg Arg Thr Pro His Lys
            20                  25                  30

Lys

<210> SEQ ID NO 392
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (5)..(6)
<223> OTHER INFORMATION: Residues at these positions can be separated by
      a linker of unknown length
<220> FEATURE:
<221> NAME/KEY: NON_CONS
<222> LOCATION: (10)..(11)
<223> OTHER INFORMATION: Residues at these positions can be separated by
      a linker of unknown length
<220> FEATURE:
<221> NAME/KEY: NON_CONS
<222> LOCATION: (12)..(13)
<223> OTHER INFORMATION: Residues at these positions can be separated by
      a linker of unknown length
<220> FEATURE:
<221> NAME/KEY: NON_CONS
<222> LOCATION: (18)..(19)
<223> OTHER INFORMATION: Residues at these positions can be separated by
      a linker of unknown length
<220> FEATURE:
<223> OTHER INFORMATION: See specification as filed for detailed
      description of substitutions and preferred embodiments

<400> SEQUENCE: 392

Lys Lys Lys Arg Lys Lys Thr Lys Lys Lys Ala Lys Lys Ala Leu Lys
1               5                   10                  15

Lys Lys Lys Lys Gly Lys Lys Lys Lys Arg Arg Arg Arg Lys Ala Ala
            20                  25                  30

Pro Lys Lys
        35

<210> SEQ ID NO 393
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Cys Lys Lys Lys Lys Lys Lys Lys Lys Lys Lys Lys Lys Lys Lys Lys
1               5                   10                  15
```

```
Lys Lys Lys Lys Lys Lys Lys Lys Lys Lys Lys Lys Lys Lys Lys
            20                  25                  30
```

```
<210> SEQ ID NO 394
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (6)..(7)
<223> OTHER INFORMATION: Residues at these positions can be separated by
      a linker of unknown length
<220> FEATURE:
<221> NAME/KEY: NON_CONS
<222> LOCATION: (9)..(10)
<223> OTHER INFORMATION: Residues at these positions can be separated by
      a linker of unknown length
<220> FEATURE:
<221> NAME/KEY: NON_CONS
<222> LOCATION: (31)..(32)
<223> OTHER INFORMATION: Residues at these positions can be separated by
      a linker of unknown length
<220> FEATURE:
<221> NAME/KEY: NON_CONS
<222> LOCATION: (34)..(35)
<223> OTHER INFORMATION: Residues at these positions can be separated by
      a linker of unknown length
<220> FEATURE:
<223> OTHER INFORMATION: See specification as filed for detailed
      description of substitutions and preferred embodiments
```

```
<400> SEQUENCE: 394
```

```
Lys Lys Arg His Arg Lys Leu Arg Glu Lys Arg His Arg Lys Leu Arg
1               5                   10                  15
```

```
Arg Arg Arg Arg Leu Lys Arg His Arg Lys Lys Arg His Arg Lys Leu
            20                  25                  30
```

```
Arg Glu Lys
        35
```

```
<210> SEQ ID NO 395
<211> LENGTH: 4431
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 395
```

```
tcgcgcgttt cggtgatgac ggtcgaggtg agccccacgt tctgcttcac tctccccatc      60 tccccccct ccccacccc aattttgtat ttatttattt tttaattatt ttgtgcagcg      120 atggggcgg ggggggggg ggggcgcgcg ccaggcgggg cggggcgggg cgaggggcgg      180
ggcggggcga ggcggagagg tgcggcggca gccaatcaga gcggcgcgct ccgaaagttt     240
ccttttatgg cgaggcggcg gcggcggcgg ccctataaaa agcgaagcgc gcggcgggcg     300
ggagtcgctg cgacgctgcc ttcgccccgt gccccgctcc gccgccgcct cgcgccgccc     360
gccccggctc tgactgaccg cgttactccc acaggtgagc gggcgggacg gcccttctcc     420
tccgggctgt aattagcgct tggtttaatg acggcttgtt tcttttctgt ggctgcgtga     480
aagccttgag gggctccggg agggcccttt gtgcgggggg gagcggctcg gggggtgcgt     540
gcgtgtgtgt gtgcgtgggg agcgccgcgt gcggcccgcg ctgcccggcg gctgtgagcg     600
ctgcgggcgc ggcgcggggc tttgtgcgct ccgcagtgtg cgcgaggggga gcgcggccgg     660
```

-continued

```
gggcggtgcc ccgcggtgcg ggggggggctg cgaggggaac aaaggctgcg tgcggggtgt    720
gtgcgtgggg gggtgagcag ggggtgtggg cgcggcggtc gggctgtaac ccccccctgc    780 accccctcc ccgagttgct gagcacggcc cggcttcggg tgcggggctc cgtacggggc     840
gtggcgcggg gctcgccgtg ccgggcgggg ggtggcggca ggtgggggtg ccgggcgggg    900
cggggccgcc tcgggccggg gagggctcgg gggaggggcg cggcggcccc cggagcgccg    960
gcggctgtcg aggcgcggcg agccgcagcc attgccttt atggtaatcg tgcgagaggg    1020
cgcagggact tcctttgtcc caaatctgtg cggagccgaa atctgggagg cgccgccgca    1080 cccccctctag cgggcgcggg gcgaagcggt gcggcgccgg caggaaggaa atgggcgggg    1140
agggccttcg tgcgtcgccg cgccgccgtc cccttctccc tctccagcct cggggctgtc    1200 cgcggggggga cggctgcctt cggggggggac ggggcagggc ggggttcggc ttctggcgtg    1260
tgaccggcgg ctctagagcc tctgctaacc atgttcatgc cttcttcttt ttcctacagc    1320
tcctgggcaa cgtgctggtt attgtgctgt ctcatcattt tggcaaaacc ggtctcgaag    1380
gcctgcaggc ggccgccgcc accgccacca tggtgagcaa gggcgaggag ctgttcaccg    1440
gggtggtgcc catcctggtc gagctggacg gcgacgtaaa cggccacaag ttcagcgtgt    1500
ccggcgaggg cgagggcgat gccacctacg gcaagctgac cctgaagttc atctgcacca    1560
ccggcaagct gcccgtgccc tggcccaccc tcgtgaccac cctgacctac ggcgtgcagt    1620
gcttcagccg ctaccccgac cacatgaagc agcacgactt cttcaagtcc gccatgcccg    1680
aaggctacgt ccaggagcgc accatcttct tcaaggacga cggcaactac aagacccgcg    1740
ccgaggtgaa gttcgagggc gacaccctgg tgaaccgcat cgagctgaag ggcatcgact    1800
tcaaggagga cggcaacatc ctggggcaca agctggagta caactacaac agccacaacg    1860
tctatatcat ggccgacaag cagaagaacg gcatcaaggt gaacttcaag atccgccaca    1920
acatcgagga cggcagcgtg cagctcgccg accactacca gcagaacacc cccatcggcg    1980
acggccccgt gctgctgccc gacaaccact acctgagcac ccagtccgcc ctgagcaaag    2040
accccaacga gaagcgcgat cacatggtcc tgctggagtt cgtgaccgcc gccgggatca    2100
ctctcggcat ggacgagctg tacaagtaat ccatggccca acttgtttat tgcagcttat    2160
aatggttaca aataaagcaa tagcatcaca aatttcacaa ataaagcatt ttttttcactg    2220 cattctagtt gtggtttgtc caaactcatc aatgtatctt atcatgtctg gatctcgtta    2280
actcgaggga tccatcgatg tcgactgcag aggcctgcat gcaagcttgg tgtaatcatg    2340
gtcatagctg tttcctgtgt gaaattgtta tccgctcaca attccacaca acatacgagc    2400
cggaagcata aagtgtaaag cctggggtgc ctaatgagtg agctaactca cattaattgc    2460
gttgcgctca ctgcccgctt tccagtcggg aaacctgtcg tgccagctgc attaatgaat    2520
cggccaacgc gcggggagag gcggtttgcg tattgggcgc tcttccgctt cctcgctcac    2580
tgactcgctg cgctcggtcg ttcggctgcg gcgagcggta tcagctcact caaaggcggt    2640
aatacggtta tccacagaat caggggataa cgcaggaaag aacatgtgag caaaaggcca    2700
gcaaaaggcc aggaaccgta aaaaggccgc gttgctggcg tttttccata ggctccgccc    2760
ccctgacgag catcacaaaa atcgacgctc aagtcagagg tggcgaaacc cgacaggact    2820
ataaagatac caggcgtttc cccctggaag ctccctcgtg cgctctcctg ttccgaccct    2880
gccgcttacc ggatacctgt ccgcctttct cccttcggga agcgtggcgc tttctcatag    2940
ctcacgctgt aggtatctca gttcggtgta ggtcgttcgc tccaagctgg gctgtgtgca    3000
cgaacccccc gttcagcccg accgctgcgc cttatccggt aactatcgtc ttgagtccaa    3060
```

-continued

```
cccggtaaga cacgacttat cgccactggc agcagccact ggtaacagga ttagcagagc     3120
gaggtatgta ggcggtgcta cagagttctt gaagtggtgg cctaactacg gctacactag     3180
aagaacagta tttggtatct gcgctctgct gaagccagtt accttcggaa aaagagttgg     3240
tagctcttga tccggcaaac aaaccaccgc tggtagcggt ggtttttttg tttgcaagca     3300
gcagattacg cgcagaaaaa aaggatctca agaagatcct ttgatctttt ctacggggtc     3360
tgacgctcag tggaacgaaa actcacgtta agggattttg gtcatgagat tatcaaaaag     3420
gatcttcacc tagatccttt taaattaaaa atgaagtttt aaatcaagcc caatctgaat     3480
aatgttacaa ccaattaacc aattctgatt agaaaaactc atcgagcatc aaatgaaact     3540
gcaatttatt catatcagga ttatcaatac catatttttg aaaaagccgt ttctgtaatg     3600
aaggagaaaa ctcaccgagg cagttccata ggatggcaag atcctggtat cggtctgcga     3660
ttccgactcg tccaacatca atacaaccta ttaatttccc ctcgtcaaaa ataaggttat     3720
caagtgagaa atcaccatga gtgacgactg aatccggtga gaatggcaaa agtttatgca     3780
tttctttcca gacttgttca acaggccagc cattacgctc gtcatcaaaa tcactcgcat     3840
caaccaaacc gttattcatt cgtgattgcg cctgagcgag acgaaatacg cgatcgctgt     3900
taaaaggaca attacaaaca ggaatcgaat gcaaccggcg caggaacact gccagcgcat     3960
caacaatatt ttcacctgaa tcaggatatt cttctaatac ctggaatgct gtttttccgg     4020
ggatcgcagt ggtgagtaac catgcatcat caggagtacg gataaaatgc ttgatggtcg     4080
gaagaggcat aaattccgtc agccagttta gtctgaccat ctcatctgta acatcattgg     4140
caacgctacc tttgccatgt ttcagaaaca actctggcgc atcgggcttc ccatacaagc     4200
gatagattgt cgcacctgat tgcccgacat tatcgcgagc ccatttatac ccatataaat     4260
cagcatccat gttggaattt aatcgcggcc tcgacgtttc ccgttgaata tggctcataa     4320 cacccettgt attactgttt atgtaagcag acagttttat tgttcatgat gatatatttt     4380
tatcttgtgc aatgtaacat cagagatttt gagacacggg ccagagctgc a             4431
```

<210> SEQ ID NO 396
<211> LENGTH: 5364
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 396

```
tcgcgcgttt cggtgatgac ggtcgaggtg agccccacgt tctgcttcac tctccccatc       60 tccccccct ccccaccccc aattttgtat ttatttattt tttaattatt ttgtgcagcg      120 atggggcgg gggggggggg ggggcgcgcg ccaggcgggg cggggcgggg cgaggggcgg      180
ggcggggcga ggcggagagg tgcggcggca gccaatcaga gcggcgcgct ccgaaagttt      240
ccttttatgg cgaggcggcg gcggcggcgg ccctataaaa agcgaagcgc gcggcgggcg      300
ggagtcgctg cgacgctgcc ttcgccccgt gccccgctcc gccgccgcct cgcgccgccc      360
gccccggctc tgactgaccg cgttactccc acaggtgagc gggcgggacg gcccttctcc      420
tccgggctgt aattagcgct tggtttaatg acggcttgtt tcttttctgt ggctgcgtga      480
aagccttgag gggctccggg agggcccttt gtgcgggggg gagcggctcg gggggtgcgt      540
gcgtgtgtgt gtgcgtgggg agcgccgcgt gcggcccgcg ctgcccggcg gctgtgagcg      600
ctgcgggcgc ggcgcggggc tttgtgcgct ccgcagtgtg cgcgagggga gcgcggccgg      660
```

-continued

```
gggcggtgcc ccgcggtgcg ggggggctg cgaggggaac aaaggctgcg tgcggggtgt      720
gtgcgtgggg gggtgagcag ggggtgtggg cgcggcggtc gggctgtaac cccccctgc      780 accccctcc ccgagttgct gagcacggcc cggcttcggg tgcggggctc cgtacggggc      840
gtggcgcggg gctcgccgtg ccgggcgggg ggtggcggca ggtgggggtg ccgggcgggg      900
cggggccgcc tcgggccggg gagggctcgg gggaggggcg cggcggcccc cggagcgccg      960
gcggctgtcg aggcgcggcg agccgcagcc attgcctttt atggtaatcg tgcgagaggg     1020
cgcagggact tcctttgtcc caaatctgtg cggagccgaa atctgggagg cgccgccgca     1080 cccctctag cgggcgcggg gcgaagcggt gcggcgccgg caggaaggaa atgggcgggg      1140
agggccttcg tgcgtcgccg cgccgccgtc cccttctccc tctccagcct cggggctgtc     1200
cgcgggggga cggctgcctt cggggggggac ggggcagggc ggggttcggc ttctggcgtg     1260
tgaccggcgg ctctagagcc tctgctaacc atgttcatgc cttcttcttt ttcctacagc     1320
tcctgggcaa cgtgctggtt attgtgctgt ctcatcattt tggcaaaacc ggtctcgaag      1380
gcctgcaggc ggccgccgcc accgccacca tggaagacgc caaaaacata aagaaaggcc      1440
cggcgccatt ctatccgctg gaagatgaa ccgctggaga gcaactgcat aaggctatga      1500
agagatacgc cctggttcct ggaacaattg cttttacaga tgcacatatc gaggtggaca     1560
tcacttacgc tgagtacttc gaaatgtccg ttcggttggc agaagctatg aaacgatatg     1620
ggctgaatac aaatcacaga atcgtcgtat gcagtgaaaa ctctcttcaa ttctttatgc     1680
cggtgttggg cgcgttattt atcggagttg cagttgcgcc cgcgaacgac atttataatg     1740
aacgtgaatt gctcaacagt atgggcattt cgcagcctac cgtggtgttc gtttccaaaa     1800
aggggttgca aaaatttttg aacgtgcaaa aaagctcccc aatcatccaa aaaattatta     1860
tcatggattc taaaacggat taccagggat ttcagtcgat gtacacgttc gtcacatctc     1920
atctacctcc cggttttaat gaatacgatt ttgtgccaga gtccttcgat agggacaaga     1980
caattgcact gatcatgaac tcctctggat ctactggtct gcctaaaggt gtcgctctgc     2040
ctcatagaac tgcctgcgtg agattctcgc atgccagaga tcctattttt ggcaatcaaa     2100
tcattccgga tactgcgatt ttaagtgttg ttccattcca tcacggtttt ggaatgttta     2160
ctacactcgg atatttgata tgtggatttc gagtcgtctt aatgtataga tttgaagaag     2220
agctgtttct gaggagcctt caggattaca agattcaaag tgcgctgctg gtgccaaccc     2280
tattctcctt cttcgccaaa agcactctga ttgacaaata cgatttatct aatttacacg     2340
aaattgcttc tggtggcgct cccctctcta aggaagtcgg ggaagcggtt gccaagaggt     2400
tccatctgcc aggtatcagg caaggatatg ggctcactga gactacatca gctattctga     2460
ttacacccga gggggatgat aaaccgggcg cggtcggtaa agttgttcca ttttttgaag     2520
cgaaggttgt ggatctggat accgggaaaa cgctgggcgt taatcaaaga ggcgaactgt     2580
gtgtgagagg tcctatgatt atgtccggtt atgtaaacaa tccggaagcg accaacgcct     2640
tgattgacaa ggatggatgg ctacattctg gagacatagc ttactgggac gaagacgaac     2700
acttcttcat cgttgaccgc ctgaagtctc tgattaagta caaaggctat caggtggctc     2760
ccgctgaatt ggaatccatc ttgctccaac accccaacat cttcgacgca ggtgtcgcag     2820
gtcttcccga cgatgacgcc ggtgaacttc ccgccgccgt tgttgttttg gagcacggaa     2880
agacgatgac ggaaaaagag atcgtggatt acgtcgccag tcaagtaaca accgcgaaaa     2940
agttgcgcgg aggagttgtg tttgtggacg aagtaccgaa aggtcttacc ggaaaactcg     3000
```

-continued

```
acgcaagaaa aatcagagag atcctcataa aggccaagaa gggcggaaag atcgccgtgt      3060
aatccatggc ccaacttgtt tattgcagct tataatggtt acaaataaag caatagcatc      3120
acaaatttca caaataaagc attttttttca ctgcattcta gttgtggttt gtccaaactc     3180
atcaatgtat cttatcatgt ctggatctcg ttaactcgag ggatccatcg atgtcgactg      3240
cagaggcctg catgcaagct tggtgtaatc atggtcatag ctgtttcctg tgtgaaattg      3300
ttatccgctc acaattccac acaacatacg agccggaagc ataaagtgta aagcctgggg      3360
tgcctaatga gtgagctaac tcacattaat tgcgttgcgc tcactgcccg ctttccagtc      3420
gggaaacctg tcgtgccagc tgcattaatg aatcggccaa cgcgcgggga gaggcggttt      3480
gcgtattggg cgctcttccg cttcctcgct cactgactcg ctgcgctcgg tcgttcggct      3540
gcggcgagcg gtatcagctc actcaaaggc ggtaatacgg ttatccacag aatcaggggga    3600 taacgcagga aagaacatgt gagcaaaagg ccagcaaaag gccaggaacc gtaaaaaggc      3660
cgcgttgctg gcgtttttcc ataggctccg ccccccctgac gagcatcaca aaaatcgacg     3720
ctcaagtcag aggtggcgaa acccgacagg actataaaga taccaggcgt ttccccctgg      3780
aagctccctc gtgcgctctc ctgttccgac cctgccgctt accggatacc tgtccgcctt      3840
tctcccttcg ggaagcgtgg cgctttctca tagctcacgc tgtaggtatc tcagttcggt      3900
gtaggtcgtt cgctccaagc tgggctgtgt gcacgaaccc cccgttcagc ccgaccgctg      3960
cgccttatcc ggtaactatc gtcttgagtc caacccggta agacacgact tatcgccact      4020
ggcagcagcc actggtaaca ggattagcag agcgaggtat gtaggcggtg ctacagagtt      4080
cttgaagtgg tggcctaact acggctacac tagaagaaca gtatttggta tctgcgctct      4140
gctgaagcca gttaccttcg gaaaaagagt tggtagctct tgatccggca aacaaaccac      4200
cgctggtagc ggtggtttttt ttgtttgcaa gcagcagatt acgcgcagaa aaaaaggatc     4260
tcaagaagat cctttgatct tttctacggg gtctgacgct cagtggaacg aaaactcacg      4320
ttaagggatt ttggtcatga gattatcaaa aaggatcttc acctagatcc ttttaaatta      4380
aaaatgaagt tttaaatcaa gcccaatctg aataatgtta caaccaatta accaattctg      4440
attagaaaaa ctcatcgagc atcaaatgaa actgcaattt attcatatca ggattatcaa      4500
taccatattt ttgaaaaagc cgtttctgta atgaaggaga aaactcaccg aggcagttcc      4560
ataggatggc aagatcctgg tatcggtctg cgattccgac tcgtccaaca tcaatacaac      4620
ctattaattt cccctcgtca aaaataaggt tatcaagtga gaaatcacca tgagtgacga      4680
ctgaatccgg tgagaatggc aaaagtttat gcatttcttt ccagacttgt tcaacaggcc      4740
agccattacg ctcgtcatca aaatcactcg catcaaccaa accgttattc attcgtgatt      4800
gcgcctgagc gagacgaaat acgcgatcgc tgttaaaagg acaattacaa acaggaatcg      4860
aatgcaaccg gcgcaggaac actgccagcg catcaacaat attttcacct gaatcaggat      4920
attcttctaa tacctggaat gctgttttttc cggggatcgc agtggtgagt aaccatgcat      4980
catcaggagt acggataaaa tgcttgatgg tcggaagagg cataaattcc gtcagccagt      5040
ttagtctgac catctcatct gtaacatcat tggcaacgct acctttgcca tgtttcagaa      5100
acaactctgg cgcatcgggc ttcccataca agcgatagat tgtcgcacct gattgcccga      5160
cattatcgcg agcccatttta tacccatata aatcagcatc catgttggaa tttaatcgcg      5220
gcctcgacgt ttcccgttga atatggctca taacacccct tgtattactg tttatgtaag      5280
cagacagttt tattgttcat gatgatatat ttttatcttg tgcaatgtaa catcagagat      5340
tttgagacac gggccagagc tgca                                            5364
```

-continued

```
<210> SEQ ID NO 397
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Lys Lys Arg His Arg Lys Tyr Pro Lys Lys Ser Arg Arg Ser Arg Leu
1               5                   10                  15

Arg Asn Phe Arg Gly Asp Tyr Asn Gln Tyr Thr Arg Arg Arg Arg
            20                  25                  30

<210> SEQ ID NO 398
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Lys Arg Lys Lys Arg His Arg Lys Arg Ile Arg Gly Arg Asp Val Lys
1               5                   10                  15

Tyr Ser Tyr Ala Arg Lys Arg His Arg Lys Phe Gln Lys Trp Asn Tyr
            20                  25                  30

Lys

<210> SEQ ID NO 399
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Lys Lys Arg His Arg Lys Ala Arg Arg Val Thr Ala Leu Arg Glu Gly
1               5                   10                  15

Arg Arg His Arg Lys Gly Glu Arg Arg Arg Arg Pro Pro Ser Tyr
            20                  25                  30

<210> SEQ ID NO 400
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Lys Lys Arg His Arg Lys Ala Leu Gly Ser Ser Asp Ser Leu Leu Ala
1               5                   10                  15

Arg Lys Arg His Arg Lys Lys Arg Lys Arg Lys Lys Arg His Arg Lys
            20                  25                  30

<210> SEQ ID NO 401
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 401

Lys Lys Arg His Arg Lys Gly Ser Ser Lys Lys Arg Pro Lys Pro Arg
1               5                   10                  15

Lys Lys Arg His Arg Lys Lys Arg His Arg Lys Lys Arg His Arg Lys
            20                  25                  30

Leu Leu

<210> SEQ ID NO 402
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Lys Lys Arg His Arg Lys Arg Ile Gln Arg Arg Ser Arg Arg Gly Ser
1               5                   10                  15

Ser Lys His Lys Gly Arg Asp Val Ile Leu Lys Lys Asp Val Arg Lys
            20                  25                  30

Arg His Arg Lys
        35

<210> SEQ ID NO 403
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Lys Lys Arg His Arg Lys Lys Lys Asp Gly Lys Lys Arg Lys Arg Leu
1               5                   10                  15

Leu Arg Lys Lys His Ala Arg Ala Leu Tyr Ile Gly Ser Arg Lys Arg
            20                  25                  30

Gly Arg Lys Pro
        35

<210> SEQ ID NO 404
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Lys Lys Arg His Arg Lys Pro Pro Lys Asp Gly Glu Ala Gln Pro Lys
1               5                   10                  15

Arg His Arg Lys Arg Arg Arg Arg Arg Lys Arg His Arg Lys Leu Arg
            20                  25                  30

Ala

<210> SEQ ID NO 405
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 405

Lys Lys Arg Lys Lys Arg His Arg Lys Leu Ala Arg Gly Pro Arg Val
1               5                   10                  15

Ala Arg Lys Arg His Arg Lys Arg Arg Arg Arg Asp Arg Tyr Gln
            20                  25                  30

Arg Leu

<210> SEQ ID NO 406
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Lys Lys Arg His Arg Lys Arg Gly Phe Arg Arg Val Ser Arg Arg Arg
1               5                   10                  15

Gly Lys Lys Lys Glu Gln Arg Arg Glu Arg Asn Ala Arg Gly Lys Lys
            20                  25                  30

Gly Lys Arg His Arg Lys
        35

<210> SEQ ID NO 407
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Lys Lys Arg His Arg Lys Arg Arg Gln Pro Pro Arg Ser Ile Ser Ser
1               5                   10                  15

His Pro Leu Arg Lys Lys Arg Lys Gly Lys Thr Arg Arg Leu Arg Gly
            20                  25                  30

Asp Leu Arg Asn Ser Arg Arg
        35

<210> SEQ ID NO 408
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Lys Lys Arg His Arg Lys Arg Leu Arg Lys Lys Arg Lys Gly Lys Gly
1               5                   10                  15

Ser Arg Pro Gly Ser Gly Phe Val Lys Lys Thr Lys Gln Arg Arg Arg
            20                  25                  30

Arg Arg

<210> SEQ ID NO 409
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409
```

-continued

```
Lys Lys Arg His Arg Lys His Arg Thr Lys Ser Gly Arg Ser Arg Ile
1               5                   10                  15

Arg Lys Lys Arg Lys Gly Lys Arg His Ala Arg Lys Lys Arg Arg Gln
                20                  25                  30

Arg Arg Arg Pro Pro Ser Tyr
            35

<210> SEQ ID NO 410
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Lys Lys Arg His Arg Lys Lys Pro Val Asn Arg Trp Ser Ala Arg Asn
1               5                   10                  15

Arg Arg Lys Lys Arg Ala Leu Leu Arg Arg Arg His Tyr Gln Arg Leu
                20                  25                  30

<210> SEQ ID NO 411
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Lys Lys Arg His Arg Lys Arg Lys Tyr Lys Gln Cys His Lys Lys Gly
1               5                   10                  15

Gly His Cys Phe Pro Lys Glu Lys Ala Arg Arg Lys Lys Arg Lys Gly
                20                  25                  30

Lys Asn Glu Ile
        35

<210> SEQ ID NO 412
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Lys Lys Arg His Arg Lys Arg Ile Lys Lys Tyr Arg Tyr Tyr Leu Lys
1               5                   10                  15

Pro Leu Lys Lys Lys Arg Lys Lys Arg Lys Gly Lys Arg His Tyr Leu
                20                  25                  30

Ile Ile Arg
        35

<210> SEQ ID NO 413
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Lys Lys Arg His Arg Lys Asp Arg Gly Arg Lys Lys Arg Arg Gln Arg
```

-continued

```
1            5               10              15

Arg Arg Pro Gln Lys Pro Arg Lys Lys Arg Arg Gln Arg Arg Phe Gln
            20              25              30

Gln Ile

<210> SEQ ID NO 414
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Lys Lys Arg His Arg Lys Gly Ser Ser Asp Pro Phe Arg Asp Asp Pro
1            5               10              15

Phe His Arg Lys Arg His Arg Lys Lys Arg His Arg Lys Lys Arg His
            20              25              30

Arg Gly Arg Arg
        35

<210> SEQ ID NO 415
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Lys Lys Arg His Arg Lys Ala Arg Ser Lys Thr Phe Asn Thr His Pro
1            5               10              15

Gln Ser Thr Pro Tyr Lys Arg His Arg Lys Arg Lys Lys Arg Lys Gly
            20              25              30

Lys Lys Arg Pro Lys
        35

<210> SEQ ID NO 416
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Arg Lys Lys Arg Lys Gly Lys Arg Ala Lys Arg His Arg Lys Lys Arg
1            5               10              15

His Arg Lys Lys Pro Lys Asn Met Thr Pro Tyr Arg Ser Pro Pro Pro
            20              25              30

Tyr Val Pro Pro
        35

<210> SEQ ID NO 417
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Lys Lys Lys Arg Lys Arg Gly Asp Lys Arg Lys Arg Lys Arg His Arg
```

-continued

```
1               5                   10                  15

Lys Lys Lys Arg Arg Arg Arg Leu Ser Ile Pro Pro Lys Ala
            20                  25                  30

<210> SEQ ID NO 418
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Lys Lys Lys Arg Lys Arg Gly Asp Lys Arg Lys Arg Lys Arg His Arg
1               5                   10                  15

Lys Lys Lys Arg Arg Arg Arg Phe Gln Thr Pro Pro Gln Leu
            20                  25                  30

<210> SEQ ID NO 419
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Lys Lys Lys Arg Lys Arg Gly Asp Lys Arg Lys Arg Lys Arg His Arg
1               5                   10                  15

Lys Lys Lys Arg Arg Arg Arg Leu Thr Pro Ala Thr Ala Ile
            20                  25                  30

<210> SEQ ID NO 420
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Lys Lys Lys Arg Lys Arg Gly Asp Lys Arg Lys Arg Lys Arg His Arg
1               5                   10                  15

Lys Lys Lys Arg Arg Arg Arg Ser Ile Gly Tyr Pro Leu Pro
            20                  25                  30

<210> SEQ ID NO 421
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Lys Lys Lys Arg Lys Arg Gly Asp Lys Arg Lys Arg Lys Arg His Arg
1               5                   10                  15

Lys Lys Lys Arg Arg Arg Arg Cys Leu Ile Arg Arg Thr Ser Ile Cys
            20                  25                  30

<210> SEQ ID NO 422
<211> LENGTH: 33
<212> TYPE: PRT
<213> ORGANISM: Artificial Sequence
<220> FEATURE:
```

-continued

```
<223> OTHER INFORMATION: Description of Artificial Sequence: Synthetic
      polypeptide

<400> SEQUENCE: 422

Lys Lys Lys Arg Lys Arg Gly Asp Lys Arg Lys Arg Lys Arg His Arg
1               5                   10                  15

Lys Lys Lys Arg Arg Arg Arg Cys Phe Phe Trp Lys Phe Arg Trp Met
            20                  25                  30

Cys

<210> SEQ ID NO 423
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Lys Lys Lys Arg Lys Arg Gly Asp Lys Arg Lys Arg Lys Arg His Arg
1               5                   10                  15

Lys Lys Lys Arg Arg Arg Arg Glu Tyr Tyr Leu Ser Ile Pro Pro Lys
            20                  25                  30

Ala

<210> SEQ ID NO 424
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Lys Lys Lys Arg Lys Arg Gly Asp Lys Arg Lys Arg Lys Arg His Arg
1               5                   10                  15

Lys Lys Lys Arg Arg Arg Asp Tyr Arg Phe Gln Thr Pro Pro Gln Leu
            20                  25                  30

<210> SEQ ID NO 425
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Lys Lys Lys Arg Lys Arg Gly Asp Lys Arg Lys Arg Lys Arg His Arg
1               5                   10                  15

Lys Lys Lys Arg Arg Arg His Tyr Arg Leu Thr Pro Ala Thr Ala Ile
            20                  25                  30

<210> SEQ ID NO 426
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426

Lys Lys Lys Arg Lys Arg Gly Asp Lys Arg Lys Arg Lys Arg His Arg
1               5                   10                  15
```

```
Lys Lys Lys Arg Arg Arg Arg Val Tyr Gln Ser Ile Gly Tyr Pro Leu
            20                  25                  30

Pro

<210> SEQ ID NO 427
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Lys Lys Lys Arg Lys Ser Tyr Arg Arg Gly Asp Lys Arg Lys Arg Lys
1               5                   10                  15

Arg His Arg Lys Lys Lys Arg Arg Arg Cys Leu Ile Arg Arg Thr
            20                  25                  30

Ser Ile Cys
        35

<210> SEQ ID NO 428
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Lys Lys Lys Arg Lys Glu Tyr Arg Gly Asp Lys Arg Lys Arg Lys Arg
1               5                   10                  15

His Arg Lys Lys Lys Arg Arg Arg Arg Cys Phe Phe Trp Lys Phe Arg
            20                  25                  30

Trp Met Cys
        35

<210> SEQ ID NO 429
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

Lys Lys Arg His Arg Lys Ala Arg Ala Arg Lys Lys Ala Ala Lys Ala
1               5                   10                  15

Arg Ile Lys Lys Ala Ala Pro Ala Lys Lys Ala Ala Asn Arg Ala Arg
            20                  25                  30

Lys Lys His
        35

<210> SEQ ID NO 430
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Lys Lys Arg His Arg Lys Gly Ser Ser Arg Arg Pro Arg Pro Gly Thr
1               5                   10                  15
```

-continued

```
Gly Pro Gly Arg Arg Pro Arg Pro Arg Pro Arg Lys Lys Arg
            20              25              30

Asn Arg Ser Arg Gln Arg Arg Arg
        35              40

<210> SEQ ID NO 431
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Lys Lys Arg His Arg Lys Lys Tyr Lys Gln Lys Ile Lys His Val Val
1               5               10              15

Lys Leu Lys Lys His Arg Lys Arg Lys Arg Asn Arg Ser Ile Lys Val
            20              25              30

Ala Val

<210> SEQ ID NO 432
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 432

Lys Lys Arg His Arg Lys Ser Ser Ser Arg Thr Leu Gln Ala His His
1               5               10              15

Asp Arg Gln Ser Asn Lys Arg Lys Arg Lys Asn Arg Ser Arg Arg Arg
            20              25              30

Arg Arg

<210> SEQ ID NO 433
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Lys Lys Arg His Arg Lys Arg Asn Arg Ser Ile His Phe Asn Pro Arg
1               5               10              15

His Arg Arg Arg Arg Arg Arg Asp Val Ala Arg Ala Arg Ala Glu Lys
            20              25              30

Ser Lys Lys Lys
        35

<210> SEQ ID NO 434
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Lys Lys Arg His Arg Lys Asn Arg Ser Lys Lys Gln Arg Phe Arg His
1               5               10              15
```

```
Arg Asn Arg Lys Gly Tyr Arg Ser Gln Arg Gly His Ser Arg Gly Arg
            20                  25                  30

Asn Gln Asn Ser Arg Arg
        35

<210> SEQ ID NO 435
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

Lys Lys Arg His Arg Lys Ala Arg Ala Arg Lys Lys Ala Ala Lys Ala
1               5                   10                  15

Arg Ile Lys Lys Ala Ala Pro Ala Lys Lys Ala Ala Arg Ala Cys Ile
            20                  25                  30

Ile Leu Arg Lys Lys His
        35

<210> SEQ ID NO 436
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Lys Lys Arg His Arg Lys Gly Ser Ser Arg Arg Pro Arg Pro Gly Thr
1               5                   10                  15

Gly Pro Gly Arg Arg Pro Arg Pro Arg Pro Arg Pro Arg Lys Lys Arg
            20                  25                  30

Cys Ala Ser Glu Arg Gln Arg Arg Arg
        35                  40

<210> SEQ ID NO 437
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Lys Lys Arg His Arg Lys Cys Ile Ile Glu Lys Tyr Lys Gln Lys Ile
1               5                   10                  15

Lys His Val Val Lys Leu Lys Lys His Arg Lys Arg Lys Arg Ile Lys
            20                  25                  30

Val Ala Val
        35

<210> SEQ ID NO 438
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Lys Lys Arg His Arg Lys Cys Gln Ala Leu Ser Ser Ser Arg Thr Leu
1               5                   10                  15
```

```
Gln Ala His His Asp Arg Gln Ser Asn Lys Arg Lys Arg Lys Arg Arg
            20                  25                  30

Arg Arg Arg
        35

<210> SEQ ID NO 439
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Lys Lys Arg His Arg Lys Arg Ile His Phe Asn Pro Arg His Arg Arg
1               5                   10                  15

Arg Arg Arg Arg Cys Ile Ala Glu Asp Val Ala Arg Ala Arg Ala Glu
            20                  25                  30

Lys Ser Lys Lys Lys
        35

<210> SEQ ID NO 440
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Lys Arg His Arg Lys Lys Lys Gln Arg Phe Arg His Arg Asn Arg Lys
1               5                   10                  15

Gly Tyr Arg Ser Gln Arg Gly His Ser Arg Gly Arg Asn Gln Asn Ser
            20                  25                  30

Arg Arg Cys Ile Ile Leu Arg
        35

<210> SEQ ID NO 441
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Lys Lys Arg His Arg Lys Ala Arg Ala Arg Lys Lys Ala Ala Lys Ala
1               5                   10                  15

Arg Ile Lys Lys Ala Ala Pro Ala Lys Lys Ala Ala Arg Ala Arg Lys
            20                  25                  30

Lys His

<210> SEQ ID NO 442
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 442

Lys Lys Arg His Arg Lys Gly Ser Ser Arg Arg Pro Arg Pro Gly Thr
1               5                   10                  15
```

```
Gly Pro Gly Arg Arg Pro Arg Pro Arg Pro Arg Pro Arg Lys Lys Arg
            20              25              30

Arg Gln Arg Arg Arg
        35

<210> SEQ ID NO 443
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Lys Lys Arg His Arg Lys Lys Tyr Lys Gln Lys Ile Lys His Val Val
1               5               10              15

Lys Leu Lys Lys His Arg Lys Arg Lys Arg Ile Lys Val Ala Val
            20              25              30

<210> SEQ ID NO 444
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Lys Lys Arg His Arg Lys Ser Ser Ser Arg Thr Leu Gln Ala His His
1               5               10              15

Asp Arg Gln Ser Asn Lys Arg Lys Arg Lys Arg Arg Arg Arg Arg
            20              25              30

<210> SEQ ID NO 445
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

Lys Lys Arg His Arg Lys Arg Ile His Phe Asn Pro Arg His Arg Arg
1               5               10              15

Arg Arg Arg Arg Asp Val Ala Arg Ala Arg Ala Glu Lys Ser Lys Lys
            20              25              30

Lys

<210> SEQ ID NO 446
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Lys Arg His Arg Lys Lys Lys Gln Arg Phe Arg His Arg Asn Arg Lys
1               5               10              15

Gly Tyr Arg Ser Gln Arg Gly His Ser Arg Gly Arg Asn Gln Asn Ser
            20              25              30

Arg Arg
```

-continued

```
<210> SEQ ID NO 447
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Lys Lys Arg His Arg Lys Gly Gly Ser Leu Leu Arg Gly Glu Lys Glu
1               5                   10                  15

Leu Lys Arg Pro Pro Arg Arg Arg Arg Lys Tyr Ile Gly Ser Arg
            20                  25                  30

<210> SEQ ID NO 448
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Lys Lys Lys Arg Lys Leu Arg Gly Asp Leu Lys Arg Lys Pro Leu Ile
1               5                   10                  15

Ser Arg Arg Leu Ile Asp Arg Tyr Gln Lys Lys Lys Arg Lys Arg Gly
            20                  25                  30

Asp Lys Arg Lys
        35

<210> SEQ ID NO 449
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Lys Lys Lys Arg Lys Leu Arg Gly Asp Leu Lys Arg Lys Ser Ser Ser
1               5                   10                  15

Val Arg Lys Lys Pro Gly Gly Ser Lys Lys Lys Arg Lys Arg Gly Asp
            20                  25                  30

Lys Arg Lys
        35

<210> SEQ ID NO 450
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Lys Lys Lys Arg Lys Leu Arg Gly Asp Leu Lys Arg Lys Gly Thr Gln
1               5                   10                  15

Pro Glu His Ser Ser Thr Asp His Lys Lys Lys Arg Lys Arg Gly Asp
            20                  25                  30

Lys Arg Lys
        35

<210> SEQ ID NO 451
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Lys Lys Lys Arg Lys Arg Gly Asp Lys Arg Lys Arg Lys Arg His Arg
1               5                   10                  15

Lys Lys Lys Arg Arg Arg Arg Leu Ser Ile Pro Pro Lys Ala
            20                  25                  30

<210> SEQ ID NO 452
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Lys Lys Lys Arg Lys Arg Gly Asp Lys Arg Lys Arg Lys Arg His Arg
1               5                   10                  15

Lys Lys Lys Arg Arg Arg Arg Phe Gln Thr Pro Pro Gln Leu
            20                  25                  30

<210> SEQ ID NO 453
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Lys Lys Lys Arg Lys Arg Gly Asp Lys Arg Lys Arg Lys Arg His Arg
1               5                   10                  15

Lys Lys Lys Arg Arg Arg Arg Asn Arg Ser Leu Thr Pro Ala Thr Ala
            20                  25                  30

Ile

<210> SEQ ID NO 454
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Lys Lys Lys Arg Lys Arg Gly Asp Lys Arg Lys Arg Lys Arg His Arg
1               5                   10                  15

Lys Lys Lys Arg Arg Arg Arg Ser Ile Gly Tyr Pro Leu Pro
            20                  25                  30

<210> SEQ ID NO 455
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455
```

-continued

Lys Lys Lys Arg Lys Arg Gly Asp Lys Arg Lys Arg Lys Arg His Arg
1               5                   10                  15

Lys Lys Lys Arg Arg Arg Arg Asn Arg Ser Cys Leu Ile Arg Arg Thr
            20                  25                  30

Ser Ile Cys
        35

<210> SEQ ID NO 456
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Lys Lys Lys Arg Lys Arg Gly Asp Lys Arg Lys Arg Lys Arg His Arg
1               5                   10                  15

Lys Lys Lys Arg Arg Arg Arg Asn Arg Ser Cys Phe Phe Trp Lys Phe
            20                  25                  30

Arg Trp Met Cys
        35

<210> SEQ ID NO 457
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Lys Lys Lys Arg Lys Asn Arg Ser Arg Gly Asp Lys Arg Lys Arg Lys
1               5                   10                  15

Arg His Arg Lys Lys Lys Arg Arg Arg Arg Ile Glu Leu Leu Gln Ala
            20                  25                  30

Arg Gly Cys
        35

<210> SEQ ID NO 458
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Lys Lys Lys Arg Lys Arg Gly Asp Lys Arg Lys Arg Lys Arg His Arg
1               5                   10                  15

Lys Lys Lys Asn Arg Ser Arg Arg Arg Arg Glu Asp Val
            20                  25                  30

<210> SEQ ID NO 459
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Lys Lys Lys Arg Lys Arg Gly Asp Lys Arg Lys Arg Lys Arg His Arg
1               5                   10                  15

```
Lys Lys Lys Arg Arg Arg Arg Val His Pro Lys Gln His Arg Gly Gly
            20                  25                  30

Ser Lys Gly Cys
        35

<210> SEQ ID NO 460
<211> LENGTH: 10664
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 460
tcgcgcgttt cggtgatcga ggtgagcccc acgttctgct tcactctccc catctccccc      60
ccctccccac ccccaatttt gtatttattt atttttaat tattttgtgc agcgatgggg     120 gcggggggg ggggggggcg cgcgccaggc ggggcggggc ggggcgaggg gcggggcggg     180
gcgaggcgga gaggtgcggc ggcagccaat cagagcggcg cgctccgaaa gtttcctttt     240
atggcgaggc ggcggcggcg gcggccctat aaaaagcgaa gcgcgcggcg ggcgggagtc     300
gctgcgacgc tgccttcgcc ccgtgccccg ctccgccgcc gcctcgcgcc gcccgccccg     360
gctctgactg accgcgttac tcccacaggt gagcgggcgg gacggcccctt ctcctccggg     420 ctgtaattag cgcttggttt aatgacggct tgtttctttt ctgtggctgc gtgaaagcct     480
tgaggggctc cgggagggcc ctttgtgcgg ggggagcgg ctcggggggt gcgtgcgtgt     540
gtgtgtgcgt ggggagcgcc gcgtgcgcc cgcgctgccc ggcggctgtg agcgctgcgg     600
gcgcggcgcg gggctttgtg cgctccgcag tgtgcgcgag gggagcgcgg ccggggcgg     660 tgccccgcgg tgcggggggg gctgcgaggg gaacaaaggc tgcgtgcggg gtgtgtgcgt     720 ggggggtga gcagggggtg tgggcgcggc ggtcgggctg taaccccccc ctgcaccccc     780 ctcccgagt gctgagcac ggcccggctt cgggtgcggg gctccgtacg gggcgtggcg     840
cggggctcgc cgtgccgggc ggggggtggc ggcaggtggg ggtgccgggc ggggcggggc     900
cgcctcgggc cgggggaggc tcgggggagg ggcgcggcgg cccccggagc gccgcggct     960 gtcgaggcgc ggcgagccgc agccattgcc ttttatggta atcgtgcgag agggcgcagg    1020
gacttccttt gtcccaaatc tgtgcggagc cgaaatctgg gaggcgccgc cgcacccct    1080 ctagcgggcg cggggcgaag cggtgcggcg ccggcaggaa ggaaatgggc gggggagggcc    1140 ttcgtgcgtc gccgcgccgc cgtccccttc tccctctcca gcctcggggc tgtccgcggg    1200
gggacggctg ccttcggggg ggacggggca gggcggggtt cggcttctgg cgtgtgaccg    1260
gcggctctag agcctctgct aaccatgttc atgccttctt cttttcctta cagctcctgg    1320
gcaacgtgct ggttattgtg ctgtctcatc attttggcaa aaccggtctc gaaggcctgc    1380
aggcggccgc cgccaccgcc accatgcaaa tagcactctt cgcttgcttc tttctgagcc    1440
ttttcaattt ctgctctagt gccatcagaa gatactacct tggtgcagtg gaattgtcct    1500
ggaactatat tcagagtgat ctgctcagtg tgctgcatac agactcaaga tttcttccta    1560
gaatgtcaac atcttttcca ttcaacacct ccatcatgta taaaaagact gtgtttgtag    1620
agtacaagga ccagctttttc aacattgcca gcccaggcc accctggatg ggtttgctag    1680
gtcctaccat ttggactgag gttcatgaca cagtggtcat tacacttaaa aacatggctt    1740
ctcatcctgt cagtcttcat gctgttggtg tgtcctactg gaaagcttct gagggagatg    1800
aatatgaaga tcagacaagc caaatggaga aggaagatga taaagtttttc cctggtgaaa    1860
```

-continued

```
gtcatactta tgtttggcaa gtcctgaaag agaatggtcc aatggcctct gaccctccat      1920
gtctcactta ctcatatatg tctcatgtgg atctggtgaa agatttgaat tcaggcctca      1980
ttggagctct gctagtatgt aaagaaggca gtctctccaa agaaagaaca cagatgttgt      2040
accaatttgt actgcttttt gctgtatttg atgaagggaa gagctggcac tcagaaacaa      2100
acgactctta tacacagtct atggattctg catctgctag agactggcct aaaatgcaca      2160
cagtcaatgg ctatgtaaac aggtctcttc caggtctgat tggatgccat aggaaatcag      2220
tctactggca cgtgattgga atgggcacca ctcctgaaat acactcaata ttcctcgaag      2280
gtcacacatt ttttgtgagg aaccaccgtc aagcttcatt ggagatatca ccaataactt      2340
tccttactgc tcaaacactc ttgatagatc ttgggcagtt cctactattt tgtcatatct      2400
cttcccataa acatgatggc atggaagctt atgtcaaagt agatagctgc cctgaggaat      2460
cccaatggca aaagaaaaat aataatgagg aaatggaaga ttatgatgat gatctttatt      2520
cagaaatgga tatgttcaca ttggattatg acagctctcc ttttatccaa attcgctcgg      2580
ttgctaaaaa gtaccctaaa acttggatac attatatttc tgctgaggag gaagactggg      2640
actatgcacc ttcagttcct acctcggata tggaagttta aaaagccag tatctgagca      2700 atggtcctca tcggattggt aggaaatata aaaaagtcag atttatagca tacacagatg      2760 aaaccttaa gactcgtgaa actattcagc atgaatcagg actcttggga cctttacttt      2820
atggagaagt tggagacaca ctgttgatta ttttttaagaa tcaagcaagc cgaccatata      2880
acatttaccc tcatggaatc actgatgtca gtcctctaca tgcaaggaga ttgccaagag      2940
gtataaagca cgtgaaggat ttgccaattc atccaggaga gatattcaag tacaagtgga      3000
cagttacagt agaagatgga ccaactaaat cagatccacg gtgcctgacc cgctattatt      3060
caagtttcat taaccctgag agagatctag cttcaggact gattggccct cttctcatct      3120
gctacaaaga atctgtagat caaaggggaa accagatgat gtcagacaaa agaaatgtca      3180
tcctgttttc tatatttgat gagaaccaaa gctggtacat cacagagaac atgcaacgct      3240
tcctccccaa tgcagctaaa acacagcccc aggaccctgg gttccaggcc tccaacatca      3300
tgcacagcat caatggctat gtttttgata gcttggagtt gacagtttgt ttgcatgagg      3360
tggcatactg gcacattctc agtgttggag cacagacaga cttcttatct atcttcttct      3420
ctggatatac tttcaaacac aaaatggtct atgaagatac acttaccctg ttcccattct      3480
caggagaaac tgtctttatg tcgatggaaa acccaggtct atgggtcttg gggtgtcata      3540
attcagactt tcggaagaga ggtatgacag cattgctgaa agtttctagt tgtgacaaga      3600
gcactagtga ttattatgaa gaaatatatg aagatattcc aacacagttg gtgaatgaga      3660
acaatgtcat tgatcccaga agcttcttcc agaatacaaa tcatcctaat actaggaaaa      3720
agaaattcaa agattccaca attccaaaaa atgatatgga gaagattgag cctcagtttg      3780
aagagatagc agagatgctt aaagtacaga gtgtctcagt tagtgacatg ttgatgctct      3840
tgggacagag tcatcctact ccacatggct tatttttatc agatggccaa gaagccatct      3900
atgaggctat tcatgatgat cattcaccaa atgcaataga cagcaatgaa ggcccatcta      3960
aagtgaccca actcaggcca gaatcccatc acagtgagaa aatagtattt actcctcagc      4020
ccggcctcca gttaagatcc aataaaagtt tggagacaac tatagaagta aagtggaaga      4080
aacttggttt gcaagtttct agtttgccaa gtaatctaat gactacaaca attctgtcag      4140
acaatttgaa agcaactttt gaaaagacag attcttcagg atttccagat atgccagttc      4200
```

-continued

```
actctagtag taaattaagt actactgcat ttggtaagaa agcatattcc cttgttgggt   4260
ctcatgtacc tttaaacgtg agtgaagaaa atagtgattc caacatattg gattcaactt   4320
taatgtatag tcaagaaagt ttaccaagag ataatatatt atcaatggag aatgatagat   4380
tactcagaga gaagaggttt catggaattg ctttattgac caaagataat actttattca   4440
aagacaatgt ctccttaatg aaaacaaaca aaacatataa tcattcaaca actaatgaaa   4500
aactacacac tgagagccca acatcaattg agaatagtac aacagacttg caagatgcca   4560
tattaaaggt caatagtgag attcaagaag taacagcttt gattcatgat ggaacacttt   4620
taggcaaaaa ttctacatat ttgagactaa accatatgct aaatagaact acctcaacaa   4680
aaaataaaga catatttcat agaaaagatg aagatcctat tccacaagat gaagagaata   4740
caatcatgcc attttccaag atgttgttct tgtcagaatc ttcaaattgg tttaaaaaga   4800
ccaatggaaa taattccttg aactctgagc aagaacatag tccaaagcaa ttagtatatt   4860
taatgtttaa aaaatatgta aaaaatcaaa gtttcttgtc agagaaaaat aaagtcacag   4920
tagaacagga tggatttaca aagaacatag gacttaaaga catggctttt ccacataata   4980
tgagcatatt tcttaccact ttgtctaacg tacatgaaaa tggtaggcac aatcaagaaa   5040
aaaatattca ggaagagata gagaaggaag cactaattga agagaaagta gttttgcccc   5100
aggtgcacga agcaactggc tctaagaatt tcttgaaaga catattgata ctaggcacta   5160
ggcaaaatat aagtttatat gaagtacatg taccagtact tcaaaacatc acatcaataa   5220
acaattcaac aaatacagta cagattcaca tggagcattt ctttaaaaga aggaaggaca   5280
aggaaacaaa ttcagaaggc ttggtaaata aaaccagaga aatggtaaaa aactatccaa   5340
gccagaagaa tattactact caacgtagta aacgggcttt gggacaattc agactgtcaa   5400
ctcaatggct taaaaccata aactgttcaa cacagtgtat cattaaacag atagaccaca   5460
gcaaggaaat gaaaaagttc attactaaat cttccttatc agattcttct gtgattaaaa   5520
gcaccactca gacaaatagt tctgactcac acattgtaaa aacatcagca tttccaccaa   5580
tagatctcaa aaggagtcca ttccaaaaca aattttctca tgttcaagca tcatcctaca   5640
tttatgactt taagacaaaa agttcaagaa ttcaagaaag caataatttc ttaaaagaaa   5700
ccaaaataaa taacccttct ttagccattc taccatggaa tatgttcata gatcaaggaa   5760
aatttacctc cccagggaaa agtaacacaa actcagtcac atataagaaa cgtgagaaca   5820
ttattttctt gaaaccaact ttgcctgaag aatctggcaa aattgaattg cttcctcaag   5880
tttccattca agaggaagaa attttaccta cagaaactag ccatggatct cctggacact   5940
tgaatctcat gaaagaggtc tttcttcaga aaatacaggg gcctactaaa tggaataaag   6000
caaagaggca tggagaaagt ataaaaggta aaacagagag ctctaaaaat actcgctcaa   6060
aactgctaaa tcatcatgct tgggattatc attatgctgc acagatacca aaagatatgt   6120
ggaaatccaa agagaagtca ccagaaatta tatccattaa gcaagaggac accattttgt   6180
ctctgaggcc tcatggaaac agtcattcaa taggggcaaa tgagaaacaa aattggcctc   6240
aaagagaaac cacttgggta aagcaaggcc aaactcaaag gacatgctct caaatcccac   6300
cagtgttgaa acgacatcaa agggaactta gtgcttttca atcagaacaa gaagcaactg   6360
actatgatga tgccatcacc attgaaacaa tcgaggattt tgacatttac agtgaggaca   6420
taaagcaagg tccccgcagc tttcaacaga aaacaaggca ctattttatt gcagctgtgg   6480
aacgactctg ggactatggg atgagtacat ctcatgttct acgaaatagg tatcaaagtg   6540
acaatgtacc tcagttcaag aaagtagttt tccaggaatt tactgatggc tcctttagtc   6600
```

-continued

```
agcccttata tcgtggagaa ttaaatgaac acctggggtt gttgggccca tatataagag    6660
cagaagttga agacaacatt atggtaactt tcaaaaacca ggcctcccgt ccctactcct    6720
tctattctag cctcatttct tataaagaag atcagagagg agaagaacct agaagaaact    6780
ttgtcaagcc taatgaaacc aaaatttatt tttggaaagt acaacatcat atggcaccca    6840
cagaagatga gtttgactgc aaggcctggg cttatttctc tgatgttgat cttgaaagag    6900
atatgcactc gggattaatt ggaccccttc tgatttgcca cgcgaacaca ctgaatcctg    6960
ctcatgggag acaagtgtca gtacaggaat ttgctctgct tttcactatc tttgatgaga    7020
ccaagagctg gtacttcact gaaaacgtga aaaggaactg caagacaccc tgcaatttcc    7080
agatggaaga ccccactttg aaagagaatt atcgcttcca tgcaatcaat ggttatgtaa    7140
tggataccct accaggctta gtaatggctc aagatcaaag gattcgatgg tatcttctca    7200
gcatgggcaa caatgagaac atccaatcta ttcatttcag tggacatgtt ttcactgtac    7260
ggaaaaaaga ggagtataaa atggcagtgt acaacctcta cccaggtgtt tttgagactc    7320
tggaaatgat accatccaga gctggaatat ggcgagtaga atgccttatt ggcgagcact    7380
tacaggctgg gatgagcact cttttttctgg tgtacagcaa gcagtgtcag attcctcttg    7440
gaatggcttc tggaagcatc cgtgatttcc agattacagc ttcaggacat tatggacagt    7500
gggccccaaa cctggcaaga cttcattatt ccggatcaat caatgcctgg agtaccaagg    7560
agcccttttc ttggatcaag gtagatctgt tggcaccaat gattgttcat ggcatcaaga    7620
ctcagggtgc tcgtcagaaa ttttccagcc tttatatctc tcaatttatc atcatgtata    7680
gcctggatgg gaagaagtgg ctgagttatc aaggaaattc cactggaacc ttaatggttt    7740
tctttggcaa tgtggactca tctgggatta agcataatag ttttaatcct ccaattattg    7800
ctcgatatat ccgtttgcac cccactcatt ctagcatccg tagtactctt cgcatggagt    7860
tgatgggctg tgatttaaac agttgcagca taccattggg aatggaaagt aaagtaaatat    7920 cagatacaca aatcactgcc tcatcctact tcaccaacat gtttgctact tggtctcctt    7980
cacaagctcg acttcacctc cagggaagga ctaatgcctg gcgacctcag gtgaatgatc    8040
caaaacaatg gttgcaagtg gacttacaaa agacaatgaa agtcactgga ataataaccc    8100
agggagtgaa atctctcttt accagcatgt ttgtgaaaga gttccttatt tccagcagtc    8160
aagatggcca tcactggact caaattttat acaatggcaa ggtaaaggtt tttcagggga    8220
atcaggactc atccacacct atgatgaatt ctctagaccc accattactc actcgctatc    8280
ttcgaattca cccccagatc tgggagcacc aaattgctct gaggcttgag attctaggat    8340
gtgaggccca gcagcaatac tgaccatggc ccaacttgtt tattgcagct tataatggtt    8400
acaaataaag caatagcatc acaaatttca caaataaagc atttttttca ctgcattcta    8460
gttgtggttt gtccaaactc atcaatgtat cttatcatgt ctggatctcg ttaactcgag    8520
ggatccatcg atgtcgactg cagaggcctg catgcaagct tggtgtaatc atggtcatag    8580
ctgtttcctg tgtgaaattg ttatccgctc acaattccac acaacatacg agccggaagc    8640
ataaagtgta aagcctgggg tgcctaatga gtgagctaac tcacattaat tgcgttgcgc    8700
tcactgcccg ctttccagtc gggaaacctg tcgtgccagc tgcattaatg aatcggccaa    8760
cgcgcgggga gaggcggttt gcgtattggg cgctcttccg cttcctcgct cactgactcg    8820
ctgcgctcgg tcgttcggct gcggcgagcg gtatcagctc actcaaaggc ggtaatacgg    8880
ttatccacag aatcagggga taacgcagga aagaacatgt gagcaaaagg ccagcaaaag    8940
```

-continued

```
gccaggaacc gtaaaaaggc cgcgttgctg gcgttttttcc ataggctccg ccccccctgac    9000 gagcatcaca aaaatcgacg ctcaagtcag aggtggcgaa acccgacagg actataaaga    9060
taccaggcgt ttccccctgg aagctccctc gtgcgctctc ctgttccgac cctgccgctt    9120
accggatacc tgtccgcctt tctcccttcg ggaagcgtgg cgctttctca tagctcacgc    9180
tgtaggtatc tcagttcggt gtaggtcgtt cgctccaagc tgggctgtgt gcacgaaccc    9240
cccgttcagc ccgaccgctg cgccttatcc ggtaactatc gtcttgagtc caacccggta    9300
agacacgact tatcgccact ggcagcagcc actggtaaca ggattagcag agcgaggtat    9360
gtaggcggtg ctacagagtt cttgaagtgg tggcctaact acggctacac tagaagaaca    9420
gtatttggta tctgcgctct gctgaagcca gttaccttcg aaaaagagt tggtagctct    9480 tgatccggca aacaaaccac cgctggtagc ggtggttttt ttgtttgcaa gcagcagatt    9540
acgcgcagaa aaaaaggatc tcaagaagat cctttgatct tttctacggg gtctgacgct    9600
cagtggaacg aaaactcacg ttaagggatt ttggtcatga gattatcaaa aaggatcttc    9660
acctagatcc ttttaaatta aaaatgaagt tttaaatcaa gcccaatctg aataatgtta    9720
caaccaatta accaattctg attagaaaaa ctcatcgagc atcaaatgaa actgcaattt    9780
attcatatca ggattatcaa taccatattt ttgaaaaagc cgtttctgta atgaaggaga    9840
aaactcaccg aggcagttcc ataggatggc aagatcctgg tatcggtctg cgattccgac    9900
tcgtccaaca tcaatacaac ctattaattt cccctcgtca aaaataaggt tatcaagtga    9960
gaaatcacca tgagtgacga ctgaatccgg tgagaatggc aaaagtttat gcatttctttt    10020 ccagacttgt tcaacaggcc agccattacg ctcgtcatca aaatcactcg catcaaccaa    10080
accgttattc attcgtgatt gcgcctgagc gagacgaaat acgcgatcgc tgttaaaagg    10140
acaattacaa acaggaatcg aatgcaaccg gcgcaggaac actgccagcg catcaacaat    10200
attttcacct gaatcaggat attcttctaa tacctggaat gctgttttttc cggggatcgc    10260 agtggtgagt aaccatgcat catcaggagt acgataaaa tgcttgatgg tcggaagagg    10320
cataaattcc gtcagccagt ttagtctgac catctcatct gtaacatcat tggcaacgct    10380 accttttgcca tgtttcagaa acaactctgg cgcatcgggc ttcccataca agcgatagat    10440
tgtcgcacct gattgcccga cattatcgcg agcccattta tacccatata aatcagcatc    10500
catgttggaa tttaatcgcg gcctcgacgt ttcccgttga atatggctca taacacccct    10560
tgtattactg tttatgtaag cagacagttt tattgttcat gatgatatat ttttatcttg    10620
tgcaatgtaa catcagagat tttgagacac gggccagagc tgca                     10664
```

```
<210> SEQ ID NO 461
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Arg Arg Arg Arg Arg
1               5

<210> SEQ ID NO 462
<211> LENGTH: 4
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 462

Asn Arg Asp Asn
1

<210> SEQ ID NO 463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Lys Leu Lys Ile Lys Arg Pro Val Lys
1               5

<210> SEQ ID NO 464
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Pro Lys Lys Lys Arg Lys Val
1               5

<210> SEQ ID NO 465
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 465

Leu Pro Xaa Thr Gly
1               5

<210> SEQ ID NO 466
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Gly Thr Ala Leu Leu
1               5

<210> SEQ ID NO 467
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Asp Ser Leu Leu

1

<210> SEQ ID NO 468
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Asn Pro Thr Tyr
1

<210> SEQ ID NO 469
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Lys Ile Leu
1

<210> SEQ ID NO 470
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Phe Tyr Gln Pro Leu
1               5

<210> SEQ ID NO 471
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Ile Lys Val Ala Val Ala
1               5

<210> SEQ ID NO 472
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Lys Arg His Arg Lys Lys Arg His Arg Lys Lys Arg His Arg Lys Lys
1               5                   10                  15

Arg His Arg Lys
            20

<210> SEQ ID NO 473
<211> LENGTH: 32
<212> TYPE: PRT

-continued

```
<213> ORGANISM: Artificial Sequence
<220> FEATURE:
<223> OTHER INFORMATION: Description of Artificial Sequence: Synthetic
      polypeptide

<400> SEQUENCE: 473

Lys Lys Arg His Arg Lys Gly Gly Ser Leu Leu Arg Gly Asp Lys Glu
1               5                   10                  15

Leu Lys Arg Pro Pro Arg Arg Arg Arg Arg His Tyr Asn Lys Ser Arg
            20                  25                  30

<210> SEQ ID NO 474
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Lys Lys Arg His Arg Lys Gly Gly Val Leu Leu Arg Gly Asp Lys Glu
1               5                   10                  15

Leu Lys Arg Pro Pro Arg Arg Arg Arg Arg His Tyr Asn Lys Ser Arg
            20                  25                  30

<210> SEQ ID NO 475
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Lys Lys Arg His Arg Lys Gly Gly Ala Leu Leu Arg Gly Asp Lys Glu
1               5                   10                  15

Leu Lys Arg Pro Pro Arg Arg Arg Arg Arg His Tyr Asn Lys Ser Arg
            20                  25                  30

<210> SEQ ID NO 476
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Lys Lys Arg His Arg Lys Gly Gly Ser Leu Leu Arg Gly Asp Lys Glu
1               5                   10                  15

Leu Lys Arg Pro Pro Arg Arg Arg Arg Arg His Tyr Cys Ala Ile Leu
            20                  25                  30

Arg

<210> SEQ ID NO 477
<211> LENGTH: 33
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 477

Lys Lys Arg His Arg Lys Lys Gly Gly Ser Leu Leu Arg Gly Asp Lys
1               5                   10                  15

Glu Leu Lys Arg Pro Pro Arg Arg Arg Arg His Tyr Asn Lys Ser
            20          25              30

Arg
```

MODIFIED MINI-NUCLEOSOME CORE PROTEINS AND USE IN NUCLEIC ACID DELIVERY

CROSS-REFERENCE TO RELATED APPLICATIONS

This application claims the benefit of U.S. Provisional Application No. 63/009,124, filed on Apr. 13, 2020, the disclosure of which is hereby incorporated by reference in its entirety.

BACKGROUND

AAV vectors are considered the current gold standard of gene therapy and have shown promise in diverse clinical trials, including clinical trials for, e.g., retinal gene therapy and systemic gene therapy in liver, CNS, and/or other tissues. With the regulatory approval of at least three different gene therapies, the field is poised for many more, so patients can access these life-changing treatments. However, despite being the industry's gold standard, AAV vectors have certain limitations. Improved and/or alternative nucleic acid delivery technologies are needed.

SUMMARY

The present disclosure provides compositions and methods relating to, among other things, polypeptides that are capable of associating with nucleic acid molecules, wherein the polypeptides include at least one modified amino acid. In various embodiments, the polypeptides can be used for, e.g., delivering the nucleic acid molecules to a subject in need of gene therapy. Accordingly, the present disclosure includes, among other things, modified polypeptides capable of associating with nucleic acid molecules, as well as compositions including modified polypeptides disclosed herein together with associated nucleic acid molecules. The present disclosure contemplates, without wishing to be bound by any particular scientific theory, that association of a nucleic acid molecule with a modified polypeptide disclosed herein can facilitate delivery of the nucleic acid to a target cell, subject, or other system.

In particular, the present disclosure includes, among other things, "modified mini-nucleosome core proteins" for delivery of nucleic acids. In various embodiments, a mini-nucleosome core protein of the present disclosure can include (a) a nucleic acid binding domain ("NABD"); (b) a nucleic acid release domain; and, optionally, (c) further domains including, e.g., one or more of a targeting domain, a stability domain, an oligomerization domain, and/or a linker domain. In various embodiments, a mini-nucleosome core protein of the present disclosure can include (a) a nucleic acid binding domain ("NABD"); (b) a nucleic acid release domain; (c) a targeting domain; and, optionally, (d) further domains including, e.g., one or more of a stability domain, an oligomerization domain, and/or a linker domain. In various embodiments, a mini-nucleosome core protein of the present disclosure can be a modified mini-nucleosome core protein that includes (a) a nucleic acid binding domain ("NABD"); (b) a nucleic acid release domain; (c) a modified amino acid residue; and, optionally, (d) further domains including, e.g., one or more of a targeting domain, a stability domain, an oligomerization domain, and/or a linker domain. In various embodiments, a mini-nucleosome core protein of the present disclosure can be a modified mini-nucleosome core protein that includes (a) a nucleic acid binding domain ("NABD"); (b) a nucleic acid release domain; (c) a targeting domain; (d) a modified amino acid residue; and, optionally, (e) further domains including, e.g., one or more of a stability domain, an oligomerization domain, and/or a linker domain. As disclosed in herein, a modified a mini-nucleosome core protein can be referred to and/or described as a mini-nucleosome core protein and/or as a protein that is or includes a mini-nucleosome core protein having at least one modified amino acid residue. Accordingly, for clarity, all references, express or implied, to "mini-nucleosome core proteins" in the present disclosure include and encompass modified mini-nucleosome core proteins of the present disclosure. One or more mini-nucleosome core proteins associated with a nucleic acid cargo can be referred to as a "loaded mini-nucleosome." Because a loaded mini-nucleosome that is for delivery of a nucleic acid to a target is non-viral, a mini-nucleosome is an example of a non-viral vehicle for nucleic acid delivery.

In particular, the present disclosure includes, among other things, "modified mini-nucleosome core proteins" for delivery of nucleic acids. In various embodiments, a mini-nucleosome core protein of the present disclosure can include (a) a nucleic acid binding domain ("NABD"); (b) a targeting domain; and, optionally, (c) further domains including, e.g., one or more of a nucleic acid release domain, a stability domain, an oligomerization domain, and/or a linker domain. In various embodiments, a mini-nucleosome core protein of the present disclosure can include (a) a nucleic acid binding domain ("NABD"); (b) a targeting domain; (c) a nucleic acid release domain; and, optionally, (d) further domains including, e.g., one or more of a stability domain, an oligomerization domain, and/or a linker domain. In various embodiments, a mini-nucleosome core protein of the present disclosure can be a modified mini-nucleosome core protein that includes (a) a nucleic acid binding domain ("NABD"); (b) a targeting domain; (c) a modified amino acid residue; and, optionally, (d) further domains including, e.g., one or more of a nucleic acid release domain, a stability domain, an oligomerization domain, and/or a linker domain. In various embodiments, a mini-nucleosome core protein of the present disclosure can be a modified mini-nucleosome core protein that includes (a) a nucleic acid binding domain ("NABD"); (b) a targeting domain; (c) a nucleic acid release domain; (d) a modified amino acid residue; and, optionally, (e) further domains including, e.g., one or more of a stability domain, an oligomerization domain, and/or a linker domain. As disclosed in herein, a modified a mini-nucleosome core protein can be referred to and/or described as a mini-nucleosome core protein and/or as a protein that is or includes a mini-nucleosome core protein having at least one modified amino acid residue. Accordingly, for clarity, all references, express or implied, to "mini-nucleosome core proteins" in the present disclosure include and encompass modified mini-nucleosome core proteins of the present disclosure. One or more mini-nucleosome core proteins associated with a nucleic acid cargo can be referred to as a "loaded mini-nucleosome." Because a loaded mini-nucleosome that is for delivery of a nucleic acid to a target is non-viral, a mini-nucleosome is an example of a non-viral vehicle for nucleic acid delivery.

The present disclosure includes the recognition that at least some modified mini-nucleosome core proteins of the present disclosure have advantageous properties including, without limitation, increased bioavailability; increased half-life; increased stability; decreased degradation; increased binding affinity, e.g., for target cells; increased uptake, e.g., by target cells; improved blood-brain barrier penetration;

reduced accumulation, e.g., in target cells or tissues; reduced aggregation; reduced precipitation; reduced thermal denaturation; and/or reduced kinetic denaturation, e.g., as set forth herein.

The present disclosure includes the recognition that at least certain compositions and methods described herein remedy one or more deficiencies associated with AAV vectors, including that:

1) AAV is associated with a payload limitation of 4.5 kb DNA length, which limitation prevents use of AAV in treatment of diseases caused at least in part by deficiency in expression of a gene product typically encoded by a nucleic acid larger than 4 kb (for example genes like CFTR, HTT, F8, DMD, ABCA4 etc. cannot fit into AAV vectors) (Lai Y. et al, 2010).

2) AAV has been known to integrate at low percentage and/or in a site-non-specific manner (Smith R. H., 2008). Random or site-non-specific integration may be deleterious if integration can or does disrupt a tumor suppressor gene or gene important for cellular functions.

3) Depending on the serotype of AAV, 25-70% of humans have preexisting neutralizing antibodies to AAV which means, they would be less likely to benefit for AAV therapy (Fitzpatrick Z., et al 2018).

4) Multiple treatments with AAV are highly unlikely to be effective because once a patient is injected, the patient produces a high number of antibodies against the virus. For some diseases where cellular turnover is high (e.g., in the turnover of liver cells or airway epithelial cells) multiple treatments maybe needed. Thus, due to increased antibodies against AAVs following a first treatment, the same vector may not be useful in follow-up treatments or doses.

5) Effective treatment of some diseases may require delivery of an enormous payload of particles administered by intravenous injection in order to transduce cells in vivo. A high dose of AAV comes with its own toxicities, which are well documented (Hinderer C. et al, 2018).

6) Most diseases are also associated with multi-organ defects and AAV may not be applied to various organs in the same body. One application at one site will raise antibodies and thus may block transduction at other locations in the body when injected in a subsequent treatment or dose.

Due at least in part to the deficiencies of AAV discussed above, there is a dire need for alternatives to AAV. In at least certain embodiments, non-viral vectors disclosed herein overcome one or more of the deficiencies of AAV discussed above.

Moreover, prior non-viral vectors are also associated with several barriers to therapeutic efficacy including: i) low transfection/transduction efficiency (Guerra-Crespo M et al, 2003) ii) low particle stability in blood, body fluids and other tissues (Barua and Mitragotri, 2014); iii) low cell entry via receptor-mediated endocytosis or cell fusion; iv) low stability in, and low escape from, endosomal and lysosomal compartments; v) low diffusion rate in the cytoplasm; vi) low nuclear pore transit; and vii) low release of DNA to permit biological function in the nucleus (Zabner J. et al, 1995). Several publications have documented inability or low efficiency of prior non-viral vectors to transfect post-mitotic cells (Wilke M. et al, 1996). Certain prior non-viral vectors lack longevity of expression and/or produce low amount of proteins that are not therapeutic enough and cannot be targeted to specific cell types in an efficient manner.

Thus, despite state-of-the-art research in the field of non-viral vectors, many prior non-viral vectors are not optimal for clinical use. Certain characteristics of at least certain embodiments discussed herein that contribute to, among other things, clinical utility, can include, without limitation:

Size and molecular weight: Many prior non-viral vectors that carry DNA molecule have a size of 10-200 nm in diameter (Konstan M. W. et. al, 2004). Their molecular weights can be greater than 300 kDa or greater than 500 kDa. The present disclosure provides, among other things, non-viral proteinaceous vehicles, and/or loaded mini-nucleosomes, that are <20 nm in diameter and have a molecular weight of <500 kDa. In particular embodiments, a non-viral proteinaceous vehicles, and/or loaded mini-nucleosomes, disclosed herein can pass into the nucleus more efficiently, perhaps, by passive diffusion, at least in part because a typical nuclear pore is only 20 nm in diameter, such that <20 nm size may allow passage.

Stability in body fluids: Many prior non-viral vectors are degraded in body fluids like blood or CSF before they can be delivered to target cells (Barua and Mitragotri, 2014). The present disclosure, provides, among other things, non-viral proteinaceous vehicles, and/or loaded mini-nucleosomes, that are physiologically stable and/or have properties that allow them to be stable in blood and/or other body fluids until and after entry into a target cell. At least one goal for these particles to safely reach the nucleus of desired cells.

Release of particles in nucleus: Many prior non-viral vectors have a very short life time because most release associated nucleic acids before entering target cells, and the remainder release associated nucleic acids in the cytoplasm, where delivered DNA encounters nucleases that destroys DNA (Zabner, J. et al, 1995). Certain prior vectors that make it into the cell nucleus and provide expression levels are very low, if they express at all. The present disclosure also recognizes, among other things, that it can be beneficial to release associated nucleic acids at a slow rate, instead of all at once, which may allow for longevity of expression.

Cell type specificity: Prior non-viral vectors are not targeted to specific cell types are associated with reduced levels of transduction and thus, reduced expression. The present disclosure provides, among other things, non-viral vectors optimized for cell-type specificity Certain means of engineering cell-type specificity are described, e.g., in Templeton and Senzer, 2011.

Taken together, there is a tremendous need for nucleic acid delivery technologies that provide effective levels of expression for a desired duration, are non-immunogenic and non-toxic, and have less limited payload capacity. Moreover, the need for millions of patients of Huntington, Stargardt, Duchenne muscular dystrophy, Cystic Fibrosis, and other conditions treatable by gene therapy clearly presents a need for technology that can help treat these patients.

The present disclosure provides safe and efficacious non-viral proteinaceous vehicles ("mini-nucleosome core proteins"), and loaded mini-nucleosomes, for delivery of nucleic acids. The present disclosure further recognizes that in at least some instances modified mini-nucleosome core proteins of the present disclosure can have advantageous properties including, without limitation, increased bioavailability; increased half-life; increased stability; decreased degradation; increased binding affinity, e.g., for target cells; increased uptake, e.g., by target cells; improved blood-brain barrier penetration; reduced accumulation, e.g., in target cells or tissues; reduced aggregation; reduced precipitation; reduced thermal denaturation; and/or reduced kinetic denaturation, e.g., as set forth herein.

In various embodiments, a mini-nucleosome core protein is associated with one or more nucleic acids. As disclosed herein a mini-nucleosome core protein associated with one or more nucleic acids can be referred to as a "loaded mini-nucleosome."

In various embodiments, a mini-nucleosome core protein includes a nucleic acid release domain that targets a loaded mini-nucleosome to one or more specific cell types for delivery and/or targeted expression of a nucleic acid, such as a gene, in or to one or more specific cell types.

In various embodiments, a mini-nucleosome core protein composition (e.g., a composition including one or more loaded mini-nucleosomes) can be titered and/or administered either once or repeatedly based on need. Furthermore, in various embodiments, a mini-nucleosome core protein or mini-nucleosome composition (e.g., a composition including one or more loaded mini-nucleosomes) is non-immunogenic and non-toxic.

Mini-nucleosome core proteins disclosed herein can, in certain embodiments, utilize principles applicable to macromolecule uptake, viral entry into cells, nucleosome formation in eukaryotic cells, cleavage of certain proteins at certain location in the cells, etc.

Various embodiments of the compositions and methods provided herein include domains that facilitate one or more of enhanced stability, targeting to specific cell types, and enhanced longevity of expression by slow nucleic acid release.

In various embodiments, a mini-nucleosome core protein and/or a mini-nucleosome is stable in body fluids and/or include domains that allow and/or target release in or to the nucleus. In at least a first aspect, the present disclosure provides an engineered polypeptide including a nucleic acid binding domain and a nucleic acid release domain, where one or more amino acids of the engineered polypeptide is a modified amino acid, optionally where the modification includes at least one of: (i) phosphorylation; (ii) sulfation; (iii) glycosylation; (iv) prenylation; (v) methylation; (vi) sialylation; (vii) lipidation and/or lipoylation; (viii) acetylation; (ix) hydroxylation; (x) palmitoylation; (xi) mannosylation; (xii) myristoylation; (xiii) fucosylation; (xiv) pegylation; and/or (xv) any combination thereof. In certain embodiments, the engineered polypeptide includes a targeting domain.

In at least a further aspect, the present disclosure provides an engineered polypeptide including a nucleic acid binding domain and a targeting domain, where one or more amino acids of the engineered polypeptide is a modified amino acid, optionally where the modification includes at least one of: (i) phosphorylation; (ii) sulfation; (iii) glycosylation; (iv) prenylation; (v) methylation; (vi) sialylation; (vii) lipidation and/or lipoylation; (viii) acetylation;

(ix) hydroxylation; (x) palmitoylation; (xi) mannosylation; (xii) myristoylation; (xiii) fucosylation; (xiv) pegylation; and/or (xv) any combination thereof; where engineered polypeptide optionally further includes a nucleic acid release domain.

In at least certain embodiments of various aspects of the present disclosure, each of two or more amino acids of an engineered polypeptide is a modified amino acid. In some embodiments, at least one of the modified amino acids includes a modification chain including two or more modifications selected from: (i) phosphorylation; (ii) sulfation; (iii) glycosylation; (iv) prenylation; (v) methylation; (vi) sialylation; (vii) lipidation and/or lipoylation; (viii) acetylation; (ix) hydroxylation; (x) palmitoylation; (xi) mannosylation; (xii) myristoylation; (xiii) fucosylation; (xiv) pegylation; and (xv) any combination thereof. In some embodiments, the modification increases the stability, half-life, and/or bioavailability of the engineered polypeptide. In some embodiments, the modification increases the affinity and/or avidity of the engineered polypeptide with a binding partner, optionally where the binding partner is a receptor, cell, or cell membrane. In some embodiments, the modification increases the affinity or avidity of the engineered polypeptide with a nucleic acid. In some embodiments, the modification decreases precipitation and/or aggregation of the engineered polypeptide.

In at least certain embodiments of various aspects of the present disclosure, a nucleic acid binding domain is derived from a histone polypeptide sequence. In some embodiments, the nucleic acid binding domain is or includes the amino acid sequence KRHRK. In some embodiments, the nucleic acid binding domain is or includes an amino acid sequence that includes KRHRK, RRRRR, RRLARR, KKAKAAAK-PKK, KKDGKKRKR, KKKLK, KKRIRK, RKKSK, KKPKK, or a combination thereof. In some embodiments, the nucleic acid binding domain is a modified nucleic acid binding domain in that the nucleic acid binding domain includes one or more modified amino acids.

In at least certain embodiments of various aspects of the present disclosure, a targeting domain is a targeting domain having the sequence of any one of SEQ ID NOs: 397-422, where the targeting domain is phosphorylated. In at least certain embodiments of various aspects of the present disclosure, a targeting domain is a targeting domain having the sequence of any one of SEQ ID NOs: 423-428, where the targeting domain is sulfated. In at least certain embodiments of various aspects of the present disclosure, a targeting domain is a targeting domain having the sequence of any one of SEQ ID NOs: 429-434, where the targeting domain is glycosylated.

In at least certain embodiments of various aspects of the present disclosure, a targeting domain is a targeting domain having the sequence of any one of SEQ ID NOs: 435-440, where the targeting domain is prenylated. In at least certain embodiments of various aspects of the present disclosure, a targeting domain is a targeting domain having the sequence of any one of SEQ ID NOs: 441-446, where the targeting domain is methylated. In at least certain embodiments of various aspects of the present disclosure, a targeting domain is a targeting domain having the sequence of any one of SEQ ID NOs: 447-459, where the targeting domain is sialylated. In at least certain embodiments of various aspects of the present disclosure, a targeting domain is a cell attachment targeting domain, a beta galactose binding domain, a fucose binding domain, a heparin binding domain, a sialic acid binding domain, a glycoprotein binding domain, a carbohydrate binding domain, a lysophosphatidic acid binding domain, a cAMP binding domain, a hyaluronan binding domain, a chondroitin sulfate binding domain, an integrin binding domain, a nucleolin binding domain, a collagen binding domain, a clathrin binding domain, a Fc receptor binding domain, an actin binding domain, an endocytosis motif, a nuclear localization signal, or a combination thereof.

In at least certain embodiments of various aspects of the present disclosure, a targeting domain is a cell attachment targeting domain. In some embodiments, the cell attachment targeting domain is or includes an amino acid sequence that includes WGREERQ, NTQIH, WNNKTPH, TPH, VNRWS, XBBBXXBX, ARKKAAKA, QRR, SRR, WEPSRPFPVD, HRRTRKAPKRIRLPHIR, KRTGQYKLGSKTGPGQK, KKTK, KLRSQLVKK, RRRCGQKKK, BX(7)B, RIQNLLKITNLRIKFVK, KKEKDIMKKTI, KGE, RGD, RGDS, TTVVNPKYEGK, ERMSQIKRLLS, WRHRARS, GFOGER, LFDLM, WGREERQ, QSTEKRG, LPNTG, or a combination thereof.

In at least certain embodiments of various aspects of the present disclosure, a targeting domain is an internalization domain. In some embodiments, the internalization domain is or includes an amino acid sequence that includes FXDXF, PPSY, FEDNFVP, YIRV, YADW, YTQV, KKRPKP, SSDDE, RRASS, (YXXL)2, LPLTG, LAFTG, or a combination thereof.

In at least certain embodiments of various aspects of the present disclosure, a targeting domain is a cell-type specific targeting domain. In some embodiments, the cell-type specific targeting domain is or includes an amino acid sequence that includes ASSLNIA, KKEEEKKEEEKKEEE, LIFH-KEQ, KFNKPFVFLI, QPEHSST, EYHHYNK, NGR, GEKGEP, KTKKK, KALKKK, KGKKK, CSVTCG, LRE, YKYNLNGRES, YRSL, KGGK7, KKKQYTSIHHG, KDEL, LADQDYTKTA, or a combination thereof.

In at least certain embodiments of various aspects of the present disclosure, a targeting domain is a modified targeting domain in that the targeting domain includes one or more modified amino acids. In some embodiments, the nucleic acid release domain is or includes an amino acid sequence that includes GRKKRRQRRRPQ, KRH, KSVKKRSV-SEIQ, NRRKKRAL, KFERQ, VRGP, NKDS, NRDN, ANNR, or a combination thereof.

In at least certain embodiments of various aspects of the present disclosure, a the nucleic acid release domain is a modified nucleic acid release domain in that the nucleic acid release domain includes one or more modified amino acids.

In at least certain embodiments of various aspects of the present disclosure, an engineered polypeptide further includes a poly-arginine domain. In some embodiments, the poly-arginine domain is a modified poly-arginine domain in that the poly-arginine domain includes one or more modified amino acids.

In at least certain embodiments of various aspects of the present disclosure, an engineered polypeptide further includes a nuclear internalization signal or a nuclear import machinery binding domain. In some embodiments, the nuclear internalization signal or nuclear import machinery binding domain is or includes an amino acid sequence that includes KKKYKLK, KKRKLE, TRSK, HRKRKR, NKRKRK, AEKSKKK, RKSK, KRVK, KRK, LQQTPLHLAVI, RRPR, PRPR, RPPP, RKKRKGK, PAAKRVKLD, KLKIKRPVK, PKKKRKV, QRKROK, DSPE, FQVT, QSTEKRG, RQGLID, Cyclic RKKH, or a combination thereof. In some embodiments, the nuclear internalization signal or a nuclear import machinery binding domain is a modified nuclear internalization signal or a nuclear import machinery binding domain in that the nuclear internalization signal or a nuclear import machinery binding domain includes one or more modified amino acids.

In at least certain embodiments of various aspects of the present disclosure, an engineered polypeptide further includes a stability domain. In some embodiments, the stability domain is or includes an amino acid sequence that includes YTRF, GDAY, LLEE, RKKRRQRRR, YKSL, YENF, FQDL, YIGSR, IKVAV, or a combination thereof. In some embodiments, the stability domain is a modified stability domain in that the stability domain includes one or more modified amino acids.

In at least certain embodiments of various aspects of the present disclosure, an engineered polypeptide further includes an oligomerization domain. In some embodiments, the oligomerization domain is selected from the oligomerization domains of Table 11, optionally where the oligomerization domain is positioned at the C-terminus of the engineered polypeptide. In some embodiments, the oligomerization domain is a modified oligomerization domain in that the oligomerization domain includes one or more modified amino acids.

In at least certain embodiments of various aspects of the present disclosure, an engineered polypeptide further includes a linker. In some embodiments, the linker is a linker according to any one of SEQ ID NOs: 154-250. In some embodiments, the linker is a modified linker in that the linker includes one or more modified amino acids.

In some embodiments, one or more amino acids of an engineered polypeptide is a phosphorylated amino acid. In some embodiments, the phosphorylated amino acid is a serine, threonine, or tyrosine amino acid. In some embodiments, the phosphorylated amino acid is present in a linker domain or targeting domain.

In some embodiments, one or more amino acids of an engineered polypeptide is a sulfated amino acid. In some embodiments, the sulfated amino acid is a serine, threonine, or tyrosine amino acid. In some embodiments, the sulfated amino acid is present in a linker domain or targeting domain.

In some embodiments, one or more amino acids of an engineered polypeptide is an acetylated amino acid. In some embodiments, the acetylated amino acid is a lysine amino acid. In some embodiments, the acetylated amino acid is present in a linker domain or targeting domain.

In some embodiments, one or more amino acids of an engineered polypeptide is a mannosylated amino acid. In some embodiments, the mannosylated amino acid is a serine amino acid. In some embodiments, the mannosylated amino acid is present in a linker domain or targeting domain.

In at least one further aspect, the present disclosure provides a polynucleotide that encodes the amino acid sequence of an engineered polypeptide of the present disclosure, such as a DNA or RNA polynucleotide. In at least one further aspect, the present disclosure provides a vector including polynucleotide of the present disclosure. In at least one further aspect, the present disclosure provides a cell including an engineered polypeptide of the present disclosure or a vector of the present disclosure.

In at least one further aspect, the present disclosure provides method of making an engineered polypeptide of the present disclosure, the method including expressing a polynucleotide of the present disclosure in a cell. In some embodiments, the method further includes isolating the engineered polypeptide from the cell.

In at least one further aspect, the present disclosure provides a composition including: (i) at least one polynucleotide, and (ii) at least one engineered polypeptide of the present disclosure. In some embodiments, the at least one polynucleotide is or includes DNA or RNA. In some embodiments, the at least one polynucleotide includes a nucleotide sequence encoding a polypeptide. In some embodiments, the at least one polynucleotide is or includes mRNA. In some embodiments, the at least one polynucleotide includes an inhibitory RNA. In some embodiments, the inhibitory RNA is a gRNA, siRNA, miRNA, or shRNA. In some embodiment, the composition includes at least two engineered polypeptides of the present disclosure, where a first engineered polypeptide of present disclosure is able to oligomerize with a second engineered polypeptide of the present disclosure. In some embodiments, the ratio of polynucleotides to engineered polypeptides is between 1:1 and 1:2,000. In some embodiments, the ratio of polynucleotides to engineered polypeptides is between 1:1 and 1:1,000, between 1:1 and 1:500, between 1:1 and 1:200, between 1:1 and 1:100, between 1:1 and 1:50, between 1:3 and 1:1,000, between 1:3 and 1:500, between 1:3 and 1:200, between 1:3 and 1:100, or between 1:3 and 1:50. In some embodiments, the ratio of polynucleotides to engineered polypeptides is between 1:200 and 1:2,000, between 1:200 and 1:1000, or between 1:200 and 1:500. In some embodiments, the composition includes a pharmaceutical carrier.

In at least one further aspect, the present disclosure provides a method that includes administering a composition of the present disclosure to a system, where the system is a cell, tissue, or subject. In some embodiments, after administration, the modification increases the stability, half-life, and/or bioavailability of the composition in the system. In some embodiments, after administration, the modification increases the affinity or avidity of the composition with a binding partner in the system, optionally where the binding partner is a receptor, cell, or cell membrane. In some embodiments, after administration, the modification decreases precipitation and/or aggregation of the composition in the system. In some embodiments, after administration, the modification increases the rate at which the composition enters one or more cells in the system. In some embodiments, after administration, the modification increases delivery of the composition to one or more cells in the system. In some embodiments, after administration, the modification increases delivery of the nucleic acid of the composition to one or more cells in the system. In some embodiments, the system is a mammalian subject and, after administration, the modification decreases accumulation of the composition in liver. In some embodiments, the system is a mammalian subject and, after administration, the modification increases the amount of composition that crosses the blood-brain barrier.

In some embodiments, the present disclosure provides a method that includes administering a composition of the present disclosure including at least one polynucleotide and at least one engineered polypeptide to a cell, tissue, or subject, wherein one or more amino acids of the engineered polypeptide is a phosphorylated amino acid. In some embodiments, the phosphorylated amino acid is a serine, threonine, or tyrosine amino acid. In some embodiments, the phosphorylated amino acid is present in a linker domain or targeting domain. In some embodiments, the composition is delivered to cells of the central nervous system (CNS).

In some embodiments, the composition is delivered to CNS neurons. In some embodiments, the composition is delivered to CNS astrocytes, microglia, oligodendrocytes, or glia. In some embodiments, the composition is delivered to spinal cord cells, optionally wherein the spina cord cells are spinal cord neurons or spinal cord glial cells. In some embodiments, the polynucleotide encodes an expression product that is expressed in cells to which the composition is delivered. In some embodiments, the subject is a mammalian subject and the administration is intrathecal, intracranial, or intra-cisterna *magna*.

In some embodiments, the present disclosure provides a method that includes administering a composition of the present disclosure including at least one polynucleotide and at least one engineered polypeptide to a cell, tissue, or subject, wherein one or more amino acids of the engineered polypeptide is a sulfated amino acid. In some embodiments, the sulfated amino acid is a serine, threonine, or tyrosine amino acid. In some embodiments, the sulfated amino acid is present in a linker domain or targeting domain. In some embodiments, the composition is delivered to cells of the central nervous system (CNS). In some embodiments, the composition is delivered to CNS neurons. In some embodiments, the composition is delivered to CNS astrocytes, microglia, oligodendrocytes, or glia. In some embodiments, the composition is delivered to spinal cord cells, optionally wherein the spina cord cells are spinal cord neurons or spinal cord glial cells. In some embodiments, the polynucleotide encodes an expression product that is expressed in cells to which the composition is delivered. In some embodiments, the subject is a mammalian subject and the administration is intrathecal, intracranial, or intra-cisterna *magna*.

In some embodiments, the present disclosure provides a method that includes administering a composition of the present disclosure including at least one polynucleotide and at least one engineered polypeptide o a cell, tissue, or subject, wherein one or more amino acids of the engineered polypeptide is an acetylated amino acid. In some embodiments, the acetylated amino acid is a lysine amino acid. In some embodiments, the acetylated amino acid is present in a linker domain or targeting domain. In some embodiments, the composition is delivered to CNS neurons. In some embodiments, the composition is delivered to retinal cells. In some embodiments, the composition is delivered to retinal neurons, optionally wherein the retinal neurons include one or more of photoreceptors, bipolar cells, retinal ganglion cells, horizontal cells, and amacrine cells. In some embodiments, the composition is delivered to photoreceptor cells, optionally wherein the photoreceptor cells include one or both of rods and cones. In some embodiments, the polynucleotide encodes an expression product that is expressed in cells to which the composition is delivered. In some embodiments, the subject is a mammalian subject and the administration is intravitreal, suprachoroidal, or subretinal.

In some embodiments, the present disclosure provides a method that includes administering a composition of the present disclosure including at least one polynucleotide and at least one engineered polypeptide to a cell, tissue, or subject, wherein one or more amino acids of the engineered polypeptide is a mannosylated amino acid. In some embodiments, the mannosylated amino acid is a serine amino acid. In some embodiments, the mannosylated amino acid is present in a linker domain or targeting domain. In some embodiments, the composition is delivered to CNS neurons. In some embodiments, the composition is delivered to retinal cells. In some embodiments, the composition is delivered to retinal neurons, optionally wherein the retinal neurons include one or more of photoreceptors, bipolar cells, retinal ganglion cells, horizontal cells, and amacrine cells. In some embodiments, the composition is delivered to photoreceptor cells include one or both of rods and cones. In some embodiments, the polynucleotide encodes an expression product that is expressed in cells to which the composition is delivered. In some embodiments, the subject is a mammalian subject and the administration is intravitreal, suprachoroidal, or subretinal.

In at least one further aspect, the present disclosure provides a method of condensing a polynucleotide, including contacting the polynucleotide with a polypeptide of the present disclosure.

In at least one further aspect, the present disclosure provides a method of neutralizing the charge of a polynucleotide, including contacting the polynucleotide with a polypeptide of the present disclosure.

In at least one further aspect, the present disclosure provides a composition including an engineered polypeptide and at least one nucleic acid, the engineered polypeptide including a nucleic acid binding domain, a targeting domain, and a nucleic acid release domain, where one or more amino acids of the engineered polypeptide is a modified amino acid, optionally where the modification includes at least one of: (i) phosphorylation; (ii) sulfation; (iii) glycosylation; (iv) prenylation; (v) methylation; (vi) sialylation; (vii) lipidation and/or lipoylation; (viii) acetylation; (ix) hydroxylation; (x) palmitoylation; (xi) mannosylation; (xii) myristoylation; (xiii) fucosylation; (xiv) pegylation; and/or (xv) any combination thereof; optionally where the composition is for use in delivering a nucleic acid to a subject or system.

In at least one further aspect, the present disclosure provides a composition including an engineered polypeptide and at least one nucleic acid, the engineered polypeptide including a nucleic acid binding domain and a targeting domain, where one or more amino acids of the engineered polypeptide is a modified amino acid, optionally where the modification includes at least one of: (i) phosphorylation; (ii) sulfation; (iii) glycosylation; (iv) prenylation; (v) methylation; (vi) sialylation; (vii) lipidation and/or lipoylation; (viii) acetylation; (ix) hydroxylation; (x) palmitoylation; (xi) mannosylation; (xii) myristoylation; (xiii) fucosylation; (xiv) pegylation; and/or (xv) any combination thereof; optionally where the composition is for use in delivering a nucleic acid to a subject or system. In some embodiments, the engineered polypeptide comprises a targeting domain.

In at least one aspect, the present disclosure provides an engineered polypeptide that includes a nucleic acid binding domain and a targeting domain, which engineered polypeptide can be a mini-nucleosome core protein. A loaded mini-nucleosome can be or provide a non-viral vector that includes an engineered polypeptide (e.g., a mini-nucleosome core protein) as described herein and at least one nucleic acid molecule as provided herein or otherwise known in the art.

In some embodiments, an engineered polypeptide (e.g., a mini-nucleosome core protein) that is or includes a nucleic acid binding domain is derived from a histone polypeptide sequence and/or a nucleic acid binding domain that is or includes the amino acid sequence KRHRK. In certain embodiments, an engineered polypeptide of the present disclosure includes a nucleic acid binding domain that is or includes an amino acid sequence that includes KRHRK, RRRRR, RRLARR, KKAKAAAKPKK, KKDGKKRKR, KKKLK, KKRIRK, RKKSK, KKPKK, or a combination thereof, but not limited to it.

In some embodiments, an engineered polypeptide of the present disclosure includes a nucleic acid binding domain derived from any histone protein sequence or those described in Table 3 or a combination of the sequences described herein but not limited to it. These nucleic acid binding domains may be derived from various human proteins or other organisms. One skilled in the art may contemplate modifying or engineering the "NABD" with changes to the amino acid sequence. One skilled in the art may also contemplate placing the "NABD" in reverse sequence or by switching amino acid positions within the domain or adding posttranslational modifications to amino acids.

In some embodiments, an engineered polypeptide of the present disclosure includes a targeting domain that is a cell attachment targeting domain, a beta galactose binding domain, a fucose binding domain, a heparin binding domain, a sialic acid binding domain, a glycoprotein binding domain, a carbohydrate binding domain, a lysophosphatidic acid binding domain, a cAMP binding domain, a hyaluronan binding domain, a chondroitin sulfate binding domain, an integrin binding domain, a nucleolin binding domain, a collagen binding domain, a clathrin binding domain, a Fc receptor binding domain, an actin binding domain, an endocytosis motif, a nuclear localization signal, or a combination thereof but not limited to it. Some examples of those domain are described in Table 5 but is not limited to these. These domains may be derived from any human proteins or other organisms. One skilled in the art may contemplate modifying or engineering the targeting domain with changes to the amino acid sequence. One skilled in the art may also contemplate placing the targeting domain in reverse sequence or by switching amino acid positions within the domain or adding posttranslational modifications to amino acids.

In some embodiments, an engineered polypeptide of the present disclosure includes a targeting domain that is an internalization domain wherein the internalization domain is or includes an amino acid sequence that includes FXDXF, PPSY, FEDNFVP, YIRV, YADW, YTQV, KKRPKP, SSDDE, RRASS, (YXXL)2, LPLTG, LAFTG, or a combination thereof but not limited to it. These domains may be derived from human proteins or other organisms. One skilled in the art may contemplate modifying or engineering the internalization domain with changes to the amino acid sequence. One skilled in the art may also contemplate placing the internalization domain in reverse sequence or by switching amino acid positions within the domain or adding posttranslational modifications to amino acids.

Those of skill in the art will appreciate that, as used in protein sequences throughout the present specification, an "X" can refer to any amino acid unless otherwise specified. Thus, unless otherwise specified, an "X" is a placeholder for a single amino acid, which position could be filled by any single amino acid known to those of skill in the art.

In some embodiments, an engineered polypeptide of the present disclosure includes a cell attachment targeting domain that is or includes an amino acid sequence selected from WGREERQ, NTQIH, WNNKTPH, TPH, VNRWS, XBBBXXBX, ARKKAAKA, QRR, SRR, WEPSRPFPVD, HRRTRKAPKRIRLPHIR, KRTGQYKLGSKTGPGQK, KKTK, KLRSQLVKK, RRRCGQKKK, BX(7)B, RIQNLLKITNLRIKFVK, KKEKDIMKKTI, KGE, RGD, RGDS, TTVVNPKYEGK, ERMSQIKRLLS, WRHRARS, GFOGER, LFDLM, WGREERQ, QSTEKRG, LPNTG, and a combination thereof, where X can be any amino acid, but not limited to it.

In some embodiments, an engineered polypeptide of the present disclosure includes a targeting domain that is an internalization domain cell-type specific targeting domain wherein the cell-type specific targeting domain is or includes an amino acid sequence that includes ASSLNIA, KKEEEK-KEEEKKEEE, LIFHKEQ, KENKPFVFLI, QPEHSST, EYHHYNK, NGR, GEKGEP, KTKKK, KALKKK, KGKKK, CSVTCG, LRE, YKYNLNGRES, YRSL, KGGK7, KKKQYTSIHHG, KDEL, LADQDYTKTA, or a combination thereof but not limited to it. These domains may be derived from human proteins or other organisms. One skilled in the art may contemplate modifying or engineering the targeting domain with changes to the amino acid sequence. One skilled in the art may also contemplate placing the targeting domain in reverse sequence or by switching amino acid positions within the domain or adding posttranslational modifications to amino acids.

In some embodiments, an engineered polypeptide of the present disclosure includes a poly-arginine domain with varying length or multiple poly-arginine domains throughout the polypeptide sequence.

In some embodiments, an engineered polypeptide of the present disclosure includes a nuclear internalization signal or a nuclear import machinery binding domain. The engineered polypeptide, the nuclear internalization signal or a nuclear import machinery binding domain can be or include an amino acid sequence that includes KKKYKLK, KKRKLE, TRSK, HRKRKR, NKRKRK, AEKSKKK, RKSK, KRVK, KRK, LQQTPLHLAVI, RRPR, PRPR, RPPP, RKKRKGK, PAAKRVKLD, KLKIKRPVK, PKKKRKV, QRKROK, DSPE, FQVT, QSTEKRG, RQGLID, Cyclic RKKH, or a combination thereof but not limited to it. These domains may be derived from human proteins or other organisms. One skilled in the art may contemplate modifying or engineering the nuclear internalization signal with changes to the amino acid sequence. One skilled in the art may also contemplate placing the nuclear internalization signal in reverse sequence or by switching amino acid positions within the domain or adding posttranslational modifications to amino acids.

In some embodiments, an engineered polypeptide of the present disclosure includes a nucleic acid release domain. The nucleic acid release domain is or includes an amino acid sequence that includes GRKKRRQRRRPQ, KRH, KSVKKRSVSEIQ, NRRKKRAL, KFERQ, VRGP, NKDS, NRDN, ANNR, or a combination thereof but not limited to it. These domains may be derived from various proteins that are substrates of peptidases, enzymes or other proteins found in humans or other organisms. Some nucleic acid release domains may also be derived from autolysis sites of various proteins. One skilled in the art may contemplate modifying or engineering the nucleic acid release domain with changes to the amino acid sequence. One skilled in the art may also contemplate placing the nucleic acid release signal in reverse sequence or by switching amino acid positions within the domain or adding posttranslational modifications to amino acids.

In some embodiments, an engineered polypeptide of the present disclosure further including a stability domain. In some embodiments, an engineered polypeptide of the present disclosure can include a stability domain that is or includes an amino acid sequence that includes YTRF, GDAY, LLEE, RKKRRQRRR, YKSL, YENF, FQDL, YIGSR, IKVAV, or a combination thereof but not limited to it. These domains may be derived from human proteins or other organisms. One skilled in the art may contemplate modifying or engineering the stability domain with changes to the amino acid sequence. One skilled in the art may also contemplate placing the stability domain in reverse sequence or by switching amino acid positions within the domain or adding posttranslational modifications to amino acids.

In some embodiments, an engineered polypeptide of the present disclosure includes an oligomerization domain. In some embodiments, an engineered polypeptide of the present disclosure can include an oligomerization domain is selected from the oligomerization domains of Table 11 but not limited to it. The position of oligomerization domain is positioned at the C-terminus of an engineered polypeptide of the present disclosure or at any other locations. These domains may be derived from human proteins or other organisms. One skilled in the art may contemplate modifying or engineering the oligomerization domain with changes to the amino acid sequence. One skilled in the art may also contemplate placing the oligomerization domain in reverse sequence or by switching amino acid positions within the domain or adding posttranslational modifications to amino acids.

In some embodiments, an engineered polypeptide of the present disclosure includes a Linker. In some embodiments, an engineered polypeptide of the present disclosure can include a Linker selected, without limitation, from the exemplary domains of Table 12. The position of linker in an engineered polypeptide of the present disclosure may be in between other domains and any other locations. These Linkers may be derived from human proteins or other organisms. One skilled in the art may contemplate modifying or engineering the linker domain with changes to the amino acid sequence. One skilled in the art may also contemplate placing the linker domain in reverse sequence or by switching amino acid positions within the domain or adding posttranslational modifications to amino acids.

In various embodiments, two or more engineered polypeptides of the present disclosure can oligomerize.

In some embodiments, the present disclosure includes a composition that includes an engineered polypeptide of the present disclosure (e.g., a mini-nucleosome core protein) together with at least one polynucleotide. In some embodiments, the polypeptide is a DNA or RNA polynucleotide In some embodiments, the polypeptide is a or includes an inhibitory RNA, wherein the inhibitory RNA is a gRNA, siRNA, miRNA, or shRNA. In various embodiments, the polypeptide(s) and polynucleotide(s) are not associated but are together in a composition, e.g., a kit or solution. In various embodiments, the polypeptide(s) and polynucleotide (s) are associated, e.g., condensed, e.g., to form a loaded mini-nucleosome. In certain embodiments, the ratio of polynucleotides to engineered polypeptides is between 1:1 and 1:2,000 or between 1:3 and 1:2,000. In certain embodiments, the ratio of polynucleotides to engineered polypeptides is between 1:1 and 1:2,000. In certain embodiments, the ratio of polynucleotides to engineered polypeptides is between 1:1 and 1:1,000, between 1:1 and 1:500, between 1:1 and 1:200, between 1:1 and 1:100, between 1:1 and 1:50. In certain embodiments, the ratio of polynucleotides to engineered polypeptides is between 1:3 and 1:1,000, between 1:3 and 1:500, between 1:3 and 1:200, between 1:3 and 1:100, or between 1:3 and 1:50. In certain embodiments, the ratio of polynucleotides to engineered polypeptides is between 1:200 and 1:2,000, between 1:200 and 1:1000, or between 1:200 and 1:500. In certain embodiments, the ratio of polynucleotides to engineered polypeptides is between 1:1 and 1:50, 1:1 and 1:40, 1:1 and 1:30, 1:1 and 1:20, 1:1 and 1:10, 1:1 and 1:5, 1:1 and 1:4, 1:1 and 1:3, or 1:1 and 1:2. One skilled in the art may also contemplate chemical modifications to the DNA or RNA molecules.

In some embodiments, a composition provided herein that includes a mini-nucleosome core protein and/or a loaded mini-nucleosome) can be administered to or contacted with a cell, tissue, or subject. The conditions of application may be in in vitro, ex vivo or in vivo Such engineered cell may include a pharmaceutical carrier, e.g, that may be used in, or is compatible with, delivery of therapeutic materials (e.g., a composition provided herein that includes a mini-nucleosome core protein and/or a loaded mini-nucleosome) to various parts of human body for example brain, retina, gut, pancreas, lung etc. without any limitations.

In some embodiments, a method of condensing a polynucleotide may include contacting a polynucleotide with a mini-nucleosome core protein as described herein The method may include process of neutralizing the charge of a polynucleotide or condensation of the polynucleotide into nano-sized particles, including contacting the polynucleotide with a mini-nucleosome core protein described herein.

In some embodiments, the mini-nucleosome core protein may be a branched peptide or a cyclic peptide but not limited to these characteristics. One skilled in the art may contemplate changing the characteristics of mini-nucleosome core protein to obtain enhanced tropism to various cell types.

The present disclosure further provides a polynucleotide encoding an engineered polypeptide (e.g., a mini-nucleosome core protein) as provided herein. The polynucleotide encoding the engineered polypeptide can be a DNA polynucleotide or an RNA polynucleotide. In some instances, the present disclosure provides a vector including a polynucleotide that encodes an engineered polypeptide of the present disclosure. In some embodiments, the present disclosure provides a cell that includes a polynucleotide encoding an engineered polypeptide (e.g., a mini-nucleosome core protein) as provided herein, a vector including such polynucleotide, or includes the sequence of such polynucleotide. In certain embodiments, an engineered polypeptide of the present disclosure can be isolated from one or more such cells.

In various embodiments, one or more amino acids of an engineered polypeptide of the present disclosure has at least 80% sequence identity with an amino acid sequence selected from SEQ ID NOs: 336-388 (e.g., at least 80%, 85%, 90%, 95%, 96%, 97%, 98%, 99%, or 100% sequence identity with an amino acid sequence selected from SEQ ID NOs: 336-388).

In various embodiments, one or more amino acids of an engineered polypeptide of the present disclosure (e.g., a mini-nucleosome core protein) is pegylated, acetylated, methylated, glycosylated, phosphorylated, sumoylated, amidated, lipidated, prenylated, lipoylated, alkylated, acylated, glycated, nitrosylated, sulfated, carbamylated, carbonylated, neddylated, biotinylated, or ribosylated.

Definitions

About: The term "about," when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referenced value.

Administration: As used herein, the term "administration" typically refers to administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or include, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Associated with: Two events or entities are "associated" with one another, as that term is used herein, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Agent: As used herein, the term "agent," may refer to a compound, molecule, or entity of any chemical class including, for example, a small molecule, polypeptide, nucleic acid, saccharide, lipid, metal, or a combination or complex thereof. In some embodiments, the term "agent" may refer to a compound, molecule, or entity that includes a polymer. In some embodiments, the term may refer to a compound or entity that includes one or more polymeric moieties. In some embodiments, the term "agent" may refer to a compound, molecule, or entity that is substantially free of a particular polymer or polymeric moiety. In some embodiments, the term may refer to a compound, molecule, or entity that lacks or is substantially free of any polymer or polymeric moiety.

Amino acid: In its broadest sense, as used herein, "amino acid" refers to any compound and/or substance that can be incorporated into a polypeptide chain, e.g., through formation of one or more peptide bonds. In some embodiments, an amino acid has the general structure $H_2N$—C(H)(R)—COOH. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy-and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Between: As used herein, the term "between" refers to content that falls between indicated upper and lower, or first and second, boundaries, inclusive of the boundaries.

Corresponding to: As used herein, the term "corresponding to" may be used to designate the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the 190th amino acid in a particular amino acid chain but rather corresponds to the residue found at 190 in the reference polypeptide; those of ordinary skill in the art readily appreciate how to identify "corresponding" amino acids. For example, those skilled in the art will be aware of various sequence alignment strategies, including software programs such as, for example, BLAST, CS-BLAST, CUDASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.). In some embodiments, a domain is or includes a characteristic portion or characteristic sequence element.

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. Those of skill in the art will appreciate that an "engineered" nucleic acid or amino acid sequence can be a recombinant nucleic acid or amino acid sequence. In some embodiments, an engineered polynucleotide includes a domain-encoding sequence regulatory sequence that is found in nature in operative association with a first sequence but not in operative association with a second sequence, is linked by the hand of man so that it is operatively associated with the second sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Gene: As used herein, the term "gene" refers to a DNA sequence that codes for a product (e.g., an RNA product and/or a polypeptide product). In some embodiments, a gene includes coding sequence (i.e., sequence that encodes a particular product); in some embodiments, a gene includes non-coding sequence. In some particular embodiments, a gene may include both coding (e.g., exonic) and non-coding (e.g., intronic) sequences. In some embodiments, a gene may include one or more regulatory elements that, for example, may control or impact one or more aspects of gene expression (e.g., a promoter). A gene can be endogenous or non-endogenous in a particular context, e.g., a cell. A gene can be a transgene.

Gene product or expression product: As used herein, the term "gene product" or "expression product" generally refers to an RNA transcribed from a gene (pre- and/or post-processing) or a polypeptide (pre- and/or post-modification) encoded by an RNA transcribed from a gene.

"Improve," "increase," "inhibit," or "reduce": As used herein, the terms "improve," "increase," "inhibit," "reduce," or grammatical equivalents thereof, indicate values that are relative to a baseline or other reference measurement. In some embodiments, an appropriate reference measurement may be or include a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or include a measurement in comparable system known or expected to respond in a particular way, in presence of the relevant agent or treatment.

Increase and decrease: As used herein, the terms "increase," "decrease," and grammatical equivalents thereof, indicate qualitative or quantitative difference from a reference.

Nucleic acid: As used herein, in its broadest sense, "nucleic acid" refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain including individual nucleic acid residues. In some embodiments, a "nucleic acid" is or includes RNA; in some embodiments, a "nucleic acid" is or includes DNA. In some embodiments, a nucleic acid is, includes, or consists of one or more natural nucleic acid residues. In some embodiments, a nucleic acid is, includes, or consists of one or more nucleic acid analogs. In some embodiments, a nucleic acid analog differs from a nucleic acid in that it does not utilize a phosphodiester backbone. For example, in some embodiments, a nucleic acid is, includes, or consists of one or more "peptide nucleic acids", which are known in the art and have peptide bonds instead of phosphodiester bonds in the backbone, are considered within the scope of the present disclosure. Alternatively or additionally, in some embodiments, a nucleic acid has one or more phosphorothioate and/or 5'-N-phosphoramidite linkages rather than phosphodiester bonds. In some embodiments, a nucleic acid is, includes, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, includes, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0 (6)-methylguanine, 2-thiocytidine, methylated bases, intercalated bases, and combinations thereof). In some embodiments, a nucleic acid includes one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments a nucleic acid has a nucleotide sequence including at least one element that encodes, or is the complement of a sequence that encodes, a polypeptide. In some embodiments, a nucleic acid has enzymatic activity.

Operably linked: As used herein, "operably linked" refers to a juxtaposition where the components described are in a relationship permitting them to function in their intended manner. For example, a control element "operably linked" to a functional element is associated in such a way that expression and/or activity of the functional element is achieved under conditions compatible with the control element. In some embodiments, "operably linked" control elements are contiguous (e.g., covalently linked) with the coding elements of interest; in some embodiments, control elements act in trans to or otherwise at a from the functional element of interest.

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Polypeptide: As used herein, "polypeptide" refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may include or consist of natural amino acids, non-natural amino acids, or both. In some embodiments, a polypeptide may include or consist of only natural amino acids or only non-natural amino acids. In some embodiments, a polypeptide may include D-amino acids, L-amino acids, or both. In some embodiments, a polypeptide may include only D-amino acids. In some embodiments, a polypeptide may include only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, phosphorylation, glycosylation, glycation, sulfation, mannosylation, nitrosylation, acylation, palmitoylation, prenylation, pegylation, etc., including combinations thereof. In some embodiments, a polypeptide may be cyclic, and/or may include a cyclic portion. In some embodiments, a polypeptide is not cyclic and/or does not include any cyclic portion. In some embodiments, a polypeptide is linear. In some embodiments, a polypeptide may be or include a stapled polypeptide. In some embodiments, the term "polypeptide" may be appended to a name of a reference polypeptide, activity, or structure; in such instances, it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence similarity (e.g., homology) or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence similarity (e.g., homology) or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or include a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may include or consist of a fragment of a parent polypeptide. In some embodiments, a useful polypeptide as may include or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Prevent or prevention: As used herein, "prevent" or "prevention," when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Promoter: As used herein, a "promoter" or "promoter sequence" can be a DNA regulatory region that directly or indirectly (e.g., through promoter-bound proteins or substances) participates in initiation and/or processivity of transcription of a coding sequence. A promoter may, under suitable conditions, initiate transcription of a coding sequence upon binding of one or more transcription factors and/or regulatory moieties with the promoter. A promoter that participates in initiation of transcription of a coding sequence can be "operably linked" to the coding sequence. In certain instances, a promoter can be or include a DNA regulatory region that extends from a transcription initiation site (at its 3' terminus) to an upstream (5' direction) position such that the sequence so designated includes one or both of a minimum number of bases or elements necessary to initiate a transcription event. A promoter may be, include, or be operably associated with or operably linked to, expression control sequences such as enhancer and repressor sequences. In some embodiments, a promoter may be inducible. In some embodiments, a promoter may be a constitutive promoter. In some embodiments, a conditional (e.g., inducible) promoter may be unidirectional or bi-directional. A promoter may be or include a sequence identical to a sequence known to occur in the genome of particular species. In some embodiments, a promoter can be or include a hybrid promoter, in which a sequence containing a transcriptional regulatory region can be obtained from one source and a sequence containing a transcription initiation region can be obtained from a second source. Systems for linking control elements to coding sequence within a transgene are well known in the art (general molecular biological and recombinant DNA techniques are described in Sambrook, Fritsch, and Maniatis, *Molecular Cloning: A Laboratory Manual*, Second Edition, Cold Spring Harbor Laboratory Press, Cold Spring Harbor, NY, 1989).

Recombinant: As used herein, "recombinant" is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc).

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantial sequence similarity: The phrase "substantial sequence similarity" is used herein to refer to a comparison between amino acid or nucleic acid sequences. As will be appreciated by those of ordinary skill in the art, two sequences are generally considered to be "substantially similar" if they contain a conservative amino acid substitution in corresponding positions. A conservative substitution is one in which an amino acid has been replaced by a non-identical residue having appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a conservative substitution. Typical amino acid categorizations are summarized in Tables 1 and 2 below:

TABLE 1

| | | | | | |
|---|---|---|---|---|---|
| Alanine | Ala | A | nonpolar | neutral | 1.8 |
| Arginine | Arg | R | polar | positive | -4.5 |
| Asparagine | Asn | N | polar | neutral | -3.5 |
| Aspartic acid | Asp | D | polar | negative | -3.5 |
| Cysteine | Cys | C | nonpolar | neutral | 2.5 |
| Glutamic acid | Glu | E | polar | negative | -3.5 |
| Glutamine | Gln | Q | polar | neutral | -3.5 |
| Glycine | Gly | G | nonpolar | neutral | -0.4 |
| Histidine | His | H | polar | positive | -3.2 |
| Isoleucine | Ile | I | nonpolar | neutral | 4.5 |
| Leucine | Leu | L | nonpolar | neutral | 3.8 |
| Lysine | Lys | K | polar | positive | -3.9 |
| Methionine | Met | M | nonpolar | neutral | 1.9 |
| Phenylalanine | Phe | F | nonpolar | neutral | 2.8 |
| Proline | Pro | P | nonpolar | neutral | -1.6 |
| Serine | Ser | S | polar | neutral | -0.8 |
| Threonine | Thr | T | polar | neutral | -0.7 |
| Tryptophan | Trp | W | nonpolar | neutral | -0.9 |
| Tyrosine | Tyr | Y | polar | neutral | -1.3 |
| Valine | Val | V | nonpolar | neutral | 4.2 |

TABLE 2

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215 (3): 403-410, 1990; Altschul, et al., Methods in Enzymology; Altschul, et al., "Gapped BLAST and PSI-BLAST: a new generation of protein database search programs," Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above typically provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues. As would be appreciated by one of ordinary skill in the art sequences with substantial sequence similarity may be homologs of one another.

Substantial sequence identity: As used herein, the phrase "substantial sequence identity" refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., Basic local alignment search tool, J. Mol. Biol., 215 (3): 403-410, 1990; Altschul et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al, (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutic regimen: A "therapeutic regimen," as that term is used herein, refers to a dosing regimen whose administration across a relevant population may be correlated with a desired or beneficial therapeutic outcome.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Variant: As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element included of a plurality of amino acids having designated positions relative to one another in linear or three-dimensional space and/or contributing to a particular structural motif and/or biological function; a nucleic acid may have a characteristic sequence element included of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence and/or one or more differences in chemical moieties (e.g., carbohydrates, lipids, phosphate groups) that are covalently components of the polypeptide or nucleic acid (e.g., that are attached to the polypeptide or nucleic acid backbone). In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid. In some embodiments, a variant polypeptide or nucleic acid lacks one or more of the biological activities of the reference polypeptide or nucleic acid. In some embodiments, a variant polypeptide or nucleic acid shows a reduced level of one or more biological activities as compared to the reference polypeptide or nucleic acid. In some embodiments, a polypeptide or nucleic acid of interest is considered to be a "variant" of a reference polypeptide or nucleic acid if it has an amino acid or nucleotide sequence that is identical to that of the reference but for a small number of sequence alterations at particular positions. Typically, fewer than about 20%, about 15%, about 10%, about 9%, about 8%, about 7%, about 6%, about 5%, about 4%, about 3%, or about 2% of the residues in a variant are substituted, inserted, or deleted, as compared to the reference. In some embodiments, a variant polypeptide or nucleic acid includes about 10, about 9, about 8, about 7, about 6, about 5, about 4, about 3, about 2, or about 1 substituted residues as compared to a reference. Often, a variant polypeptide or nucleic acid includes a very small number (e.g., fewer than about 5, about 4, about 3, about 2, or about 1) number of substituted, inserted, or deleted, functional residues (i.e., residues that participate in a particular biological activity) relative to the reference. In some embodiments, a variant polypeptide or nucleic acid includes not more than about 5, about 4, about 3, about 2, or about 1 addition or deletion, and, in some embodiments, includes no additions or deletions, as compared to the reference. In some embodiments, a variant polypeptide or nucleic acid includes fewer than about 25, about 20, about 19, about 18, about 17, about 16, about 15, about 14, about 13, about 10, about 9, about 8, about 7, about 6, and commonly fewer than about 5, about 4, about 3, or about 2 additions or deletions as compared to the reference. In some embodiments, a reference polypeptide or nucleic acid is one found in nature. In some embodiments, a reference polypeptide or nucleic acid is a human polypeptide or nucleic acid.

BRIEF DESCRIPTION OF THE DRAWING

FIG. 3 includes panel A and panel B. Panel A is a schematic representation of how a mini-nucleosome core protein modified with 1 kDa PEG, shown in Panel B, at a lysine residue can undergo a condensation reaction with a DNA molecule to produce a loaded mini-nucleosome. Each nucleic acid molecule may require several (1 to 1000) mini-nucleosome core proteins to neutralize the negative charges in the DNA to form a loaded mini-nucleosome. The schematic is intended only as a cartoon diagram, and is not intended to be representative of the actual structure of loaded mini-nucleosomes except to the extent that loaded mini-nucleosome includes nucleic acids associated with core proteins.

Figure 4:
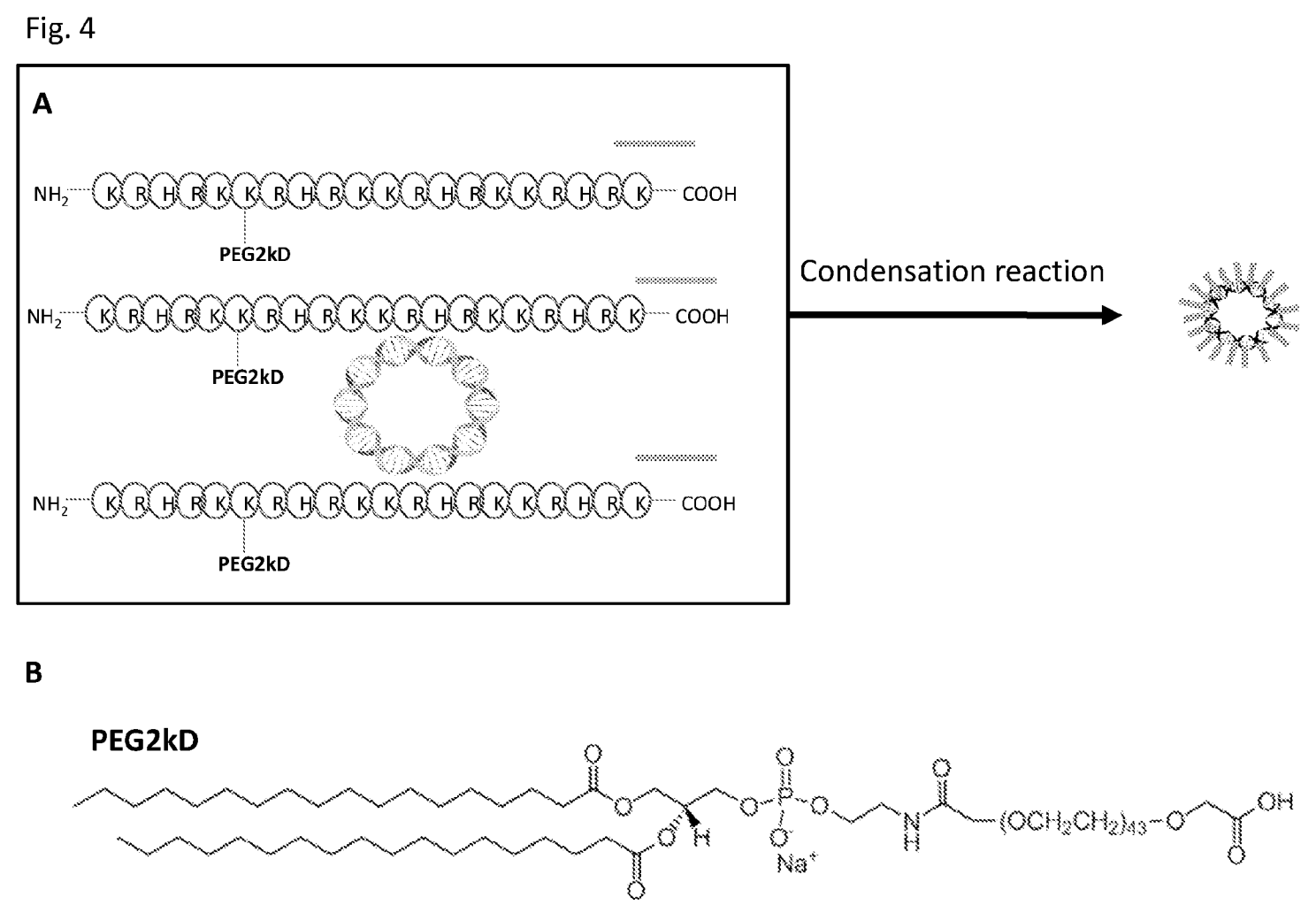

FIG. 4 includes panel A and panel B. Panel A is a schematic representation of how a mini-nucleosome core protein modified with 2 kDa PEG, shown in Panel B, at a lysine residue can undergo a condensation reaction with a DNA molecule to produce a loaded mini-nucleosome. Each nucleic acid molecule may require several (1 to 1000) mini-nucleosome core proteins to neutralize the negative charges in the DNA to form a loaded mini-nucleosome. The schematic is intended only as a cartoon diagram, and is not intended to be representative of the actual structure of loaded mini-nucleosomes except to the extent that loaded mini-nucleosome includes nucleic acids associated with core proteins.

Figure 20:
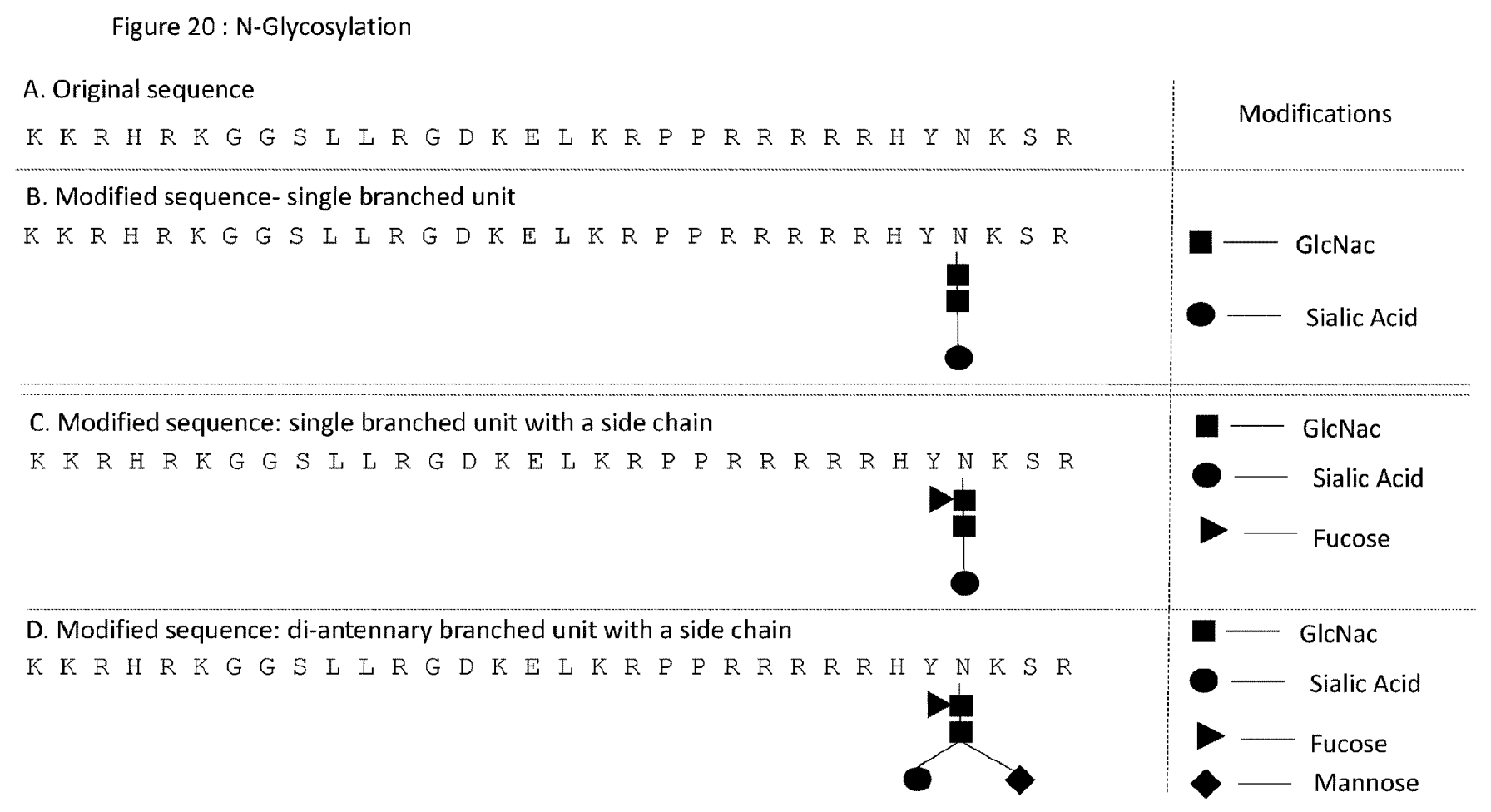

FIG. 20 includes panels A, B, C, and D. Panel A is a schematic representation of an unmodified mini-nucleosome core protein. Panel B is a schematic representation of a modified mini-nucleosome core protein, where an asparagine residue (N) is modified with an unbranched modification chain including GlcNac, GlcNac, and sialic acid. Panel C is a schematic representation of a modified mini-nucleosome core protein, where an asparagine residue (N) is modified with a branched modification chain including a trunk including GlcNac, a branch including GlcNac and sialic acid, and a branch including fucose. Panel D is a schematic representation of a modified mini-nucleosome core protein, where an asparagine residue (N) is modified with a branched modification chain including a trunk including GlcNac, a branch including fucose, and a branch including a secondary trunk including GlcNac, a secondary branch including sialic acid, and a secondary branch including mannose.

FIG. 22 includes panels A, B, C, D, E, F, G, H, I, and J. Panel A is a schematic representation of a GlcNac modification that could modify a serine residue of a mini-nucleosome core protein. Panel B is a schematic representation of an unbranched glycan modification chain including GalNac and galactose. Panel C is a schematic representation of a di-antennary branched glycan modification including a GalNac trunk, a GlcNac branch, and a galactose branch, which branched modification could modify a serine residue of a mini-nucleosome core protein. Panel D is a schematic representation of an unbranched modification including mannose, GlcNac, galactose, and NeuAc, which unbranched modification could modify a serine residue of a mini-nucleosome core protein. Panel E is a schematic representation of an unbranched modification including fucose, GlcNac, galactose, and sialic acid, which unbranched modification could modify a serine residue of a mini-nucleosome core protein. Panel F is a schematic representation of a di-antennary branched modification including a GalNac trunk, a galactose branch, and a branch including GlcNac, galactose, GlcNac, galactose, and NeuAc, which branched modification could modify a serine residue of a mini-nucleosome core protein. Panel G is a schematic representation of a di-antennary branched modification including a GalNac trunk, a galactose branch, and branch including a secondary trunk including GlcNac, galactose, GlcNac, and galactose with a fucose secondary branch and a NeuAc secondary branch, which branched modification could modify a serine residue of a mini-nucleosome core protein. Panel H is a schematic representation of single sugar addition that could modify a serine or threonine, which single sugar modification could be, e.g., a galactose, glucose, mannose, fucose, or sialic acid. Panel I is a schematic representation of an unmodified mini-nucleosome core protein. Panel J is a schematic representation of a modified mini-nucleosome core protein, where a serine residue is modified with an unbranched glycan modification including GalNac, GalNac, and galactose.

FIG. 23 includes panels A, B, C, D, and E. Panel A is a schematic representation of an unmodified mini-nucleosome core protein. Panel B is a schematic representation of a modified mini-nucleosome core protein, where a lysine residue (K) is modified with an acetyl group. Panel C is a schematic representation of a modified mini-nucleosome core protein, where two lysines residues (K) are each modified with an acetyl group. Panel D is a schematic representation of a modified mini-nucleosome core protein, where each of a lysine residue (K) and a valine (V) is modified with an acetyl group. Panel E is a schematic representation of a modified mini-nucleosome core protein, where each of a lysine residue (K) and an alanine (A) residue is modified with an acetyl group.

FIG. 24 is a schematic representation of an acetylated lysine.

FIG. 25 includes panels A, B, and C. Panel A is a schematic representation of an unmodified mini-nucleosome core protein. Panel B is a schematic representation of a modified mini-nucleosome core protein, where a tyrosine residue (Y) is modified with a sulfate group. Panel C is a schematic representation of a sulfated tyrosine FIG. 26 includes panels A, B, C, and D. Panel A is a schematic representation of an unmodified mini-nucleosome core protein. Panel B is a schematic representation of a modified mini-nucleosome core protein, where a cysteine residue (C) is modified with prenyl group. Panel C is a schematic representation of a farnesyl group linked with a polypeptide. Panel D is a schematic representation of a geranylgeranyl group linked with a polypeptide.

FIG. 27 includes panels A, B, C, D, E, and F. Panel A is a schematic representation of an unmodified mini-nucleosome core protein. Panel B is a schematic representation of a modified mini-nucleosome core protein, where a serine residue(S) is modified with a phospho group. Panel C is a schematic representation of phosphotyrosine. Panel D is a schematic representation of phosphoserine. Panel E is a schematic representation of phosphothreonine. Panel F is a schematic representation of bis-phosphohistidine.

FIG. 28 includes panels A, B, C, D, and E. Panel A is a schematic representation of an unmodified mini-nucleosome core protein. Panel B is a schematic representation of a modified mini-nucleosome core protein sequence, where a lysine residue (K) is methylated. Panel C is a schematic representation of mono-methyl lysine. Panel D is a schematic representation of di-methyl lysine. Panel E is a schematic representation of tri-methyl lysine.

FIG. 29 includes panels A, B, C, and D. Panel A is a schematic representation of an unmodified mini-nucleosome core protein. Panel B is a schematic representation of a modified mini-nucleosome core protein, where a proline residue (P) is hydroxylated. Panel C is a schematic representation of 4-hydroxylated proline. Panel D is a schematic representation of 3-hydroxylated proline.

FIG. 30 includes panels A, B, C, D and E. Panel A is a schematic representation of an unmodified mini-nucleosome core protein. Panel B is a schematic representation of a modified mini-nucleosome core protein, where a lysine residue (K) is lipidated and/or lipoylated. Panel C is a schematic representation of S-myristoylated glycine. Panel D is a schematic representation of S-palmitoylated cysteine. Panel E is a schematic representation of O-palmitoylated cysteine.

FIG. 32 includes panels A and B. Panel A is an IVIS® Spectrum In Vivo Imaging System (IVIS) image of a mouse administered an unmodified mini-nucleosome core protein according to SEQ ID NO: 388 loaded with a nucleic acid payload including a gene encoding luciferase as a representative expression product. Panel B is an IVIS® Spectrum In Vivo Imaging System (IVIS) image of a mouse administered a sulfated mini-nucleosome according to SEQ ID NO: 388 loaded with a nucleic acid payload including a gene encoding luciferase as a representative expression product. Panel B shows that the modified mini-nucleosome core protein, but not the unmodified mini-nucleosome core protein, results in robust expression of the representative nucleic acid payload-encoded expression product (here, luciferase) in certain tissues including central nervous system cells including neurons, and including spinal cord cells and brain neurons.

DETAILED DESCRIPTION

Figure 1:
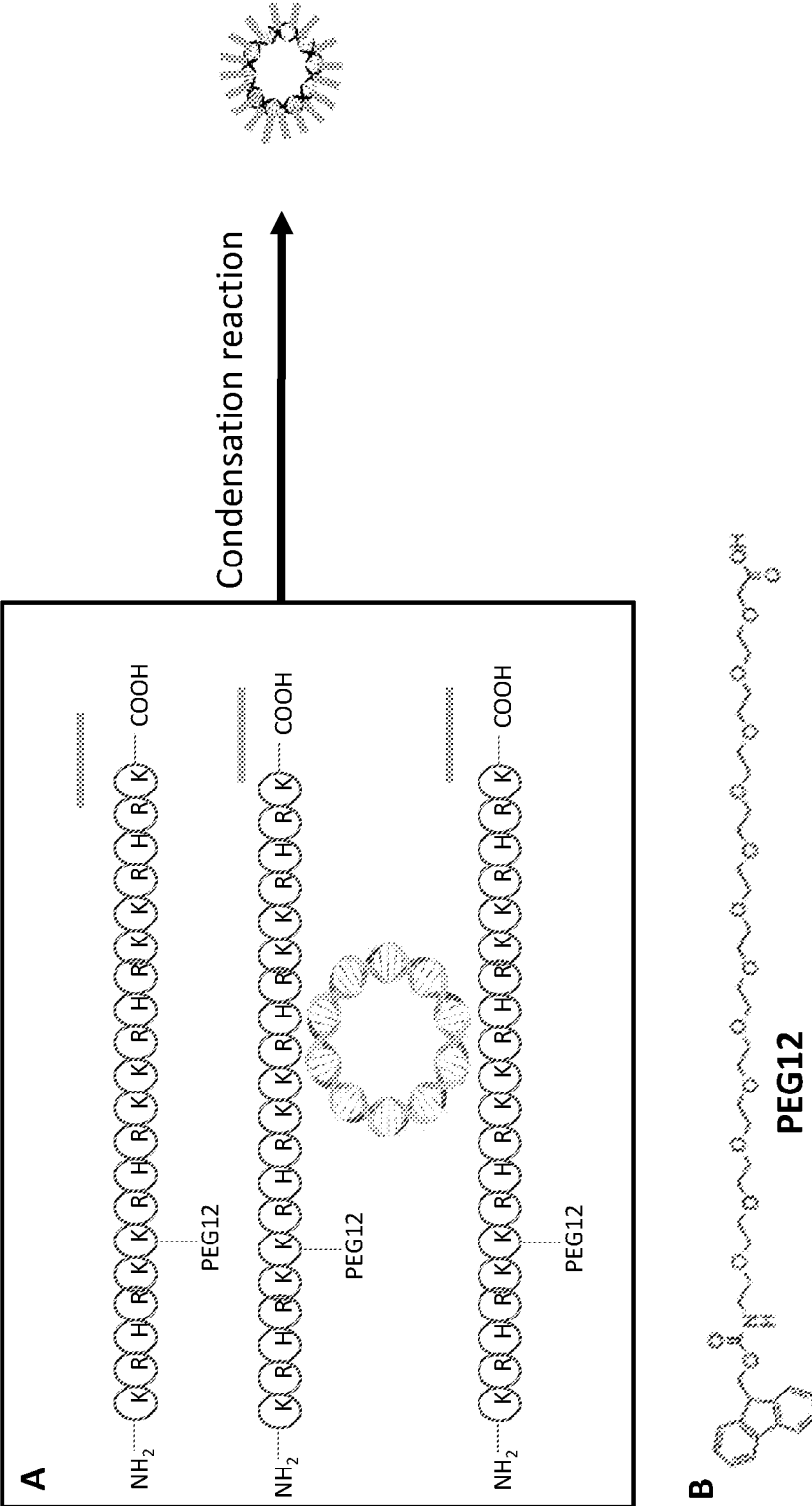
FIG. 1 includes panel A and panel B. Panel A is a schematic representation of how a mini-nucleosome core protein modified with PEG12, shown in Panel B, at a lysine residue can undergo a condensation reaction with a DNA molecule to produce a loaded mini-nucleosome. Each nucleic acid molecule may require several (1 to 1000) mini-nucleosome core proteins to neutralize the negative charges in the DNA to form a loaded mini-nucleosome. The schematic is intended only as a cartoon diagram, and is not intended to be representative of the actual structure of loaded mini-nucleosomes except to the extent that loaded mini-nucleosome includes nucleic acids associated with core proteins.

The present disclosure provides, among other things, methods and compositions relating to mini-nucleosome core proteins and uses thereof. Mini-nucleosome core proteins disclosed herein include, among other things, (a) a nucleic acid binding domain (NABD), (b) a targeting domain and/or (c) a nucleic acid release domain, and/or a stability domain, and/or an oligomerization domain, and/or a linker domain. Certain mini-nucleosome core proteins disclosed herein include (a) a nucleic acid binding domain (NABD); (b) a targeting domain; (c) a nucleic acid release domain; and, optionally, (d) further domains including, e.g., one or more of a stability domain, an oligomerization domain, and/or a linker domain. In various embodiments, mini-nucleosome core protein of the present disclosure is a modified mini- nucleosome core protein, i.e., a mini-nucleosome core pro- tein that is modified in that it includes one or more modified amino acid residues, such as an amino acid residue modified to include a modification provided herein, including without limitation any of one or more of (i) phosphorylation; (ii) sulfation; (iii) glycosylation (e.g., N-glycosylation, C-gly- cosylation, and/or O-glycosylation); (iv) prenylation (e;g., geranylation and/or farnesylation); (v) methylation;; (vi) sialylation; (vii) lipidation and/or lipoylation;; (viii) acety- lation; (ix) hydroxylation;; (x) palmitoylation; (xi) manno- sylation; (xii) myristoylation; (xiii) fucosylation; (xiv) pegy- lation; and/or; (xv) any combination thereof, including any number of one or more of the modifications or variants thereof, e.g., in a branched or unbranched modification chain. In various embodiments, a mini-nucleosome core protein of the present disclosure can be a modified mini- nucleosome core protein that includes (a) a nucleic acid binding domain ("NABD"); (b) a targeting domain; (c) a modified amino acid residue; and, optionally, (d) further domains including, e.g., one or more of a nucleic acid release domain, a stability domain, an oligomerization domain, and/or a linker domain. In various embodiments, a mini-nucleosome core protein of the present disclosure can be a modified mini-nucleosome core protein that includes (a) a nucleic acid binding domain ("NABD"); (b) a targeting domain; (c) a nucleic acid release domain; (d) a modified amino acid residue; and, optionally, (e) further domains including, e.g., one or more of a stability domain, an oligomerization domain, and/or a linker domain. In various embodiments, a mini-nucleosome core protein is associated with one or more nucleic acid molecules, thereby forming a loaded mini-nucleosome core protein (the mini-nucleosome core protein and associated nucleic acid molecules also referred to together herein as a loaded mini-nucleosome). In various embodiments, a loaded mini-nucleosome includes two or more mini-nucleosome core proteins and one or more nucleic acid molecules. In various embodiments, a loaded mini-nucleosome is administered to a subject in need thereof.

Polynucleotide chains typically carry phosphates with negative charge. Accordingly, positive charges in proteins such as histones help condense nucleic acids. The present disclosure appreciates that nucleic acid binding domains, derived, e.g., from histones, can be utilized in artificially constructed mini-nucleosome core proteins as a non-viral proteinaceous vector.

Most mammalian cells possess cell surface binding moi- eties or receptors that recognize (and/or are recognized by), bind, and internalize molecules or entities like viruses and bacteria. Various compositions and methods disclosed herein make use of such cell surface binding motifs in combination with nucleic acid binding domains and poly- Arginine domains in a mini-nucleosome core protein. In various embodiments, a mini-nucleosome core protein is capable of condensing, or participating in or facilitating the condensation of, one or more nucleic acids. In various embodiments, a mini-nucleosome core protein facilitates internalization of associated nucleic acids, e.g., in a loaded mini-nucleosome, into specific cell types, e.g., via endocy- tosis or via other cellular entry mechanisms. Accordingly, in various embodiments, the present disclosure includes mini- nucleosome core proteins that incorporate targeting moieties capable of binding with cell surface moieties or receptors that are naturally present on cells of a system, e.g., a system that is a human, where the cell surface moiety or receptor provides a cell entry mechanism. In various instances, the cell surface moiety or receptor is cell-type specific and thus facilitates specific delivery of nucleic acids to selected cell types.

Nucleic acid molecules can have a large negative charge, are vulnerable for degradation in body fluids, e.g., after administration to subjects, and cannot enter a cell via simple injections or exposure to the cell. That large negative charge can be neutralized by mini-nucleosome core-proteins, including modified mini-nucleosome core proteins, to form loaded mini-nucleosomes of certain shape, size, and charge and/or that are capable of entering into cells by passive diffusion or active transport. Various mini-nucleosome core proteins described herein allow proper binding, condensa- tion and targeting of nucleic acids. These domains described herein, may be derived from human proteins or other organ- isms. One skilled in the art may contemplate modifying or engineering domains and/or mini-nucleosome core proteins described herein, e.g., with changes to the amino acid sequence for enhancing certain functions such as cell attach- ment, internalization etc. but not limited to these. One skilled in the art may also contemplate placing the domain in reverse sequence or by switching amino acid positions within the domain or adding various posttranslational modifications such as acetylation, glycation etc. to amino acids but not limited to these. Various mini-nucleosome core proteins described herein include at least one modified amino acid residue.

Nucleic Acid Binding Domains

The present disclosure includes the recognition that positively charged domains associate with nucleic acids. The present disclosure provides nucleic acid binding domains, e.g., DNA and RNA binding domains, that can be included in a mini-nucleosome core protein. In some instances, a DNA binding domain present in a mini-nucleosome core protein is a DNA binding domain disclosed herein. In some instances, a RNA binding domain present in a mini-nucleosome core protein is a RNA binding domain disclosed herein.

In some particular instances, an NABD that is a DNA binding domain present in a mini-nucleosome core protein disclosed herein can be derived from a histone polypeptide sequence. Non-viral vectors such as DNA nanoparticles utilizing poly-lysine peptides to compact DNA into smaller particles for gene delivery (Liu G. et al, 2003) have been used, at least some instances, with no success or significant responses in treatment of diseases (Konstan M.W. et al, 2004). The present disclosure provides a significantly different approach that includes, in various embodiments, use of DNA binding domain of histones, for example the amino acid sequence KRHRK. This amino acid sequence serves two purpose-first it gives the highly positive charge that is needed to associate with nucleic acids, Secondly, it also gives stability to the mini-nucleosome core protein structure. Thirdly, the amino acid sequence KRH in this NABD also is a cleavage site for proprotein convertases thus allows efficient release of the genetic cargo in cells.

Other examples of NABDs are provided in Table 3.

A poly-arginine tract such as RRRRR can be included in a mini-nucleosome core protein to increase nucleic acid binding as well as to enhance positive charge and/or cell penetration ability of the composition. A poly-arginine tract can be present in a mini-nucleosome core protein in a position suitable to facilitate penetration of cells by the mini-nucleosome core protein and/or by loaded mini-nucle-osomes including the mini-nucleosome core protein. Those of skill in the art will be aware of the methods and techniques that allow determination of such a position. Arginine interacts with phospholipids to form of bi-or multi-dentate hydrogen bonding from simultaneous association with the phosphates of more than one lipid head therefore interacts with the phosphate on a single lipid head group. Since, only arginine can form bi-dentate hydrogen-bonds, poly-argin-ines could bond with more zwitterionic and anionic lipids and therefore generate positive curvature along its contour length, thus resulting in negative Gaussian curvature (Roth-bard, J. B., et al. 2005). A poly-Arginine tract may also be modified to include specifically one or more Histidine (H) amino acid (or any other amino acid) to improve stability of the mini-nucleosome core protein. Histidine (or any other amino acid) may be inserted in any position in the poly-Arginine tract as shown in Table 3. Other arginine-rich peptides such as ANTP Penetratin, and TAT have also shown similar impact on cell penetration.

The present disclosure includes the recognition that local-ization of a mini-nucleosome core protein to a euchromatin area of the nucleus can be facilitated by acetylation of lysines in mini-nucleosome core proteins. The mechanism of this stabilization may be related, at least in part, to mechanisms that stabilize post-translationally modified his-tones. Methylated histones pack more tightly. Histone methylation can be dynamic. Other post translational modifications that can be applied are: phosphorylation, glycosylation, prenylation, lipoylation, alkylation, acylation, glycation, nitrosylation, sulfation, carbamylation, carbonylation, sumoylation, neddylation, biotinylation, ribosylation etc. Modifications may not be limited to these mentioned here. Other modifications may include attachment of co-factors, co-enzymes, hydrophobic groups, hydrophilic groups, smaller chemical groups, smaller peptides etc. Such modification could also be applied to amino acids in these mini-nucleosome core proteins described herein. Nucleic acid binding domains mentioned herein, in Table 3 can be incorporated in polypeptides at any location to enhance nucleic acid binding in combination with other domains provided in Tables 4, 5, 6, 7, 9, 10, 11 and 12.

TABLE 3

| Exemplary Domains | SEQ ID NO: | Name | Exemplary Utility | Reference |
|---|---|---|---|---|
| KRHRK | 1 | DNA binding domain | Enhanced DNA binding | Bottomley M.J., 2004 |
| RRR, RRRR, RRRRR, (RR)X | 2, 3, 4, 5 | Poly-Arginines: DNA binding domain | Enhanced cell penetration | Mishra, A. et al, 2008 |
| RRLARR | 6 | Condensing domain (part of) | Enhanced DNA binding; condensation | John P. H. Th'ng et al. 2005 |
| KKAKAAAKPKK | 7 | Condensing domain (part of) | Enhanced DNA binding and condensation | John P. H. Th'ng et al. 2005 |
| KKDGKKRKR | 8 | Condensing domain (part of) | Enhanced DNA binding and condensation | John P. H. Th'ng et al. 2005 |
| KKKLK | 9 | HTH motif (part of | Enhanced DNA binding | Uniprot |
| KKRIRK, RKKSK | 10, 11 | RUNX1 binding (part of) | Enhanced DNA binding | Uniprot |
| KKPKK | 12 | Condensing domain (part of) | Enhanced DNA binding and condensation | John P. H. Th'ng et al. 2005 |
| RRHRR | 13 | Nucleic acid binding | Enhanced nucleic acid binding and stability | Uniprot |

TABLE 3-continued

| Exemplary Domains | SEQ ID NO: | Name | Exemplary Utility | Reference |
|---|---|---|---|---|
| RHRRR | 14 | Nucleic acid binding | Enhanced nucleic acid binding and stability | Uniprot |
| RRRRHR | 15 | Nucleic acid binding | Enhanced nucleic acid binding and stability | Uniprot |
| KRTVRK | 16 | Nucleic acid binding | Enhanced nucleic acid binding | Uniprot |
| KRQRNR | 17 | Nucleic acid binding | Enhanced nucleic acid binding | Uniprot |
| RVCACPGR | 18 | P53 DNA interaction | Enhanced nucleic acid binding | Uniprot |
| (KKK)x | 19 | Nucleic acid binding | Enhanced nucleic acid binding | Uniprot |
| DEMGLGKT | 20 | Nucleic acid binding | Nucleotide binding | Uniprot |
| QRE, HLSQHLN, KTQK, RFKW, RVY, NRRK | 21, 22, 23, 24, 25, 26 | Nucleic acid binding | Interaction with DNA | Uniprot |
| TFF | 27 | Nucleic acid binding | RNA binding | Uniprot |
| RPRGRPRKHTVTS | 28 | Nucleic acid binding | Enhanced nucleic acid binding | Uniprot |

For the avoidance of doubt, the present disclosure includes modified nucleic acid binding domains, including without limitation a nucleic acid binding domain of the present disclosure in which at least one amino acid of the nucleic acid binding domain includes a modification disclosed herein.

Targeting Domains

Mini-nucleosome core proteins disclosed herein include targeting domains that target mini-nucleosomes to one or more cells or cell types.

In some embodiments, a targeting domain of a mini-nucleosome core protein is an amino acid domain that allows attachment to and enter into one or more cells or cell types. It is to be understood that targeting domains can be specific to certain cell types but can also include domains that facilitate entry into cells generally. In general, a targeting domain of a mini-nucleosome core protein can contribute to one or more of attachment, cell-type specific binding, and internalization. A targeting domain can be, for example, a cell attachment targeting domain, beta galactose binding domain, fucose binding domain, heparin binding domain, sialic acid binding domain, glycoprotein binding domain, carbohydrate binding domain, lysophosphatidic acid binding, cAMP binding domain, hyaluronan binding domain, chondroitin sulfate binding domain, integrin binding domain, nucleolin binding domain, collagen binding domain, clathrin binding domain, Fc receptor binding domain, actin binding domain, endocytosis motif or a nuclear localization signal. In some embodiments, a targeting domain of a mini-nucleosome core protein is an amino acid domain that allows binding and entry into one or more cells or cell types and that is derived from a mammal, virus, viral particle, prion, bacteria or fungal amino acid sequence.

For the avoidance of doubt, the present disclosure includes modified targeting domains, including without limitation a targeting domain of the present disclosure in which at least one amino acid of the targeting domain includes a modification disclosed herein.

Cell Attachment Targeting Domains

Cell attachment is a means by which a mini-nucleosome core protein, or loaded mini-nucleosome include the mini-nucleosome core protein, can adhere to cell and, in various instances, facilitate entry to into the cell. Various viruses have adhesion molecules or domains that allow binding to host cells and enhance entry into them. For example, flu virus has hemagglutinin on its surface that allows it to bind to sialic acid on the cell surface. The present disclosure provides, among other things, several such domains that allow mini-nucleosome core protein binding to sialic acid, galactose, fucose, hyaluronic acid, and chondroitin sulfate, as well as glycoproteins that enhance cell attachment for internalization. A mini-nucleosome core protein disclosed herein can include one or more cell attachment targeting domains. Cell attachment targeting domains include the domains shown in Table 4. A cell attachment targeting domain of the present disclosure can be present in a mini-nucleosome core protein at any position and/or in combination with any of one or more other domains provide herein, e.g., in Tables 3, 5, 6, 78, 9, 10, 11 and 12.

TABLE 4

| Exemplary Domains | SEQ ID NO: | Name | Exemplary Utility | Reference |
|---|---|---|---|---|
| WGREERQ | 29 | Cell attachment site on LGALS3 | Enhanced cell surface attachment via beta-galactose binding | Uniprot |

TABLE 4-continued

| Exemplary Domains | SEQ ID NO: | Name | Exemplary Utility | Reference |
|---|---|---|---|---|
| NTQIH & WNNKTPH | 30, 31 | CTxB domain | Enhanced cell surface attachment via galactose binding | Uniprot |
| TPH | 32 | CTxB domain | Enhanced cell surface attachment via Fucose binding | Uniprot |
| VNRWS | 33 | Sialic acid binding domain | Enhanced muscle cell surface attachment via Sialic acid binding | Uniprot |
| XBBBXXBX, ARKKAAKA | 34, 35 | Heparin binding domain | Enhanced cell surface attachment via Heparin binding. | Cardin and Weintraub, 1989 |
| QRR, SRR | 36, 37 | CPC motif | Enhanced cell surface attachment via Heparin binding | Torrent M. et. al, 2012 |
| WEPSRPFPVD | 38 | B3GAT3 motif | Enhanced cell surface attachment via galactose binding | Uniprot |
| HRRTRKAPKRIRLPHIR | 39 | Herpes glycoprotein gD motif | Enhanced cell surface attachment via glycoprotein binding | Uniprot |
| KRTGQYKLGSKTGPGQK | 40 | Heparin binding domain in FGF2 | Enhanced cell surface attachment via heparin binding | Uniprot |
| KKTK | 41 | Heparin sulfate binding | Enhanced cell surface attachment via heparin sulfate binding domain | Nelson C. Di Paolo et al, 2007 |
| KLRSQLVKK | 42 | Hyaluronan binding motif | Enhanced cell surface attachment via Hyaluronan binding | Uniprot |
| RRRCGQKKK | 43 | Hyaluronan binding motif | Enhanced cell surface attachment via Hyaluronan binding | Uniprot |
| BX(7)B | 44 | BX7B domain | Enhanced cell surface attachment via Hyaluronan binding | Jean L. et al, 2001 |
| RIQNLLKITNLRIKFVK | 45 | AC15 domain | Enhanced cell surface attachment via heparin binding | Kokona Kouzi-K. et al. 1989 |
| KKEKDIMKKTI | 46 | Sgl MOTIF of integrin | Enhanced cell surface attachment via chondroitin sulfate binding domain | Joji I. et al, 1998 |
| HGSRFTFHRGSM, HRPH, DVAR, HFNPR, WGTE | 47, 48, 49, 50, 51 | Lectin binding | Enhanced cell surface attachment via Beta-galactoside binding binding domain | Uniprot |
| KKQFGAEC | 52 | Chondroitin sulfate binding | Enhanced cell surface attachment | Uniprot |
| RRPRPGTGPGRRPRPRPRP | 53 | Heparan sulfate binding | Enhanced cell surface attachment | Uniprot |

Cell attachment can also be achieved by domains such as RGD, RGDS etc. (D'Souza S E et al, 1991). Binding to cell surface proteins such as integrins, nucleolin, collagen, clathrins, Fc receptors also help viruses and other particles get entry to the cell. The present disclosure provides, among other things, domains that allow binding to as integrins, nucleolin, collagen, clathrins, Fc receptors for increased cellular uptake. Cell attachment targeting domains include the domains shown in Table 5. A cell attachment targeting domain provided in Table 5 can be present in a mini-nucleosome core protein at any position and/or in combination with any of one or more other domains provide herein, e.g., in Tables 3, 4, 6, 7, 8, 9, 10, 11 and 12.

TABLE 5

| Exemplary Domains | SEQ ID NO: | Name | Exemplary Utility | Reference |
|---|---|---|---|---|
| KGE | 54 | Cell attachment motif | Enhanced cell attachment via Integrin binding | Maginnis M. S. et al, 2006 |
| RGD, RGDS | 55, 56 | Cell attachment motif | Can be used to block RPE transduction. | D'Souza SE et al, 1991 |
| TTVVNPKYEGK, ERMSQIKRLLS | 57, 58 | Betal integrin cell attachment domain | Enhanced cell attachment via Integrin binding | Reszka A. A. et al, 1992 |
| WRHRARS | 59 | NS5B domain | Enhanced cell attachment via Nucleolin binding | Kusakawa T. et al, 2007 |
| GFOGER | 60 | A-domains of Integrins | Enhanced cell attachment via Collagen I and IV binding to Integrins | Knight C. G. et al, 2000 |
| LFDLM | 61 | ENTH domain | Enhanced cell attachment via Clathrin terminal domain binding | Kalthoff et al, 2002 |
| WGREERQ | 62 | Galactose binding motif | Enhanced cell attachment via galactose binding site on LGALS3 | Uniprot |
| QSTEKRG | 63 | Cclec6A motif | Enhanced cell attachment via association with Fc receptor gamma chain (FCER1G) | Uniprot |
| LPNTG | 64 | LPXTG motif | Enhanced cell attachment | Dramsi et al, 2008 |
| DSPE, FQVT | 65, 65 | Popeye domain | CAMP binding | Brand, T. 2016 |
| QSTEKRG | 66 | CLEC6a motif | Carbohydrate binding | Uniprot |
| RQGLID | 67 | domain in LPAR1 | Lysophosphatidic acid binding | Uniprot |
| RKKH | 68 | Midas motif | Echo virus 1 and integrin binding motif. Collagen binding. | Pentikainen O. et al, 1999 |
| YPK, YNQYT | 69, 70 | Sialoadhesion domain | Myelin associated glycoprotein | Kelm S. et al, 1994 |
| KWNYK | 71 | Sialic acid binding domain | Siglec7 | Uniprot |
| GPQSVKFKSPDQI | 72 | Adhesion domain | Cytoadherence | Uniprot |
| RVGENWWY, RTLQAHHDR, RESPFSGSSR, REEIQERMR, QDSSSFHHQ, KKQFGAEC, KRALHNAEC | 73, 74, 75, 76, 77, 78, 79 | Chondroitin sulfate binding | Cell surface attachment | Uniprot |
| KQKIKHVVKLK, KLRCQLAKKK | 80, 81 | Hyaluronic acid binding | Cell surface attachment | Uniprot |

For the avoidance of doubt, the present disclosure includes modified cell attachment targeting domains, including without limitation a cell attachment targeting domain of the present disclosure in which at least one amino acid of the cell attachment targeting domain includes a modification disclosed herein.

Internalization Targeting Domains

Certain domains in viral and mammalian proteins can directly impact cellular internalization. For example, domains of certain proteins, and sequential arrangement, is described in Oleson et al., 2008. For example, a PPxY-Motif is required for adenovirus entry into cells (Wodrich et al, 2010), where x could be any amino acid. Another example of an internalization targeting domain is the GTALL motif-a five-amino acid residue domain, in the carboxyl-terminus tail of leutinizing hormone (LH) receptor directs the ligand-receptor complexes from a degradative to recycling pathway (Pandey, 2009). The GTALL motif also shows sequence homology to carboxyl-terminus tetrapeptide sequence motif DSLL, which has been suggested to participate in the internalization of β-adrenergic receptors. Pandey also discusses that the clathrin-dependent cargo usually contains a short sequence motif such as YXXQ (where X could be any amino acid), recognized by adaptor protein-2 (AP-2) and may contain Asn-Pro-X-Tyr sequence (NPXY) motifs, which are recognized by the accessory clathrin adaptor proteins. Transferrin. NPXY motif has also been discussed by Kirchhausen, 1999. NPTY is also the Endocytosis motif of APP. Another example of clathrin binding domain that allows internalization is FXDXF (where X could be any amino acid) (Lene E. Oleson. 2008). Internalization targeting domains include the domains provided in Table 6.

Other features provided by the present disclosure include one or more leucine and isoleucine residues, which residues are highly hydrophobic in nature. In fact, leucine is the second most hydrophobic amino acid. In various embodiments, leucine residues can serve multiple functions in the composition of mini-nucleosome core proteins. First, the hydrophobicity of the nonpolar face of an amphipathic molecule plays an important role in stabilizing the peptide secondary structure (Chen Y. et al, 2007). Secondly, dileucine-type of signal motifs have been shown to be essential for internalization and trafficking of membrane receptors and membrane proteins into subcellular compartments. For example, GLUT4 (glucose transporter 4), LDL (low density lipoprotein); LH (leutinizing hormone), TGN (Trans-Golgi network) all have dileucine motifs that help internalization into cells. Fc receptor dileucine motif also signals for endocytosis (Wu Z. and Simister N.E., 2001). An internalization targeting domain provided in Table 4 can be present in a mini-nucleosome core protein at any position and/or in combination with any of one or more other domains provide herein, e.g., in Tables 3, 4, 5, 7, 8, 9, 10, 11 and 12.

TABLE 6

| Exemplary Domains | SEQ ID NO: | Name | Exemplary Utility | Reference |
|---|---|---|---|---|
| FXDXF | 82 | FXDXF-motif | Clathrin binding motif facilitates internalization | Lene E. Oleson JBC. 2008 |
| PPSY | 83 | PPxY-Motif | Facilitates Adenovirus Entry. At the end of the sequence. | H Wodrich et al, 2010 |
| FEDNFVP | 84 | 7-mer peptide from amphiphysin. | Enhanced Internalization | Lene E. Oleson JBC. 2008 |
| YIRV, YADW, YTQV | 85, 86, 87 | Internalization motif | Enhanced Internalization | Zrarate et al, 2007 |
| KKRPKP | 88 | Prion internalization motif | Is sufficient to direct internalization. | (Sunyach, 2003). |
| SSDDE, RRASS | 89, 90 | CcN motif | Efficient nuclear transport and localization | (David A Jans. 1995 JBC) |
| (YXXL)2 | 91 | Internalization motif of bovine leukemia virus | For viral entry and incorporation of viral envelope protein into virions. | Inabe K et al, 1999 |
| LPLTG, LAFTG | 92, 93 | Sorting signal | Sortase dependent entry. | Ton-That, H., and O. Schneewind. 2003 |
| L, I, LI, IL | 94, 95, 96, 97 | Leucines, Isoleucine | Increased hydrophobicity for polypeptide stability | Chen Y. et al, 2007 |
| LL | 98 | Dileucine | Enhanced cellular internalization | Wu Z. and Simister N. E., 2001 |
| KRRHPKK | 99 | Cardin-Weintraub motif | Heparan sulfate binding | Uniprot |
| EPS, EPNLPEE, ND | 100, 101, 102 | Mannose binding domian | Enhanced cellular internalization | Uniprot |
| NFR | 103 | N-acetyl-D-glucosamine binding | Enhanced cellular internalization | Uniprot |

TABLE 6-continued

| Exemplary Domains | SEQ ID NO: | Name | Exemplary Utility | Reference |
|---|---|---|---|---|
| YWV | 104 | PDZ binding | Enhanced cellular internalization | Uniprot |
| AICKRIPNKKPGKRT | 105 | Heparin binding | Enhanced cellular internalization | Uniprot |
| VAR, KIL | 106 | Receptor binding (CXCL12) | Enhanced cellular internalization | Uniprot |
| RCPCR, RANVKHLKILN, VARLKNNNRQV | 107, 108 109 | Heparin binding | Enhanced cellular internalization | Uniprot |
| VRKKP, YVRKKPKLK | 110, 111 | PDGFA binding to its receptor | Enhanced cellular internalization | Uniprot |
| ISRRLI | 112 | PDGFB binding to its receptor | Enhanced cellular internalization | Uniprot |
| LTKRSRQ, NRKISVQRL | 113, 114 | Gag binding | Enhanced cellular internalization | Uniprot |
| YYKQRLI | 115 | Nucleocytoplasmic transport | Enhanced cellular internalization | Uniprot |

For the avoidance of doubt, the present disclosure includes modified internalization targeting domains, including without limitation an internalization targeting domain of the present disclosure in which at least one amino acid of the internalization targeting domain includes a modification disclosed herein.

Nucleus Targeting Domains

In various embodiments, it is important that, following cellular entry, a nucleic acid cargo reaches the nucleus. Nuclear internalization signals or binding to the nuclear import machinery are key to nuclear localization. Functional eukaryotic nuclear localization signals are widespread in terminal proteins of bacteriophages (Redrejo-Rodríguez et. al, 2012). Chan and Jans have shown that polylysine by itself doesn't function as a nuclear localization signal. Thus, adding a nuclear targeting signals to enhance non-viral gene transfer is a logical approach (Chan and Jans, 1999). Location of NLS in the polypeptide is also key for its function. We have listed the NLS sequences in Table 7 for enhanced nuclear entry and provided certain preferred locations of NLS signal within mini-nucleosome core proteins for efficient nuclear entry in Table 13. Domains mentioned herein, in Table 7 can be incorporated in mini-nucleosome core protein at any location to enhance nucleic acid binding in combination with other domains provided in Table 3, 4, 5, 6, 8, 9, 10, 11 and 12.

TABLE 7

| Exemplary Domains | SEQ ID NO: | Source protein | Exemplary Utility | Reference |
|---|---|---|---|---|
| KKKYKLK | 116 | Gag pol | Nuclear localization signal | Uniprot |
| KKRKLE | 117 | LMNA | Nuclear localization signal | Uniprot |
| TRSK | 118 | VP22 | Nuclear localization signal | Uniprot |
| HRKRKR | 119 | Aprataxin | Nuclear localization signal | Uniprot |
| NKRKRK | 120 | SAP30L | Nuclear localization signal | Uniprot |
| AEKSKKK | 121 | HMGB1 | Nuclear localization signal | Uniprot |
| RKSK, KRVK | 122, 123 | HIPK2 | Nuclear localization signal | Uniprot |
| KRK | 124 | NFATC1 | Nuclear localization signal | Uniprot |

TABLE 7-continued

| Exemplary Domains | SEQ ID NO: | Source protein | Exemplary Utility | Reference |
|---|---|---|---|---|
| LQQTPLHLAVI | 125 | NFKB inhibitor alpha | Nuclear localization signal contains ankyrin repeats | Uniprot |
| RRPR, PRPR, RPPP | 126, 127, 128 | Bovine Herpes Virus | Nuclear localization signal for bovine herpes. (dystroglycan). In the c-terminal | Uniprot |
| RKKRKGK | 129 | DAG1 | | Uniprot |
| PAAKRVKLD | 130 | c-Myc | Nuclear localization signal | Uniprot |
| KLKIKRPVK | 131 | TUS | Nuclear localization signal | Uniprot |
| PKKKRKV | 132 | SV40 | Nuclear localization signal | Uniprot |
| QRKRQK | 133 | NFKB | Nuclear localization signal | Uniprot |
| KRPR | 134 | TOPBP1 | Nuclear localization signal | Uniprot |
| RKRRRP | 135 | DEDD2 | Nuclear localization signal | Uniprot |
| KKGRRNRFK | 136 | HNF1A | Nuclear localization signal | Uniprot |
| RHRDRLNTELDRLASLLPFPQDVINKLDK | 137 | AHR | Nuclear localization signal | Uniprot |
| KRGRKP | 138 | CBX2 | Nuclear localization signal | Uniprot |
| KKRAGRRIFKETR | 139 | DREBE1 | Nuclear localization signal | Uniprot |

For the avoidance of doubt, the present disclosure includes modified nucleus targeting domains, including without limitation a nucleus targeting domain of the present disclosure in which at least one amino acid of the nucleus targeting domain includes a modification disclosed herein. Cell-type Specific Targeting Domains In various embodiments, it is most desirable that larger concentration of the particles home into the desired cell type. This allows for increased uptake and increased expression-two favorable gene therapy output. In literature, there are very few motifs that have been discovered for such properties. Most of these come from experiments that have shown viral tropism to be different from different capsids. The present disclosure includes, in various embodiments, use of some of those defined motifs, to enhance expression in neurons, muscles, liver, lung, kidney, endothelial cells or tumor sites. Cell-type specific targeting domains include the domains shown in Table 8. A cell-type specific targeting domain of Table 8 can be present in a mini-nucleosome core protein at any position and/or in combination with any of one or more other motifs provide herein, e.g., in Tables 3, 4, 5, 6, 7, 9, 10, 11 and 12.

TABLE 8

| Exemplary Domains | SEQ ID NO: | Exemplary Utility | Reference |
|---|---|---|---|
| ASSLNIA | 140 | Muscle targeting | Yu C-Y. et al. 2009 |
| SKIFNTHPQSTP | 141 | Muscle targeting | Y Seow et al. 2010 |
| YKQCHKKGGHCFPKEK | 142 | Muscle targeting | Uniprot |
| LGKMDCRWKWKCCKKGSG | 143 | Muscle targeting | Uniprot |
| HGSRFTFHRGSM | 144 | Muscle targeting | Uniprot |
| KKEEEKKEEEKKEEE | 145 | Renal targeting | Wischnjow A, et al, 2016 |
| LIFHKEQ | 146 | LIVER targeting | Uniprot |
| KFNKPFVFLI | 147 | Lung targeting | Buning H. et al, 2003 |
| QPEHSST | 148 | Endothelial cell targeting | Work, L. M. et. al, 2006 |
| EYHHYNK | 149 | Vascular smooth muscle cell targeting | Work, L. M, et. al, 2004 |

TABLE 8-continued

| Exemplary Domains | SEQ ID NO: | Exemplary Utility | Reference |
|---|---|---|---|
| NGR | 150 | Tumor homing | Arap W, et. al, 1998 |
| GEKGEP | 151 | Facilitate phagocytosis by monocytes | Uniprot |
| KTKKK, KALKKK, KGKKK | 152, 153, 154 | Phagocytosis of the particles. | Caberoy N. B. et al, 2010 |
| CSVTCG | 155 | Interaction with CD36; bind to cancerous cells. | Asch A. S., et. al 1992 |
| LRE | 156 | Neuron targeting by enhanced neuronal attachment. | Hunter D. D. et al, 1989 |
| YKYNLNGRES | 157 | Lung targeting | Asokan A, et al, 2006 |
| YRSL | 158 | Basolateral targeting | Anderson E., et al, 2005 |
| KGGK7 | 159 | Actin-binding | Dahlin-Huppe K. et al., 1997 |
| KKKQYTSIHHG | 160 | Basolateral sorting | Zheng P. et al, 1998 |
| KDEL | 161 | Endosomal Reticulum targeting | Chinnapen D. J. et al, 2007 |
| LADQDYTKTA | 162 | Retrograde transport | Tervo D. G. R., et. al, 2016 |
| DDNN | 163 | Corin surface targeting | Uniprot |
| SAVTTVVN | 164 | ITGB1 interaction with ITGB1BP1 | Uniprot |

For the avoidance of doubt, the present disclosure includes modified cell-type specific targeting domains, including without limitation a cell-type specific targeting domain of the present disclosure in which at least one amino acid of the cell-type specific targeting domain includes a modification disclosed herein.

Nucleic Acid Release Domains

In some embodiments, a "nucleic acid release domain" ("NARD") of a mini-nucleosome is an amino acid domain that causes or facilitates release of a nucleic acid cargo of a loaded mini-nucleosome (e.g., release of one or more of the nucleic acids associated with a mini-nucleosome core protein of a loaded mini-nucleosome). In various embodiments, by controlling or regulating the conditions under which a nucleic acid cargo is released, a nucleic acid release domain can improve delivery a nucleic acid cargo to cells, e.g., to the cytoplasm or nucleus of cells.

It is highly desirable that nucleic acids associated with a loaded mini-nucleosome core protein (e.g., when delivered to a subject or system) do not release from a loaded mini-nucleosome prior to the loaded mini-nucleosome entering a cell (e.g., a cell of the subject or system). Within a cell, release of nucleic acid cargo in the cytoplasm or nucleus may be preferred. Various proteases and endopeptidases known in the art could cause or facilitate release of one or more nucleic acids of a loaded mini-nucleosome inside cells, e.g., causing or facilitating disassociation of one or more nucleic acids of a loaded mini-nucleosome from the mini-nucleosome core protein of the loaded mini-nucleosome. Proprotein convertases and endopeptidases are exemplary agents that cleave polypeptides at certain amino acid domains, which phenomenon is utilized herein to provide mini-nucleosome core proteins that can release an associated nucleic acid cargo upon delivery into a cell (e.g., a cell of a subject or system), e.g., into the cytoplasm or nucleus of a cell.

KRH is an exemplary cleavage domain that can be included in a mini-nucleosome core protein as a nucleic acid release domain. KRH is the cleavage site for Pcsk 1 and Pcsk2. To provide one non-limiting example of a KRH cleavage site, proglucagon is post-translationally processed in a tissue-specific manner in pancreatic A cells and intestinal cells by Pcsk1 or Pcsk2.

NRRKKRAL is an exemplary cleavage domain that can be included in a mini-nucleosome core protein as a nucleic acid release domain. To provide one non-limiting example of an NRRKKRAL cleavage domain, NRRKKRAL is a Furin cleavage site of for TGFB1. Another exemplary cleavage domain is KSVKKRSVSEIQ, which is a Furin cleavage site in parathyroid hormone.

Various other cleavage domains are known in the art and can be included in a mini-nucleosome core protein as a nucleic acid release domain. As those of skill in the art will appreciate, cleavage sites can also be predicted in silico using bioinformatics platforms such as Expasy, OmicX, PROSPERous, Prop1.0, SignalP-5.0, MEROPS, CutDB, Peptide Cutter etc.

The present disclosure provides that cleavage domains of the present disclosure can be included in mini-nucleosome core proteins to cause or facilitate release of a nucleic acid cargo of a loaded mini-nucleosomes in cells (e.g., cells of a subject or system), e.g., in cytoplasm or nucleus. Domains provided herein, including those provided in Table 9, can be present in a mini-nucleosome core protein of the present disclosure (e.g., a modified mini-nucleosome core protein) at any position within the mini-nucleosome core protein. For the avoidance of doubt, a nucleic acid release domain of the present disclosure can be present in a mini-nucleosome core protein in combination with other domains provided herein, including without limitation those provided in Tables 3, 4, 5, 6, 7, 8, 10, 11 and 12. When present anywhere within a mini-nucleosome core protein of the present disclosure, a nucleic acid release domain of the present disclosure can enhance release of a nucleic acid cargo of a loaded mini-nucleosome.

TABLE 9

| Exemplary Domains | SEQ ID NO: | Exemplary Utility | Reference |
|---|---|---|---|
| GRKKRRQRRRPQ | 165 | Release at extracellular or intracellular sites depending on tissues expressing furin. | Tian and Huang et al, 2011 |

TABLE 9-continued

| Exemplary Domains | SEQ ID NO: | Exemplary Utility | Reference |
|---|---|---|---|
| KRH | 166 | Release at extracellular or intracellular sites depending on tissues expressing Pcsk1 and Pcsk2 | Uniprot |
| KSVKKRSVSEIQ | 167 | Release at extracellular or intracellular sites depending on tissues expressing Pesk1 and Pcsk2 | Uniprot |
| NRRKKRAL | 168 | Release at extracellular or intracellular sites depending on tissues expressing furin. | Tian and Huang et al, 2011 |
| KFERQ | 169 | Breakdown in the lysosomes. | Park J. S. et al., 2016 |
| VRGP | 170 | Cleavage by Thrombin | Uniprot |
| NKDS, NRDN | 171 | Cleavage by Plasmin | Uniprot |
| ANNR | 172 | Cleavage by Hementin | Uniprot |
| HL | 173 | Cleavage by MMP9 | Uniprot |
| RI, ET, GQ, RS, RD, RN, RC, RG, RL, DA, RA, GS, LT, FS, GL, SA, DP, GT, GC, RQ, LS, HA | 174, 175, 176, 177, 178, 179, 180, 181, 182, 183, 184, 185, 186, 187, 188, 189, 190, 191, 192, 193, 194, 195 | Cleavage by autolysis | Uniprot |
| FV, QH, EA, AL, LY, YL, GF, PS, RE, DP, PI, QS | 196, 197, 198, 199, 200, 201, 202, 203, 204, 205, 206, 207 | Cleavage by Pepsin | Uniprot |
| ND | 208 | Cleavage by BMP1 | Uniprot |

For the avoidance of doubt, the present disclosure includes modified nucleic acid release domains, including without limitation a nucleic acid release domain of the present disclosure in which at least one amino acid of the nucleic acid release domain includes a modification disclosed herein.

Stability Domains

In some embodiments, a "stability domain" of a mini-nucleosome is an amino acid domain that allows loaded mini-nucleosomes to stay stable in bodily fluids, cytoplasm and the nucleus.

Particle stability is important for safe passage into cells and longevity of expression. There are several reasons for particles to lose stability. First, particles should be stable in blood and other bodily fluids. Secondly, particles need to safely traverse the endosomal entry and escape safely to make it out to the cytoplasm. Viral particles or recycled receptors use several domains to enter the endosome and escape it. We provide examples of mini-nucleosome core proteins that incorporate endosomal entry and escape domains to increase stability. Domains mentioned herein, in Table 10 can be incorporated in mini-nucleosome core protein preferably at the C-terminal but also at any location to enhance stability of the mini-nucleosome core protein when combined with other domains provided in Table 3, 4, 5, 6, 7, 8, 9, 11 and 12. One skilled in the art may also contemplate fluorination of hydrophobic amino acids in the peptides to provide means of increasing protein stability, enhanced assembly etc. and to strengthen ligand-receptor interactions. One skilled in the art may also contemplate other post translational modifications to amino acids in the peptides to provide means of increasing protein stability, enhanced assembly etc. and to strengthen ligand-receptor interactions.

TABLE 10

| Exemplary Domains | SEQ ID NO: | Exemplary Utility | Reference |
|---|---|---|---|
| YTRF | 209 | Endocytosis signal for Transferrin receptor | Pandey K. N. 2009 |
| GDAY | 210 | Internalization signal for endocytosis of NPRA | Pandey K. N. 2009 |
| LLEE | 211 | Endosomal entry of Cd209 | Uniprot |
| RKKRRQRRR | 212 | Allows for endosomal escape | Najjar K, et. al., 2015 |
| YKSL | 213 | Endosomal entry of Cd209 | Uniprot |
| YENF | 214 | Endosomal entry of CELC10a | Uniprot |
| FQDL | 215 | Endosomal entry of CELC10a | Uniprot |
| YIGSR | 216 | Integrin conjugation, increased cell attachment | Graf, J et al, 1987 |
| IKVAV | 217 | Cell Membrane Penetrating Peptide, cell attachment | Tashiro, K, et al 1989 |

TABLE 10-continued

| Exemplary Domains | SEQ ID NO: | Exemplary Utility | Reference |
|---|---|---|---|
| EFAKFE | 218 | Recycling endosomes | Uniprot |
| LLEEEQLRGLGFRQTRGYKSL | 219 | Endosomal entry of Cd209 | Uniprot |

For the avoidance of doubt, the present disclosure includes modified nucleic acid release domains, including without limitation a nucleic acid release domain of the present disclosure in which at least one amino acid of the nucleic acid release domain includes a modification disclosed herein.

Oligomerization Domains

Oligomerization is a chemical process by which monomers associate to form multimers, including dimers and higher order macromolecular complexes. Oligomerization of proteinaceous molecules is often facilitated by domains that promote association of monomers.

In some embodiments, an "oligomerization domain" of a mini-nucleosome is an amino acid domain that allows mini-nucleosome core proteins or loaded mini-nucleosomes to associate in higher order structures such as homodimer, heterodimer, tetramer, octamers or other higher order structures. Oligomerization can reduce the size of a loaded mini-nucleosome. A multimers of mini-nucleosome core proteins can include two or more of the same mini-nucleosome core protein (e.g., two mini-nucleosome core proteins having the same amino acid sequence) and/or can include two more distinct mini-nucleosome core proteins (e.g., two mini-nucleosome core proteins having different amino acid sequences). Examples of oligomerization domains provided herein are not in any way limiting and one skilled in the art can appreciated that such domains may be recognized or identified by various methods including yeast-two hybrid screening, affinity purification coupled to mass spectrometry, text mining, or by application of artificial intelligence and machine learning. One skilled in the art can also create an inducible system of forming loaded mini-nucleosomes using an inducible homodimerization system and/or chemically induced dimerization.

In some embodiments, an oligomerization domain can include 3 or more amino acids. Oligomerization domains disclosed herein, e.g., in Table 11, can be incorporated in mini-nucleosome core protein at any position of a mini-nucleosome core protein, e.g., in combination with other domains provided herein, e.g., in Table 3, 4, 5, 6, 7, 8, 9,10 and 12. In certain particular embodiments, an oligomerization domain is positioned at the C-terminus of a mini-nucleosome core protein.

TABLE 11

| Exemplary Domains | SEQ ID NO: | Exemplary Utility | Reference |
|---|---|---|---|
| LIRERTE | 220 | Dimerization | Tucker C. L., et al, 1999 |
| LVEERTQ | 221 | Dimerization | Tucker C. L., et al, 1999 |
| IITFTK | 222 | Human PTB Domain helps dimerization | Markovtsov, V et al, 2000 |
| ILFNK | 223 | Human PTB Domain helps dimerization | Markovtsov, V et al, 2000 |
| PIRTLSK | 224 | Human PTB Domain helps dimerization | Markovtsov, V et al, 2000 |
| YGNSPLHRFK | 225 | Human PTB Domain helps dimerization | Markovtsov, V et al, 2000 |
| FFQKDR | 226 | Human PTB Domain helps dimerization | Markovtsov, V et al, 2000 |
| KSRP | 227 | Human PTB Domain helps dimerization | Markovtsov, V et al, 2000 |
| YVM | 228 | GRB2 domain mediated interaction | Uniprot |
| YMKM | 229 | YXXL domain helps oligomerization | Uniprot |
| RSSSFG | 230 | Protein-protein interaction | Uniprot |
| LKIRGRER, LKIRGRKR | 231, 232 | P53 oligomerization (part of) | Uniprot |
| HVIFKKVSR | 233 | Heterodimerization of SAG with Rho | Uniprot |
| RGPRV | 234 | Polymerization of Fibrin | Uniprot |
| RANVKHLK | 235 | Polymerization of CXCL12 | Uniprot |
| YPKAG, YPRTG | 236, 237 | Dimerization of DPP-IV | Tang, H-K et. al, 2011 |

For the avoidance of doubt, the present disclosure includes modified oligomerization domains, including without limitation an oligomerization domain of the present disclosure in which at least one amino acid of the oligomerization domain includes a modification disclosed herein.

Linkers

Figure 10:
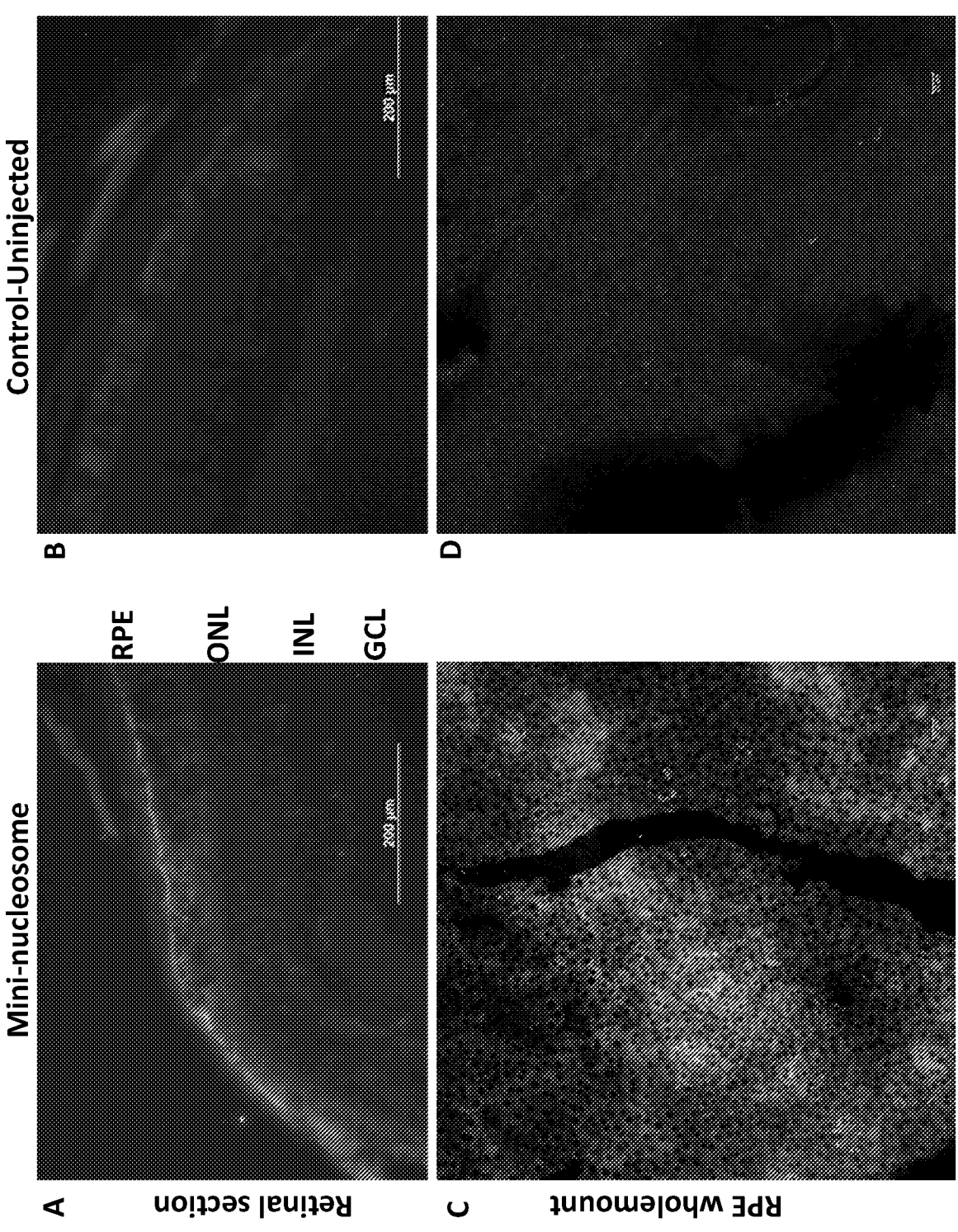
FIG. 10 is a set of images including panels A, B, C & D each of which is a fluorescent microscopy image that illustrates gene expression in mice RPE tissue of proteins encoded by nucleic acids present in loaded mini-nucleosomes. Panel A is a retinal section that demonstrates RPE specific expression. Panels B is a RPE wholemount that demonstrates RPE specific expression. Panels B and D represent untreated control samples of a retina section and RPE wholemount respectively.

It is known in the art of creating fusion proteins that proteins can, some instances, benefit from inclusion of a linker. The present disclosure includes mini-nucleosome core proteins that include one or more linkers, e.g., between two domains of a mini-nucleosome core protein. Linkers can contribute to protein structure stability. In some cases, linkers work as a separation between domains and in others they can directly affect function of proteins. Some linkers increase stiffness thus allowing effective separation of protein domains. Linkers also may be implemented to introduce cleavage sites. Linkers have been used for these reasons in the field of protein engineering. However, in the context of non-viral gene transfer this strategy hasn't been utilized. We show here that linkers can be successfully used to engineer domains for functional purposes such as selective transduction, gene delivery and transgene expression in desired cell types (FIG. 10). In some cases, linkers separate domains and those of skill in the art will appreciate that non-functional amino acids between functional domains have been referred to in the art as spacers. For the avoidance of doubt, the term linker as used herein includes spacers.

In some embodiments, a linker sequence can include 1 or more amino acids. Linker amino acid sequences disclosed herein, e.g., in Table 12, can be incorporated in mini-nucleosome core protein between domains as shown in SEQ ID NOS: 238-335, where a linker could be a linker having any of the amino acids or amino acid sequences provided in Table 1 and 12. The linkers may contain other amino acid sequences not limited to those provided in Table 12. Linker sequences may also be generated via program called LINKER, which searches database of linker sequences using user-chosen inputs and generate output of linker sequences that fit the criteria. Threonine, serine, glycine, proline, arginine and alanine are preferred residues in natural linkers and thus, in mini-nucleosome core proteins.

TABLE 12

| Linkers | SEQ ID NO: |
|---|---|
| L | 238 |
| LL | 239 |
| GSS | 240 |
| GSSGSS | 241 |
| GGS | 242 |
| SSS | 243 |
| SSSSSS | 244 |
| GGSGG | 245 |
| GGSGGGGG | 246 |
| GGSGGHMGSGG | 247 |
| A(EAAAK)$_n$A | 248 |
| (AP)$_n$ | 249 |
| (KP)$_n$ | 250 |
| (EP)$_n$ | 251 |
| GT | 252 |
| AAGAATAA | 253 |
| GSGSGSGS | 254 |
| GGSSG | 255 |
| PP | 256 |
| WW | 257 |
| MH | 258 |
| QP | 259 |
| PL | 260 |
| CM | 261 |

TABLE 12-continued

| Linkers | SEQ ID NO: |
|---|---|
| RM | 262 |
| RK | 263 |
| QR | 264 |
| HR | 265 |
| FW | 266 |
| PW | 267 |
| HR | 268 |
| DH | 269 |
| QS | 270 |
| WG | 271 |
| GM | 272 |
| KP | 273 |
| LF | 274 |
| YQ | 275 |
| RI | 276 |
| FY | 277 |
| FN | 278 |
| TA | 279 |
| HY | 280 |
| QV | 281 |
| DW | 282 |
| AW | 283 |
| YI | 284 |
| HT | 285 |
| CH | 286 |
| HP | 287 |
| TA | 288 |
| EM | 289 |
| KH | 290 |
| ML | 291 |
| AQ | 292 |
| YL | 293 |
| FI | 294 |
| KY | 295 |
| WR | 296 |
| LA | 297 |
| FS | 298 |
| AR | 299 |
| FN | 300 |
| ET | 301 |
| LW | 302 |
| NE | 303 |
| LH | 304 |
| MH | 305 |
| FY | 306 |
| PH | 307 |
| YE | 308 |
| HK | 309 |
| PW | 310 |
| HF | 311 |
| IM | 312 |
| DH | 313 |
| VH | 314 |
| DR | 315 |
| RI | 316 |
| QS | 317 |
| FC | 318 |
| GM | 319 |
| HR | 320 |
| HN | 321 |
| EC | 322 |
| VT | 323 |
| TH | 324 |
| CR | 325 |
| FQ | 326 |
| EV | 327 |
| KT | 328 |
| TD | 329 |
| SF | 330 |
| ST | 331 |
| QV | 332 |
| YK | 333 |
| NO | 334 |
| QK | 335 |

For the avoidance of doubt, the present disclosure includes a modified linker, including without limitation a linker of the present disclosure in which at least one amino acid of the linker includes a modification disclosed herein.

Mini-Nucleosome Core Proteins

A mini-nucleosome core protein can include one or more domains provided herein.

Mini-nucleosome proteins disclosed herein include at least a positively charged amino acid sequence that contains a nucleic acid binding domain, a targeting domain and/or a nucleic acid release domain and/or a stability domain. The mini-nucleosome core protein can be sequences that have e.g., at least 65%, at least 70%, at least 75%, at least 80%, at least 85%, at least 90%, at least 95%, at least 96%, at least 97%, at least 98%, at least 99%, or 100% sequence identity with a mini-nucleosome core protein as set forth in any of SEQ ID NOs: 336-388. In various embodiments, a mini-nucleosome core protein has at least 65%, at least 70%, at least 75%, at least 80%, at least 85%, at least 90%, at least 95%, at least 96%, at least 97%, at least 98%, at least 99%, or 100% sequence identity with a mini-nucleosome core protein as set forth in one of SEQ ID NOs: 388-394, 399, 401, or 447.

In some embodiments, a mini-nucleosome core protein may contain amino acid sequence length from 10 to 100 amino acids. Amino acids, e.g., 10, 12, 15, 20, 25, 30, 35, 40, 45, 50, 55, 60, 55, 70, 75, 80, 85, 90, 95, or 100 amino acids. In certain embodiments, a mini-nucleosome core protein can have a length of, e.g., 15 to 90 amino acids, 20 to 80 amino acids, 20 to 70 amino acids, 20 to 60 amino acids, or 30 to 40 amino acids.

In certain embodiments, a mini-nucleosome core protein includes one or more domains disclosed herein and one or more amino acids that is not present in a domain disclosed herein. In certain instances, amino acids not present in a domain disclosed herein that are N-terminal or C-terminal of a domain disclosed herein can be referred to as "flanking amino acids," and the sum of all amino acids present in a mini-nucleosome not present in any domain disclosed herein can be referred to as the "non-domain amino acids."

In various embodiments, non-domain amino acids of a mini-nucleosome core protein can have a sequence that contributes to the charge of the mini-nucleosome core protein. In various embodiments, non-domain amino acids of a mini-nucleosome core protein include at least 10% positively charged amino acids, e.g., at least 20%, at least 30%, at least 40%, at least 50%, at least 60%, at least 70%, at least 80%, at least 90%, or 100% positively charged amino acids.

In some embodiments, at pH7, a mini-nucleosome core protein may have a total positive charge in between 10 and 100.

In some embodiments, a mini-nucleosome core protein can contain one or more nucleic acid binding domains placed at any location of the amino acid sequence. In some cases, the mini-nucleosome core protein may contain only the nucleic acid binding domains. In some cases, the mini-nucleosome core protein may contain on the nucleic acid binding domains and the poly-Arginine domains. In some cases, the mini-nucleosome core protein may contain on the nucleic acid binding domains and the targeting domains. In some cases, the mini-nucleosome core protein may contain only the poly-Arginine domains and the targeting domains. In some cases, the mini-nucleosome core protein may contain only the poly-Arginine domains, nucleic acid release domains and the targeting domains.

In some embodiments, a mini-nucleosome core protein may contain one or more poly-Arginines placed at any location of the amino acid sequence. The poly-Arginine sequence may contain 4-30 Arginines.

In some embodiments, a mini-nucleosome core protein may contain one or more targeting domains The targeting domain may be placed at any location in the amino acid sequence of the mini-nucleosome core protein.

In some embodiments, a mini-nucleosome core protein may contain one or more nucleic acid release domains. Preferably, the nucleic acid release domains are placed in the middle of the amino acid sequence of the mini-nucleosome core protein. Preferably, the nucleic acid release domains are placed after 6 amino acids from the N-terminus or before 6 amino acids from the C-terminus.

In some embodiments, a mini-nucleosome core protein can contain one or more stability domains. Preferably, the stability domains are placed in the C-terminal of the amino acid sequence of the mini-nucleosome core protein. In some cases, the stability domains are placed in the N-terminal of the amino acid sequence of the mini-nucleosome core protein.

In some embodiments, a mini-nucleosome core protein can include one or more oligomerization domains. In certain particular embodiments, the oligomerization domains are positioned at the C-terminus of the amino acid sequence of a mini-nucleosome core protein. In some cases, the oligomerization domain is positioned at the N-terminus of the amino acid sequence of a mini-nucleosome core protein.

Thus, for the avoidance of doubt, a mini-nucleosome core protein, as set forth herein, can include (a) a nucleic acid binding domain (NABD), and (b) a targeting domain, and in some embodiments can include (a) a nucleic acid binding domain (NABD), (b) a targeting domain, and (c) a nucleic acid release domain. Those of skill in the art will appreciate from the present disclosure that a polypeptide including these components will constitute a mini-nucleosome core protein as disclosed herein, optionally subject to additional limitations set forth herein and/or including, without limitation, one or more further domains provided herein or otherwise known in the art. In some embodiments, a mini-nucleosome core protein can include a nucleic acid binding domain having at least 65% sequence identity with a nucleic acid binding domain as set forth in any of SEQ ID NOs: 1-28 (e.g., as set forth in Table 3), e.g., at least 65%, at least 70%, at least 75%, at least 80%, at least 85%, at least 90%, at least 95%, and/or that differs from a nucleic acid binding domain as set forth in any of SEQ ID NOs: 1-28 by no more than two amino acid changes (e.g., a deletion, addition, or substitution, e.g., a conservative substitution) or no more than one amino acid changes. In some embodiments, a mini-nucleosome core protein can include a targeting domain that is a cell attachment targeting domain having at least 65% sequence identity with a cell attachment targeting domain as set forth in any of SEQ ID NOs: 29-53 (e.g., as set forth in Table 4), e.g., at least 65%, at least 70%, at least 75%, at least 80%, at least 85%, at least 90%, at least 95%, and/or that differs from a cell attachment targeting domain as set forth in any of SEQ ID NOs: 29-53 by no more than two amino acid changes (e.g., a deletion, addition, or substitution, e.g., a conservative substitution) or no more than one amino acid changes. In some embodiments, a mini-nucleosome core protein can include a targeting domain that is a cell attachment targeting domain having at least 65% sequence identity with a cell attachment targeting domain as set forth in any of SEQ ID NOs: 54-81 (e.g., as set forth in Table 5), e.g., at least 65%, at least 70%, at least 75%, at least 80%, at least 85%, at least 90%, at least 95%, and/or that differs from a cell attachment targeting domain as set forth in any of SEQ ID NOs: 54-81 by no more than two amino acid changes (e.g., a deletion, addition, or substitution, e.g., a conservative substitution) or no more than one amino acid changes. In some embodiments, a mini-nucleosome core protein can include a targeting domain that is an internalization targeting domain having at least 65% sequence identity with an internalization targeting domain as set forth in any of SEQ ID NOs: 82-115 (e.g., as set forth in Table 6), e.g., at least 65%, at least 70%, at least 75%, at least 80%, at least 85%, at least 90%, at least 95%, and/or that differs from an internalization targeting domain as set forth in any of SEQ ID NOs: 82-115 by no more than two amino acid changes (e.g., a deletion, addition, or substitution, e.g., a conservative substitution) or no more than one amino acid changes. In some embodiments, a mini-nucleosome core protein can include a targeting domain that is a nucleus targeting domain having at least 65% sequence identity with a nucleus targeting domain as set forth in any of SEQ ID NOs: 116-139 (e.g., as set forth in Table 7), e.g., at least 65%, at least 70%, at least 75%, at least 80%, at least 85%, at least 90%, at least 95%, and/or that differs from a nucleus targeting domain as set forth in any of SEQ ID NOs: 116-139 by no more than two amino acid changes (e.g., a deletion, addition, or substitution, e.g., a conservative substitution) or no more than one amino acid changes. In some embodiments, a mini-nucleosome core protein can include a targeting domain that is a cell-type specific targeting domain having at least 65% sequence identity with a cell-type specific targeting domain as set forth in any of SEQ ID NOs: 140-164 (e.g., as set forth in Table 8), e.g., at least 65%, at least 70%, at least 75%, at least 80%, at least 85%, at least 90%, at least 95%, and/or that differs from a cell-type specific targeting domain as set forth in any of SEQ ID NOs: 140-164 by no more than two amino acid changes (e.g., a deletion, addition, or substitution, e.g., a conservative substitution) or no more than one amino acid changes. In some embodiments, a mini-nucleosome core protein can include a nucleic acid release domain having at least 65% sequence identity with a nucleic acid release domain as set forth in any of SEQ ID NOs: 165-208 (e.g., as set forth in Table 9), e.g, at least 65%, at least 70%, at least 75%, at least 80%, at least 85%, at least 90%, at least 95%, and/or that differs from a nucleic acid release domain as set forth in any of SEQ ID NOs: 165-208 by no more than two amino acid changes (e.g., a deletion, addition, or substitution, e.g., a conservative substitution) or no more than one amino acid changes. In some embodiments, a mini-nucleosome core protein can include a stability domain having at least 65% sequence identity with a stability domain as set forth in any of SEQ ID NOs: 209-219 (e.g., as set forth in Table 10), e.g., at least 65%, at least 70%, at least 75%, at least 80%, at least 85%, at least 90%, at least 95%, and/or that differs from a stability domain as set forth in any of SEQ ID NOs: 209-219 by no more than two amino acid changes (e.g., a deletion, addition, or substitution, e.g., a conservative substitution) or no more than one amino acid changes. In some embodiments, a mini-nucleosome core protein can include an oligomerization domain having at least 65% sequence identity with an oligomerization domain as set forth in any of SEQ ID NOs: 220-237 (e.g., as set forth in Table 11), e.g., at least 65%, at least 70%, at least 75%, at least 80%, at least 85%, at least 90%, at least 95%, and/or that differs from an oligomerization domain as set forth in any of SEQ ID NOs: 220-237 by no more than two amino acid changes (e.g., a deletion, addition, or substitution, e.g., a conservative substitution) or no more than one amino acid changes. In some embodiments, a mini-nucleosome core protein can include a linker domain having at least 65% sequence identity with a linker domain as set forth in any of SEQ ID NOs: 238-335 (e.g., as set forth in Table 12), e.g., at least 65%, at least 70%, at least 75%, at least 80%, at least 85%, at least 90%, at least 95%, and/or that differs from a linker domain as set forth in any of SEQ ID NOs: 238-335 by no more than two amino acid changes (e.g., a deletion, addition, or substitution, e.g., a conservative substitution) or no more than one amino acid changes.

Those of skill in the art that domains of a mini-nucleosome core protein provided herein can be arranged in any order, orientation, or sequence as provided herein or as will otherwise be understood from the present disclosure by those of skill in the art. For instance, those of skill in the art will appreciate the intended use of linkers, e.g., as optional sequences that can be included individually or in a tandem plurality between any pair of domains or adjacent to any domain, with or without one or more intervening amino acids not specifically disclosed herein. Thus, for example, a NABD can be C-terminal or N-terminal of a targeting domain. Additional domains provided herein, including without limitation additional NABDs or additional targeting domains, can be C-terminal or N-terminal of NABD and C-terminal or N-terminal of a targeting domain. Moreover, for each domain present in mini-nucleosome core protein, including a linker, one or more linker domains can be included C-terminal of the domain or N-terminal of the domain. Exemplary mini-nucleosome proteins are provided herein. As will be readily apparent to those of skill in the art from the present disclosure, domains provided herein are modular and can be included with their intended function in any order and/or thereby provide the mini-nucleosome with the intended utility or functionality regardless of the order in which they are present.

Those of skill in the art will further appreciate that mini-nucleosome core proteins of the present disclosure can include any number or type of modifications (e.g., posttranslational modifications) known in the art. Such modifications include, without limitation, pegylation, acetylation, methylation, glycosylation, phosphorylation, sumoylation, amidation, lipidation, and/or methylation. In various embodiments, a mini-nucleosome core protein can be pegylated.

In some embodiments, a mini-nucleosome core protein is modified by association of the mini-nucleosome core protein with polyethylene glycol (PEG). PEG are nonionic, nontoxic, biocompatible and highly hydrophilic polymers. PEG is mostly used for the covalent modification of biological macromolecules and surfaces. PEG conjugation increases the apparent size of the polypeptide, thus reducing the renal filtration and altering biodistribution. PEGylation of peptides can enhance therapeutic properties due to their increased solubility (for hydrophobic peptides), prolonged half-life through reduced renal clearance, and masked antigenicity for minimum immune response in the host. PEGs of varying PEG chain lengths have been used in FDA cleared drugs with molecular weights ranging from 5-40 kDa. In FIGS. 1, 3, 4, 5 and 6, we show schematics of how PEGs of varying PEG chain lengths can be utilized to provide mini-nucleosome core proteins of varying size.

Figure 2:
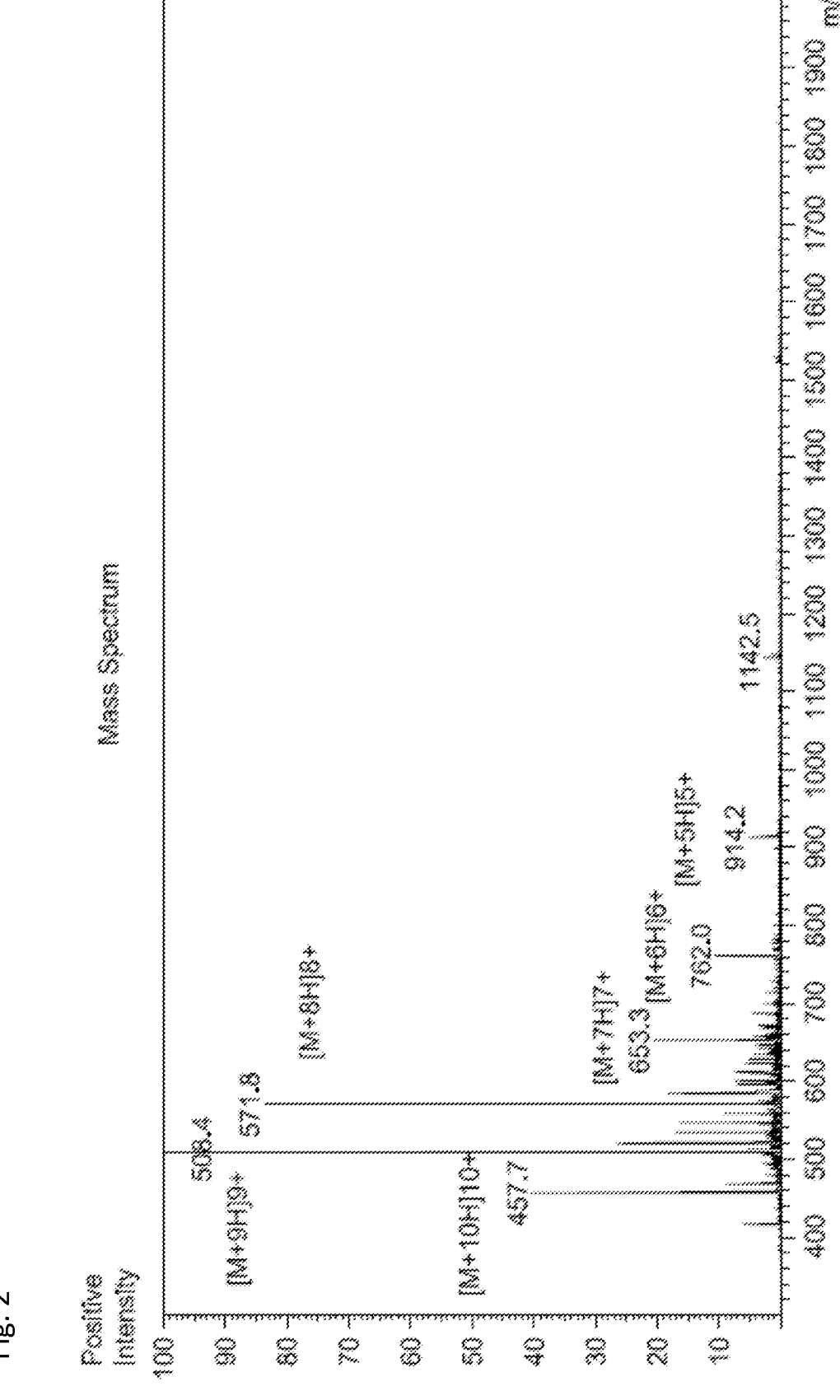
FIG. 2 is a chart showing data obtained from mass spectrometry analyses after the formulation of the mini-nucleosome core protein modified with PEG12 at the first lysine residue in the sequence.
Figure 3:
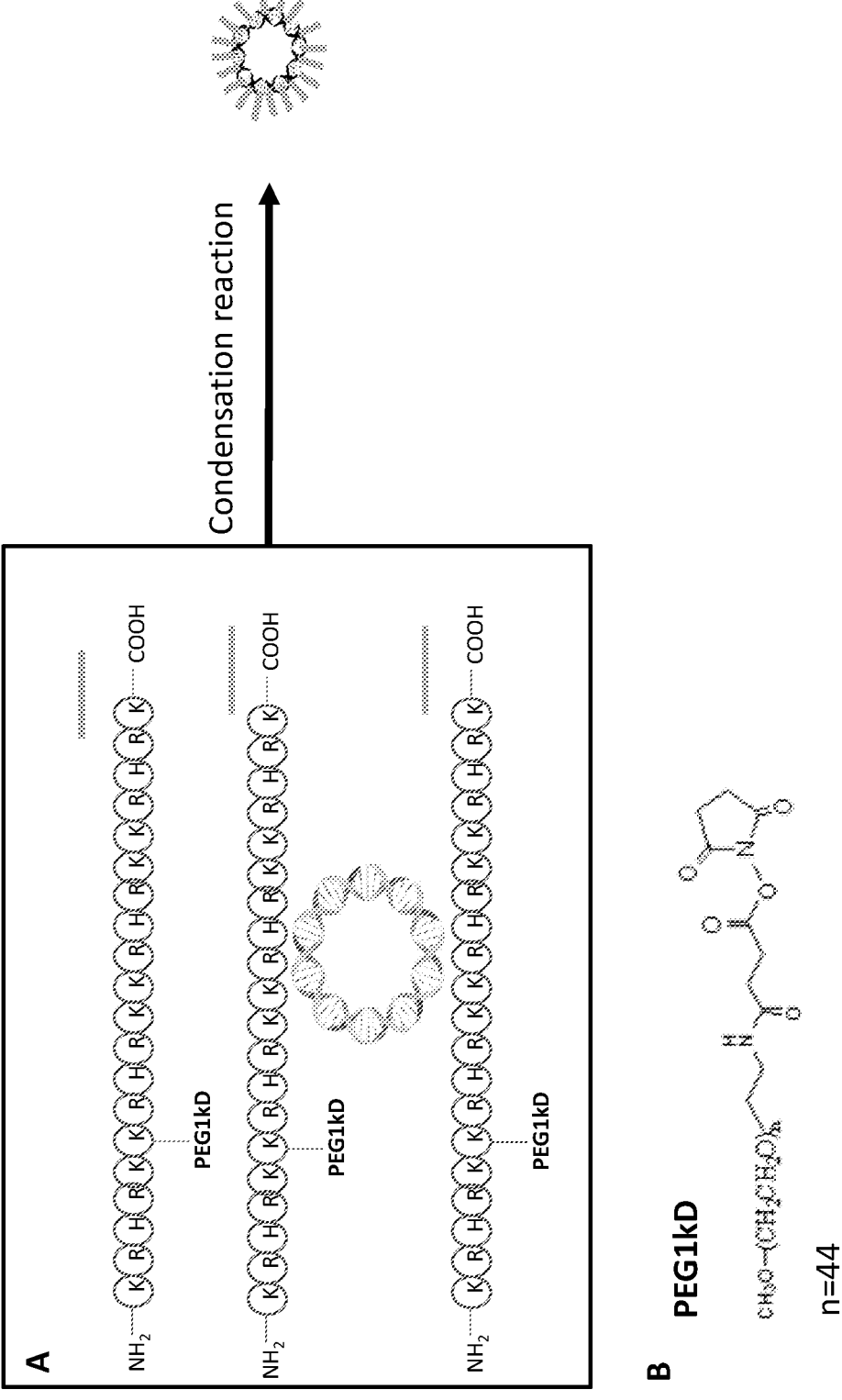
FIG. 3 is a schematic representation of how a mini-nucleosome core protein modified with 1 kDa PEG at a lysine residue can undergo a condensation reaction with a DNA molecule to produce a loaded mini-nucleosome.
Figure 5:
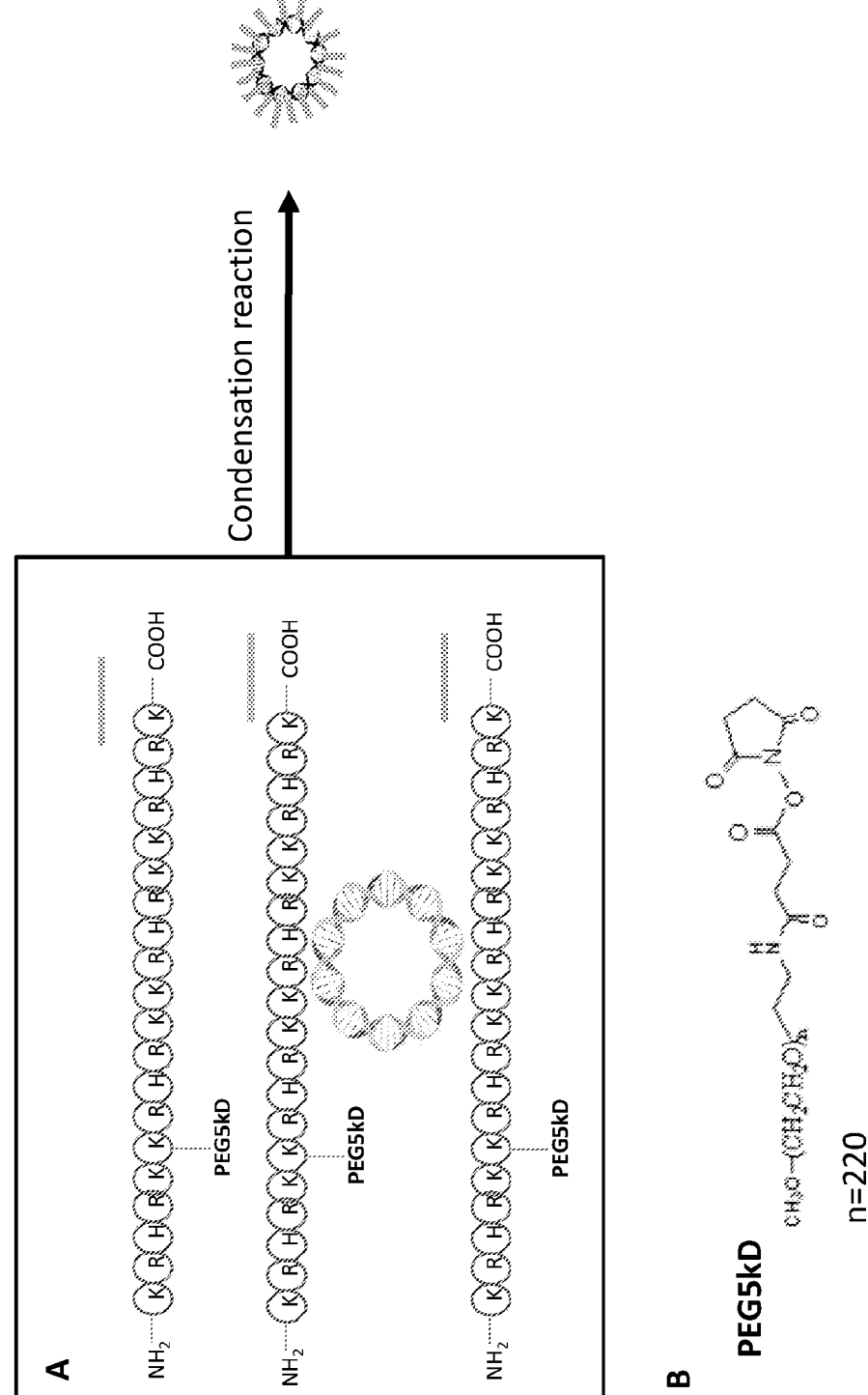
FIG. 5 includes panel A and panel B. Panel A is a schematic representation of how a mini-nucleosome core protein modified with 5 kDa PEG, shown in Panel B, at a lysine residue can undergo a condensation reaction with a DNA molecule to produce a loaded mini-nucleosome. Each nucleic acid molecule may require several (1 to 1000) mini-nucleosome core proteins to neutralize the negative charges in the DNA to form a loaded mini-nucleosome. The schematic is intended only as a cartoon diagram, and is not intended to be representative of the actual structure of loaded mini-nucleosomes except to the extent that loaded mini-nucleosome includes nucleic acids associated with core proteins.
Figure 6:
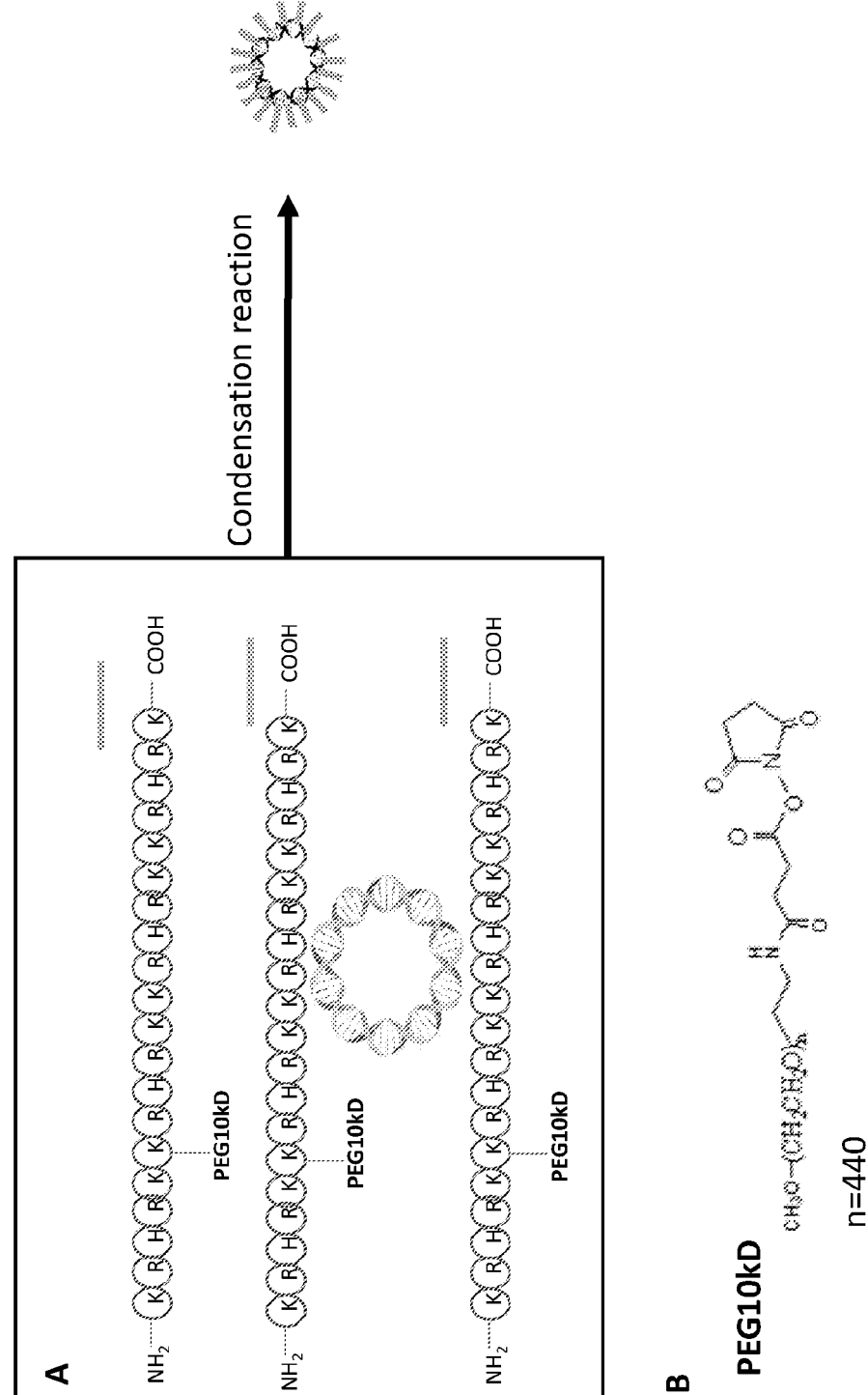
FIG. 6 includes panel A and panel B. Panel A is a schematic representation of how a mini-nucleosome core protein modified with 10 kDa PEG, shown in panel B, at a lysine residue can undergo a condensation reaction with a DNA molecule to produce a loaded mini-nucleosome. Each nucleic acid molecule may require several (1 to 1000) mini-nucleosome core proteins to neutralize the negative charges in the DNA to form a loaded mini-nucleosome. The schematic is intended only as a cartoon diagram, and is not intended to be representative of the actual structure of loaded mini-nucleosomes except to the extent that loaded mini-nucleosome includes nucleic acids associated with core proteins.

Many current particles use PEG of size 10 kDa or larger, however, a drawback to using larger PEG size is that it also increases particle size. (Feuz L. et al. 2007). The present disclosure provides, among other things, particles with varying PEG length to formulate mini-nucleosomes with varying size-preferably smaller than 20 μm in diameter. In FIG. 1, we show a minimal PEG length of 12 chains and how it can be utilized to modify amino acids in the mini-nucleosome core proteins. The final size of the loaded mini-nucleosome also depends on the PEG size used to modify the mini-nucleosome core proteins. FIG. 2 shows that by attaching PEG12, the molecular weight of the peptide increases accordingly, however doesn't change the physical characteristics such as solubility of the peptide.

In some embodiments, a mini-nucleosome core protein can have a total molecular weight between 1700 g/mol and 20000 g/mol, e.g., 1700, 1800, 1900, 2000, 2500, 3000, 3500, 4000, 4500, 5000, 5500, 6000, 6500, 7000, 7500, 8000, 8500, 9000, 9500, 10000, 10500, 11000, 11500, or 20000 g/mol. In various embodiments, a mini-nucleosome core protein can have a total molecular weight between 100Kda and 10,000 kDa, e.g, 100, 200, 500, 1000, 2,000, 3000, 5000, 8000, and 10000 kDa.

The amino acid sequence may be used in reverse or in any order. One may also contemplate changing one or non-essential amino acid in the domain to obtain same charge or other properties of the domain. For the avoidance of doubt, any mini-nucleosome core protein provided herein, including the exemplary mini-nucleosome core proteins provided in Table 13 below, can be modified at any amino acid and/or with any of one or more of the modifications provided herein.

TABLE 13

| Exemplary Mini-nucleosome core protein sequences | SEQ ID NO. | Net charge at pH7 | Number of residues | Molecular weight (g/mol) | Iso-electric point (pH) |
|---|---|---|---|---|---|
| KRHRKLREKRHRKLRRRRRLKRHRKKRHRKLREK | 336 | 22.4 | 34 | 4773.77 | 12.72 |
| KRHRKGSSLREKRHRKLRRRRRLKRHRKKRHRKLR EGGSK | 337 | 22.4 | 40 | 5206.16 | 12.72 |
| KRHRKREGSSLREKRHRKNDLRRRRRLKRHRKKRH RKLREGGSK | 338 | 21.4 | 44 | 5720.65 | 12.46 |
| KKPKKREGSSLREKRHRKNDLRRRRRLKRHRKKRH RKLREGGSK | 339 | 21.3 | 44 | 5624.6 | 12.38 |
| RRLARRGSSLREKRHRKLRRRRRLKKPKKKRHRKLR EGGSK | 340 | 22.2 | 41 | 5213.23 | 12.72 |
| KRHRKLREKRHRKLREKRHRKLKRHRKKRHRKLRE K | 341 | 21.5 | 36 | 4984 | 12.48 |
| KRHRKRILREKRHRKLREARKRHRKLKRHRKKRHR KLREK | 342 | 23.5 | 40 | 5480.61 | 12.56 |
| KRHRKKGKKKKGEKGKKKLKGKKKLRRRRRRRQR R | 343 | 25.1 | 35 | 4507.55 | 12.78 |
| KRHRKAPAPKGKKKKGEKGKKKLKGKKKLKPKPRR RRRRQRR | 344 | 27.1 | 43 | 5294.51 | 12.79 |
| KRHRKGGSGGKGKKKKGEKGKKKLKGKKKLARRR RRRQRR | 345 | 25.1 | 41 | 4893.91 | 12.78 |
| KRHRKLREKRHRKRRRRRRRKRHRKLREKRRQRR | 346 | 24.3 | 34 | 4906.85 | 12.84 |
| KRHRKKRHRKKRVKKKRHRKRRRRRRDSLL | 347 | 21.3 | 30 | 4141.02 | 12.86 |
| KRHRKKRHRKYQKRVKKKRHRKSSSRRRRRRDSLL | 348 | 21.3 | 35 | 4693.55 | 12.64 |
| KRHRKKKEEEKKEEEKKEEEKRRRRRRRQRRR | 349 | 12.1 | 32 | 4473.09 | 11.61 |
| KRHRKWRKKEEEKKEEEKKEEEKRIRRRRRRRQRRR | 350 | 14.1 | 36 | 5084.83 | 11.79 |
| KRHRKRGDKRHRKRRRRRKRHRKTPHKKK | 351 | 20.4 | 29 | 3964.72 | 12.82 |
| KRHRKFIRGDKRHRKRRRRRKRHRKLATPHKKK | 352 | 20.4 | 33 | 4409.28 | 12.82 |
| KRHRKRGDKRHRKRRRRRKRHRKGSSRNTPHQKKK K | 353 | 22.4 | 36 | 4722.51 | 12.86 |
| KRHRKRGDKRHRKLKRHRKRRRRKRHRKTPHKK | 354 | 22.5 | 33 | 4499.37 | 12.86 |
| KRHRKRGDKRHRKKRHRKKRHRKRGDKKTK | 355 | 19.4 | 30 | 3983.71 | 12.5 |
| KRHRKRGDKKRKKKKRGDKKRRRRRKKKPPSY | 356 | 21.1 | 32 | 4172.01 | 12.33 |
| KRHRKRKRKRKRRRRRKKKRASSLNIAKRRRR | 357 | 24.1 | 32 | 4308.23 | 13.26 |
| KRKKRKGKRLKRRREKRHRKRASSLNIAKKKK | 358 | 20.1 | 32 | 4054.95 | 12.68 |
| KRKKRRLKRKRKRRRRREKRHRKRRRQRRRKK | 359 | 27.1 | 32 | 4618.63 | 13.01 |
| KRKKRKRKRKRRRRKRHRKLRERKRRLREKK | 360 | 24.1 | 31 | 4420.4 | 12.75 |
| KRKNGRKRKRKKRHRKKKKRRRRRKRHRKNGRKKK | 361 | 28.2 | 34 | 4587.61 | 13.2 |

TABLE 13-continued

| Exemplary Mini-nucleosome core protein sequences | SEQ ID NO. | Net charge at pH7 | Number of residues | Molecular weight (g/mol) | Iso-electric point (pH) |
|---|---|---|---|---|---|
| KRHRKWRHRARSKRHRKKKKKKRKKRKGK | 362 | 22.3 | 29 | 3902.77 | 13.03 |
| KRHRKRGDKRHRKKKKNRRKKRALRKKRKGK | 363 | 22.2 | 31 | 4047.92 | 12.73 |
| KKRKRGGKTKKKAKKALKKKKKGKKKKRRRRKKA APKK | 364 | 28 | 38 | 4541.77 | 12.87 |
| KKKAYPKALKKPKKKKKAYPKALKRRRRRKNRRK KRALKRHRK | 365 | 29.1 | 43 | 5481.83 | 12.53 |
| KTRSKKKKKRGDKKKKNRRKKRALNTQIHKKKKKA APKK | 366 | 23.1 | 39 | 4725.78 | 12.4 |
| KGKKKKGEKGKKKLKGKKKLRRRRRSPKKRRQRR | 367 | 23 | 34 | 4242.23 | 12.68 |
| KRHRKLREKRHRKLRRRRRLKRHRKKRHRKLREK | 368 | 22.4 | 34 | 4773.77 | 12.72 |
| KRHRKLREKRHRKLREKRHRKLKRHRKKRHRKLRE K | 369 | 21.5 | 36 | 4984 | 12.48 |
| KRHRKKGKKKKGEKGKKKLKGKKKLRRRRRRQR R | 370 | 25.1 | 35 | 4507.55 | 12.78 |
| KRHRKLREKRHRKRRRRRRRKRHRKLREKRRQRR | 371 | 24.3 | 34 | 4906.85 | 12.84 |
| KRHRKKRHRKKRVKKKRHRKRRRRRRDSLL | 372 | 21.3 | 30 | 4141.02 | 12.86 |
| KRHRKKKEEEKKEEEKKEEEKRRRRRRRQRRR | 373 | 12.1 | 32 | 4473.09 | 11.61 |
| KRHRKQSKKEEEKKEEEKKEEEKNQRRRRRRRQRR R | 374 | 12.1 | 36 | 4930.53 | 11.61 |
| KRHRKRGDKRHRKRRRRRKRHRKTPHKKK | 375 | 20.4 | 29 | 3964.72 | 12.82 |
| KRHRKRGDKRHRKLKRHRKRRRRRKRHRKTPHKK | 376 | 22.5 | 33 | 4499.37 | 12.86 |
| KRHRKRGDKRHRKKRHRKKRHRKRGDKKTK | 377 | 19.4 | 30 | 3983.71 | 12.5 |
| KRHRKRGDKRKKKKRGDKKRRRRRKKKPPSY | 378 | 21.1 | 32 | 4172.01 | 12.33 |
| KRHRKGGSRGDKKRKKKKRGDSSSKKRRRRRKKKP PSY | 379 | 21.1 | 38 | 4634.43 | 12.33 |
| KRHRKRKRKRKRRRRRKKKRASSLNIAKRRRR | 380 | 24.1 | 32 | 4308.23 | 13.26 |
| KRKKRKGKRLKRRREKRHRKRASSLNIAKKKK | 381 | 20.1 | 32 | 4054.95 | 12.68 |
| KRKKRRLKRKRKRRRRREKRHRKRRRQRRRKK | 382 | 27.1 | 32 | 4618.63 | 13.01 |
| KRKKRRKRKRRRRRKRHRKLRERKRRLREKK | 383 | 24.1 | 31 | 4420.4 | pH 12.75 |
| KRKNGRKRKRKKRHRKKKKRRRRKRHRKNGRKKK | 384 | 28.2 | 34 | 4587.61 | 13.2 |
| KRKWRNGRKRKRQKRHRKKKKKRARRRRKRHRKNG RKHKKK | 385 | 30.3 | 40 | 5422.54 | 13.26 |
| KRHRKWRHRARSKRHRKKKPKKRKKRKGK | 386 | 21.3 | 29 | 3871.71 | 13.03 |
| KRHRKPKPRIWRHRARSRDKRHRKKKPKKRKKRKG K | 387 | 23.3 | 36 | 4734.73 | 12,78 |
| KKKRKLRGDLKRKGSSYQPLAPAPKKKRKRGDKRK LFYQPL | 388 | 16.0 | 41 | 4894.87 | 11.77 |

For the avoidance of doubt, the present disclosure includes modified mini-nucleosome core proteins, including without limitation a mini-nucleosome core protein of the present disclosure in which at least one amino acid of the mini-nucleosome core protein includes a modification disclosed herein.

Modified Mini-Nucleosome Core Proteins

The present disclosure provides, among other things, mini-nucleosome core proteins that include at least one modified amino acid residue. Various modifications and certain advantageous thereof are provided throughout the present disclosure. For the avoidance of doubt, the present disclosure provides that any and/or all residues of any and/or all domains, mini-nucleosome core proteins, or other polypeptides provided herein, and/or any and all residues of any portion(s) thereof, can be modified in accordance with the present disclosure of modifications. Moreover, various advantages resulting from any such amino acid modification as disclosed herein do not depend upon the specific residue within a domain, mini-nucleosome core protein, or other polypeptide that is modified, and/or the position thereof within a domain, mini-nucleosome core protein, or other polypeptide. In various embodiments, various advantages resulting from any such amino acid modification as disclosed herein are realized upon inclusion of the modification at any of one or more residues of a domain, mini-nucleosome core protein, or other polypeptide in accordance with the present disclosure.

In various embodiments, a modification of an amino acid present in a domain, mini-nucleosome core protein, or other polypeptide can be any of:

(i) phosphorylation;

(ii) sulfation;

(iii) glycosylation (e.g., N-glycosylation, C-glycosylation, and/or O-glycosylation);

(iv) prenylation (e;g., geranylation and/or farnesylation);

(v) methylation;

(vi) sialylation;

(vii) lipidation and/or lipoylation;

(viii) acetylation;

(ix) hydroxylation;

(x) palmitoylation;

(xi) mannosylation;

(xii) myristoylation;

(xiii) fucosylation;

(xiv) pegylation; and/or (xv) any combination thereof, including any number of one or more of the modifications or variants thereof, e.g., in a branched or unbranched modification chain.

Examples of modifications and modified mini-nucleosome core proteins are found, e.g., in FIGS. 20-31. Those of skill in the art will appreciate that, even absent express disclosure of the atoms of any given chemical linkage between a modification and amino acid, or between two modifications in a modification chain, that such linkages are well known in the art of amino acids and amino acid modifications.

Phosphorylated Mini-Nucleosome Core Proteins

Phosphorylation typically occurs on serine, threonine, tyrosine, and/or histidine residues (S, Y, T, and/or H; see, e.g., FIG. 27). Phosphorylation includes covalent linkage of a phosphate group to an amino acid residue, such as to a hydroxyl side chain of a serine residue, a hydroxyl side chain of a threonine residue, or a phenolic side chain of a tyrosine residue. Phosphorylation is known to mediate protein functions including target binding, cellular localization, and enzymatic activity, among others. The present disclosure includes modified mini-nucleosome core proteins in which one or more threonine, tyrosine, and/or histidine residues are phosphorylated, e.g., mono-phosphorylated or bis-phosphorylated. In some embodiments, a modified mini-nucleosome core protein is phosphorylated by incorporation of protected phosphor-amino acids during polypeptide synthesis. In some embodiments, a modified mini-nucleosome core protein is phosphorylated by post-synthesis phosphorylation of residues, e.g., serine, threonine, or tyrosine residues. In general, at least certain advantages of phosphorylation have been demonstrated, e.g., by Kobayashi et. Al. 1996 (showing phosphorylation of ATF-1 increased DNA binding capabilities), Robin et. Al, 2003 (showing phosphorylation of GSTA4-4 increased targeting of GSTA4-4 to mitochondria by interaction with mitochondrial surface proteins), Rossetto D et al. 2012 (showing that phosphorylation of extra-nucleosomal histone $H_1$, a linker Histone, increases stabilization of the nucleosome), and Anai et al, 2007

(showing a bis-phosphorylated peptide with increased binding affinity and selectivity for WW domains).

In various embodiments, phosphorylation of one more residues of a modified mini-nucleosome core protein increases the stability of the modified mini-nucleosome core protein, or loaded mini-nucleosome core proteins including the same, as compared to a reference mini-nucleosome core protein that does not include one or more of the phosphorylation modifications. In various embodiments, phosphorylation of one more residues of a modified mini-nucleosome core protein increases the half-life and/or bioavailability of the modified mini-nucleosome core protein, or loaded mini-nucleosome core proteins including the same, as compared to a reference mini-nucleosome core protein that does not include one or more of the phosphorylation modifications. In various embodiments, phosphorylation of one more residues of a modified mini-nucleosome core protein increases the affinity or avidity with a target cell or other binding partner of the modified mini-nucleosome core protein, or loaded mini-nucleosome core proteins including the same, as compared to a reference mini-nucleosome core protein that does not include one or more of the phosphorylation modifications. In various embodiments, phosphorylation of one more residues of a modified mini-nucleosome core protein increases the rate at which the modified mini-nucleosome core protein, or loaded mini-nucleosome core proteins including the same, enters one or more target cells (i.e., crosses the cell membranes of target cells) as compared to a reference mini-nucleosome core protein that does not include one or more of the phosphorylation modifications. In various embodiments, phosphorylation of one more residues of a modified mini-nucleosome core protein increases the affinity or avidity of the mini-nucleosome core protein with one or more nucleic acid cargos as compared to a reference mini-nucleosome core protein that does not include one or more of the phosphorylation modifications. Thus, in some embodiments, phosphorylation of one more residues of a modified mini-nucleosome core protein increases delivery of a mini-nucleosome core protein, loaded mini-nucleosome core protein, or nucleic acid cargo of a mini-nucleosome core protein to a target cell, tissue, or organ.

In certain particular embodiments of the present disclosure, phosphorylation of one more residues of a modified mini-nucleosome core protein decreases accumulation in liver of the modified mini-nucleosome core protein, or loaded mini-nucleosome core proteins including the same, as compared to a reference mini-nucleosome core protein that does not include one or more of the phosphorylation modifications. This is particularly advantageous in view of the empirical observation that most molecules and drug products, including adeno-associated viruses injected intravenously, accumulate in liver cells. Thus, phosphorylated mini-nucleosome core proteins of the present disclosure advantageously provide a means of nucleic acid delivery that reduces accumulation in liver of mini-nucleosome core proteins and/or loaded mini-nucleosome core proteins.

In certain particular embodiments of the present disclosure, targeting of a phosphorylated mini-nucleosome core protein, or loaded mini-nucleosome core protein including the same, to a target, target cell, or target tissue, e.g., by inclusion in the mini-nucleosome core protein of a targeting domain as provided herein, is increased in affinity, avidity, or rate as compared to a reference mini-nucleosome core protein that does not include one or more of the phosphorylation modifications. For example, phosphorylated mini-nucleosome core proteins, and loaded mini-nucleosome core proteins including the same, that are targeted to neurons, e.g., by inclusion of targeting domain for neuronal targeting, can deliver nucleic acid cargos to neurons with increased affinity, avidity, or rate as compared to a reference mini-nucleosome core protein that does not include one or more of the phosphorylation modifications.

Exemplary domains that can be included in mini-nucleosome core proteins, and which can optionally be modified by phosphorylation at one more residues, are provided in below Tables 14-16.

Table 14 includes exemplary targeting domains that target neurons, and which target neurons with greater affinity, avidity, or rate when phosphorylated at one or more under-lined serine, threonine, and/or tyrosine residues.

Table 15 includes exemplary targeting domains that target muscle cells, and which target muscle cells with greater affinity, avidity, or rate when phosphorylated at one or more underlined serine, threonine, and/or tyrosine residues.

Table 16 includes exemplary targeting domains that target endothelial cells, and which target endothelial cells with greater affinity, avidity, or rate when phosphorylated at one or more underlined serine, threonine, and/or tyrosine residues.

TABLE 14

| Exemplary mini-nucleosome core protein domain | SEQ ID NO. |
| --- | --- |
| KKRHRKYPKKSRRSRLRNFRGDYNQYTRRRRR | 397 |
| KRKKRHRKRIRGRDVKYSYARKRHRKFQKWNYK | 398 |
| KKRHRKARRVTALREGRRHRKGERRRRRPPSY | 399 |
| KKRHRKALGSSDSLLARKRHRKKRKRKKRHRK | 400 |
| KKRHRKGSSKKRPKPRKKRHRKKRHRKKRHRKLL | 401 |
| KKRHRKRIQRRSRRGSSKHKGRDVILKKDVRKRHRK | 402 |
| KKRHRKKKDGKKRKRLLRKKHARALYIGSRKRGRKP | 403 |
| KKRHRKPPKDGEAQPKRHRKRRRRRKRHRKLRA | 404 |
| KKRKKRHRKLARGPRVARKRHRKRRRRRDRYQRL | 405 |

TABLE 15

| Exemplary mini-nucleosome core protein domain | SEQ ID NO. |
| --- | --- |
| KKRHRKRGFRRVSRRRGKKKEQRRERNARGKKGKRHRK | 406 |
| KKRHRKRRQPPRSISSHPLRKKRKGKTRRLRGDLRNSRR | 407 |
| KKRHRKRLRKKRKGKGSRPGSGFVKKTKQRRRRR | 408 |
| KKRHRKHRTKSGRSRIRKKRKGKRHARKKRRQRRRPPSY | 409 |
| KKRHRKKPVNRWSARNRRKKRALLRRRHYQRL | 410 |
| KKRHRKRKYKQCHKKGGHCFPKEKARRKKRKGKNEI | 411 |
| KKRHRKRIKKYRYYLKPLKKKRKKRKGKRHYLIIR | 412 |
| KKRHRKDRGRKKRRQRRRPQKPRKKRRQRRFQQI | 413 |
| KKRHRKGSSDPFRDDPFHRKRHRKKRHRKKRHRGRR | 414 |
| KKRHRKARSKTFNTHPQSTPYKRHRKRKKRKGKKRPK | 415 |
| RKKRKGKRAKRHRKKRHRKKPKNMTPYRSPPPYVPP | 416 |

TABLE 16

| Exemplary mini-nucleosome core protein domain | SEQ ID NO. |
| --- | --- |
| KKKRKRGDKRKRKRHRKKKRRRRLSIPPKA | 417 |
| KKKRKRGDKRKRKRHRKKKRRRRFQTPPQL | 418 |
| KKKRKRGDKRKRKRHRKKKRRRRLTPATAI | 419 |
| KKKRKRGDKRKRKRHRKKKRRRRSIGYPLP | 420 |
| KKKRKRGDKRKRKRHRKKKRRRRCLIRRTSIC | 421 |
| KKKRKRGDKRKRKRHRKKKRRRRCFFWKFRWMC | 422 |

Sulfated Mini-Nucleosome Core Proteins

Sulfation refers to the covalent linkage of sulfate to a tyrosine (Y) residue (see, e.g., FIG. 25). In certain embodiments, an amino acid immediately N-terminal to a sulfated tyrosine in a polypeptide is an amino acid selected from E, N, S, H, V, and D, and/or an amino acid immediately C-terminal to a sulfated tyrosine in a polypeptide is an amino acid selected from E, L, D, Q, P, T, R and Y. In general, sulfation is known to increase the affinity and/or avidity of protein-protein interactions. For example, sulfation is predicted to increase selectin binding for increased update into endothelial cells, and Farzan et al. 1999 demonstrated that sulfation of CCR5 facilitates HIV entry. Proteins known to undergo sulfation include G-protein-coupled receptors, adhesion molecules, hormones, and extracellular matrix proteins. Sulfation is known to contribute to L- and P-selectin-mediated neutrophil recruitment, and leukocyte rolling (Somers et al, 2003).

In various embodiments, sulfation of one more residues of a modified mini-nucleosome core protein increases affinity or avidity with a target cell or other binding partner of the modified mini-nucleosome core protein, or loaded mini-nucleosome core proteins including the same, as compared to a reference mini-nucleosome core protein that does not include one or more of the sulfation modifications. In various embodiments, sulfation of one more residues of a modified mini-nucleosome core protein increases affinity or avidity of binding with a target receptor of the modified mini-nucleosome core protein, or loaded mini-nucleosome core proteins including the same, as compared to a reference mini-nucleosome core protein that does not include one or more of the sulfation modifications. Thus, in some embodiments, sulfation of one more residues of a modified mini-nucleosome core protein increases delivery of a mini-nucleosome core protein, loaded mini-nucleosome core protein, or nucleic acid cargo of a mini-nucleosome core protein to a target cell, tissue, or organ.

In various embodiments, sulfation of one more residues of a modified mini-nucleosome core protein increases the rate at which the modified mini-nucleosome core protein, or loaded mini-nucleosome core proteins including the same, enters one or more target cells (i.e., crosses the cell membranes of target cells) as compared to a reference mini-nucleosome core protein that does not include one or more of the sulfation modifications.

In various embodiments, sulfation of one more residues of a modified mini-nucleosome core protein increases blood-brain barrier penetration by the modified mini-nucleosome core protein, or loaded mini-nucleosome core proteins including the same, as compared to a reference mini-nucleosome core protein that does not include one or more of the sulfation modifications.

In various embodiments, sulfation of one more residues of a modified mini-nucleosome core protein increases selectivity of the modified mini-nucleosome core protein, or loaded mini-nucleosome core proteins including the same, for target receptors, and/or selectivity of internalization after receptor binding, as compared to a reference mini-nucleosome core protein that does not include one or more of the sulfation modifications.

Table 17 includes exemplary sulfated domains for inclusion in mini-nucleosome core proteins that enhance binding to endothelial cell surface markers and/or increase update of mini-nucleosome core proteins and/or loaded mini-nucleosome core proteins by endothelial cells.

TABLE 17

| Exemplary mini-nucleosome core protein domain | SEQ ID NO. |
| --- | --- |
| KKKRKRGDKRKRKRHRKKKRRRREYYLSIPPKA | 423 |
| KKKRKRGDKRKRKRHRKKKRRRDYRFQTPPQL | 424 |
| KKKRKRGDKRKRKRHRKKKRRRHYRLTPATAI | 425 |
| KKKRKRGDKRKRKRHRKKKRRRRVYQSIGYPLP | 426 |
| KKKRKSYRRGDKRKRKRHRKKKRRRRCLIRRTSIC | 427 |
| KKKRKEYRGDKRKRKRHRKKKRRRRCFFWKFRWMC | 428 |

Glycosylated Mini-Nucleosome Core Proteins

Glycosylation includes, among other things, N-glycosylation, O-glycosylation, and C-glycosylation. N glycosylation, refers to covalent linkage of a glycan to a nitrogen atom of a side chain of an amino acid, typically the amide nitrogen of an asparagine (N) residue. Examples of N glycosylation include GlcNAc-$\beta$-Asn, GlcNac-$\alpha$-Asn, and Glc-Asn. O-glycosylation refers to covalent linkage of a glycan to an oxygen atom of a hydroxyl side chain of an amino acid, typically an oxygen atom of a hydroxyl side chain of a serine(S) or threonine (T) residue. Examples of O-glycosylation include GlcNac-$\beta$-Ser/Thr and GalNac-$\alpha$-Ser/Thr. C-glycosylation refers to covalent linkage of mannose to a carbon atom of a side chain of an amino acid, typically a carbon atom of a tryptophan (W) residue. An example of C-glycosylation is $\alpha$-mannosyl tryptophan. Accordingly, in various embodiments, glycosylation can refer to one or more modifications, each of which modifications can be any of N-glycosylation, C-glycosylation, or O-glycosylation. Known functions of glycosylation modifications include contributions to protein folding and cell signaling. In general, glycosylation is also known to improve protein stability and serve as an epitope for association with binding partners.

In various embodiments, glycosylation of one more residues of a modified mini-nucleosome core protein increases the stability of the modified mini-nucleosome core protein, or loaded mini-nucleosome core proteins including the same, as compared to a reference mini-nucleosome core protein that does not include one or more of the glycosylation modifications. In some embodiments, glycosylation increases stability of the modified mini-nucleosome core protein, or loaded mini-nucleosome core proteins including the same, in that physical properties of the modified mini-nucleosome core protein, or loaded mini-nucleosome core proteins including the same, including protein structure and protein charge, are maintained and/or maintained for a longer period of time, e.g., after administration to a subject.

In some embodiments, glycosylation decreases the occurrence or rate of thermal and/or kinetic denaturation of the modified mini-nucleosome core protein, or loaded mini-nucleosome core proteins including the same, as compared to a reference mini-nucleosome core protein that does not include one or more of the glycosylation modifications.

In various embodiments, glycosylation of one more residues of a modified mini-nucleosome core protein increases half-life and/or bioavailability of the modified mini-nucleosome core protein, or loaded mini-nucleosome core proteins including the same, as compared to a reference mini-nucleosome core protein that does not include one or more of the glycosylation modifications.

In various embodiments, glycosylation of one more residues of a modified mini-nucleosome core protein increases affinity or avidity with a target cell or other binding partner of the modified mini-nucleosome core protein, or loaded mini-nucleosome core proteins including the same, as compared to a reference mini-nucleosome core protein that does not include one or more of the glycosylation modifications. In various embodiments, glycosylation of one more residues of a modified mini-nucleosome core protein increases affinity or avidity of binding with a target receptor of the modified mini-nucleosome core protein, or loaded mini-nucleosome core proteins including the same, as compared to a reference mini-nucleosome core protein that does not include one or more of the glycosylation modifications. Thus, in some embodiments, glycosylation of one more residues of a modified mini-nucleosome core protein increases delivery of a mini-nucleosome core protein, loaded mini-nucleosome core protein, or nucleic acid cargo of a mini-nucleosome core protein to a target cell, tissue, or organ.

In various embodiments, glycosylation of one more residues of a modified mini-nucleosome core protein increases the rate at which the modified mini-nucleosome core protein, or loaded mini-nucleosome core proteins including the same, enters one or more target cells (i.e., crosses the cell membranes of target cells) as compared to a reference mini-nucleosome core protein that does not include one or more of the glycosylation modifications.

In various embodiments, glycosylation of one more residues of a modified mini-nucleosome core protein decreases precipitation and/or aggregation of the modified mini-nucleosome core protein, or loaded mini-nucleosome core proteins including the same, as compared to a reference mini-nucleosome core protein that does not include one or more of the glycosylation modifications.

Table 18 includes exemplary glycosylated domains, in particular galactose-modified targeting domains that target mini-nucleosome core proteins to liver.

TABLE 18

| Exemplary mini-nucleosome core protein domain | SEQ ID NO. |
| --- | --- |
| KKRHRKARARKKAAKARIKKAAPAKKAANRARKKH | 429 |
| KKRHRKGSSRRPRPGTGPGRRPRPRPRPRKKRNRSRQRRR | 430 |
| KKRHRKKYKQKIKHVVKLKKHRKRKRNRSIKVAV | 431 |
| KKRHRKSSSRTLQAHHDRQSNKRKRKNRSRRRRR | 432 |
| KKRHRKRNRSIHFNPRHRRRRRRDVARARAEKSKKK | 433 |
| KKRHRKNRSKKQRFRHRNRKGYRSQRGHSRGRNQNSRR | 434 |

Prenylated Mini-Nucleosome Core Proteins

Prenylation typically occurs on cysteine residues (see, e.g., FIG. 26 for an example of a prenylated mini-nucleosome core protein). Prenylation includes covalent linkage of a lipid chain farnesyl (C15) or geranylgeranyl (C20) isoprenoid moiety to a free thiol group of a cysteine residue. Accordingly, prenylation includes modifications including farnesylation, geranylation, and geranylgeranylation. Prenylation is often found on C-terminal residues of polypeptides; in mammals, approximately 2% of proteins are prenylated at their C-terminal residues. Prenylation of a polypeptide such as a mini-nucleosome core protein significantly impacts hydrophobicity of the polypeptide. For at least that reason, prenylation of a mini-nucleosome core protein increases the strength (e.g., affinity or avidity) of interaction between a mini-nucleosome core protein and plasma membranes, facilitating efficient cellular uptake. Prenylation of a polypeptide such as a mini-nucleosome core protein also increases cell penetrating ability and/or uptake by target cells (see, e.g., Ochocki J D et al, 2011). Prenylation has also been shown to strengthen (e.g., increase the affinity or avidity of) protein-protein interactions (e.g., promoting protein-protein and protein-membrane interactions of proteins such as Ras, Rho, and Rab, etc., as reported by Gelb et al, 1998). Prenylation of proteins is also known to facilitate homing to target subcellular localizations.

In various embodiments, prenylation of one more residues of a modified mini-nucleosome core protein increases affinity or avidity with a target cell or other binding partner of the modified mini-nucleosome core protein, or loaded mini-nucleosome core proteins including the same, as compared to a reference mini-nucleosome core protein that does not include one or more of the prenylation modifications. In various embodiments, prenylation of one more residues of a modified mini-nucleosome core protein increases affinity or avidity of binding with a target receptor of the modified mini-nucleosome core protein, or loaded mini-nucleosome core proteins including the same, as compared to a reference mini-nucleosome core protein that does not include one or more of the prenylation modifications. Thus, in some embodiments, prenylation of one more residues of a modified mini-nucleosome core protein increases delivery of a mini-nucleosome core protein, loaded mini-nucleosome core protein, or nucleic acid cargo of a mini-nucleosome core protein to a target cell, tissue, or organ.

In various embodiments, prenylation of one more residues of a modified mini-nucleosome core protein increases strength (e.g., affinity or avidity) of association with cell membranes of the modified mini-nucleosome core protein, or loaded mini-nucleosome core proteins including the same, as compared to a reference mini-nucleosome core protein that does not include one or more of the prenylation modifications. In various embodiments, prenylation of one more residues of a modified mini-nucleosome core protein increases the rate at which the modified mini-nucleosome core protein, or loaded mini-nucleosome core proteins including the same, penetrates cell membranes as compared to a reference mini-nucleosome core protein that does not include one or more of the prenylation modifications. In various embodiments, prenylation of one more residues of a modified mini-nucleosome core protein increases the rate at which the modified mini-nucleosome core protein, or loaded mini-nucleosome core proteins including the same, enters one or more target cells (i.e., crosses the cell membranes of target cells) as compared to a reference mini-nucleosome core protein that does not include one or more of the prenylation modifications.

In various embodiments, prenylation of one more residues of a modified mini-nucleosome core protein increases the rate at which the modified mini-nucleosome core protein, or loaded mini-nucleosome core proteins including the same, home to target subcellular localization as compared to a reference mini-nucleosome core protein that does not include one or more of the prenylation modifications.

Table 19 includes exemplary prenylated domains, in particular prenylated targeting domains that target mini-nucleosome core proteins to liver cells and other cell types.

TABLE 19

| Exemplary mini-nucleosome core protein domain | SEQ ID NO. |
| --- | --- |
| KKRHRKARARKKAAKARIKKAAPAKKAARACIILRKKH | 435 |
| KKRHRKGSSRRPRPGTGPGRRPRPRPRPRKKRCASERQRRR | 436 |
| KKRHRKCIIEKYKQKIKHVVKLKKHRKRKRIKVAV | 437 |
| KKRHRKCQALSSSRTLQAHHDRQSNKRKRKRRRRR | 438 |
| KKRHRKRIHFNPRHRRRRRRCIAEDVARARAEKSKKK | 439 |
| KRHRKKKQRFRHRNRKGYRSQRGHSRGRNQNSRRCIILR | 440 |

Methylated Mini-Nucleosome Core Proteins

Methylation typically occurs on lysine (K) and arginine (R) residues (see, e.g., FIG. 28). Methylated residues include mono-methylated residues, di-methylated residues, and tri-methylated residues, among others. In particular, lysine residues are typically mono-methylated, di-methylated, or tri-methylated, and arginine residues are typically mono-methylated or di-methylated. Studies have demonstrated that histones methylated on certain residues cause and/or contribute to epigenetic control of gene expression. Methylation of polypeptides such as methylated mini-nucleosome core proteins increases targeting of the polypeptides to the nucleus.

In various embodiments, methylation of one more residues of a modified mini-nucleosome core protein increases the rate of delivery to the nuclei of target cells of the modified mini-nucleosome core protein, or loaded mini-nucleosome core proteins including the same, as compared to a reference mini-nucleosome core protein that does not include one or more of the methylation modifications. In various embodiments, methylation of one more residues of a modified mini-nucleosome core protein increases the rate of delivery to the nuclei of target cells of a nucleic acid cargo of a loaded mini-nucleosome core protein including the modified mini-nucleosome core protein, as compared to delivery of the nucleic acid cargo of a reference loaded mini-nucleosome core protein that includes a mini-nucleosome core protein that does not include one or more of the methylation modifications. In various embodiments, methylation of one more residues of a modified mini-nucleosome core protein increases expression in target cells of a coding sequence of a nucleic acid cargo of a loaded mini-nucleosome core protein including the modified mini-nucleosome core protein, as compared to expression of a coding sequence of a nucleic acid cargo of a reference loaded mini-nucleosome core protein that includes a mini-nucleosome core protein that does not include one or more of the methylation modifications.

Table 20 includes exemplary methylated domains, in particular methylated targeting domains that target mini-nucleosome core proteins to cell nuclei and/or increase expression of nucleic acid cargos when included in a mini-nucleosome core protein of a loaded mini-nucleosome core protein.

TABLE 20

| Exemplary mini-nucleosome core protein domain | SEQ ID NO. |
| --- | --- |
| KKRHRKARARKKAAKARIKKAAPAKKAARARKKH | 441 |
| KKRHRKGSSRRPRPGTGPGRRPRPRPRPRKKRRQRRR | 442 |
| KKRHRKKYKQKIKHVVKLKKHRKRKRIKVAV | 443 |
| KKRHRKSSSRTLQAHHDRQSNKRKRKRRRRR | 444 |
| KKRHRKRIHFNPRHRRRRRRDVARARAEKSKKK | 445 |
| KRHRKKKQRPRHRNRKGYRSQRGHSRGRNQNSRR | 446 |

Sialylated Mini-Nucleosome Core Proteins

Sialylation refers to the covalent addition of sialic acid to the terminal end of a glycoprotein oligosaccharide chain. Sialylation can occur, e.g., on asparagine (N) and serine(S) residues. Sialylation can increase endothelial cell targeting and/or blood brain barrier penetration. In some instances, endothelial cell targeting provides a means of increased blood brain barrier penetration.

In various embodiments, sialylation of one more residues of a modified mini-nucleosome core protein increases blood-brain barrier penetration by the modified mini-nucleosome core protein, or loaded mini-nucleosome core proteins including the same, as compared to a reference mini-nucleosome core protein that does not include one or more of the sialylation modifications.

In various embodiments, sialylation of one more residues of a modified mini-nucleosome core protein increases strength (e.g., affinity or avidity) of association with cell membranes (e.g., endothelial cell membranes) of the modified mini-nucleosome core protein, or loaded mini-nucleosome core proteins including the same, as compared to a reference mini-nucleosome core protein that does not include one or more of the sialylation modifications. In various embodiments, sialylation of one more residues of a modified mini-nucleosome core protein increases the rate at which the modified mini-nucleosome core protein, or loaded mini-nucleosome core proteins including the same, penetrates cell membranes (e.g., endothelial cell membranes) as compared to a reference mini-nucleosome core protein that does not include one or more of the sialylation modifications. In various embodiments, sialylation of one more residues of a modified mini-nucleosome core protein increases the rate at which the modified mini-nucleosome core protein, or loaded mini-nucleosome core proteins including the same, enters one or more target cells (i.e., crosses the cell membranes of target cells), such as endothelial cells, as compared to a reference mini-nucleosome core protein that does not include one or more of the sialylation modifications.

Table 21 includes exemplary sialylated domains, in particular sialylated targeting domains that increase endothelial cell targeting and/or blood brain barrier penetration when included in a mini-nucleosome core protein.

TABLE 21

| Exemplary mini-nucleosome core protein domain | SEQ ID NO. |
| --- | --- |
| KKRHRKGGSLLRGEKELKRPPRRRRRKYIGSR | 447 |
| KKKRKLRGDLKRKPLISRRLIDRYQKKKRKRGDKRK | 448 |
| KKKRKLRGDLKRKSSSVRKKPGGSKKKRKRGDKRK | 449 |
| KKKRKLRGDLKRKGTQPEHSSTDHKKKRKRGDKRK | 450 |
| KKKRKRGDKRKRKRHRKKKKRRRRLSIPPKA | 451 |
| KKKRKRGDKRKRKRHRKKKKRRRRFQTPPQL | 452 |
| KKKRKRGDKRKRKRHRKKKKRRRRNRSLTPATAI | 453 |
| KKKRKRGDKRKRKRHRKKKKRRRRSIGYPLP | 454 |
| KKKRKRGDKRKRKRHRKKKKRRRRNRSCLIRRTSIC | 455 |
| KKKRKRGDKRKRKRHRKKKKRRRRNRSCFFWKFRWMC | 456 |
| KKKRKNRSRGDKRKRKRHRKKKKRRRRIELLQARGC | 457 |
| KKKRKRGDKRKRKRHRKKKNRSRRRRREDV | 458 |
| KKKRKRGDKRKRKRHRKKKKRRRRVHPKQHRGGSKGC | 459 |

Lipidated and or Lipoylated Mini-Nucleosome Core Proteins

Amino acids can be covalently modified by linkage to a variety of lipids, including fatty acids, isoprenoids, and cholesterol (see, e.g., FIG. 30). Fatty acids that can be linked to amino acid residues for lipidation and/or lipoylation include caprylic acid (C8), capric acid (C10), lauric acid (C12), myristic acid (C14), palmitic acid (C16) or Stearic acid (C18). Fatty acids can be conjugated to the N-terminus of a polypeptide or to a side-chain of a lysine residue. Cysteine residues can also be covalently linked to fatty acids. Lipoylation is a form of acylation that includes linkage of an amino acid to a lipoate (C8) functional group. Lipoylation can occur, e.g., on lysine residues. In some instances, a polypeptide such as a mini-nucleosome core protein can be covalently linked to cholesterol. Cholesterol can be conjugated to a mini-nucleosome core protein at a N-terminal residue or at a C-terminal residue, and/or at a cysteine residue.

Lipidation and/or lipoylation can contribute to polypeptide localization and function. Lipidation and/or lipoylation can improve pharmacokinetic properties of a polypeptide such as a mini-nucleosome core protein, e.g., to increase half-life in circulation. Lipidation and/or lipoylation, e.g., with long-chain fatty acids, can also increase targeting of polypeptides such as a mini-nucleosome core protein (see, e.g., Hossieni et al., 2019, demonstrating that palmitoylation can significantly improve targeting in Wnt trafficking). Linkage of a mini-nucleosome core protein to cholesterol can increase membrane anchoring and thereby increase delivery to target cells.

In various embodiments, lipidation and/or lipoylation of one more residues of a modified mini-nucleosome core protein increases affinity or avidity with a target cell or other binding partner of the modified mini-nucleosome core protein, or loaded mini-nucleosome core proteins including the same, as compared to a reference mini-nucleosome core protein that does not include one or more of the lipidation and/or lipoylation modifications. In various embodiments, lipidation and/or lipoylation of one more residues of a modified mini-nucleosome core protein increases affinity or avidity of binding with a target receptor of the modified mini-nucleosome core protein, or loaded mini-nucleosome core proteins including the same, as compared to a reference mini-nucleosome core protein that does not include one or more of the lipidation and/or lipoylation modifications. Thus, in some embodiments, lipidation and/or lipoylation of one more residues of a modified mini-nucleosome core protein increases delivery of a mini-nucleosome core protein, loaded mini-nucleosome core protein, or nucleic acid cargo of a mini-nucleosome core protein to a target cell, tissue, or organ.

In various embodiments, lipidation and/or lipoylation of one more residues of a modified mini-nucleosome core protein increases half-life and/or bioavailability of the modified mini-nucleosome core protein, or loaded mini-nucleosome core proteins including the same, as compared to a reference mini-nucleosome core protein that does not include one or more of the lipidation and/or lipoylation modifications.

Acetylated Mini-Nucleosome Core Proteins

Acetylation can occur, e.g., on alanine (A), valine (V), and/or lysine (K) residues. An acetyl group can be covalently linked to an α-amino group of the N-terminus of a polypeptide or to an ε-amino group of a lysine residue (see, e.g., FIGS. 23 and 24). Acetylation refers to the substitution of hydrogen with an acetyl group in a residue of a polypeptide, such as a mini-nucleosome core protein. Acetylation can increase the stability and/or biological activity of a polypeptide, such as a mini-nucleosome core protein. For example, acetylation can increase stability of modified polypeptides by preventing N-terminal degradation. Acetylation is a reversible modification.

In various embodiments, acetylation of one more residues of a modified mini-nucleosome core protein increases the stability of the modified mini-nucleosome core protein, or loaded mini-nucleosome core proteins including the same, as compared to a reference mini-nucleosome core protein that does not include one or more of the acetylation modifications. In some embodiments, acetylation increases stability of the modified mini-nucleosome core protein, or loaded mini-nucleosome core proteins including the same, in that physical properties of the modified mini-nucleosome core protein, or loaded mini-nucleosome core proteins including the same, including protein structure and protein charge, are maintained and/or maintained for a longer period of time, e.g., after administration to a subject. In some embodiments, acetylation decreases the occurrence or rate of thermal and/or kinetic denaturation of the modified mini-nucleosome core protein, or loaded mini-nucleosome core proteins including the same, as compared to a reference mini-nucleosome core protein that does not include one or more of the acetylation modifications.

In various embodiments, acetylation of one more residues of a modified mini-nucleosome core protein increases half-life and/or bioavailability of the modified mini-nucleosome core protein, or loaded mini-nucleosome core proteins including the same, as compared to a reference mini-nucleosome core protein that does not include one or more of the acetylation modifications.

Hydroxylated Mini-Nucleosome Core Proteins

Hydroxylation can occur, e.g., on proline (P) and lysine (K) residues, as well as other amino acids including without limitation asparagine, aspartate and histidine (see, e.g., FIG. 29). Proline and/or lysine hydroxylation is associated with a variety of physiological molecules and/or processes, including certain molecules and/or process of certain pathological states. For example, proline hydroxylation can increase stability of a polypeptide such as a mini-nucleosome core protein.

In various embodiments, hydroxylation of one more residues, e.g., one or more proline residues, of a modified mini-nucleosome core protein increases the stability of the modified mini-nucleosome core protein, or loaded mini-nucleosome core proteins including the same, as compared to a reference mini-nucleosome core protein that does not include one or more of the hydroxylation modifications. In some embodiments, hydroxylation of one more residues, e.g., one or more proline residues, increases stability of the modified mini-nucleosome core protein, or loaded mini-nucleosome core proteins including the same, in that physical properties of the modified mini-nucleosome core protein, or loaded mini-nucleosome core proteins including the same, including protein structure and protein charge, are maintained and/or maintained for a longer period of time, e.g., after administration to a subject. In some embodiments, hydroxylation of one more residues, e.g., one or more proline residues, decreases the occurrence or rate of thermal and/or kinetic denaturation of the modified mini-nucleosome core protein, or loaded mini-nucleosome core proteins including the same, as compared to a reference mini-nucleosome core protein that does not include one or more of the hydroxylation modifications.

In various embodiments, hydroxylation of one more residues, e.g., one or more proline residues, of a modified mini-nucleosome core protein increases half-life and/or bioavailability of the modified mini-nucleosome core protein, or loaded mini-nucleosome core proteins including the same, as compared to a reference mini-nucleosome core protein that does not include one or more of the hydroxylation modifications.

Palmitoylated Mini-Nucleosome Core Proteins

Palmitoylation is a lipid modification that typically occurs on cysteine I residues, and can also occur, e.g., on serine(S) and threonine (T) residues. Palmitoylation includes the covalent attachment of a fatty acid, such as palmitic acid, to a residue of a polypeptide such as a mini-nucleosome core protein. Palmitoylation can be present, e.g., on residues of membrane proteins.

In various embodiments, palmitoylation of one more residues of a modified mini-nucleosome core protein increases strength (e.g., affinity or avidity) of association with cell membranes (e.g., endothelial cell membranes) of the modified mini-nucleosome core protein, or loaded mini-nucleosome core proteins including the same, as compared to a reference mini-nucleosome core protein that does not include one or more of the palmitoylation modifications. In various embodiments, palmitoylation of one more residues of a modified mini-nucleosome core protein increases the rate at which the modified mini-nucleosome core protein, or loaded mini-nucleosome core proteins including the same, penetrates cell membranes (e.g., endothelial cell membranes) as compared to a reference mini-nucleosome core protein that does not include one or more of the palmitoylation modifications. In various embodiments, palmitoylation of one more residues of a modified mini-nucleosome core protein increases the rate at which the modified mini-nucleosome core protein, or loaded mini-nucleosome core proteins including the same, enters one or more target cells (i.e., crosses the cell membranes of target cells), such as endothelial cells, as compared to a reference mini-nucleosome core protein that does not include one or more of the palmitoylation modifications.

Mannosylated Mini-Nucleosome Core Proteins

Mannosylation can refer to modification of an amino acid to include a mannose glycoside. Mannosylation can occur, e.g., on threonine (T) residues of a polypeptide, e.g., a mini-nucleosome core protein. To provide one particular example, mono-O-mannosyl glycans concentrate in inhibitory GABAergic neurons, and the present disclosure includes mono-O-mannosylation of mini-nucleosome core proteins to target mini-nucleosome core proteins to GABAergic neurons.

Myristoylated Mini-Nucleosome Core Proteins

Myristoylation is a lipid modification that includes covalent linkage of a myristoyl group with an amino acid, e.g., a residue of a polypeptide such as a mini-nucleosome core protein. Myristoylation can occur, e.g., on a glycine (G) residue of a polypeptide such as a mini-nucleosome core protein. For instance, protein N-myristoylation is a lipidic modification that can be present on the alpha-amino group of an N-terminal glycine residue. Myristoylation can contribute to cellular signaling, protein-protein interaction, and targeting of proteins to endomembrane and plasma membrane systems In various embodiments, myristoylation of one more residues of a modified mini-nucleosome core protein increases affinity or avidity with a target cell or other binding partner of the modified mini-nucleosome core protein, or loaded mini-nucleosome core proteins including the same, as compared to a reference mini-nucleosome core protein that does not include one or more of the myristoylation modifications. In various embodiments, myristoylation of one more residues of a modified mini-nucleosome core protein increases affinity or avidity of binding with a target receptor of the modified mini-nucleosome core protein, or loaded mini-nucleosome core proteins including the same, as compared to a reference mini-nucleosome core protein that does not include one or more of the myristoylation modifications. Thus, in some embodiments, myristoylation of one more residues of a modified mini-nucleosome core protein increases delivery of a mini-nucleosome core protein, loaded mini-nucleosome core protein, or nucleic acid payload of a mini-nucleosome core protein to a target cell, tissue, or organ.

In various embodiments, myristoylation of one more residues of a modified mini-nucleosome core protein increases strength (e.g., affinity or avidity) of association with cell membranes (e.g., endothelial cell membranes) of the modified mini-nucleosome core protein, or loaded mini-nucleosome core proteins including the same, as compared to a reference mini-nucleosome core protein that does not include one or more of the myristoylation modifications. In various embodiments, myristoylation of one more residues of a modified mini-nucleosome core protein increases the rate at which the modified mini-nucleosome core protein, or loaded mini-nucleosome core proteins including the same, penetrates cell membranes (e.g., endothelial cell membranes) as compared to a reference mini-nucleosome core protein that does not include one or more of the myristoylation modifications. In various embodiments, myristoylation of one more residues of a modified mini-nucleosome core protein increases the rate at which the modified mini-nucleosome core protein, or loaded mini-nucleosome core proteins including the same, enters one or more target cells (i.e., crosses the cell membranes of target cells), such as endothelial cells, as compared to a reference mini-nucleosome core protein that does not include one or more of the myristoylation modifications.

Fucosylated Mini-Nucleosome Core Proteins

Fucosylation is a form of glycosylation that refers to the addition of fucose to an amino acid, e.g., a threonine (T) residue. Fucosylation includes attachment of a fucose residue to N-glycans, O-glycans, and glycolipids.

Pegylated Mini-Nucleosome Core Proteins

Pegylation (sometimes written PEGylation) includes the modification of biological molecules by covalent conjugation with polyethylene glycol (PEG), a non-toxic, non-immunogenic polymer. PEG is generally understood to be biocompatible and/or to lack immunogenicity, antigenicity, and/or toxicity. PEG is soluble in water and other organic solvents, is readily cleared from the body, and has high mobility in solution. Pegylation can impact physical and chemical properties of a polypeptide such as a mini-nucleosome core protein, including properties such as conformation, electrostatic binding, and hydrophobicity. Pegylation can cause an improvement in pharmacokinetic behavior of a polypeptide such as a mini-nucleosome core protein. Pegylation can improve drug solubility and decreases immunogenicity of a polypeptide such as a mini-nucleosome core protein. PEGylation can increases drug stability and/or retention time of a polypeptide such as a mini-nucleosome core protein in blood. Pegylation can reduce proteolysis and/or renal excretion polypeptide such as a mini-nucleosome core protein, which can reduce the therapeutically effective dose of a polypeptide such as a mini-nucleosome core protein. As those of skill in the art will appreciate, techniques for use of PEG and pegylation in combination with polypeptide agents are well known in the art. The present disclosure includes, without limitation, modified mini-nucleosome core proteins that include a pegylated amino acid alone or in combination with other modifications of the same or other amino acids of the mini-nucleosome core protein.

Modified Mini-Nucleosome Core Proteins with Multiple and or Branched Modifications Those of skill in the art will appreciate that a polypeptide such as a mini-nucleosome core protein can include one or more amino acids that each include one or more modifications provided herein. Accordingly, a mini-nucleosome core protein can include a plurality of modified amino acids each including the same modification, or can include a plurality of modified amino acids of which at least two include different modifications. Moreover, as those of skill in the art will further appreciate, in some embodiments a single modified amino acid can include two or more modifications (see, e.g., FIGS. 20-22). In some embodiments, a single modified amino acid can include two or more modifications, where each of the modifications is covalently linked to the canonical core structure of the amino acid at a different position thereof. In some embodiments, a single modified amino acid can include two or more modifications, where the two or more modifications are present in a modification chain (i.e., a moiety comprising two or more covalently linked modifications, which is itself covalently linked to an atom of the canonical core structure of the amino acid). Accordingly, as disclosed herein, an amino acid can be referred to as modified by a particular modification when the canonical core structure of the amino acid is directly covalently linked to the modification and/or when the canonical core structure of the amino acid is indirectly covalently linked to the modification, e.g., when the modification is present in a modification chain and is not directly linked to an atom of the canonical core structure of the amino acid.

Modification chains of the present disclosure can include a plurality of modifications. In some embodiments, a modification chain includes a plurality of linearly associated modifications, which modifications are directly or indirectly covalently linked in a single linear chain. A modification chain including a single covalently linked linear chain of directly or indirectly linked modifications can be referred to as an "unbranched" modification chain. Modification chains of the present disclosure can be "branched", e.g., where the modification chain includes a "trunk" that is covalently linked to an atom of the canonical core structure of an amino acid, and which trunk is covalently linked to two or more branches of covalently linked atoms, each of which branches can include one or more modifications. In such branched modification chains, the trunk and two or more branches do not form a single covalently linked linear chain. As provided herein, a trunk or unbranched modification chain can include any number of modifications provided herein, e.g., 0, 1, 2, 3, 4, 5, 6, 7, 8, 9, or 10 modifications provided herein, any of which may be the same modification as any other in the trunk or chain or a different modifications from any other in the trunk or chain. As provided herein, a branch can include any number of modifications provided herein, e.g., 0, 1, 2, 3, 4, 5, 6, 7, 8, 9, or 10 modifications provided herein, any of which may be the same modification as any other in the branch or chain or a different modifications from any other in the branch or chain.

Thus, for the avoidance of doubt, a mini-nucleosome core protein, as set forth herein, can include (a) a nucleic acid binding domain (NABD), and (b) a targeting domain, and in some embodiments can include (a) a nucleic acid binding domain (NABD), (b) a targeting domain, and (c) a nucleic acid release domain, where any of the various mini-nucleosome core proteins provided herein can optionally include one or more modified amino acid residues.

Nucleic Acid Cargos

Loaded mini-nucleosomes disclosed herein can be loaded with a nucleic acid cargo that is, e.g., RNA, DNA, or a nucleic acid analog thereof. A nucleic acid cargo can be single stranded or double stranded. A nucleic acid cargo can be linear or circular. A nucleic acid cargo can encode one or more of each of a protein, an RNA, an shRNA, an miRNA, an antibody, a nanobody, a Darpin, an Ankyrin repeat, or a polypeptide. For example, a nucleic acid cargo can be a cDNA molecule that encodes at least one functional protein. In various embodiments, a nucleic acid cargo can be an inhibitory RNA, e.g., a gRNA, siRNA, miRNA, or shRNA.

A nucleic acid cargo can encode, e.g., an RNA, protein, polypeptide, antibody, nanobody, miRNA, shRNA, gRNA, Cas9, non-coding RNA when delivered into a nucleus of any cell. Expression may not be limited to entities mentioned herein.

Loaded Mini-Nucleosomes

A loaded mini-nucleosome of the present disclosure can include one or more mini-nucleosome core proteins of the present disclosure and one or more polynucleotides. Those of skill in the art will appreciate from the present disclosure that such loaded mini-nucleosomes can be generated from combining mini-nucleosome core proteins and polynucleotides in a variety of ways. Those of skill in the art will appreciate that, in at least one embodiment, loaded mini-nucleosome assembly will occur simply upon inclusion of one or more mini-nucleosome core proteins provided herein and one or more polynucleotides in a solution, e.g., without limitation, an aqueous solution, e.g., at a standard temperature and e.g., vortexing at a standard speed. Methods of generating loaded mini-nucleosome core proteins therefore include approaches provided herein and others that will be apparent to those of skill in the art. Those of skill in the art will appreciate that, in at least one embodiment, loaded mini-nucleosome assembly will occur upon inclusion of one or more mini-nucleosome core proteins provided herein and one or more polynucleotides in a solution, e.g., without limitation, an aqueous solution, e.g., at a standard temperature in the presence of catalysts that help enhance condensation of nucleic acids.

A loaded mini-nucleosome of the present disclosure can be at an uncondensed state and a condensed state. A loaded mini-nucleosome is in a condensed state where at least 90%, 91%, 92%, 93%, 94%, 95%, 96%, 97%, 98%, 99%, or 100% of negative charges in the nucleic acid molecule has been neutralized. A loaded mini-nucleosome is considered in an uncondensed state when less than 90% of negative charges in the nucleic acid molecule has been neutralized. Unless specified, references to mini-nucleosomes in the present disclosure encompass at least condensed and uncondensed states and, where applicable, characteristics thereof.

A mini-nucleosome can include, e.g., 1 to 10,000 mini-nucleosome core proteins. A mini-nucleosome can include, e.g., 1 to 100 nucleic acid cargo molecules.

In some embodiments, loaded mini-nucleosome can be of size between 0.5 to 50 nanometers in diameter. Mini-nucleosomes can include nucleic acid cargo molecules that can have a length of up to 50 kb while maintaining a small diameter of between 0.5 and 50 nm.

In some embodiments, loaded mini-nucleosome can have a molecular weight of between 100 and 10000 kDa, e.g., 100, 200, 500, 1000, 3000, 5,000, 8000, 10000 kDa.

In various embodiments, loaded mini-nucleosome can have a net charge of $-100$ to 100. In some embodiments, the zeta potential of the loaded mini-nucleosome formulation may range from $-10$ milliVolts to 100 millivolts. In some examples, a complex of nucleic acid cargo and mini-nucleosome core protein is condensed to a minimal size compared to the nucleic acid molecule and polypeptide molecules used to construct the mini-nucleosome particle. The final positive to negative charge ratio is approximately 1:1, thereby forming a non-charged, slightly positively charged or slightly negatively charged molecule. The final particle may form in several shapes including rod, spherical or circular but not limited to these.

In various embodiments, the mini-nucleosome core protein may be modified with one or more molecules of polyethylene glycol of molecular weight of 5 Daltons to 20 kDa A polyethylene glycol (PEG) moiety maybe attached to any amino acid residue in the polypeptide.

In certain embodiments, a loaded mini-nucleosome includes a ratio of nucleic acid molecules to mini-nucleosome core proteins that is between 1:1 and 1:2,000 or between 1:3 and 1:2,000. In certain embodiments, a loaded mini-nucleosome includes a ratio of nucleic acid molecules to mini-nucleosome core proteins that is between 1:1 and 1:2,000. In certain embodiments, a loaded mini-nucleosome includes a ratio of nucleic acid molecules to mini-nucleosome core proteins that is between 1:1 and 1:1,000, between 1:1 and 1.500, between 1:1 and 1:200, between 1:1 and 1:100, between 1:1 and 1:50. In certain embodiments, a loaded mini-nucleosome includes a ratio of nucleic acid molecules to mini-nucleosome core proteins that is between 1:3 and 1:1,000, between 1:3 and 1:500, between 1:3 and 1:200, between 1:3 and 1:100, or between 1:3 and 1:50. In certain embodiments, a loaded mini-nucleosome includes a ratio of nucleic acid molecules to mini-nucleosome core proteins that is between 1:200 and 1:2,000, between 1:200 and 1.1000, or between 1:200 and 1.500. In certain embodiments, a loaded mini-nucleosome includes a ratio of nucleic acid molecules to mini-nucleosome core proteins that is between 1:1 and 1:50, 1:1 and 1:40, 1:1 and 1:30, 1:1 and 1:20, 1:1 and 1:10, 1:1 and 1:5, 1:1 and 1:4, 1:1 and 1:3, or]: 1 and 1:2.

In various embodiments, a loaded mini-nucleosome includes a ratio of nucleic acid molecules to mini-nucleosome core proteins that is between 1 nucleic acid molecule to 3 mini-nucleosome core proteins (1:3) and 1 nucleic acid molecule to 3,000 mini-nucleosome core proteins (1:3,000), or within any range there between.

In various embodiments, a loaded mini-nucleosome includes a ratio of nucleic acid molecules to mini-nucleosome core proteins that is between 1 nucleic acid molecule to 3 mini-nucleosome core proteins (1:3) and 1 nucleic acid molecule to 2,000 mini-nucleosome core proteins (1:2,000).

In various embodiments, a loaded mini-nucleosome includes a ratio of nucleic acid molecules to mini-nucleosome core proteins that is between 1 nucleic acid molecule to 3 mini-nucleosome core proteins (1:3) and 1 nucleic acid molecule to 1,000 mini-nucleosome core proteins (1:1,000).

In various embodiments, a loaded mini-nucleosome includes a ratio of nucleic acid molecules to mini-nucleosome core proteins that is between 1 nucleic acid molecule to 3 mini-nucleosome core proteins (1:3) and 1 nucleic acid molecule to 500 mini-nucleosome core proteins (1:500)

In various embodiments, a loaded mini-nucleosome includes a ratio of nucleic acid molecules to mini-nucleosome core proteins that is between 1 nucleic acid molecule to 3 mini-nucleosome core proteins (1:3) and 1 nucleic acid molecule to 200 mini-nucleosome core proteins (1:200).

In various embodiments, a loaded mini-nucleosome includes a ratio of nucleic acid molecules to mini-nucleosome core proteins that is between 1 nucleic acid molecule to 3 mini-nucleosome core proteins (1:3) and 1 nucleic acid molecule to 100 mini-nucleosome core proteins (1:100).

In various embodiments, a loaded mini-nucleosome includes a ratio of nucleic acid molecules to mini-nucleosome core proteins that is between 1 nucleic acid molecule to 3 mini-nucleosome core proteins (1:3) and 1 nucleic acid molecule to 50 mini-nucleosome core proteins (1:50).

In various embodiments, a loaded mini-nucleosome includes a ratio of nucleic acid molecules to mini-nucleosome core proteins that is between 1 nucleic acid molecule to 50 mini-nucleosome core proteins (1:50) and 1 nucleic acid molecule to 2,000 mini-nucleosome core proteins (1:2,000).

In various embodiments, a loaded mini-nucleosome includes a ratio of nucleic acid molecules to mini-nucleosome core proteins that is between 1 nucleic acid molecule to 50 mini-nucleosome core proteins (1:50) and] nucleic acid molecule to 1,000 mini-nucleosome core proteins (1:1,000).

In various embodiments, a loaded mini-nucleosome includes a ratio of nucleic acid molecules to mini-nucleosome core proteins that is between 1 nucleic acid molecule to 50 mini-nucleosome core proteins (1:50) and 1 nucleic acid molecule to 500 mini-nucleosome core proteins (1:500).

In various embodiments, a loaded mini-nucleosome includes a ratio of nucleic acid molecules to mini-nucleosome core proteins that is between 1 nucleic acid molecule to 50 mini-nucleosome core proteins (1:50) and 1 nucleic acid molecule to 200 mini-nucleosome core proteins (1:200).

In various embodiments, a loaded mini-nucleosome includes a ratio of nucleic acid molecules to mini-nucleosome core proteins that is between 1 nucleic acid molecule to 50 mini-nucleosome core proteins (1:50) and 1 nucleic acid molecule to 100 mini-nucleosome core proteins (1:100).

In various embodiments, a loaded mini-nucleosome includes a ratio of nucleic acid molecules to mini-nucleosome core proteins that is between 1 nucleic acid molecule to 200 mini-nucleosome core proteins (1:200) and 1 nucleic acid molecule to 2,000 mini-nucleosome core proteins (1:2,000).

In various embodiments, a loaded mini-nucleosome includes a ratio of nucleic acid molecules to mini-nucleosome core proteins that is between 1 nucleic acid molecule to 200 mini-nucleosome core proteins (1:200) and 1 nucleic acid molecule to 1,000 mini-nucleosome core proteins (1:1,000).

In various embodiments, a loaded mini-nucleosome includes a ratio of nucleic acid molecules to mini-nucleosome core proteins that is between 1 nucleic acid molecule to 200 mini-nucleosome core proteins (1:200) and 1 nucleic acid molecule to 500 mini-nucleosome core proteins (1:500)

The skilled artisan will appreciate that mini-nucleosome core protein molecules can be produced and/or constituted by various means, including without limitation in several different salt conditions including acetate, trifluoroacetate, bicarbonate, and chloride. Final formulation of the loaded mini-nucleosome may be constituted in normal saline, water or any other pharmaceutically acceptable buffers.

Delivery of Loaded Mini-Nucleosomes to Target Cells or Tissues

In certain embodiments, a mini-nucleosome can deliver a nucleic acid where the target cell is the retinal pigment epithelium (RPE). For efficient gene therapy, some embodiments include delivery of a large copy number of genetic cargo such as DNA or RNA into one cell type. For example, in wet-age-related macular degeneration, expressing anti-VEGF in the RPE may provide therapeutic levels of proteins necessary for inhibiting endothelial cell proliferation and vascular leakage. We provide herein, examples of mini-nucleosomes core proteins (SEQ ID NO. 392) that allow enhanced uptake into the RPE (FIG. 10, 11).

Figure 12:
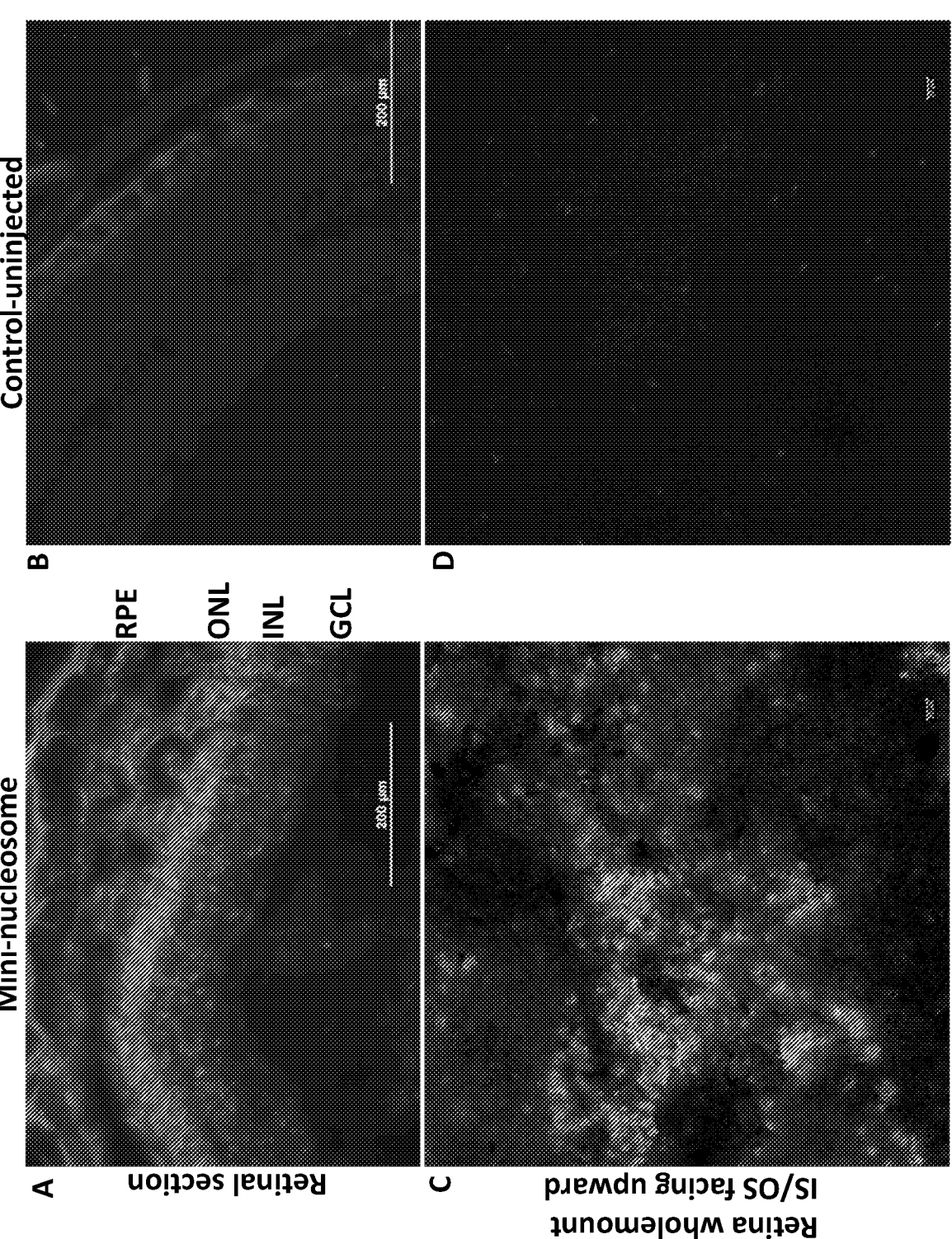
FIG. 12 is a set of images including panels A, B, C & D each of which is a fluorescent microscopy image that illustrates gene expression in mice retinal tissue of proteins encoded by nucleic acids present in loaded mini-nucleosomes. Panel A is a retinal section that demonstrates GFP expression in retinal neurons. Panel C is a retinal wholemount that demonstrates GFP expression in retinal photoreceptors. Panels B and D represent untreated control samples of a retinal section and RPE wholemount respectively.

In certain embodiments, a mini-nucleosome can deliver a nucleic acid where the target cell is a neuron in the retina. It has been described that amino acid domain LRE (SEQ ID NO. 156) could be used for enhanced neuronal attachment (Dale D, et al, 1989). We have made use of such domain in a non-viral vector using a GFP construct (SEQ ID NO. 395) with mini-nucleosome core protein (SEQ ID NO. 394) to express GFP to target neuronal cells in the retina (FIG. 12). This maybe particularly useful for delivering DNA or RNA to treat retinal degeneration caused by genetic mutations in genes expressed in retinal neurons.

In various embodiments, a mini-nucleosome can deliver a nucleic acid where the target cell is for e.g. a muscle cell, a liver cell, an endothelial cell, hematopoietic stem cell, lung epithelial, cell, a pericyte, a beta cell, gut epithelial cell, a microglial cell, a macrophage cell, a neuronal cell, skin cell, a blood cell, etc. but not limited to these. Various combination of domains described herein (Table 3-12), may allow delivery of loaded mini-nucleosomes to certain target cell type for therapeutic effects in other parts of the body including brain, retina, gut, liver, lung, kidney, muscle, pancreas but not limited to it.

Pharmaceutical Compositions

The present disclosure contemplates a "loaded mini-nucleosome therapeutic" that includes a loaded mini-nucleosome and at least one pharmaceutically acceptable carrier. Formulations of pharmaceutically acceptable carrier solutions are well-known to those skilled in the art, as is the development of suitable dosing and treatment regimens. Typically, these formulations can contain 102 genome copies or more of desired transgenes. Other factors such as solubility, bioavailability, half-life, shelf-life will be contemplated by one skilled in the art. As such, various doses and treatment regiments may be desirable. Loaded mini-nucleosome therapeutic could be used to deliver nucleotides to variety of cell types, tissue types or organs in a human body including retina, liver, CNS, gut etc. but not limited to it.

A loaded mini-nucleosome therapeutic can be formulated such that it is pharmaceutically acceptable for administration to cells or animals. Loaded mini-nucleosome therapeutic may be administered in vitro, ex vivo or in vivo. A loaded mini-nucleosome therapeutic can be administered to a subject either alone or in combination with one or more other therapeutic modalities, e.g., antibodies, steroids, vitamins, AAVs etc.

In certain instances, a loaded mini-nucleosome therapeutic can include one or more nucleic acid cargos that each or together encode one or more distinct expression products.

In certain circumstances, it will be desirable to deliver the loaded mini-nucleosome formulations in suitably formulated pharmaceutical compositions disclosed herein either by subcutaneous, intraocular, intravitreal, parenteral, intravenous, intramuscular, intrathecal, topical, oral, intraperitoneal injections, or by nasal inhalation but not limited to these techniques. Solutions of the loaded mini-nucleosome formulations may be prepared in sterile water, sterile saline and may also suitably mixed with one or more surfactants, such as pluronic acid. Dispersions may also be prepared in glycerol, liquid polyethylene glycols, and mixtures thereof. Storage preparations may contain preservatives to prevent microorganisms from growing.

A suitable means of administration of a loaded mini-nucleosome therapeutic agent can be selected based on the condition or disease to be treated and upon the age and condition of a subject. Dose and method of administration can vary depending on the weight, age, condition, and the like of a patient, and can be suitably selected as needed by those skilled in the art.

In various instances, a loaded mini-nucleosome therapeutic agent composition can be formulated to include a pharmaceutically acceptable carrier or excipient. Examples of pharmaceutically acceptable carriers include, without limitation, any and all solvents, dispersion media, coatings, antibacterial and antifungal agents, isotonic and absorption delaying agents, and the like that are physiologically compatible. Compositions of the present invention can include a pharmaceutically acceptable salt, e.g., an acid addition salt or a base addition salt.

In various embodiments, a composition including a loaded mini-nucleosome therapeutic agent as described herein, e.g., a sterile formulation for injection, can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

As disclosed herein, a loaded mini-nucleosome therapeutic agent composition may be in any form known in the art. Such forms include, e.g., liquid, semi-solid and solid dosage forms, such as liquid solutions (e.g., injectable and infusible solutions), dispersions or suspensions, tablets, pills, powders, liposomes and suppositories.

Selection or use of any particular form may depend, in part, on the intended mode of administration and therapeutic application. For example, compositions containing a composition intended for systemic or local delivery can be in the form of injectable or infusible solutions. Accordingly, a loaded mini-nucleosome therapeutic agent composition can be formulated for administration by a parenteral mode (e.g., intravenous, subcutaneous, intraperitoneal, or intramuscular injection). As used herein, parenteral administration refers to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

A parenteral route of administration can be, for example, administration by injection, transnasal administration, transpulmonary administration, or transcutaneous administration. Administration can be systemic or local by intravenous injection, intramuscular injection, intraperitoneal injection, subcutaneous injection.

In various embodiments, a loaded mini-nucleosome therapeutic agent composition of the present invention can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

A loaded mini-nucleosome therapeutic agent composition can be administered parenterally in the form of an injectable formulation comprising a sterile solution or suspension in water or another pharmaceutically acceptable liquid. For example, the loaded mini-nucleosome therapeutic agent composition can be formulated by suitably combining the therapeutic molecule with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of loaded mini-nucleosome therapeutic agent included in the pharmaceutical preparations is such that a suitable dose within the designated range is provided. Non-limiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampule.

In some embodiments, a loaded mini-nucleosome therapeutic agent composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 11/2 years, or 2 years) at 2-8° C. (e.g., 4° C.). Thus, in some embodiments, the compositions described herein are stable in storage for at least 1 year at 2-8° C. (e.g., 4° C.).

In particular instances, a loaded mini-nucleosome therapeutic agent composition can be formulated as a solution. In some embodiments, a composition can be formulated, for example, as a buffered solution at a suitable concentration and suitable for storage at 2-8° C. (e.g., 4° C.).

Compositions including a loaded mini-nucleosome therapeutic agent as described herein can be formulated in immunoliposome compositions. Such formulations can be prepared by methods known in the art. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions can be formulated in a composition suitable for intrapulmonary administration (e.g., for administration via an inhaler or nebulizer) to a mammal such as a human. Methods for formulating such compositions are well known in the art. Dry powder inhaler formulations and suitable systems for administration of the formulations are also known in the art. Pulmonary administration may be oral and/or nasal. Examples of pharmaceutical devices for pulmonary delivery include metered dose inhalers, dry powder inhalers (DPIs), and nebulizers. For example, a composition described herein can be administered to the lungs of a subject by way of a dry powder inhaler. These inhalers are propellant-free devices that deliver dispersible and stable dry powder formulations to the lungs. Dry powder inhalers are well known in the art of medicine and include, without limitation: the TURBO-HALER® (AstraZeneca; London, England) the AIR® inhaler (ALKERMES®; Cambridge, Mass.); ROTAHALER® (GlaxoSmithKline; London, England); and ECLIPSE™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, a composition described herein can be intrapulmonarily administered by way of a metered dose inhaler. These inhalers rely on a propellant to deliver a discrete dose of a compound to the lungs. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, loaded mini-nucleosome therapeutic agent compositions can be formulated for delivery to the eye, e.g., in the form of a pharmaceutically acceptable solution, suspension or ointment. A preparation for use in treating an eye can be in the form of a sterile aqueous solution containing, e.g., additional ingredients such as, but not limited to, preservatives, buffers, tonicity agents, antioxidants and stabilizers, nonionic wetting or clarifying agents, and viscosity-increasing agents. A preparation as described herein can be administered topically to the eye of the subject in need of treatment (e.g., a subject afflicted with AMD) by conventional methods, e.g., in the form of drops, or by bathing the eye in a therapeutic solution, containing one or more compositions.

A variety of devices for introducing drugs into the vitreal cavity of the eye may be appropriate, in certain embodiments, for administration of a composition as described herein. For example, U.S. Publication No. 2002/0026176 describes a pharmaceutical-containing plug that can be inserted through the sclera such that it projects into the vitreous cavity to deliver the pharmaceutical agent into the vitreous cavity. In another example, U.S. Pat. No. 5,443,505 describes an implantable device for introduction into a suprachoroidal space or an avascular region for sustained release of drug into the interior of the eye. U.S. Pat. Nos. 5,773,019 and 6,001,386 each disclose an implantable drug delivery device attachable to the scleral surface of an eye. Additional methods and devices (e.g., a transscleral patch and delivery via contact lenses) for delivery of a loaded mini-nucleosome therapeutic agent to the eye are described in, e.g., Ambati and Adamis (2002) Prog Retin Eye Res 21 (2): 145-151; Ranta and Urtti (2006) Adv Drug Delivery Rev 58 (11): 1164-1181; Barocas and Balachandran (2008) Expert Opin Drug Delivery 5 (1): 1-10 (10); Gulsen and Chauhan (2004) Invest Opthalmol Vis Sci 45:2342-2347; Kim et al. (2007) Ophthalmic Res 39:244-254; and PCT publication no. WO 04/073551, the disclosures of which are incorporated herein by reference in their entirety.

In various embodiments, subcutaneous administration can be accomplished by means of a device, such as a syringe, a prefilled syringe, an auto-injector (e.g., disposable or reusable), a pen injector, a patch injector, a wearable injector, an ambulatory syringe infusion pump with subcutaneous infusion sets, or other device for subcutaneous injection.

In some embodiments, a loaded mini-nucleosome therapeutic agent composition described herein can be therapeutically delivered to a subject by way of local administration. As used herein, "local administration" or "local delivery," can refer to delivery that does not rely upon transport of the loaded mini-nucleosome therapeutic agent composition or loaded mini-nucleosome therapeutic agent to its intended target tissue or site via the vascular system. For example, the loaded mini-nucleosome therapeutic agent composition may be delivered by injection or implantation of the composition or agent or by injection or implantation of a device containing the composition or agent. In certain embodiments, following local administration in the vicinity of a target tissue or site, the composition or agent, or one or more components thereof, may diffuse to an intended target tissue or site that is not the site of administration.

In some embodiments, the compositions provided herein are present in unit dosage form, which unit dosage form can be suitable for self-administration. Such a unit dosage form may be provided within a container, typically, for example, a vial, cartridge, prefilled syringe or disposable pen. A doser such as the doser device described in U.S. Pat. No. 6,302,855, may also be used, for example, with an injection system as described herein.

A suitable dose of a loaded mini-nucleosome therapeutic agent composition described herein, which dose is capable of treating or preventing a disorder in a subject, can depend on a variety of factors including, e.g., the age, sex, and weight of a subject to be treated, the condition or disease to be treated, and the particular loaded mini-nucleosome therapeutic agent used. Other factors affecting the dose administered to the subject include, e.g., the type or severity of the condition or disease. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject can also be adjusted based upon the judgment of a medical practitioner.

A loaded mini-nucleosome therapeutic agent solution can include a therapeutically effective amount of a composition described herein. Such effective amounts can be readily determined by one of ordinary skill in the art based, in part, on the effect of the administered composition, or the combinatorial effect of the composition and one or more additional active agents, if more than one agent is used. A therapeutically effective amount can be an amount at which any toxic or detrimental effects of the composition are outweighed by therapeutically beneficial effects.

Pharmaceutical forms of loaded mini-nucleosome therapeutic formulations suitable for injection can include sterile aqueous solutions or dispersions. A formulation can be sterile and must be fluid to allow proper flow in and out of a syringe. A formulation can also be stable under the conditions of manufacture and storage. A carrier can be a solvent or dispersion medium containing, for example, water and saline or buffered aqueous solutions. Preferably, isotonic agents, for example, sugars or sodium chloride can be used in the formulations. For human administration, final preparations and compositions should meet sterility, pyrogenicity, and the general endotoxin levels, safety and purity standards as required by the US FDA and EU regulatory standards. Temperature and exposure to other proteins can alter the properties of loaded mini-nucleosomes. The final preparations and compositions must be stored at appropriate temperatures, preferably at 2-8 degree Celsius or at room temperature (20-25 degree Celsius).

In addition, one skilled in the art may also contemplate additional delivery method may be via electroporation, sonophoresis, intraosseous injections methods or by using gene gun. Vectors may also be implanted into microchips, nano-chips or nanoparticles.

In certain embodiments, the compositions described herein may be formulated in a kit. Such kits may be used for therapeutic or diagnostic purposes. The present disclosure provides, among other things, one or more compositions together with one or more pharmaceutically-acceptable excipients, carriers, diluents, adjuvants, and/or other components, as may be employed in the formulation of a composition consisting of mini-nucleosome core proteins and nucleic acids, and in the preparation of therapeutic agents for administration to a mammal, and in particularly, to a human, for one or more diseases described herein. In particular, such kits may include one or more of the disclosed mini-nucleosome core protein compositions in combination with instructions for using nucleic acids in the treatment various disorders in a mammal, and may typically include containers prepared for convenient commercial packaging.

Compositions described herein can be administered to an animal that is a mammal, e.g., a human. Compositions described herein are also applicable to animals of commercial interest, livestock, and household pets such as dogs and cats. Compositions in kits can include partially or significantly purified loaded mini-nucleosomes compositions, either alone, or in combination with one or more other ingredients or drugs for therapeutic or diagnostic use. Therapeutic kits can also be prepared that include at least one loaded mini-nucleosome component based gene therapy compositions disclosed herein and instructions for using the composition as a therapeutic agent. The container means for such kits may typically include at least one vial, test tube, flask, bottle, syringe or other container means, into which the disclosed mini-nucleosomes composition(s) may be placed, and preferably suitably aliquoted.

Applications

Mini-nucleosomes provided herein can, in various embodiments, be characterized by small size, ability to enter cells by receptor mediated or passive diffusion processes, precision in the location of gene expression, precision in the duration of gene expression, and/or retention until release of nucleic acids in the cytoplasm of the nucleus of a target cell. Some of the desired application of the mini-nucleosome technology are described herein.

The present disclosure further includes the recognition that modified mini-nucleosomes of the present disclosure can target delivery of nucleic acid payloads to particular cells or tissues and/or to achieve expression of an expression product encoded by a nucleic acid payload in one or more particular cells or tissues. As will be readily apparent from the present disclosure, delivery and/or expression of a nucleic acid payload in a particular cell or tissue can be useful in a variety of methods and compositions that benefit from the presence of a particular expression product (e.g., a particular protein) in a particular targeted cell or tissue.

In certain embodiments, a modified mini-nucleosome of the present disclosure includes one or more phosphorylated residues (e.g., where one or more, or all, of the phosphorylated residues are selected from serine, threonine, or tyrosine residues). The present disclosure includes the recognition that the presence, rather than the specific number or position, of the phosphorylated residue mediates the ability of the modified mini-nucleosome to target delivery of nucleic acid payloads to particular cells or tissues and/or to achieve expression of an expression product encoded by a nucleic acid payload in one or more particular cells or tissues. Without wishing to be bound by any particular scientific theory, the present disclosure includes that at least certain advantages that characterize phosphorylated mini-nucleosome core proteins (e.g., targeting of particular cell or tissues) result from interaction of the modification with cell surface receptors of target cells and are therefore not sequence specific or specific to the position of any modified residue. The present disclosure specifically includes the recognition that phosphorylated mini-nucleosome core proteins can deliver a nucleic acid payload to, and/or cause expression of a nucleic acid payload in, target cells that are cells of the central nervous system (CNS). In certain embodiments, a phosphorylated mini-nucleosome core proteins can deliver a nucleic acid payload to, and/or cause expression of a nucleic acid payload in, CNS neurons. In certain embodiments, a phosphorylated mini-nucleosome core proteins can deliver a nucleic acid payload to, and/or cause expression of a nucleic acid payload in, CNS astrocytes, microglia, oligodendrocytes, or glia. In certain embodiments, a phosphorylated mini-nucleosome core protein can deliver a nucleic acid payload to, and/or cause expression of a nucleic acid payload in, spinal cord cells, e.g., spinal cord neurons or spinal cord glial cells. In various embodiments, expression of an expression product encoded by a nucleic acid payload associated with a modified mini-nucleosome core protein (e.g., a phosphorylated mini-nucleosome core protein, e.g., in a loaded mini-nucleosome) is increased as compared to expression achieved under reference (e.g., same or similar) conditions using a reference (e.g., unmodified) mini-nucleosome core protein. The present disclosure recognizes that expression in various such target cell types is significant for treatment of certain conditions that effect or are effected by target cell types, e.g., diseases of the CNS.

In certain embodiments, delivery of a nucleic acid payload and/or expression of a nucleic acid payload in target cells is facilitated by a particular route of delivery. In various embodiments in which a phosphorylated mini-nucleosome core protein delivers a nucleic acid payload to, and/or cause expression of a nucleic acid payload in, one or more target cells, cell types, or tissues disclosed herein, administration to a subject is by a route that achieves delivery to cells of the central nervous system. In various embodiments in which a phosphorylated mini-nucleosome core protein delivers a nucleic acid payload to, and/or cause expression of a nucleic acid payload in, one or more target cells, cell types, or tissues disclosed herein, administration to a subject is by a route that achieves delivery to CNS neurons. In various embodiments in which a phosphorylated mini-nucleosome core protein delivers a nucleic acid payload to, and/or cause expression of a nucleic acid payload in, one or more target cells, cell types, or tissues disclosed herein, administration to a subject is by a route that achieves delivery to CNS astrocytes, microglia, oligodendrocytes, or glia. In various embodiments in which a phosphorylated mini-nucleosome core protein delivers a nucleic acid payload to, and/or cause expression of a nucleic acid payload in, one or more target cells, cell types, or tissues disclosed herein, administration to a subject is by a route that achieves delivery to spinal cord cells, e.g., spinal cord neurons or spinal cord glial cells. Those of skill in the art will be familiar with routes of administration to particular cells, cell types, and tissues. In certain particular embodiments, administration to a subject is by injection, e.g., injection to the CNS (e.g., to a cell or tissue of the CNS). In certain particular embodiments, administration to a subject is intrathecal, intracranial, or intra-cisterna magna. In certain particular embodiments, administration to a subject is intrathecal.

In various embodiments, a phosphorylated mini-nucleosome core protein can include multiple phosphorylated residues, e.g., one, two, three, or four phosphorylated residues. In various embodiments, a phosphorylated mini-nucleosome core protein can include one or more amino acid modifications disclosed herein that is not phosphorylation. Accordingly, the present disclosure includes combinations of different modifications present in a single modified mini-nucleosome core protein. A phosphorylated amino acid of a modified mini-nucleosome can be present in any domain or at any amino acid position of a modified mini-nucleosome.

A phosphorylated amino acid of a modified mini-nucleosome can be present, without limitation, in a linker domain or targeting domain.

In certain embodiments, a modified mini-nucleosome of the present disclosure includes one or more sulfated residues (e.g., where one or more, or all, of the sulfated residues are selected from serine, threonine, or tyrosine residues). The present disclosure includes the recognition that the presence, rather than the specific number or position, of the sulfated residue mediates the ability of the modified mini-nucleosome to target delivery of nucleic acid payloads to particular cells or tissues and/or to achieve expression of an expression product encoded by a nucleic acid payload in one or more particular cells or tissues. Without wishing to be bound by any particular scientific theory, the present disclosure includes that at least certain advantages that characterize sulfated mini-nucleosome core proteins (e.g., targeting of particular cell or tissues) result from interaction of the modification with cell surface receptors of target cells and are therefore not sequence specific or specific to the position of any modified residue. The present disclosure specifically includes the recognition that sulfated mini-nucleosome core proteins can deliver a nucleic acid payload to, and/or cause expression of a nucleic acid payload in, target cells that are cells of the central nervous system. In certain embodiments, a sulfated mini-nucleosome core protein can deliver a nucleic acid payload to, and/or cause expression of a nucleic acid payload in, CNS neurons. In certain embodiments, a sulfated mini-nucleosome core protein can deliver a nucleic acid payload to, and/or cause expression of a nucleic acid payload in, CNS astrocytes, microglia, oligodendrocytes, or glia. In certain embodiments, a sulfated mini-nucleosome core protein can deliver a nucleic acid payload to, and/or cause expression of a nucleic acid payload in, spinal cord cells, e.g., spinal cord neurons or spinal cord glial cells. In various embodiments, expression of an expression product encoded by a nucleic acid payload associated with a modified mini-nucleosome core protein (e.g., a sulfated mini-nucleosome core protein, e.g., in a loaded mini-nucleosome) is increased as compared to expression achieved under reference (e.g., same or similar) conditions using a reference (e.g., unmodified) mini-nucleosome core protein. The present disclosure recognizes that expression in various such target cell types is significant for treatment of certain conditions that effect or are effected by target cell types, e.g., diseases of the CNS.

In certain embodiments, delivery of a nucleic acid payload and/or expression of a nucleic acid payload in target cells is facilitated by a particular route of delivery. In various embodiments in which a sulfated mini-nucleosome core protein delivers a nucleic acid payload to, and/or cause expression of a nucleic acid payload in, one or more target cells, cell types, or tissues disclosed herein, administration to a subject is by a route that achieves delivery to cells of the central nervous system. In various embodiments in which a sulfated mini-nucleosome core protein delivers a nucleic acid payload to, and/or cause expression of a nucleic acid payload in, one or more target cells, cell types, or tissues disclosed herein, administration to a subject is by a route that achieves delivery to CNS neurons. In various embodiments in which a sulfated mini-nucleosome core protein delivers a nucleic acid payload to, and/or cause expression of a nucleic acid payload in, one or more target cells, cell types, or tissues disclosed herein, administration to a subject is by a route that achieves delivery to CNS astrocytes, microglia, oligodendrocytes, or glia. In various embodiments in which a sulfated mini-nucleosome core protein delivers a nucleic acid payload to, and/or cause expression of a nucleic acid payload in, one or more target cells, cell types, or tissues disclosed herein, administration to a subject is by a route that achieves delivery to spinal cord cells, e.g., spinal cord neurons or spinal cord glial cells. Those of skill in the art will be familiar with routes of administration to particular cells, cell types, and tissues. In certain particular embodiments, administration to a subject is by injection, e.g., injection to the CNS (e.g., to a cell or tissue of the CNS). In certain particular embodiments, administration to a subject is intrathecal, intracranial, or intra-cisterna magna. In certain particular embodiments, administration to a subject is intrathecal.

In various embodiments, a sulfated mini-nucleosome core protein can include multiple sulfated residues, e.g., one, two, three, or four sulfated residues. In various embodiments, a sulfated mini-nucleosome core protein can include one or more amino acid modifications disclosed herein that is not sulfation. Accordingly, the present disclosure includes combinations of different modifications present in a single modified mini-nucleosome core protein. A sulfated amino acid of a modified mini-nucleosome can be present in any domain or at any amino acid position of a modified mini-nucleosome. A sulfated amino acid of a modified mini-nucleosome can be present, without limitation, in a linker domain or targeting domain.

In certain embodiments, a modified mini-nucleosome of the present disclosure includes one or more acetylated residues (e.g., where one or more, or all, of the acetylated residues are lysine residues). The present disclosure includes the recognition that the presence, rather than the specific number or position, of the acetylated residue mediates the ability of the modified mini-nucleosome to target delivery of nucleic acid payloads to particular cells or tissues and/or to achieve expression of an expression product encoded by a nucleic acid payload in one or more particular cells or tissues. Without wishing to be bound by any particular scientific theory, the present disclosure includes that at least certain advantages that characterize acetylated mini-nucleosome core proteins (e.g., targeting of particular cell or tissues) result from interaction of the modification with cell surface receptors of target cells and are therefore not sequence specific or specific to the position of any modified residue. The present disclosure specifically includes the recognition that acetylated mini-nucleosome core proteins can deliver a nucleic acid payload to, and/or cause expression of a nucleic acid payload in, target cells that are CNS neurons and/or retinal cells. In certain embodiments, an acetylated mini-nucleosome core protein can deliver a nucleic acid payload to, and/or cause expression of a nucleic acid payload in, CNS neurons. In certain embodiments, an acetylated mini-nucleosome core protein can deliver a nucleic acid payload to, and/or cause expression of a nucleic acid payload in, retinal cells, e.g., retinal neurons including one or more of photoreceptors, bipolar cells, retinal ganglion cells, horizontal cells and amacrine cells). In certain embodiments, an acetylated mini-nucleosome core protein can deliver a nucleic acid payload to, and/or cause expression of a nucleic acid payload in, photoreceptor cells (e.g., rods and/or cones). In various embodiments, expression of an expression product encoded by a nucleic acid payload associated with a modified mini-nucleosome core protein (e.g., an acetylated mini-nucleosome core protein, e.g., in a loaded mini-nucleosome) is increased as compared to expression achieved under reference (e.g., same or similar) conditions using a reference (e.g., unmodified) mini-nucleosome core protein. The present disclosure recognizes that expression in various such target cell types is significant for treatment of certain conditions that effect or are effected by target cell types, e.g., diseases of the CNS, including diseases of the retina (e.g., Retinitis pigmentosa and/or Stargardt's disease).

In certain embodiments, delivery of a nucleic acid payload and/or expression of a nucleic acid payload in target cells is facilitated by a particular route of delivery. In various embodiments in which an acetylated mini-nucleosome core protein delivers a nucleic acid payload to, and/or cause expression of a nucleic acid payload in, one or more target cells, cell types, or tissues disclosed herein, administration to a subject is by a route that achieves delivery to CNS neurons and/or retinal cells. In various embodiments in which an acetylated mini-nucleosome core protein delivers a nucleic acid payload to, and/or cause expression of a nucleic acid payload in, one or more target cells, cell types, or tissues disclosed herein, administration to a subject is by a route that achieves delivery to CNS neurons. In various embodiments in which an acetylated mini-nucleosome core protein delivers a nucleic acid payload to, and/or cause expression of a nucleic acid payload in, one or more target cells, cell types, or tissues disclosed herein, administration to a subject is by a route that achieves delivery to retinal cells, e.g., retinal neurons including one or more of photoreceptors, bipolar cells, retinal ganglion cells, horizontal cells and amacrine cells). In various embodiments in which an acetylated mini-nucleosome core protein delivers a nucleic acid payload to, and/or cause expression of a nucleic acid payload in, one or more target cells, cell types, or tissues disclosed herein, administration to a subject is by a route that achieves delivery to photoreceptor cells (e.g., rods and/or cones). Those of skill in the art will be familiar with routes of administration to particular cells, cell types, and tissues. In certain particular embodiments, administration to a subject is by injection, e.g., injection to the eye (e.g., to a cell or tissue of the eye). In certain particular embodiments, administration to a subject is intravitreal, suprachoroidal, or subretinal.

In various embodiments, an acetylated mini-nucleosome core protein can include multiple acetylated residues, e.g., one, two, three, or four acetylated residues. In various embodiments, an acetylated mini-nucleosome core protein can include one or more amino acid modifications disclosed herein that is not acetylation. Accordingly, the present disclosure includes combinations of different modifications present in a single modified mini-nucleosome core protein. An acetylated amino acid of a modified mini-nucleosome can be present in any domain or at any amino acid position of a modified mini-nucleosome. An acetylated amino acid of a modified mini-nucleosome can be present, without limitation, in a linker domain or targeting domain.

In certain embodiments, a modified mini-nucleosome of the present disclosure includes one or more mannosylated residues (e.g., where one or more, or all, of the mannosylated residues are serine residues). The present disclosure includes the recognition that the presence, rather than the specific number or position, of the mannosylated residue mediates the ability of the modified mini-nucleosome to target delivery of nucleic acid payloads to particular cells or tissues and/or to achieve expression of an expression product encoded by a nucleic acid payload in one or more particular cells or tissues. Without wishing to be bound by any particular scientific theory, the present disclosure includes that at least certain advantages that characterize mannosylated mini-nucleosome core proteins (e.g., targeting of particular cell or tissues) result from interaction of the modification with cell surface receptors of target cells and are therefore not sequence specific or specific to the position of any modified residue. The present disclosure specifically includes the recognition that mannosylated mini-nucleosome core proteins can deliver a nucleic acid payload to, and/or cause expression of a nucleic acid payload in, target cells that are CNS neurons and/or retinal cells. In certain embodiments, a mannosylated mini-nucleosome core protein can deliver a nucleic acid payload to, and/or cause expression of a nucleic acid payload in, CNS neurons. In certain embodiments, a mannosylated mini-nucleosome core protein can deliver a nucleic acid payload to, and/or cause expression of a nucleic acid payload in, retinal cells, e.g., retinal neurons including one or more of photoreceptors, bipolar cells, retinal ganglion cells, horizontal cells and amacrine cells). In certain embodiments, a mannosylated mini-nucleosome core protein can deliver a nucleic acid payload to, and/or cause expression of a nucleic acid payload in, photoreceptor cells (e.g., rods and/or cones). In various embodiments, expression of an expression product encoded by a nucleic acid payload associated with a modified mini-nucleosome core protein (e.g., a mannosylated mini-nucleosome core protein, e.g., in a loaded mini-nucleosome) is increased as compared to expression achieved under reference (e.g., same or similar) conditions using a reference (e.g., unmodified) mini-nucleosome core protein. The present disclosure recognizes that expression in various such target cell types is significant for treatment of certain conditions that effect or are effected by target cell types, e.g., diseases of the CNS, including diseases of the retina (e.g., Retinitis pigmentosa and/or Stargardt's disease.

In certain embodiments, delivery of a nucleic acid payload and/or expression of a nucleic acid payload in target cells is facilitated by a particular route of delivery. In various embodiments in which a mannosylated mini-nucleosome core protein delivers a nucleic acid payload to, and/or cause expression of a nucleic acid payload in, one or more target cells, cell types, or tissues disclosed herein, administration to a subject is by a route that achieves delivery to CNS neurons and/or retinal cells. In various embodiments in which a mannosylated mini-nucleosome core protein delivers a nucleic acid payload to, and/or cause expression of a nucleic acid payload in, one or more target cells, cell types, or tissues disclosed herein, administration to a subject is by a route that achieves delivery to CNS neurons. In various embodiments in which a mannosylated mini-nucleosome core protein delivers a nucleic acid payload to, and/or cause expression of a nucleic acid payload in, one or more target cells, cell types, or tissues disclosed herein, administration to a subject is by a route that achieves delivery to retinal cells, e.g., retinal neurons including one or more of photoreceptors, bipolar cells, retinal ganglion cells, horizontal cells and amacrine cells). In various embodiments in which a mannosylated mini-nucleosome core protein delivers a nucleic acid payload to, and/or cause expression of a nucleic acid payload in, one or more target cells, cell types, or tissues disclosed herein, administration to a subject is by a route that achieves delivery to photoreceptor cells (e.g., rods and/or cones). Those of skill in the art will be familiar with routes of administration to particular cells, cell types, and tissues. In certain particular embodiments, administration to a subject is by injection, e.g., injection to the eye (e.g., to a cell or tissue of the eye). In certain particular embodiments, administration to a subject is intravitreal, suprachoroidal, or subretinal.

In various embodiments, a mannosylated mini-nucleosome core protein can include multiple mannosylated residues, e.g., one, two, three, or four mannosylated residues. In various embodiments, a mannosylated mini-nucleosome core protein can include one or more amino acid modifications disclosed herein that is not mannosylation. Accordingly, the present disclosure includes combinations of different modifications present in a single modified mini-nucleosome core protein. A mannosylated amino acid of a modified mini-nucleosome can be present in any domain or at any amino acid position of a modified mini-nucleosome. A mannosylated amino acid of a modified mini-nucleosome can be present, without limitation, in a linker domain or targeting domain.

Gene Therapy

In various embodiments, mini-nucleosomes provided herein can be used in methods of gene therapy. The general principles of gene therapy are well known in the art and include the delivery of a polynucleotide to a subject in need thereof to provide an expression product (e.g., an mRNA, protein, or inhibitory RNA) of therapeutic value. In some embodiments, gene therapy can include gene or protein replacement therapy (e.g., enzyme replacement therapy), augmentation, or target inhibition. In various embodiments, mini-nucleosomes provided herein can be applied to rescue deleterious effects of any mutations that cause diseases including, without limitation, Cystic fibrosis, Duchenne muscular dystrophy, Stargardt's disease, Age-related macular degeneration, Huntington, Hemophilia A, Spinal muscular atrophy, Usher syndrome etc. In such diseases, a genetic mutation renders a gene nonfunctional or not available. In such cases, replacing the mutated gene by a functional copy may be beneficial to the patients. By incorporating a functional cDNA or whole gene into a loaded mini-nucleosome, and delivering it to desired cells or tissues, one may receive, in various embodiments, a therapeutic benefit.

In some embodiments, mini-nucleosomes provided herein can be applied to inhibit genes that are upregulated and disease causing. For example, P53 overexpression has been described in various diseases. In some instances, it is also beneficial to knock down genes at specific cells or tissues to downregulate genes that cause inflammation, hypoxia etc. to have therapeutic effects.

Ex-vivo Engineered Cells

Mini-nucleosomes of the present disclosure can be used to engineer cells ex vivo. Cells can be engineered to express therapeutics in various ways. One such cell is immune cell, e.g., T cell. Immune cells can be genetically engineered to express new proteins or receptors that may allow immune recognition of cancerous cells or other harmful cell types for killing and clearance. Such genetic engineering may be performed ex vivo. In various embodiments, mini-nucleosomes provided herein can be used in methods of genetically engineering cells ex vivo. Combination of domains provided herein, may allow loaded mini-nucleosome entry to variety of T cells and deliver a genetic cargo to the nucleus in such cells. The genetic cargo may encode and/or allow expression of chimeric receptors, knockdown of genes or other therapeutic entity. Such cells may then be infused into patients for therapy. One skilled in the art, may contemplate using loaded mini-nucleosomes for creating chimeric antigen receptor T cells (CAR T cells) for use in immunotherapy.

In some embodiments, mini-nucleosomes provided herein can be applied to engineering stem cells ex vivo to express new proteins or receptors for therapeutic purposes. Combination of domains provided herein, may allow loaded mini-nucleosome entry to variety of stem cells to deliver a genetic cargo to the nucleus/cytoplasm in such cells. The genetic cargo may allow expression of chimeric receptors, knockdown of genes or other therapeutic entity. Such cells may then be infused into patients for therapy. One skilled in the art, may contemplate using loaded mini-nucleosomes for creating chimeric stem cells or chimeric hematopoietic stem cells for use in immunotherapy.

Gene Editing And Base Excision Repair

Gene editing, base editing and manipulation is also an applicable area for this mini-nucleosome technology described herein. Gene editing and base excision repair are state-of-the-art technologies that allow correcting a genetic mutation or editing the genes at the DNA or RNA level. Towards this application, a loaded mini-nucleosome may incorporate nucleic acids that encode for gRNA, sgRNA, spCas9, saCas9, dCas9, cytidine deaminase and several other enzymes that help cleave DNA or convert one base to another. One skilled in the art can appreciate that incorporating multiple gRNAs and Cas9 or similar editing enzymes in an AAV is a cumbersome and often inefficient process. Hence, using the method and compositions described herein, that enables easy compaction of nucleic acids onto loaded mini-nucleosomes allows incorporation of several gRNAs and even the largest of Cas9 genes to deliver to desired cells.

Antibody Delivery

Antibodies are a class of drugs that have been life changing for millions of patients worldwide. However, one big drawback in this therapy is the requirement of repeat administration which poses immense burden to patients, physicians and caregivers. One skilled in the art can appreciate that a DNA molecule can be used to express antibodies. Mini-nucleosome technology described herein, provides an opportunity to vectorize the antibody and deliver to desired cells in the patients to create a long-term depot in their bodies to reduce the burden of multiple administration. These DNA molecules that express part or whole of antibody domains can be incorporated into loaded mini-nucleosomes to create a long term therapeutic option for patients that take antibody drugs. One skilled in the art may also vectorize and deliver other antibody like molecules such as nanobody, antibody mimetics, fusion peptides, antibody fragments, camelid or camelid single-domain antibody fragments using mini-nucleosome core proteins.

Vaccine Delivery

Genetically engineered DNA or RNA can produce an antigen to provide a protective immunological response. Nucleic acid vaccines have several potential advantages such as wide-range immunological response over conventional vaccines. Mini-nucleosome technology described herein, can incorporate and deliver such DNA or RNA constructs to desired cells or tissues in animals including humans to protect from several viral, bacterial or parasitic infections.

Cosmetics

Genetically engineered DNA or RNA can be developed for several cosmetic applications for example to enhance muscle mass, repair skin in burn victims, for weight loss, to improve immune function, to slow aging and many other applications. Mini-nucleosome technology described herein, can incorporate and deliver applicable DNA or RNA constructs to desired cells or tissues in animals including humans for desired cosmetic effect.

In various embodiments, the present disclosure further provides vectors relating to preventing or treating a disease in humans or other animals. A prophylactically or therapeutically effective amount of a composition could be administered via intravenous, intramuscular, intranasal, intraperitoneal, subcutaneous, intracerebral, subretinal, intravitreal, via lumbar puncture, topical, rectal, or direct delivery to local organs or tumors but not limited to these techniques. The composition includes of nucleic acid complexes, each complex consisting essentially of a single or more nucleic acid molecule and one or more mini-nucleosome core protein molecules.

The present disclosure provides, among other things, improved methods of condensing DNA, RNA and their analogs etc. for efficient delivery into human cells to treat certain diseases and/or cosmetic applications. The nucleic acid delivered may also have applications to deliver vaccines.

Examples

Example 1: Design and Synthesis of
Mini-Nucleosome Core Proteins

This Example is representative of methods and compositions relating to mini-nucleosome core proteins. In this Example, amino acid sequences of peptides (that can condense nucleic acids into loaded-mini-nucleosomes) and their synthesis process are described.

Loaded mini-nucleosomes of the present Example are produced for efficient gene transfer and release of loaded nucleic acid cargo to various cell types. Loaded mini-nucleosomes of the present Example are designed to actively engage with cell surface via binding to cell surface proteins, to be translocated to the cytoplasm/nucleus in cells, and to allow release of the nucleic acid cargo. These characteristics can be achieved by mini-nucleosome core protein and loaded mini-nucleosomes designed based on structured protein/DNA interaction. Accordingly, the present Example includes mini-nucleosome core proteins that include one or more amino acid domains that enhance one or more of cellular attachment, enhanced uptake, enhanced stability, active transport to the nucleus of a target cell, and release via peptidases.

In the present Example, synthesized mini-nucleosome core proteins may include, without limitation, a sequence according to any one of SEQ ID NOS: 389-394, or other sequences derived from domains disclosed herein in Table 3-12, or any combination thereof. Mini-nucleosome core proteins of the present Example are peptides with net positive charge >8 at pH 7 and isoelectric point >9. For example, SEQ ID NO: 394 is a mini-nucleosome core protein sequence including multiple DNA binding domains (KRHRK) combined with multiple Neuronal attachment domains (LRE) and a poly-Arginine domain (RRRRR). In this same construct, Leucines (L) surround the poly-Arginine domain to separate charged domains with hydrophobic amino acids, enabling the cell attachment targeting domain to bind to the cell surface. In this construct, the mini-nucleosome core protein (SEQ ID NO: 394) is designed for enhanced attachment to neurons via LRE domain while the poly-Arginine domain would help cell entry. The present Example also includes mini-nucleosome core proteins with various linkers positioned between certain domains, and examples of linkers include those provided in SEQ ID NOS: 389-394. By design, KRH in SEQ ID NO: 394 also serves as a cut site for PCSK1 for enhanced release of nucleic acids. Other nucleic acid release domains or cleavage domains that could be included in mini-nucleosome core proteins include, without limitation, those described in Table 9. Domains for inclusion in mini-nucleosome core proteins can also be derived for other peptidases, including without limitation those in Table 9.

Mini-nucleosome core proteins of the present Example, including mini-nucleosome core proteins according to SEQ ID NOS: 389-394, include various combinations of sequence features that allows efficient condensation with nucleic acid molecules and delivery of loaded mini-nucleosomes to desired cell types, e.g., animal cells and tissues. In certain mini-nucleosome core proteins of the present Example, an oligomerization domain is included in a mini-nucleosome core protein in order to cause a loaded mini-nucleosome core protein formed by association of the mini-nucleosome core protein with a nucleic acid cargo to have a relatively smaller size as compared to a reference loaded mini-nucleosome core protein, e.g., as compared to a loaded mini-nucleosome including mini-nucleosome core proteins that lack the oligomerization domain(s) but otherwise are identical in amino acid sequence. Exemplary oligomerization domains include those provided in Table 11. Similarly, endosomal entry and escape signals may also be included in mini-nucleosome core proteins for enhanced stability and release.

Mini-nucleosome core proteins of the present Example can be synthesized by various methods. One method of synthesizing mini-nucleosome core proteins is peptide synthesis. Peptide synthesis allows linking of amino acids via amide bonds. For example, mini-nucleosomes core proteins can be chemically synthesized via a condensation reaction between carboxyl group of one amino acid to the amino group of the next desired amino acid, in order of the sequence of a mini-nucleosome core protein. An established method of peptide syntheses is known in the art as solid phase peptide synthesis.

Several strategies can optionally be applied to protect the amino (N-terminal) and carboxy-terminal (C-terminal) of mini-nucleosome core proteins of the present disclosure. If the mini-nucleosome core protein is lyophilized, the lyophilized peptide may contain traces of salts used during the synthesis process. Other methods of mini-nucleosome core protein production include expressing the mini-nucleosome core protein in a cell system or in vivo form DNA constructs encoding the mini-nucleosome core protein. Produced mini-nucleosome core proteins can be purified by a variety of methods known in the art. For instance, several resins may be utilized during the process. Mini-nucleosomes core proteins, in various instances of the present Example, are >90% pure. However, a less pure <90% core protein may also be used to form a loaded mini-nucleosome. Mini-nucleosomes core proteins, in various instances of the present Example, are >90% conjugated with PEG. However, a less conjugated (<90%) or non-conjugated core protein may also be used to form a loaded mini-nucleosome. Mini-nucleosomes core protein purity can be determined by high-pressure liquid chromatography (HPLC) and identity confirmed by mass spectrometry to the very least.

Example 2. Production of loaded Mini-nucleosomes

This Example describes techniques relating to production of a loaded mini-nucleosome, including without limitation a loaded mini-nucleosome of Example 1. Loaded mini-nucleosomes of the present Example include a nucleic acid cargo (DNA or RNA) condensed with mini-nucleosome core proteins with net positive charges. The mini-nucleosome core protein net positive charge neutralizes negative charges of the nucleic acid cargo, resulting in nanometer sized particles. Conjugation of the said mini-nucleosomes core proteins and DNA or RNA can occur in small or large quantities. There are 2 phosphates meaning 2 negative charges associated with every base. The present Example provides that at least 90% of DNA negative charges are neutralized by a nucleosome core protein positive charge. For example, 90-95 percent of DNA negative charges need to be neutralized for efficient condensation of the nucleic acids with a mini-nucleosome core protein. Various mini-nucleosome core proteins of the present Example can include amino acid domains that enhance one or more of cellular attachment, cellular uptake, protein stability, active transport to the nucleus of a target cell, and release of nucleic acid cargo. Thus, certain mini-nucleosome core proteins provided herein can be particularly useful in certain contexts. During the process of mixing the nucleic acids and mini-nucleosomes core proteins to produce a loaded mini-nucleosome, the mixture of nucleic acids and mini-nucleosome core proteins can be mixed or vortexed between 100rpms to 4000rpms. In the process of conjugation of nucleic acids, certain catalysts, such as NaOH and spermidines, that enhance the condensation reaction may be added. These catalysts can be added to the reactor prior to adding the polypeptides and nucleic acids. The nucleic acids may be added in concentrations ranging from 0.1 microgram/microliter to 100 grams/liter. Mini-nucleosomes core proteins may be added at a concentration of 0.1 microgram/microliter to 100 grams/liter. The nucleic acids may be added at once or may be added gradually, e.g., steadily or in sequentially in drops to a vortexing solution. Once the mixing is over, the condensed materials, i.e., loaded mini-nucleosomes may be allowed to be equilibrated for a period of several minutes to several hours, e.g., a period of 2 minutes to a period of 6 hours, prior to purification. Dialysis may be performed to remove impurities and exchange buffers at this stage. Loaded mini-nucleosomes may be purified using several techniques. One such technique is to centrifuge the particles at high speed in a column with molecular weight cutoff parameters of 1kiloDalton or higher. The centrifugation speed may range from 7000 xg to 10,000 xg depending on the sample volume. Similarly, duration of centrifugation may vary from 20 minutes at room temperature to one hour depending in sample volume. Another technique available to purify the mini-nucleosomes is dialysis. The purification technique may not be limited to these two techniques and those of skill in the art will be aware of various further purification techniques from literature that can be used to purify protein/nucleic acid complexes. Finally, the loaded mini-nucleosomes may be eluted or collected in endotoxin free water, normal saline or any other buffered solution but not limited to these. The expected recovery of DNA is ~30-70%. Loaded mini-nucleosomes may also undergo further centrifugation in molecular weight cut-off columns to further concentrate the amount of vector genome in the solution. In the present Example, the loaded mini-nucleosome is formulated to minimize the presence of endotoxin. Typical sources of endotoxin are known to include plasmids, peptide synthesis, or from materials used in the prep. Hence, endotoxin free plasmids can be used, and materials and equipment that have been scrubbed of endotoxin can be used, during preparations described in this Example.

A bioreactor can also be used to formulate loaded mini-nucleosomes for consistent mixing of the nucleic acids and peptides to produce particles for commercial and clinical use.

Example 3: Favorable Shapes/Sizes and Formulations for Loaded Mini-Nucleosomes

Figure 7:
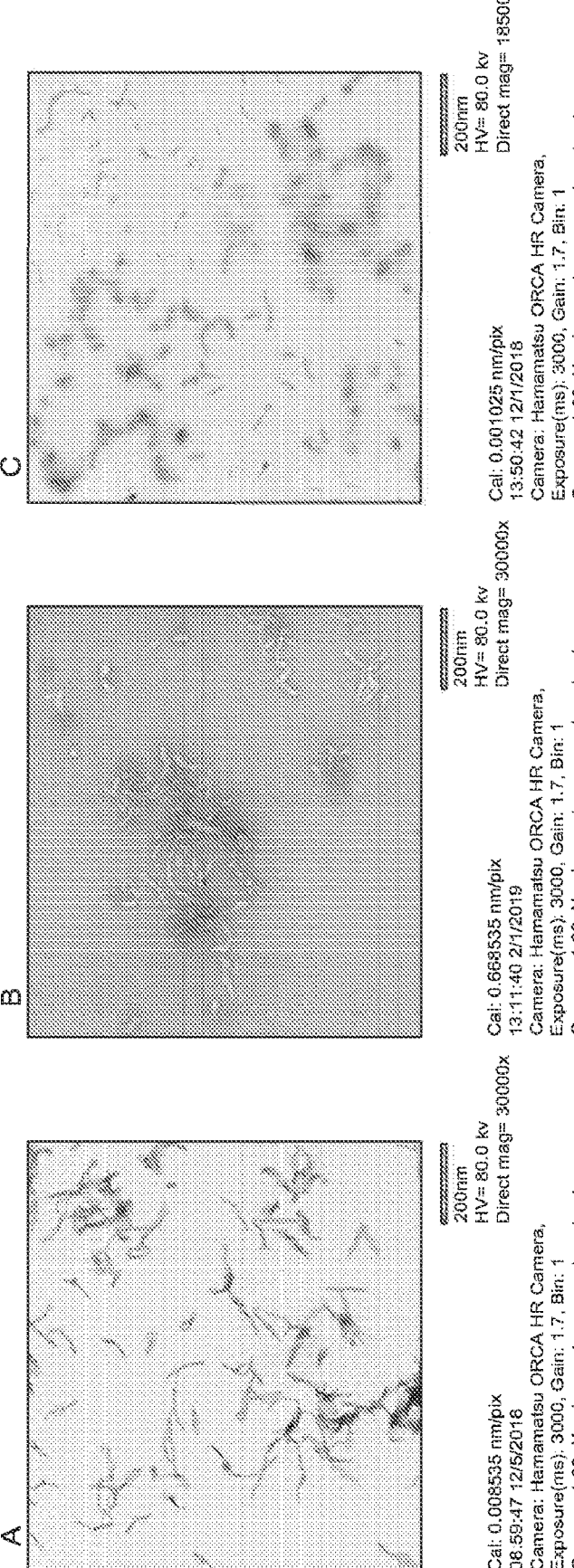
FIG. 7 is a set of images that includes panels A, B, and C, each of which presents an image from Transmission Electron Microscopy (TEM) of loaded mini-nucleosomes.
Figure 18:
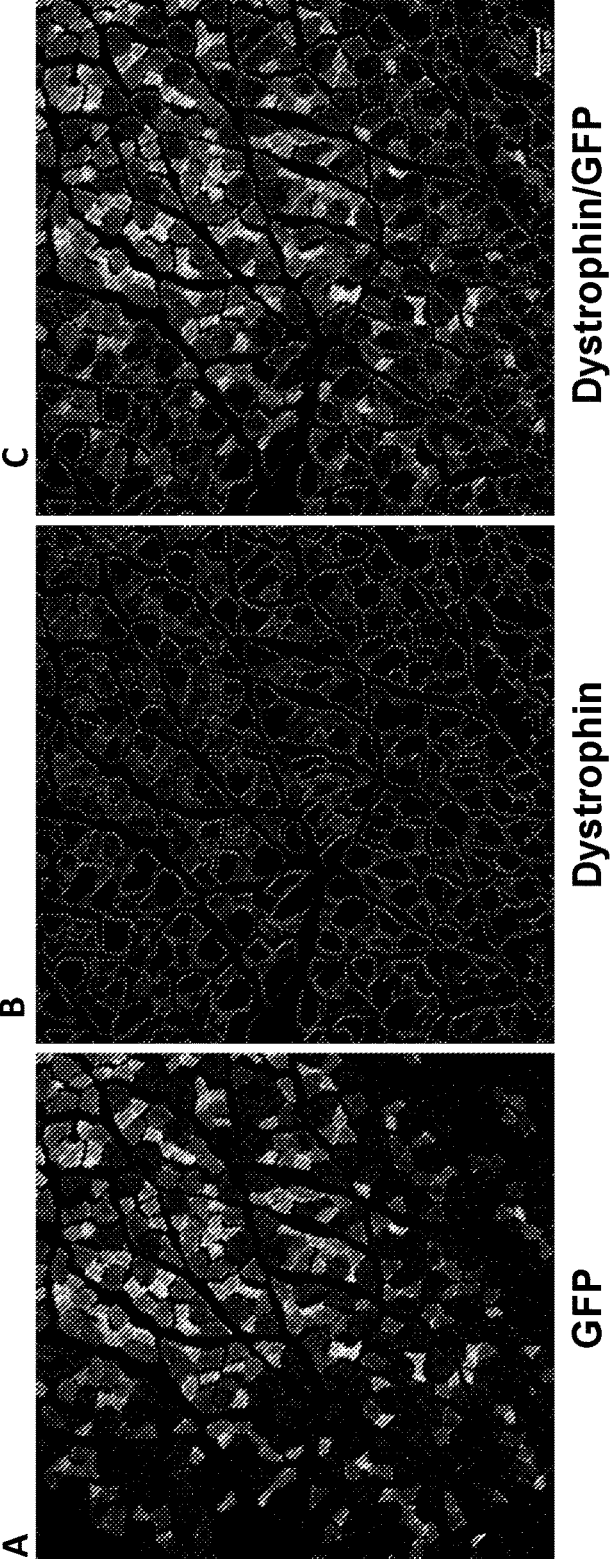
FIG. 18 is a set of images including panels A, B & C that illustrates gene expression in mice muscle tissue of proteins encoded by nucleic acids present in loaded mini-nucleosomes. Panel A demonstrates GFP expression in mouse muscle cells. Panel B demonstrates dystrophin staining pattern in expression in mouse muscle cells. Panel C is a merge of panel A and B that demonstrates colocalization of dystrophin staining pattern with GFP in mouse muscle cells.

Provided in this Example are techniques to produce loaded mini-nucleosomes in various formulations, including formulations useful for administration to cells and to mammalian subjects, e.g., humans. Loaded mini-nucleosomes can be formulated to different shape and/or sizes parameters based on the mini-nucleosome core protein amino acid sequence and the buffer conditions in which the synthesis occurs. Loaded mini-nucleosomes can be formulated in different conditions, e.g., with solubility suitable for therapeutic use. Solubility of loaded mini-nucleosomes in water and/or normal saline is one means to allow non-toxic formulation of compositions for administration to patients, and to ease of delivery into patients. To form loaded mini-nucleosomes represented in FIG. 7, core proteins were synthesized by solid phase synthesis using trifluoroacetate buffers. 200 micrograms of DNA (SEQ ID NO: 396) were added to 1 milligram of lyophilized core proteins and vortexed together, and purified to produce loaded mini-nucleosomes (FIG. 7). Buffer exchange was performed and final formulation of mini-nucleosome was made in sterile, endotoxin free water. 1 microgram of each kind of mini-nucleosomes was diluted in water and then placed on grids that were stained with freshly prepared in 0.75% uranyl acetate in methanol solution for two minutes. Grids were dipped in 100% ethanol and then blotted into lens absorbent paper. The grids were then air-dried for few minutes with film side up and taken for imaging with Hammatsu ORCA HR camera (FIG. 7). The polynucleotide utilized in generating loaded mini-nucleosome core proteins of the present disclosure as a plasmid encoding luciferase, but those of skill in the art will appreciate that the present Example is broadly demonstrative of the general capacity of mini-nucleosome core proteins of the present disclosure to associate with polynucleotides and form loaded mini-nucleosomes. Luciferase plasmid is representative of nucleic acid in general, including, without limitation, plasmids, linear nucleic acids, RNA and DNA of all kinds. In other cases, e.g., RNA or DNA of other sequences or structures could be used in producing loaded mini-nucleosomes. Luciferase plasmid condensed with core protein of SEQ ID NO: 393, led to spiral/helical-shaped loaded mini-nucleosome (FIG. 7A). Luciferase plasmid condensed with core protein with SEQ ID NO: 390, led to rod/lobular shaped loaded mini-nucleosomes (FIG. 7B). A mixture of circular and rod like molecules were observed for loaded mini-nucleosome produced by condensation of luciferase plasmid with core protein SEQ ID NO: 391 (FIG. 7C). There are other buffer conditions and amino acid sequence with varying charge and iso-electric point that could produce spherical or circular loaded mini-nucleosomes. Molecules of different shapes and sizes can enhance tropism to certain cell types. Differently shaped viruses transduce different cell types more effectively. For example, the tobacco mosaic virus is a rod/helical shaped nucleocapsid structure that transduces tobacco plant cells, HIV is round or ball-shaped that infects white blood cells, and AAV2 is an icosahedral shape that transduces liver cells effectively. We observed better transduction tropism of spiral shaped mini-nucleosomes compared to rod shaped ones in muscle cells (FIG. 18). We have been able to formulate differently shaped loaded mini-nucleosomes as described herein. Distinct mini-nucleosomes can also be purified based on unique shapes and sizes.

Figure 8:
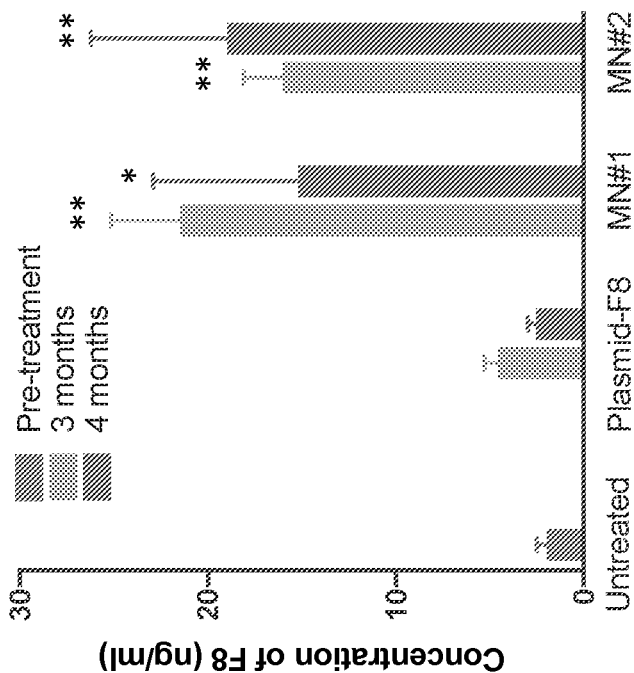
FIG. 8 is a graph showing concentration of expressed Factor 8 protein as measured by Elisa.

Example 4: Route of Administration-Intravenous (Systemic) and Application in Systemic Diseases Such as Hemophilia A This Example demonstrates that loaded mini-nucleosomes can be delivered by intravenous routes to express proteins in the liver and other organs. Balb/c mice were restrained using standard techniques and insulin syringes were used to deliver loaded mini-nucleosomes and plasmid controls via tail vein injections. F8 expressing plasmid constructs ("F8 plasmid"; see, e.g., MN #1 and MN #2, FIG. 8) were prepared by condensation of SEQ ID NO: 390 and SEQ ID NO: 391, respectively, with F8 plasmid DNA (SEQ ID NO: 460). Plasmid sequence for GFP expressing construct is provided in SEQ ID NO: 8. In the present Example, to target loaded mini-nucleosomes to liver cells, we incorporated 2 NGR amino acid domains alongside nucleic acid binding domains (SEQ ID NO: 3). NGR domains in AAV2 have been shown to promote $\alpha V\beta 5$ integrin binding. NGR domains are implicated in heparan sulfate binding, known as receptor for AAV2. AAV2 is known for high liver tropism. KRH amino acid motif also incorporated in these core proteins serve as a cut site for PCSK1 for enhanced release of nucleic acids. Inclusion of multiple KRH amino sequences should enhance release of loaded mini-nucleosomes. Each mouse received 40 micrograms dose of either MN #1, MN #2 or naked plasmid F8 (SEQ ID NO: 460). To test for expression of F8 protein, ~150 μl blood was collected by cheek bleed technique before (1 day prior) and after treatments (post treatment-3 days, 1 week, 2 weeks, 1 month, 3 months and 4 months). Serum was prepared from blood using standard techniques. F8 Elisa (Aviva Systems Biology) was performed according to manufacturer's instructions using 1:6 serum dilutions. Loaded mini-nucleosomes #1 (MN #1 includes SEQ ID NO: 390+F8 plasmid) and MN #2 (MN #2 includes SEQ ID NO: 391+F8 plasmid) expressed approximately six folds more F8 compared the level of F8 detected by ELISA in pre-treatment samples. MN #1 sustained significantly elevated levels of expression at 3 months and 4 months after a single injection of loaded mini-nucleosome (FIG. 8). Control mice treated with naked plasmid encoding F8 (not complexed with mini-nucleosome core proteins) did not demonstrate significant increase in F8 expression at either time points (FIG. 8).

Figure 9:
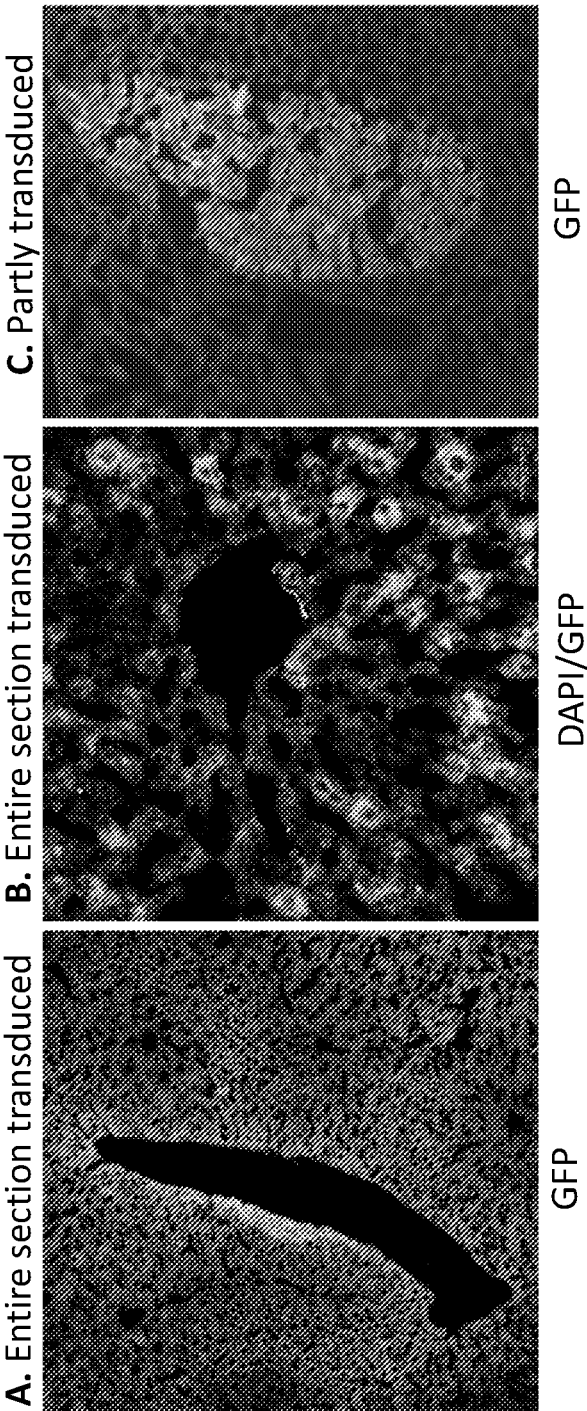
FIG. 9 is a set of images including panels A, B, and C, each of which is a fluorescent microscopy image that illustrates gene expression in liver tissue of proteins encoded by nucleic acids present in loaded mini-nucleosomes.

In another experiment, direct GFP fluorescence was observed in tissues collected from mice that underwent intravenous injection of loaded-mini-nucleosomes carrying GFP expressing plasmid (SEQ ID NO: 390+GFP plasmid, SEQ ID NO: 395) (FIG. 9). Briefly, mice were perfused with 1×PBS and sacrificed. Entire liver was collected following dissection. The liver tissues were fixed in 4% paraformaldehyde overnight then washed in 1×PBS, immersed in 15% sucrose for few hours and then in 30% sucrose solution overnight for cryopreservation. The tissues were then placed in a plastic vial and frozen using OCT compound for sectioning. 10-micron thick tissue sections were obtained using a cryotome. The liver sections were mounted with mounting media with or without DAPI, coverslip and sealed. Images were acquired by Leica SP5 confocal and epi-fluorescent scopes.

Results demonstrated that when delivered by intravenous route, mini-nucleosomes successfully reached liver and mini-nucleosome cargo-encoded genes were expressed in liver cells (FIG. 9). Expression in multiple liver cell types was observed. The observations of the present Example suggest that delivery of loaded mini-nucleosomes to liver is not dependent upon targeting domains. One of skill in the art, in view of the data provided in the present Examples, would understand that loaded mini-nucleosomes can be delivered to cells in kidney and spleen via intravenous delivery, since, like the liver, these organs normally function in clearance of, e.g., drugs.

One example of a condition that, in view of the present disclosure, can be treated by use of a loaded mini-nucleosome therapeutic agent is Hemophilia A. Hemophilia A is a severe bleeding disorder caused by mutation in factor 8, a clotting factor. It is inherited in an X-lined recessive manner. It occurs in approximately 1 in 5,000 live births. Most serious implications are internal bleeding that may lead to death. Severity depends on amount of F8 circulating in the body. 75% of the hemophilia patients take a recombinant F8 product as therapy. Subjects receiving F8 therapy are repeatedly infused intravenously, leading to huge burden for patients, physicians, and caregivers over time. Currently, gene therapy trials are underway to deliver long term expression of F8 via AAVs. However, F8 is a large gene that cannot be fully incorporated in AAV. Thus, mini-F8 has been utilized to deliver functional domains of F8 to treat this disease. It is well known that mini-F8 doesn't have the same functional capability and stability as of full-length F8. Moreover, 20-40% of population already has neutralizing antibodies against AAV that will render a large population of Hemophilic patients unable to receive the AAV-based medicine. In addition, if a further treatment were to be needed after a first discontinued course of AAV treatment, AAV vectors cannot be redosed due to immunogenicity. By being able to deliver full size of F8 gene (FIG. 8) and because of its redosable nature (FIG. 17), loaded mini-nucleosomes solve these two problems of AAV gene therapy. Thus, the present disclosure provides techniques to deliver loaded mini-nucleosomes into different cell types in the systemic space such as liver, kidney, spleen etc. using intravenous mode of delivery, for use in many conditions of which Hemophilia A is exemplary.

Other systemic diseases that often stem from defects in secreted proteins could also be treated using loaded mini-nucleosomes therapeutic agents. The present Example (FIG. 8) demonstrated that loaded-mini-nucleosomes, delivered intravenously (systemic administration), produce proteins at levels higher than the therapeutic threshold which is approximately 10% of endogenous levels determined by various clinical trials demonstrating, among other things, therapeutic potential of mini-nucleosomes as therapeutic agents for treatment of, e.g., systemic diseases where a secreted protein can be expressed by variety of cell types. In some cases, expression can be restricted to certain cell types by using a cell-type specific promoter. One skilled in the art would also understand from the present disclosure that other tissues such as brain, heart, muscles etc. may also be accessed and transduced via intravenous delivery. The targeting mechanism built into the mini-nucleosome core proteins shall aid in that context.

When injected intravenously, loaded mini-nucleosomes may be delivered at a dose greater than 1e5 genome copies per kg and up to a dose of 1e25 copies per kg of body weight (e.g., at about 1e5, 1e6, 1e7, 1e8, 1e9, 1e10, 1e15, 1e20, or 1e25 copies per kg body weight, or any range there between). Volume of the material may range from 1-900 milliliters (e.g., 1, 5, 10, 20, 30, 40, 50, 100, 200, 300, 400, 500, 600, 700, 800, or 900 milliliters). The loaded mini-nucleosomes may also be administered repeatedly (e.g., a selected volume and/or number of genome copies can be administered multiple times or divided among two or more does).

Example 5: Route of administration-Intraocular

Figure 11:
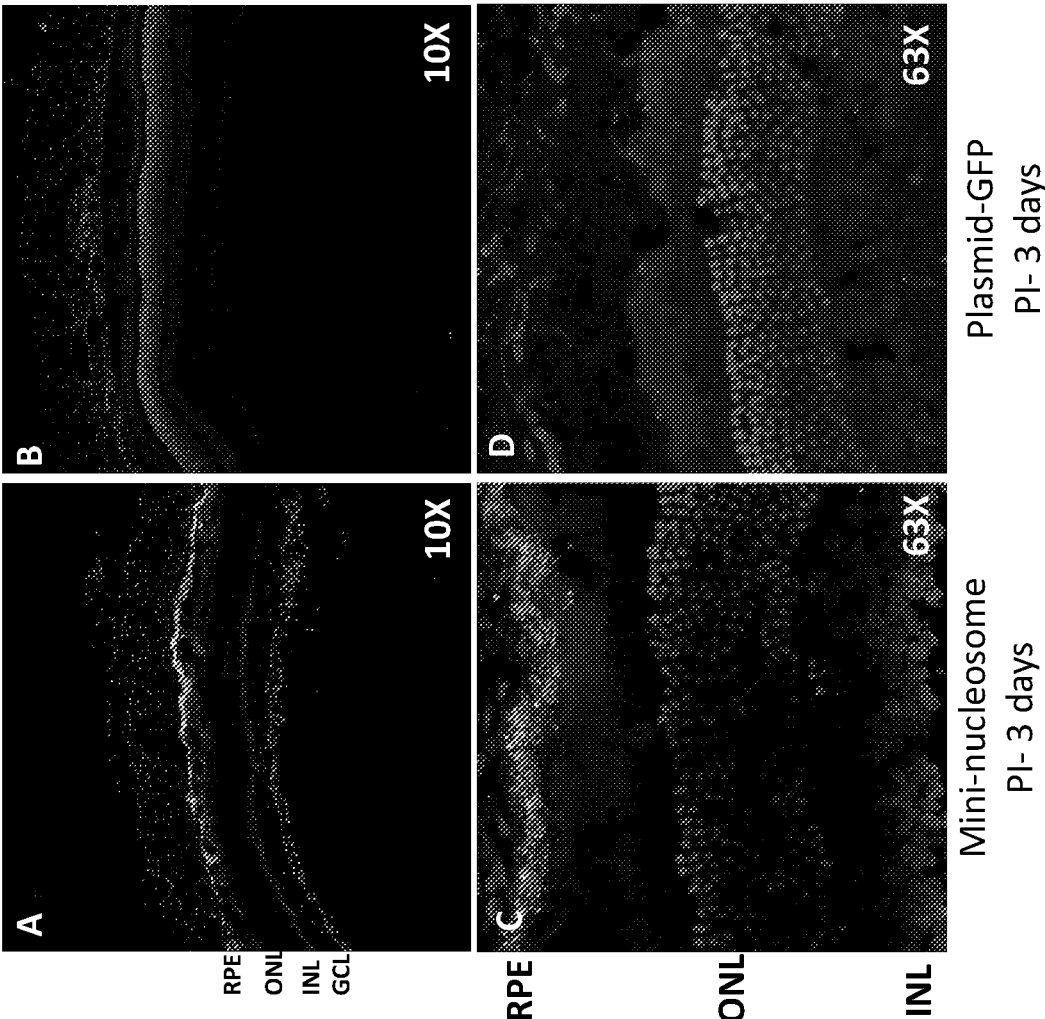
FIG. 11 is a set of images including panels A, B, C & D each of which is a fluorescent microscopy image that illustrates gene expression in rat retinal tissue of proteins encoded by nucleic acids present in loaded mini-nucleosomes. Panels A and C are retinal sections that demonstrates RPE specific expression and panels B and D present plasmid injected control samples.

This example demonstrates that loaded mini-nucleosomes can be delivered by intra-ocular route to express proteins in the retinal pigment epithelium (RPE) or in other retinal neurons such as photoreceptors, bipolar cells and ganglion cells. In the present Example, Balb/c mice were anesthetized by IP injection with Ketamine/Xylazine (90-100 mg/kg+10 mg/kg) and positioned underneath a microscope. Mice eyes were dilated with topical Tropicamide (1%) and 1 μl of loaded mini-nucleosomes (total dose 1.5 micrograms in mice) were injected into the vitreous cavity using 32 gauge blunt needle passing through the incision made by a 25-gauge needle below the limbus. At various time points, mice were perfused with 10 ml of 1xPBS, and then sacrificed using standard techniques. Mice were enucleated and eyecups were collected and incubated in 4% paraformaldehyde overnight. The eyecups were washed with 1xPBS, then immersed in 15% sucrose for few hours and then in 30% sucrose solution overnight for cryopreservation. The eyecups were then placed in a plastic vial and frozen using OCT compound for cryo-sectioning. 10-micron thick tissue sections were obtained for staining. The retinal sections were mounted with mounting media with or without DAPI, coverslip and sealed. Images were acquired by Leica SP5. For wholemount imaging, eyecups were fixed in 4% paraformaldehyde overnight. Eyecups were washed in 1xPBS, retina was removed and the remaining eyecup or RPE wholemount was processed for staining. The RPE tissue was wholemounted with mounting media, coverslip and sealed. Images were acquired by Leica SP5. Native GFP fluorescence were observed in retina and RPE cells (FIGS. 10, 11 & 12).

To target the RPE cells, the present Example utilized a mini-nucleosome core protein (SEQ ID NO: 392) that could bind to the phagocytic proteins like MERTK. RPE are phagocytic cells, that extend their microvilli to the photoreceptor inner/outer segment junction. MERTK is expressed in those microvilli. In SEQ ID NO: 392, we incorporated the "eat me" signals as descried in Table 8. In literature, "eat me" signals are described as domains exposed in cellular debris that are primed for phagocytosis (Wei Li, Journal of Cell physiology, 2016, which is incorporated herein by reference). To the present inventor's knowledge, these "eat me" signals have never been utilized in the context of non-viral vectors before. These "eat me" signal domains have not been previously applied for non-viral vectors to target the RPE cells.

To selectively transduce photoreceptors, the present Example utilized core proteins like those of SEQ ID NO:394. SEQ ID NO:394 included a neuronal attachment element (LRE) described herein Table 8, that could allow transduction into ganglion cells, bipolar cells and photoreceptors which are all neurons in the retina (FIG. 12). This neuronal attachment domain has not been previously applied for non-viral vectors to target neurons. The present disclosure provides that this neuronal targeted vector can transduce neurons in the brain via local or systemic administration. The present disclosure further provides for targeting photoreceptor binding and internalization by incorporating lectin binding domains (described in Table 4) in mini-nucleosomes for attachment to photoreceptor extracellular matrix to enhance uptake. An integrin binding domain incorporated in the mini-nucleosome core protein (SEQ ID NO: 390) also could transduce RPE cells in rat eyes exclusively when delivered intraocular (FIG. 11). Moreover, more than one domain could be utilized to selectively transduce a plurality of diverse cell types. This core protein (SEQ ID NO: 390) with integrin binding properties may also be utilized for delivery of nucleic acids to other cell types that express high levels of aVB5 integrin. The present disclosure further provides use of other intra-ocular injection techniques such as subretinal, suprachoroidal, intra-cameral, or topical administration to target photoreceptors, RPE, Mueller cells or other cell types in the retina.

Provided herein are techniques to deliver loaded mini-nucleosomes into different cell types in the retina using intravitreal, suprachoroidal, or subretinal mode of delivery. Diseases like retinal degeneration are mostly caused by mutations in genes expressed in the photoreceptors. Age-related macular degeneration (AMD), is a disease of retinal pigment epithelium (RPE) and choriocapillaries, that affects >10 million Americans and >100 million people worldwide, Currently, the predominant technology to deliver gene therapy vectors to photoreceptors and RPE is a surgical technique where viruses are injected subretinally into the retina. However, subretinal procedure is a complex surgery performed in the operating room by a trained Ophthalmic surgeon. There is an unmet need at least in that, in the United states, there are only a handful of surgeons trained to perform this surgery. One way to reduce the burden for patients and physicians is to develop vectors that can be injected intravitreally that can pass through the retina to transduce the photoreceptors and RPE. Intravitreal injection can be performed by all ophthalmologist in an in-patient visit. Loaded mini-nucleosome therapy solves this problem as intravitreal injections could transduce photoreceptors and RPE selectively (FIGS. 10, 11 and 12). This makes mini-nucleosomes highly suitable for treating most retinal diseases with genetic defects.

When injected intraocular, the loaded mini-nucleosomes may be delivered at a dose greater than 1e5 genome copies per eye and up to a dose of 1e25 copies per eye (e.g., at about 1e5, 1e6, 1e7, 1e8, 1e9, 1e10, 1e15, 1e20, or 1e25 copies per, or any range there between). Volume of the material may range from 10-500 microliters when injected subretinally (e.g., 1, 5, 10, 20, 30, 40, 50, 100, 200, 300, 400, or 500 microliters) and 10-250 microliters when injection is intravitreal, suprachoroidal, or intracameral (e.g., 1, 5, 10, 20, 30, 40, 50, 100, 150, 200, or 250 microliters). A loaded mini-nucleosome therapeutic agent may also be administered repeatedly (e.g., a selected volume and/or number of genome copies can be administered multiple times or divided among two or more does).

Example 6: Route of administration-Intranasal

This example demonstrates that loaded mini-nucleosomes can be delivered by intra-nasal route to express proteins in lung, trachea, and gut cells. In the present Example, to target epithelial cells in the lung epithelium, 2 NGR amino acid domains were included in a mini-nucleosome core protein alongside nucleic acid binding domains (see use of NGR amino acid domains SEQ ID NO: 390). To the present inventor's knowledge, NGR domains have never been utilized to create and deliver non-viral DNA/protein complexes to retinal cells as disclosed herein. NGR domains in AAV2 have been shown to promote $\alpha V\beta 5$ integrin binding. NGR domains are implicated in heparan sulfate binding, known as receptor for AAV2.

Figure 13:
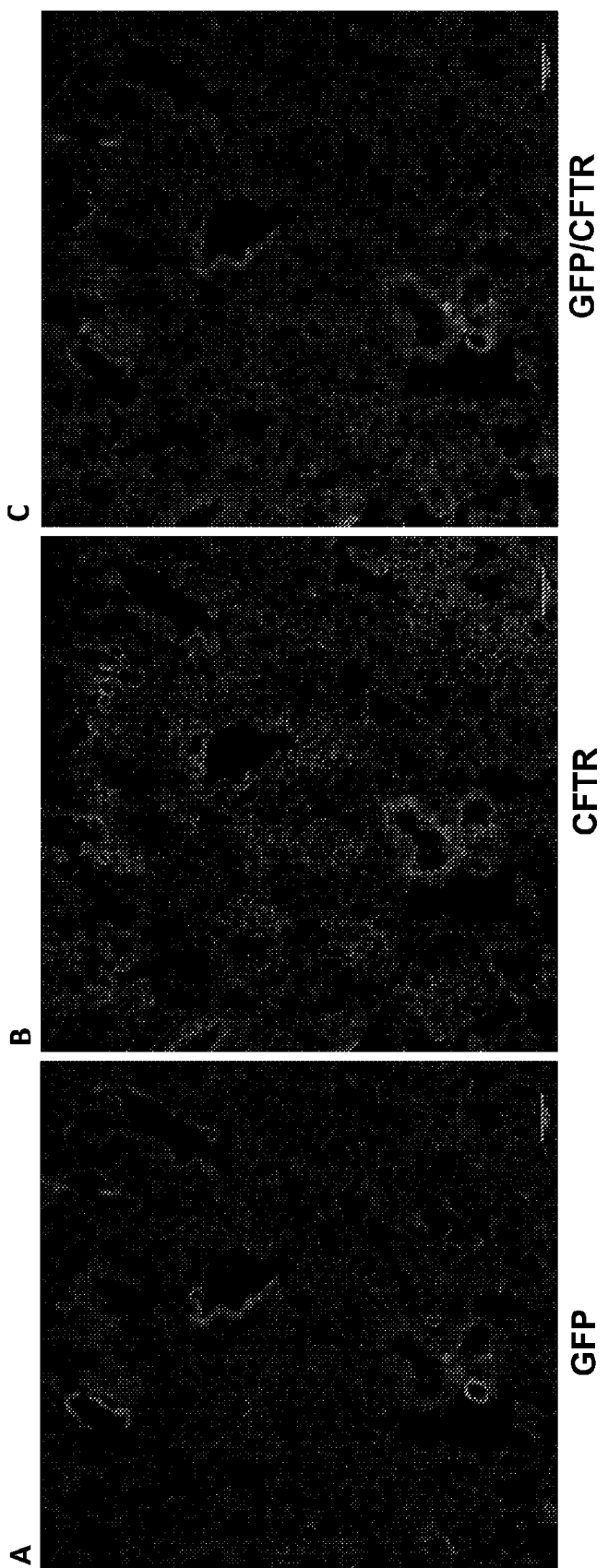
FIG. 13 is a set of images including panels A, B & C each of which is a fluorescent microscopy image that illustrates gene expression in mice lung of proteins encoded by nucleic acids present in loaded mini-nucleosomes. Panel A demonstrates GFP expression in alveoli and bronchioles. Panel B demonstrates CFTR staining. Panel C is a merge for panels A and B demonstrating colocalization of GFP and CFTR staining.
Figure 14:
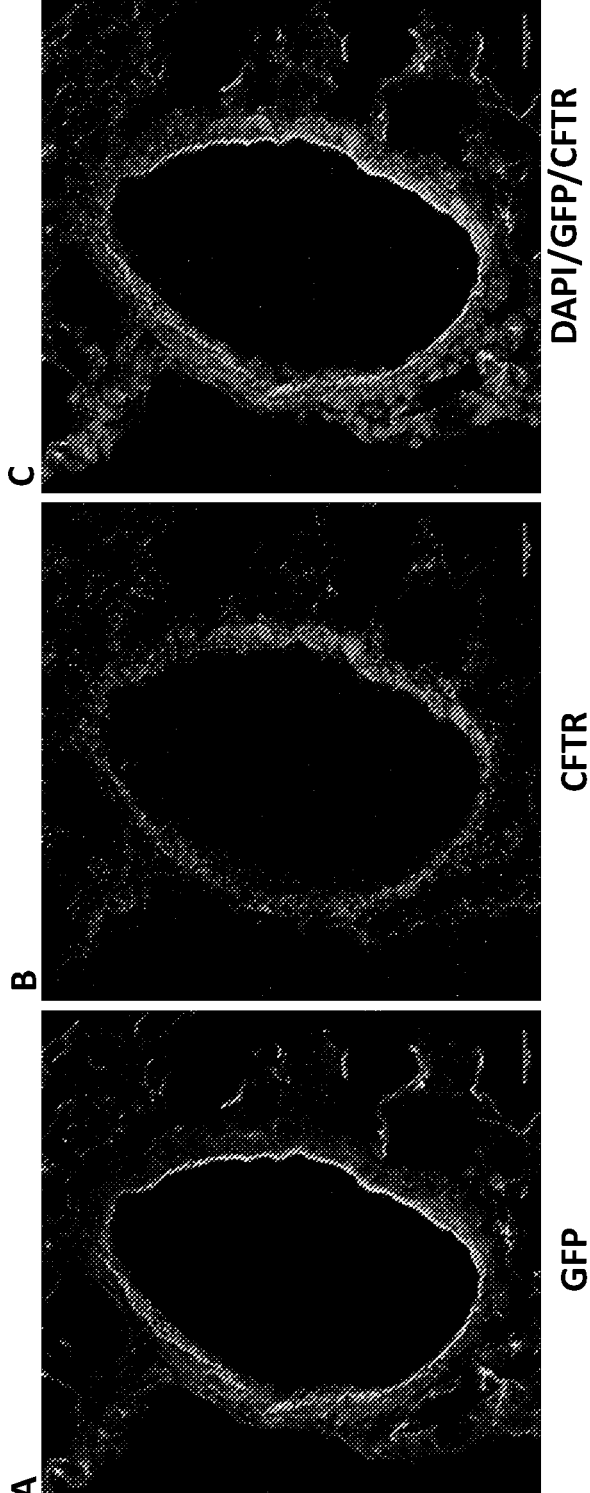
FIG. 14 is a set of images including panels A, B & C each of which is a fluorescent microscopy image at higher magnification that illustrates gene expression in mice lung epithelium of proteins encoded by nucleic acids present in loaded mini-nucleosomes. Panel A demonstrates GFP expression in alveoli and bronchioles. Panel B demonstrates CFTR staining. Panel C is a merge for panels A and B demonstrating colocalization of GFP and CFTR including DAPI staining.

In the present Example, Balb/c mice were anesthetized by IP injection with Ketamine/Xylazine (90-100 mg/kg+10 mg/kg) and the anesthetized mice were positioned underneath a microscope for visual of the nasal area for intranasal delivery. 1 µl of loaded mini-nucleosome (SEQ ID NO: 390+GFP plasmid) solution was delivered into the nasal cavity every few seconds until 12 microliters were delivered to each nasal side. Total dose of 25 micrograms was delivered. Following sacrifice, mice lung was processed to obtain 10 micron thick sections. Sections were washed in PBS and incubated in blocking buffer (0.1% TritonX-100, 1% BSA, 3% donkey serum) for 1 hr and then incubated in CFTR antibody (prepared on blocking buffer) blocking buffer overnight at 4 degree Celsius. Next day wash in PBS 3×5 min and incubated in AlexaFlour-555 (Donkey Anti-rabbit IgG secondary) in blocking buffer at RT for 1 hour and washed in PBS 3×5 min. Mounting media was added and coverslip was applied and sealed. Native fluorescence of GFP was obtained in the 486 nm channel of Leica SP5 scope in the 486-nm wavelength and CFTR expression in the 555-nm channel. We observed loaded mini-nucleosomes expression as early as 3 days and at PI-3 months as well (FIG. 13). We observed expression in the epithelium of both alveoli and bronchioles (FIGS. 13A and 13C) depicted by sharp green fluorescence along with CFTR staining. Co-localization of CFTR and GFP (FIG. 13C) demonstrates expression of genes encoded by mini-nucleosomes in lung epithelium. Higher magnification images taken from an alveoli ring (FIGS. 14A, B and C) also clearly exhibit bright green ring of GFP fluorescence in the epithelium together with red fluoresce in CFTR stained cells.

Figure 15:
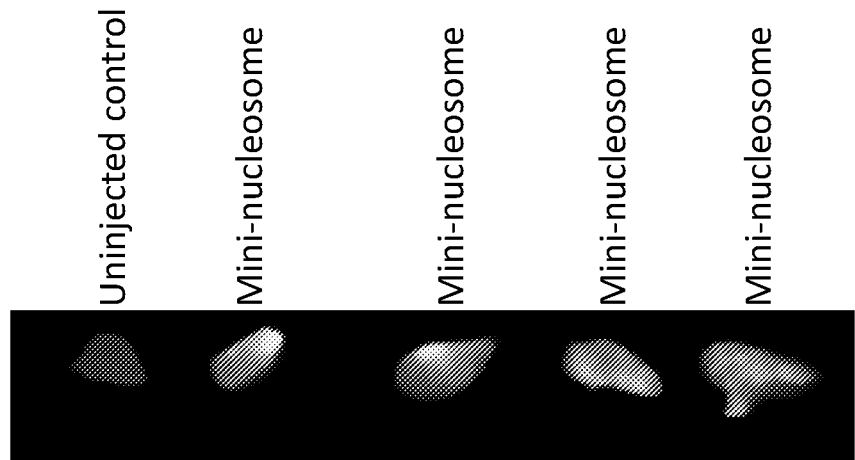
FIG. 15 is a set of images that illustrates gene expression in mice whole lung tissue of proteins encoded by nucleic acids present in loaded mini-nucleosomes.

In the present Example, whole lung tissue and biodistribution via mini-nucleosome was also evaluated (FIG. 15). Whole lung tissue was extracted form mice following perfusion and sacrifice. Lung tissue was fixed in 4% PFA and washed with 1xPBS. Whole tissues were placed in the Odyssey imager for detecting GFP native fluorescence. Uninjected control did not exhibit any fluorescence (FIG. 15). Loaded mini-nucleosomes including plasmid nucleic acid cargo encoding GFP demonstrated GFP fluorescence in whole lung tissue in 5-week post injection samples (FIG. 15).

Figure 16:
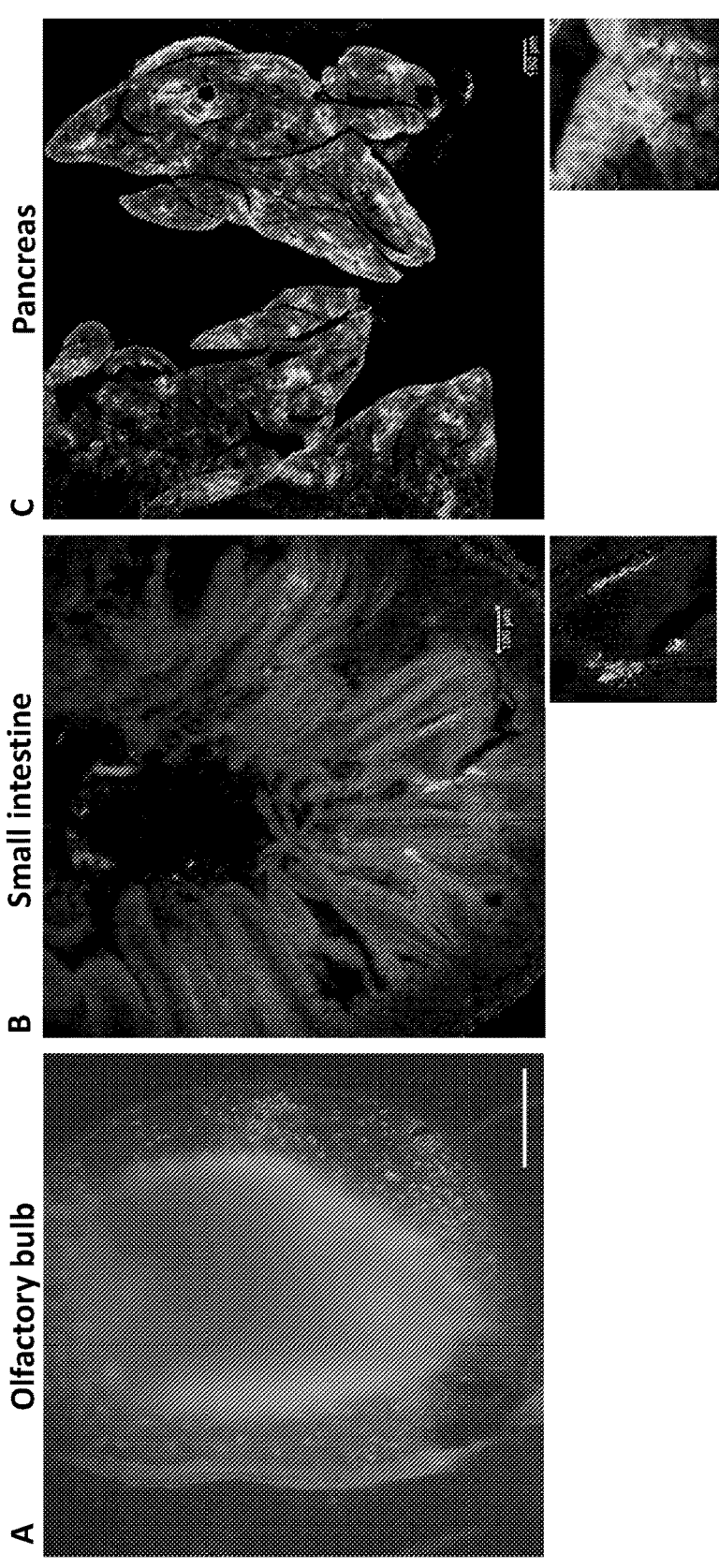
FIG. 16 is a set of images including panels A, B & C that illustrates gene expression in mice brain, gut and pancreas tissue of proteins encoded by nucleic acids present in loaded mini-nucleosomes. Panel A demonstrates expression pattern in olfactory neurons. Panel B and its inset below demonstrates expression pattern in small intestine. Panel C and its inset below demonstrates expression pattern in pancreas.
Figure 17:
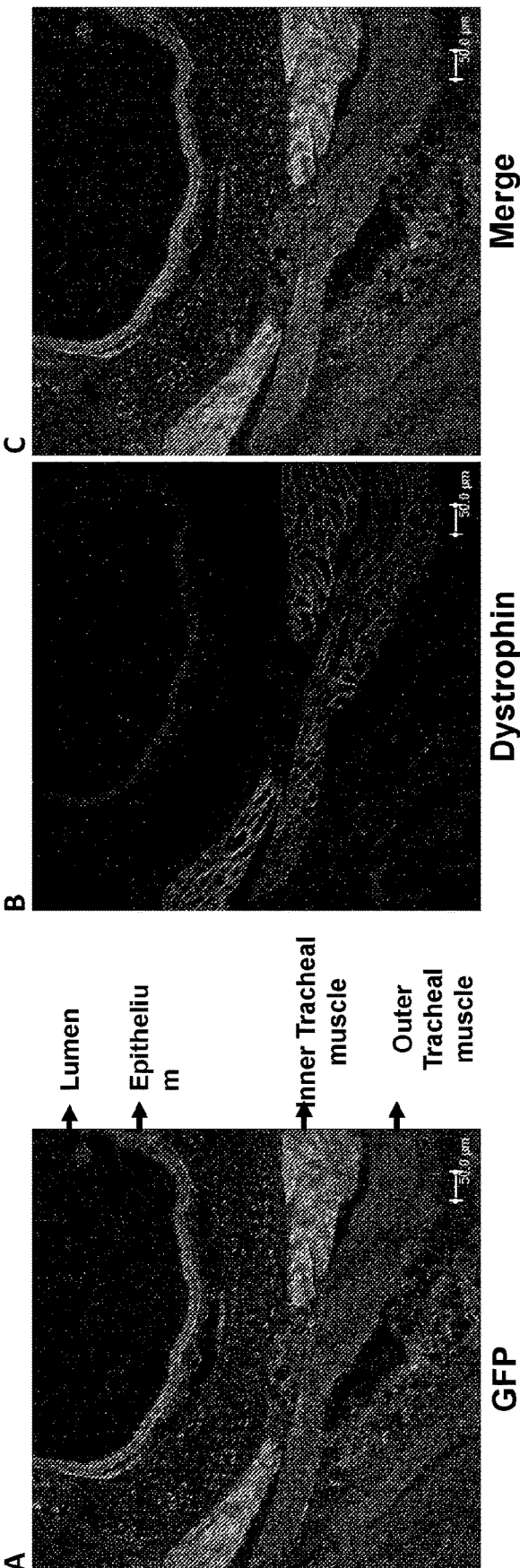
FIG. 17 is a set of images including panels A, B & C that illustrates gene expression in mice tracheal tissue of proteins encoded by nucleic acids present in loaded mini-nucleosomes. Panel A demonstrates GFP expression in tracheal epithelium and inner tracheal muscle. Panel B demonstrates dystrophin staining pattern in expression in inner and outer tracheal muscle. Panel C is a merge of panel A and B that demonstrates colocalization of dystrophin staining pattern with GFP in inner tracheal muscle cells.

Provided herein are techniques to deliver loaded mini-nucleosomes into different cell types in tissues of the pulmonary space such as lung epithelium, and/or trachea using intranasal mode of delivery. Genetic diseases such as cystic fibrosis affect the lung and other organs. To deliver genes to the lung, the intranasal is one of the routes of choices. We observed that loaded-mini-nucleosomes when delivered intranasally, expresses proteins in the alveoli and bronchioles (FIG. 13). These are tissues that would normally express the CFTR protein implicated in cystic fibrosis. In other diseases, this route of administration can be used to produce therapeutic proteins that could alleviate other diseases. Intranasal route may also provide access to other organs such as the gut and brain (FIG. 16). Inclusion of NGR domains in the mini-nucleosome core proteins (SEQ ID NO: 390), allowed enhanced uptake and release of DNA molecules into the nucleus for high levels of sustained expression. This is evidenced in FIG. 16 by the bright green fluorescence observed from loaded-mini-nucleosomes vs no such pattern in the untreated animals (lung image in the first row in FIG. 16) at 5-weeks post treatment. We also observed transduction of expression of GFP in tracheal epithelium and tracheal muscle following intranasal delivery of loaded mini-nucleosomes (FIG. 17).

When injected intranasally, the loaded mini-nucleosomes may be delivered at a dose greater than 1e5 genome copies per kg and up to a dose of 1e25 copies per kg of body weight (e.g., at about 1e5, 1e6, 1e7, 1e8, 1e9, 1e10, 1e15, 1e20, or 1e25 copies per kg of body weight, or any range there between). Volume of the material may range from 1-200 milliliters (e.g., 1, 5, 10, 20, 30, 40, 50, 100, or 200 milliliters). The loaded mini-nucleosomes may also be administered repeatedly. The loaded mini-nucleosomes may also be delivered orally to access gut, pancreas etc.

Example 7: Route of Administration-Intramuscular

This example demonstrates that loaded mini-nucleosomes can be delivered by intra-muscular route to express proteins in the muscle cells. Balb/c mice were anesthetized by IP injection with Ketamine/Xylazine (90-100 mg/kg+10 mg/kg) and several loaded mini-nucleosomes were injected into both leg muscle at 17.5 µg doses per leg using an insulin syringe (Total dose 35 micrograms per mice). Mice were sacrificed at various time points and leg muscle were obtained for tissue sections. Constructs that contained core proteins such as polylysine (SEQ ID NO: 393) or mini-nucleosome with other domain combinations (SEQ ID NO: 389) didn't exhibit GFP fluorescence at the 3-month time point. Surprisingly, in muscle tissue sections obtained from 3-months post injections, we observed sharp green fluorescence in skeletal muscle cells injected with loaded mini-nucleosomes with containing galactose and fucose binding domain as shown in SEQ ID NO: 391 (FIGS. 18A, B and C). This demonstrates that some domains have a higher propensity of attachment and internalization into muscle cells and could be utilized for efficient gene transfer to muscle cells. One skilled in the art may contemplate combining such domains with other domains known for muscle tropism.

To validate muscle specificity of expression of genes encoded by the nucleic acid cargo, we utilized dystrophin immunolabeling as an endogenous secondary marker. Regions of sharp green fluorescence (panel A) encircled by red fluorescence (panel B; merged in panel C) of Dystrophin staining clearly demonstrates that loaded mini-nucleosomes injected intramuscularly can deliver genes to muscle cells (FIG. 18). Native fluorescence of GFP was obtained in the 486-nm channel of Leica SP5 scope. Dystrophin in red is the RFP channel (555-nm). Untransduced muscle cells in figure also serve as internal control for differentiation between GFP signal and autofluorescence.

Provided herein are techniques to deliver loaded mini-nucleosomes into muscle cells by intramuscular mode of delivery. Many genetic muscular dystrophies lead to atrophy of the muscle cells. To deliver functional genes to these muscle cells, intramuscular route provides direct routes of administration. We demonstrated the muscle tropism and ability of loaded-mini-nucleosomes to express genes in the skeletal muscle cells (FIG. 18). Expression was observed in muscle cells as early as day 2 after delivery. Provided herein are muscle-tropic domains that could enhance vector uptake and gene expression, however is not limited to it. We also observed that spiral shaped loaded mini-nucleosomes delivered via intramuscular route, transduce muscle cells effectively and for longer durations—in this case 3 months (FIG. 18) compared to lobular shaped molecule (data not shown). The shape of vectors has not been described before in the context of delivering genes to the muscle cells. One skilled in the art may contemplate, utilizing other structures for increased cell tropism for muscle cells. Overall, the expression of GFP in dystrophin expressing muscle cells demonstrates the ability of loaded mini-nucleosomes to rescue diseases like Duchenne muscular dystrophy or other muscular dystrophies. Muscle tropism may also be enhanced by inclusion of other domains described in Table 4. Muscle tropism may also be achieved by intravenous delivery.

When injected via intramuscular route, the loaded mini-nucleosomes may be delivered at a dose greater than 1e5 genome copies per kg and up to a dose of 1e25 copies per kg of body weight (e.g., at about 1e5, 1e6, 1e7, 1e8, 1e9, 1e10, 1e15, 1e20, or 1e25 copies per kg body weight, or any range there between). Volume of the material may range from 1-900 milliliters (e.g., 1, 5, 10, 20, 30, 40, 50, 100, 200, 300, 400, 500, 600, 700, 800, or 900 milliliters). The loaded mini-nucleosomes may also be administered repeatedly (e.g., a selected volume and/or number of genome copies can be administered multiple times or divided among two or more does). The loaded mini-nucleosomes may also be administered intravenously to access muscle cells.

Example 8: Loaded Mini-Nucleosomes are Redosable

Figure 19:
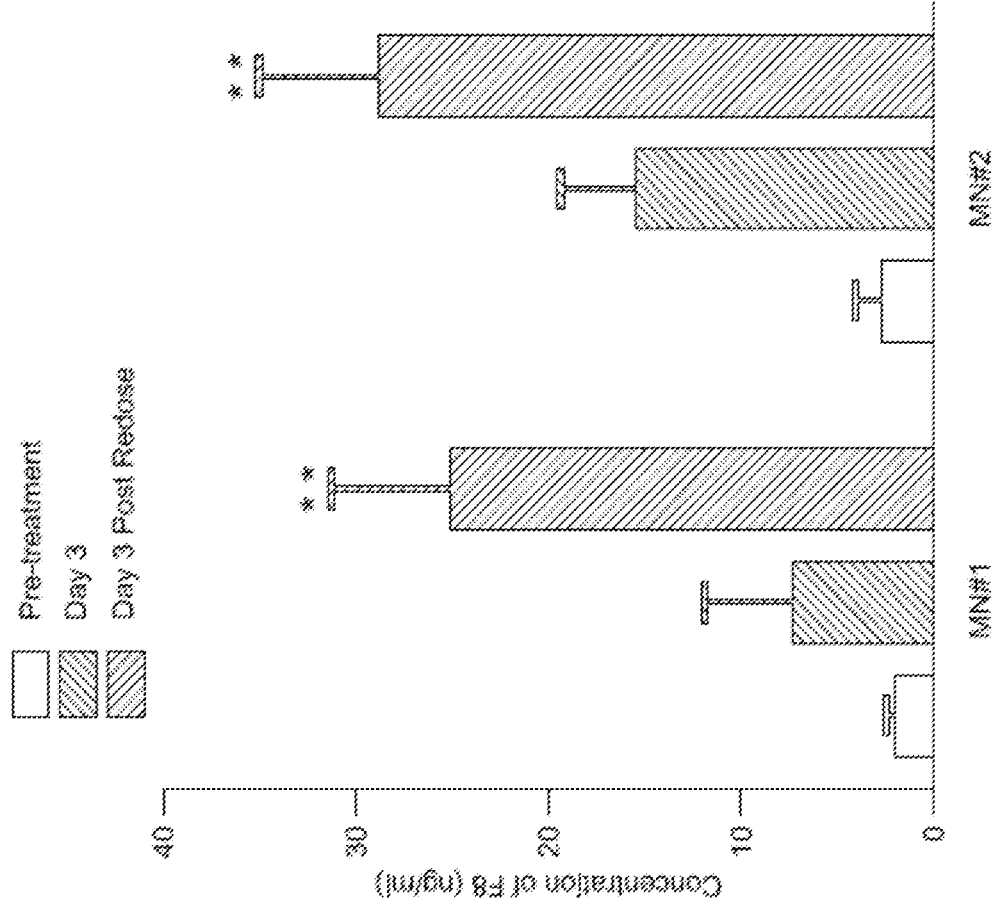
FIG. 19 is a graph showing increase in concentration of expressed Factor 8 protein as measured by Elisa following a first dose and a second dose suggesting lack of neutralizing effect or in other words lack neutralizing antibody activity.
Figure 21:
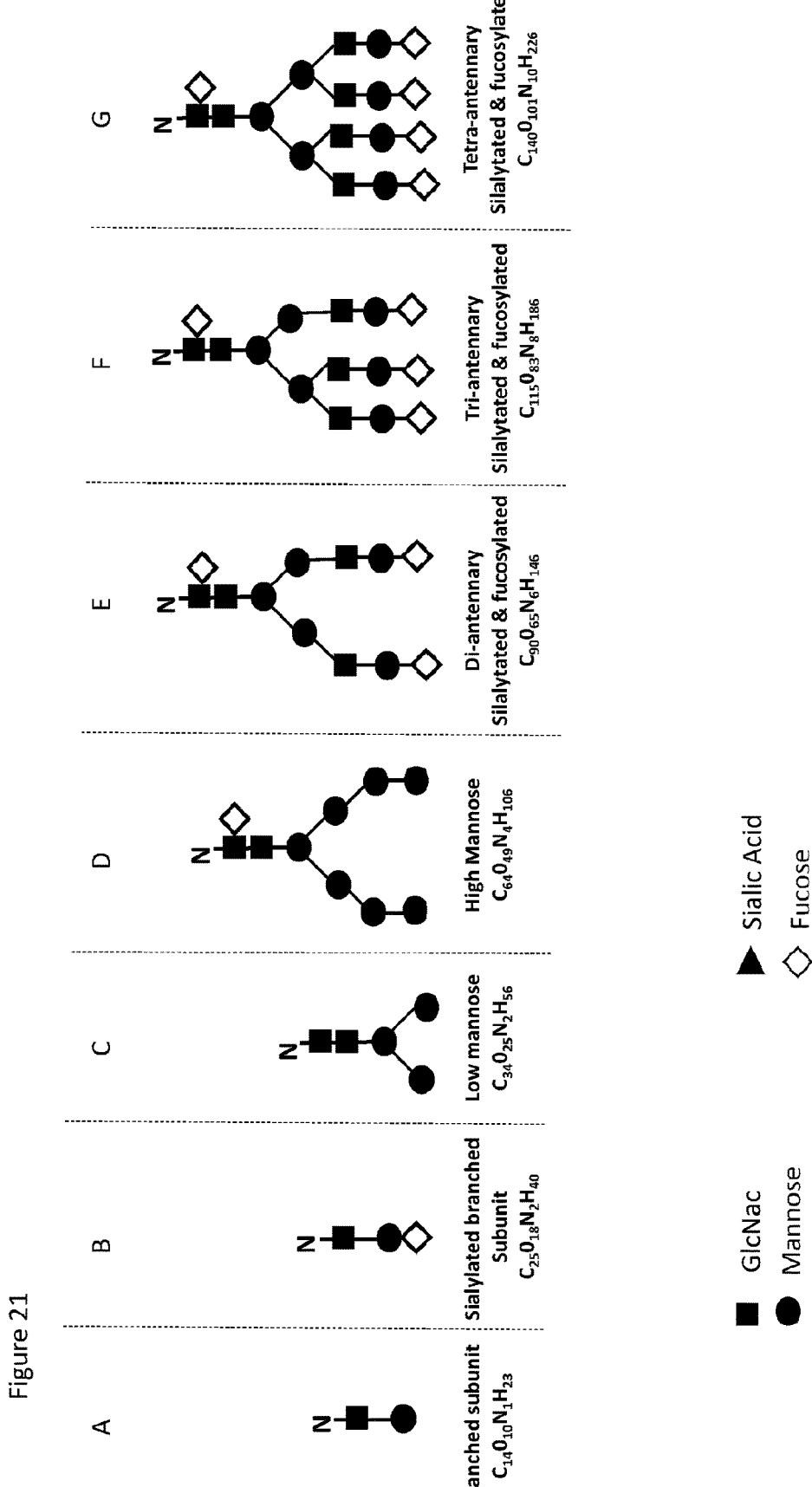
FIG. 21 includes panels A, B, C, D, E, F and G. Panel A is a schematic representation of an unbranched modification chain ($C_{14}O_{10}N_1H_{23}$) including GlcNac and mannose that could, e.g., modify an asparagine residue in a mini-nucleosome core protein. Panel B is a schematic representation of an unbranched modification chain ($C_{25}O_{18}N_2H_{40}$) including GlcNac, mannose, and fucose that could, e.g., modify an asparagine residue in a mini-nucleosome core protein. Panel C is a schematic representation of a di-antennal branched modification chain ($C_{34}O_{25}N_2H_{56}$) including a trunk including GlcNac, GlcNac, and Mannose and two branches, each including mannose, which modification chain could modify, e.g., an asparagine residue in a mini-nucleosome core protein. A modification chain having this structure can be referred to as low mannose. Panel D is a schematic representation of di-antennal branched modification chain ($C_{64}O_{49}N+H_{106}$) that includes a trunk including GlcNac, a branch including fucose, and a branch including a secondary trunk including GlcNac and mannose and two secondary branches each including three mannose modifications, which modification chain could, e.g., modify an asparagine residue in a mini-nucleosome core protein. A modification chain having this structure can be referred to as high mannose. Panel E is a schematic representation of a di-antennary silalylated & fucosylated branched modification chain ($C_{90}O_{65}N_6H_{146}$) that includes a trunk including GlcNac, a branch including fucose, and a branch including a secondary trunk including GlcNac and mannose, two secondary branches each including mannose, GlcNac, mannose, and fucose, which modification chain could, e.g., modify an asparagine residue in a mini-nucleosome core protein. Panel F is a schematic representation of tri-antennary silalylated and fucosylated branched modification chain ($C_{115}O_{83}N\&H_{186}$) that that includes a trunk including GlcNac, a branch including fucose, and a branch including a secondary trunk including GlcNac and mannose with two secondary branches. One of the secondary branches includes mannose, GlcNac, mannose, and fucose, while the other includes a tertiary trunk including mannose, and two tertiary branches each including GlcNac, mannose, and fucose. The branched modification chain could, e.g., modify an asparagine residue in a mini-nucleosome core protein. Panel G is a schematic representation of tetra-antennary sialylated & fucosylated branched modification chain ($C_{140}O_{101}N_{10}H_{226}$) that includes a trunk including GlcNac, a branch including fucose, and a branch including a secondary trunk including GlcNac and mannose with two secondary branches. Each of the secondary branches includes a tertiary trunk including mannose, and two tertiary branches each including GlcNac, mannose, and fucose. The branched modification chain could, e.g., modify an asparagine residue in a mini-nucleosome core protein.

This example demonstrates that mini-nucleosomes can be re-administered without any neutralizing effect on the expression of proteins (FIG. 19). Balb/c mice were simply restrained using standard restraining techniques and Insulin syringe were used to deliver the loaded mini-nucleosomes MN #1 (SEQ ID NO: 390+F8 plasmid), and MN #2 (SEQ ID NO: 391+F8 plasmid, SEQ ID NO: 393) via tail vein injection. Each mouse received 20 micrograms 1st dose and 40 micrograms 2nd dose (30 days after 1st dose). Serum were collected by cheek bleed technique at day 3 post 1st and 2nd doses. ~ 150 µl blood were collected each time and serum was collected from blood using standard techniques. F8 Elisa was performed to determine expression levels of F8 in serum in Balb/c mice following intravenous delivery of loaded mini-nucleosomes. F8 Elisa was performed according to manufacturer's (Aviva Systems Biology) instructions. 1:6 serum dilutions were made for all assays. We observed that when delivered a second time, there was no neutralizing effect in the expression levels, as evidenced by increase in protein levels of F8 (FIG. 19).

Provided herein are examples of mini-nucleosome core proteins and loaded mini-nucleosome that can be delivered repeatedly to boost expression levels of desired proteins. Redosability is a very important feature for any drug that may require repeat administration. In gene therapy, currently one of the most undesirable features of viral vectors is the inability to re-administer drug products. Viral vector once injected into the patient leads to formation of neutralizing antibodies. This causes immunogenicity and inexpressibility when they are administered the second time. We show here that, mini-nucleosome mediated gene delivery solves this problem. The non-immunogenic nature of mini-nucleosome is engineered in by design: by combining self-peptides or human derived amino acid sequences and enhanced by pegylation. In literature, pegylated proteins have been shown to evade the immune system. In this case, in mice, lack of immunogenicity for artificial human derived core proteins, further validates the case for pegylation. This redosability feature will allow multiple treatments to patients when needed. In case of diminishing expression levels over time, this redosable feature will allow repeat treatment to boost the expression to desired levels. This piece of data also shows that in some patients that need multi-organ injections, mini-nucleosome mediated gene transfer will be most desirable. One skilled in the art may also contemplate repeat dosing via many other routes of administration such as topical, oral, vaginal, intraperitoneal, intraocular, intrathecal, intracerebral, subcutaneous etc. or via encapsulation in liposomes or other synthetic materials.

Repeat doses may be delivered at a concentration greater than 1e5 genome copies per kg and up to a dose of 1e25 copies per kg of body weight (e.g., at about 1e5, 1e6, 1e7, 1e8, 1e9, 1e10, 1e15, 1e20, or 1e25 copies per kg body weight, or any range there between). Volume of the material may range from 1-900 milliliters (e.g., 1, 5, 10, 20, 30, 40, 50, 100, 200, 300, 400, 500, 600, 700, 800, or 900 milliliters). The loaded mini-nucleosomes may also be administered repeatedly (e.g., a selected volume and/or number of genome copies can be administered multiple times or divided among two or more does).

Example 9: General techniques

This example describes general techniques for cloning, delivery of min-nucleosomes into cells. Some of the cloning techniques that can be applied to constructing these vectors may include-synthesis of transgene constructs, TOPO PCR cloning, blunt end cloning, seamless cloning, long fragment cloning, restriction enzyme digestion and ligation but not limited to these techniques. DNA or RNA molecules may express one or more expression markers such as GFP, YFP and Luciferase but not limited to it. DNA or RNA molecules may express one or more therapeutic RNA or proteins but not limited to it.

Loaded mini-nucleosomes can be tested for their function and characterized in vitro by expressing them in HEK cells or other animal cell lines. Ability of synthesized and/or purified loaded mini-nucleosomes to transduce hematopoietic stem cells or differentiated peripheral blood mononuclear cells can be assayed by exposing the cells to the loaded mini-nucleosomes in culture. Loaded mini-nucleosomes can also be tested for their function and ability to form chimeric T cells in vitro by exposure to mini-nucleosomes or via techniques of transfection, or other physical methods for insertions. Loaded mini-nucleosomes can be tested for their function and characterized in vivo by delivering in mice or any other animal models but not limited to it.

Example 10: Phosphorylated Mini-Nucleosome Core Proteins Deliver Nucleic Acid Payloads to Neurons and Central Nervous System Cells The present Example demonstrates that a mini-nucleosome core protein including one or more residues modified by phosphorylation is particularly advantageous at least for expression of a nucleic acid payload (i.e., expression of an expression product encoded by a nucleic acid payload) in certain cells or tissues. For example, a mini-nucleosome core protein including one or more residues modified by phosphorylation can be particularly advantageous for expression of a nucleic acid payload in central nervous system cells including neurons, and particularly including spinal cord cells and brain neurons.

Modified mini-nucleosome core proteins were prepared by phosphorylation of a mini-nucleosome core protein having an amino acid sequence according to SEQ ID NO: 399. In particular, a threonine residue at position 11 of the mini-nucleosome core protein was phosphorylated. This residue is positioned in a linker domain (VT) of the mini-nucleosome core protein. However, the present disclosure provides that the presence of the modification, rather than the particular position of the modification within the mini-nucleosome core protein, determines the characteristics of the mini-nucleosome core proteins disclosed herein. Without wishing to be bound by any particular scientific theory, the present Example includes the recognition that modifications of mini-nucleosome core proteins according the present Example can interact with cell surface receptors, improving delivery of loaded mini-nucleosomes to certain target cells. Accordingly, the present disclosure provides that phosphorylation of any amino acid residue(s) of a mini-nucleosome core protein, in particular a serine, threonine, or tyrosine, would provide equivalent advantages and characteristics as phosphorylation of the particular residue of the particular mini-nucleosome core protein modified in the present Example. Unmodified mini-nucleosome core proteins according to the same amino acid sequence were also included in the present example as a control.

Mini-nucleosome core proteins of the present Example were loaded with a nucleic acid payload that included a gene encoding luciferase. In the present Example, luciferase is representative of protein expression generally, in that expression of luciferase is indicative of the ability of a mini-nucleosome core protein modified as disclosed herein and discussed in the present Example to successfully delivery any nucleic acid payload for expression of any expression product. Loaded mini-nucleosomes of the present Example were administered intrathecally to one or more 9-10 week old Balb/c mice (3e10 gc/mouse; 10 µl volume).

Figure 31:
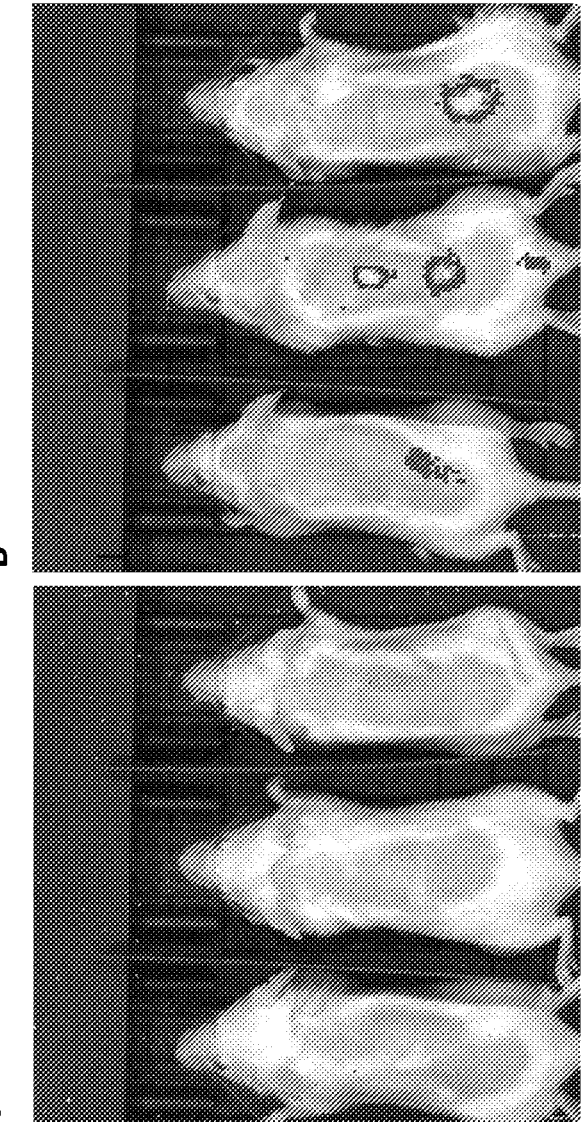
FIG. 31 includes panels A and B. Panel A is an IVIS® Spectrum In Vivo Imaging System (IVIS) image of a mouse administered an unmodified mini-nucleosome core protein according to SEQ ID NO: 399 loaded with a nucleic acid payload including a gene encoding luciferase as a representative expression product. Panel B is an IVIS® Spectrum In Vivo Imaging System (IVIS) image of a mouse administered a phosphorylated mini-nucleosome according to SEQ ID NO: 399 loaded with a nucleic acid payload including a gene encoding luciferase as a representative expression product. Panel B shows that the modified mini-nucleosome core protein, but not the unmodified mini-nucleosome core protein, results in robust expression of the representative nucleic acid payload-encoded expression product (here, luciferase) in certain tissues including central nervous system cells including neurons, and including spinal cord cells and brain neurons.

Results are shown in FIG. 31. On day 11 post dose administration, mice were dosed with luciferin at 150 mg/kg (60 mg/mL) via intraperitoneal (IP) injection at 2.5 ml/kg. At ~15 minutes post each luciferin administration (+5%), all animals underwent an IVIS imaging session. Panel A of FIG. 31 shows results using loaded mini-nucleosomes including an unmodified mini-nucleosome core protein, while Panel B of FIG. 31 shows results using loaded mini-nucleosomes including a phosphorylated mini-nucleosome core protein. All mini-nucleosome core proteins were loaded with a nucleic acid payload including a gene encoding luciferase. Panel B shows that the modified mini-nucleosome core protein, but not the unmodified mini-nucleosome core protein results in robust expression of the representative nucleic acid payload-encoded expression product (here, luciferase) in certain tissues including central nervous system cells including neurons, and including spinal cord cells and brain neurons. Expression levels observed in the present Example were highly unexpected. Detection of expression by IVIS imaging requires a very high level of expression, and the present data therefore reflects remarkable efficiency of both cellular uptake and payload expression. Levels of expression dramatically exceed those that would be expected for a non-viral vector.

Example 11: Sulfated Mini-Nucleosome Core Proteins Deliver Nucleic Acid Payloads to Neurons and Central Nervous System Cells The present Example demonstrates that a mini-nucleosome core protein including one or more residues modified by sulfation is particularly advantageous at least for expression of a nucleic acid payload (i.e., expression of an expression product encoded by a nucleic acid payload) in certain cells or tissues. For example, a mini-nucleosome core protein including one or more residues modified by sulfation can be particularly advantageous for expression of a nucleic acid payload in central nervous system cells including neurons, and particularly including spinal cord cells and brain neurons.

Modified mini-nucleosome core proteins were prepared by sulfation of a mini-nucleosome core protein having an amino acid sequence according to SEQ ID NO: 388. In particular, a tyrosine residue at position 38 of the mini-nucleosome core protein was sulfated. This residue is positioned in a targeting domain (FYQPL) of the mini-nucleosome core protein. However, the present disclosure provides that the presence of the modification, rather than the particular position of the modification within the mini-nucleosome core protein, determines the characteristics of the mini-nucleosome core proteins disclosed herein. Without wishing to be bound by any particular scientific theory, the present Example includes the recognition that modifications of mini-nucleosome core proteins according the present Example can interact with cell surface receptors, improving delivery of loaded mini-nucleosomes to certain target cells. Accordingly, the present disclosure provides that sulfation of any amino acid residue(s) of a mini-nucleosome core protein, in particular a serine, threonine, or tyrosine, would provide equivalent advantages and characteristics as sulfation of the particular residue of the particular mini-nucleosome core protein modified in the present Example. Unmodified mini-nucleosome core proteins according to the same amino acid sequence were also included in the present example as a control.

Mini-nucleosome core proteins of the present Example were loaded with a nucleic acid payload that included a gene encoding luciferase. In the present Example, luciferase is representative of protein expression generally, in that expression of luciferase is indicative of the ability of a mini-nucleosome core protein modified as disclosed herein and discussed in the present Example to successfully delivery any nucleic acid payload for expression of any expression product. Loaded mini-nucleosomes of the present Example were administered intrathecally to one or more 9-10 week old Balb/c mice (3e10 gc/mouse; 10 µl volume).

Figure 33:
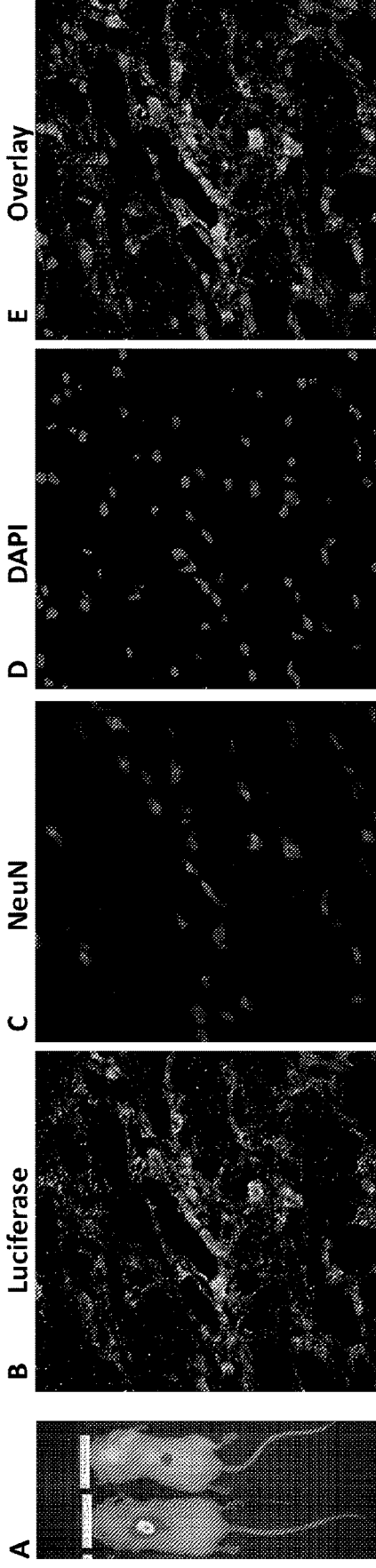
FIG. 33 includes panels A, B, C, D and E. Panel A is an IVIS® Spectrum In Vivo Imaging System (IVIS) image of a mouse administered a sulfated mini-nucleosome according to SEQ ID NO: 388 loaded with a nucleic acid payload including a gene encoding luciferase as a representative expression product. Panel A shows a high degree of expression in certain tissues including central nervous system cells including neurons, and including spinal cord cells and brain neurons. Panels B, C, D, and E are images of a representative tissue section from the brain of an animal shown in Figure A (left), each of which represents a different imaging or overlay. Panel B shows a luciferase stain. Panel C shows an anti-NeuN (neuronal marker) antibody stain. Panel D shows a D-DAPI (nuclear) stain. Panel E shows an overlay of the luciferase, anti-NeuN antibody, and D-DAPI stains. Images demonstrate robust expression of the representative nucleic acid payload-encoded expression product (here, luciferase) in brain cells, particularly including brain neurons, when the mini-nucleosome is sulfated but not when the mini-nucleosome is unmodified.

Results are shown in FIGS. 32 and 33. On day 11 post dose administration, mice were dosed with luciferin at 150 mg/kg (60 mg/mL) via intraperitoneal (IP) injection at 2.5 ml/kg. At ~15 minutes post each luciferin administration (+5%), all animals underwent an IVIS imaging session. Panel A of FIG. 32 shows results using loaded mini-nucleosomes including an unmodified mini-nucleosome core protein, while Panel B of FIG. 32 shows results using loaded mini-nucleosomes including a sulfated mini-nucleosome core protein. All mini-nucleosome core proteins were loaded with a nucleic acid payload including a gene encoding luciferase. Panel B of FIG. 32 shows that the modified mini-nucleosome core protein, but not the unmodified mini-nucleosome core protein results in robust expression of the representative nucleic acid payload-encoded expression product (here, luciferase) in certain tissues including central nervous system cells including neurons, and including spinal cord cells and brain neurons. FIG. 33 includes brain tissue sections of a mouse administered a sulfated mini-nucleosome core protein loaded with the luciferase-encoding payload, which mouse showed a high degree of expression in certain tissues including central nervous system cells including neurons, and including spinal cord cells and brain neurons (Panel A). Panels B, C, and D respectively show luciferase, anti-NeuN antibody, and D-DAPI stains, with an overlay of these stains shown in Panel E. Images of FIG. 33 demonstrate robust expression of the representative nucleic acid payload-encoded expression product (here, luciferase) in brain cells, particularly including brain neurons, when the mini-nucleosome is sulfated but not when the mini-nucleosome is unmodified. Expression levels observed in the present Example were highly unexpected. Detection of expression by IVIS imaging requires a very high level of expression, and the present data therefore reflects remarkable efficiency of both cellular uptake and payload expression. Levels of expression dramatically exceed those that would be expected for a non-viral vector. Moreover, it was unexpected that sulfation would increase expression in brain cells, particularly including brain neurons.

Example 12: Acetylated Mini-Nucleosome Core Proteins Deliver Nucleic Acid Payloads to Neurons and Central Nervous System Cells The present example demonstrates that a mini-nucleosome core protein including one or more residues modified by acetylation is particularly advantageous at least for expression of a nucleic acid payload (i.e., expression of an expression product encoded by a nucleic acid payload) in certain cells or tissues. For example a mini-nucleosome core protein including one or more residues modified by acetylation can be particularly advantageous for expression of a nucleic acid payload in retinal cells, in particular photoreceptors Modified mini-nucleosome core proteins were prepared by acetylation of a mini-nucleosome core protein having an amino acid sequence according to SEQ ID NO: 401. In particular, a lysine residue at position 10 of the mini-nucleosome core protein was acetylated. This residue is positioned in a targeting domain (KKRPKP) of the mini-nucleosome core protein. However, the present disclosure provides that the presence of the modification, rather than the particular position of the modification within the mini-nucleosome core protein, determines the characteristics of the mini-nucleosome core proteins disclosed herein. Without wishing to be bound by any particular scientific theory, the present Example includes the recognition that modifications of mini-nucleosome core proteins according the present Example can interact with cell surface receptors, improving delivery of loaded mini-nucleosomes to certain target cells. Accordingly, the present disclosure provides that acetylation of any amino acid residue(s) of a mini-nucleosome core protein, in particular a lysine, would provide equivalent advantages and characteristics as acetylation of the particular residue of the particular mini-nucleosome core protein modified in the present Example. Unmodified mini-nucleosome core proteins according to the same amino acid sequence were also included in the present example as a control.

Mini-nucleosome core proteins of the present Example were loaded with a nucleic acid payload that included a gene encoding GFP. In the present Example, GFP is representative of protein expression generally, in that expression of GFP is indicative of the ability of a mini-nucleosome core protein modified as disclosed herein and discussed in the present Example to successfully delivery any nucleic acid payload for expression of any expression product. Loaded mini-nucleosomes of the present Example were administered intravitreally to one or more mice. For intravitreal injections, mice were anesthetized by IP injection with Ketamine/Xylazine (90-100 mg/kg+10 mg/kg), a target pupil was dilated under a microscope using topical Tropicamide (1%), and an incision/insertion was made on the sclera ~1 mm below the limbus using a 30-gauge needle. 1 µl of loaded mini-nucleosome was injected into the vitreous cavity using 32 gauge blunt needle passing through the incision made by the 25-gauge needle.

Figure 34:
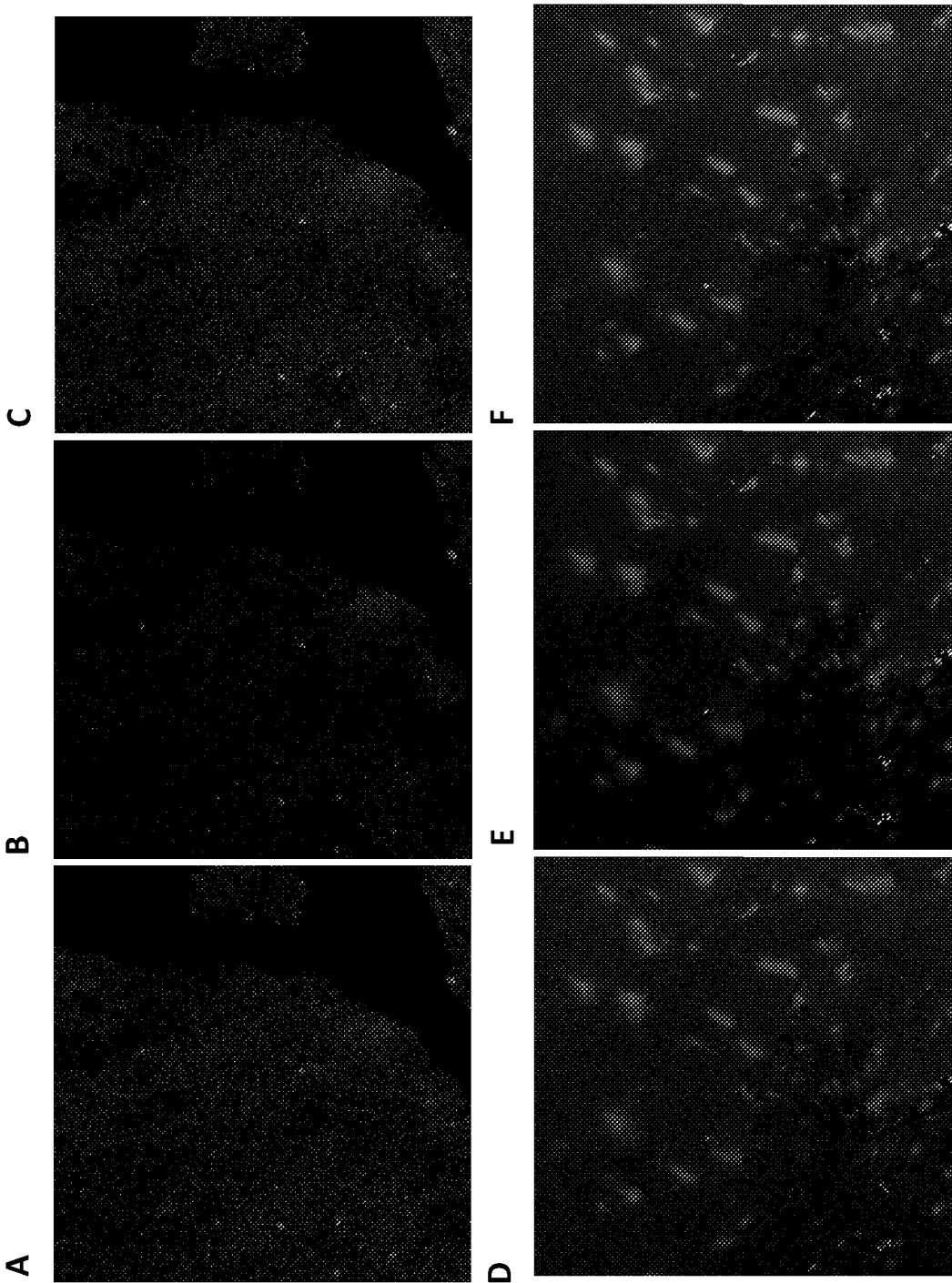
FIG. 34 includes panels A, B, C, D, E, and F, each of which shows a retinal wholemount. Panels A, B, and C show a representative retinal wholemount from a mouse administered an unmodified mini-nucleosome core protein according to SEQ ID NO: 401 loaded with a nucleic acid payload including a gene encoding green fluorescent protein (GFP) as a representative expression product. Panel A shows native GFP fluorescence. Panel B shows an anti-GFP antibody stain. Panel C shows an overlay of native GFP fluorescence and anti-GFP antibody stain. Panels D, E, and F show a representative retinal wholemount from a mouse adminis- tered an acetylated mini-nucleosome according to SEQ ID NO: 401 loaded with a nucleic acid payload including a gene encoding GFP as a representative expression product. Panel D shows native GFP fluorescence. Panel E shows an anti- GFP antibody stain. Panel F shows an overlay of native GFP fluorescence and anti-GFP antibody stain. Images demon- strate robust expression of the representative nucleic acid payload-encoded expression product (here, GFP) in retinal cells, in particular photoreceptors, when the mini-nucle- osome is acetylated but not when the mini-nucleosome is unmodified.

Results are shown in FIG. 34. Eyes were enucleated at 4 weeks post injection and placed in 4% PFA for fixation. Lenses were removed from the eyes by dissection and the retinal wholemount was dissected from eyecup. Retinal wholemounts were hydrated with 1xPBS, blocked using 2% BSA and stained with GFP antibodies coupled to Alexa-flour 555 at room temperature for 1 hr and washed with 1xPBS 4 times, 5 minutes each. Images were obtained using Leica SP5 confocal microscope.

Panels A-C of FIG. 34 show results using loaded mini-nucleosomes including an unmodified mini-nucleosome core protein, while Panel D-F of FIG. 34 shows results using loaded mini-nucleosomes including an acetylated mini-nucleosome core protein. All mini-nucleosome core proteins were loaded with a nucleic acid payload including a gene encoding GFP. Images demonstrate robust expression of the representative nucleic acid payload-encoded expression product (here, GFP) in retinal cells, in particular photoreceptors, when the mini-nucleosome is acetylated but not when the mini-nucleosome is unmodified. Expression levels observed in the present Example were highly unexpected. Detection of expression by IVIS imaging requires a very high level of expression, and the present data therefore reflects remarkable efficiency of both cellular uptake and payload expression. Levels of expression dramatically exceed those that would be expected for a non-viral vector. Moreover, it was unexpected that acetylation would increase expression in retinal cells, in particular photoreceptors.

Example 13: Phosphorylated Mini-Nucleosome Core Proteins Deliver Nucleic Acid Payloads to Neurons and Central Nervous System Cells The present Example demonstrates that a mini-nucleosome core protein including one or more residues modified by mannosylation is particularly advantageous at least for expression of a nucleic acid payload (i.e., expression of an expression product encoded by a nucleic acid payload) in certain cells or tissues. For example, a mini-nucleosome core protein including one or more residues modified by mannosylation can be particularly advantageous for expression of a nucleic acid payload in retinal cells, in particular photoreceptors.

Modified mini-nucleosome core proteins were prepared by mannosylation of a mini-nucleosome core protein having an amino acid sequence according to SEQ ID NO: 447. In particular, a serine residue at position 9 of the mini-nucleosome core protein was mannosylated. This residue is positioned in a linker domain (GGS) of the mini-nucleosome core protein. However, the present disclosure provides that the presence of the modification, rather than the particular position of the modification within the mini-nucleosome core protein, determines the characteristics of the mini-nucleosome core proteins disclosed herein. Without wishing to be bound by any particular scientific theory, the present Example includes the recognition that modifications of mini-nucleosome core proteins according the present Example can interact with cell surface receptors, improving delivery of loaded mini-nucleosomes to certain target cells. Accordingly, the present disclosure provides that mannosylation of any amino acid residue(s) of a mini-nucleosome core protein, in particular a serine, would provide equivalent advantages and characteristics as mannosylation of the particular residue of the particular mini-nucleosome core protein modified in the present Example. Unmodified mini-nucleosome core proteins according to the same amino acid sequence were also included in the present example as a control.

Mini-nucleosome core proteins of the present Example were loaded with a nucleic acid payload that included a gene encoding GFP. In the present Example, GFP is representative of protein expression generally, in that expression of GFP is indicative of the ability of a mini-nucleosome core protein modified as disclosed herein and discussed in the present Example to successfully delivery any nucleic acid payload for expression of any expression product. Loaded mini-nucleosomes of the present Example were administered subretinally to one or more mice. For subretinal injections, mice were anesthetized by IP injection with Ketamine/Xylazine (90-100 mg/kg+10 mg/kg), a target pupil was dilated under a microscope using topical Tropic-amide (1%), and an incision/insertion was made on the sclera ~1 mm below the limbus using a 30-gauge needle. 1 μl of loaded mini-nucleosome was injected into the vitreous cavity using 32 gauge blunt needle passing through the incision made by the 25-gauge needle behind the retina. A micropump controlled injector was utilized for this procedure.

Figure 35:
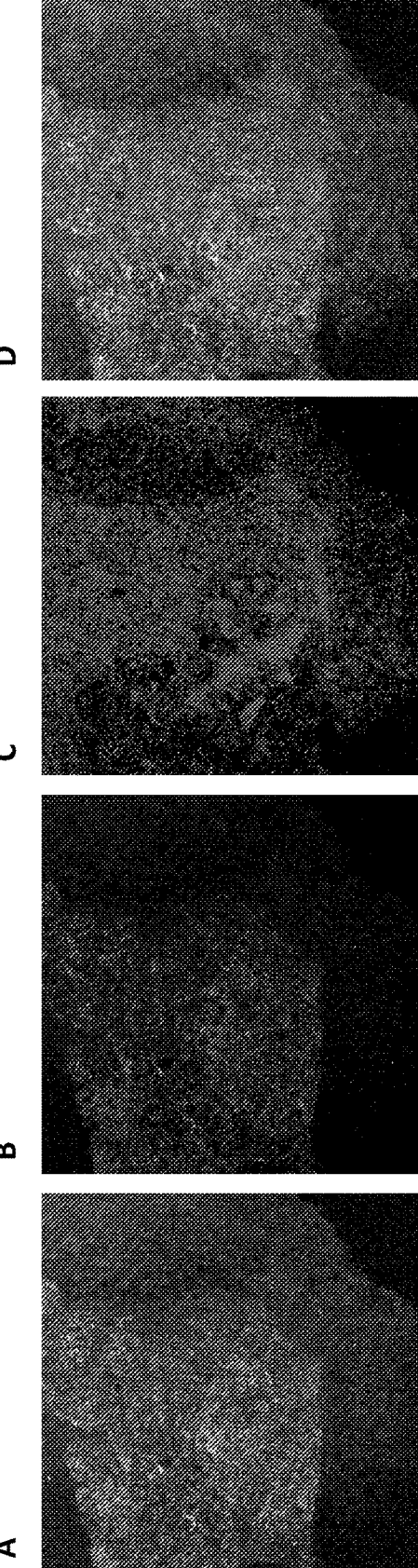
FIG. 35 includes panels A, B, C, and D, each of which is an image of a representative retinal wholemount from a mouse administered a mannosylated mini-nucleosome according to SEQ ID NO: 447 loaded with a nucleic acid payload including a gene encoding GFP as a representative expression product. Panel A shows native GFP fluorescence. Panel B shows an anti-GFP antibody stain. Panel C shows a peanut agglutinin (PNA; marker for photoreceptors) stain. Panel D shows an overlay of native GFP fluorescence, anti-GFP antibody stain, and PNA stain. Images demonstrate robust expression of the representative nucleic acid payload- encoded expression product (here, GFP) in retinal cells, in particular photoreceptors, when the mini-nucleosome is mannosylated. An unmodified control loaded with the same nucleic acid payload was not robustly expressed in retinal cells or photoreceptors.

Results are shown in FIG. 35. Eyes were enucleated at 2 weeks post injection and placed in 4% PFA for fixation. Lenses were removed from the eyes by dissection and the retinal wholemount was dissected from eyecup. Retinal wholemounts were hydrated with 1xPBS, blocked using 2% BSA and stained with GFP antibodies coupled to Alexa-flour 555 at room temperature for 1 hour and washed with 1xPBS 4 times, 5 minutes each. Images were obtained using Leica SP5 confocal microscope.

FIG. 35, panels A-D, show a representative retinal wholemount from a mouse administered loaded mini-nucleosomes including mannosylated mini-nucleosome core protein. Images demonstrate robust expression of the representative nucleic acid payload-encoded expression product (here, GFP) in retinal cells, in particular photoreceptors, when the mini-nucleosome is mannosylated. An unmodified control loaded with the same nucleic acid payload was not robustly expressed in retinal cells or photoreceptors. Expression levels observed in the present Example were highly unexpected. Detection of expression by IVIS imaging requires a very high level of expression, and the present data therefore reflects remarkable efficiency of both cellular uptake and payload expression. Levels of expression dramatically exceed those that would be expected for a non-viral vector.

```
CERTAIN SEQUENCES:

SEQ ID NO: 394

KKRHRK-[LINKER]-LRE-[LINKER]KRHRKLRRRRRLKRHRKKRHRK-[LINKER]-

LRE-[LINKER]-K (where [LINKER] could be any amino acid sequence described in Table 12 but not limited to it)

SEQ ID NO: 389

KKKRHRKRKRKRKRRRRKKK-[LINKER]-ASSLNIAK-[LINKER]-RRRR (where [LINKER] could be any amino acid sequence described in Table 12 but not lim-
ited to it)
```

-continued

SEQ ID NO: 390

KKKRK-[LINKER]-NGR-[LINKER]-KRKRKKRHRKKKKRRRRKRHRK-[LINKER]-
NGR-[LINKER]-KKK
(where [LINKER] could be any amino acid sequence described in Table 12 but not lim-
ited to it)

SEQ ID NO: 391

KKKRHRKKKKK-[LINKER]-RGD-[LINKER]-KKKK-[LINKER]-NTQIH-[LINKER]-
RRRRR-[LINKER]-TPH-[LINKER]-KK
(where [LINKER] could be any amino acid sequence described in Table 12 but not
limited to it)

SEQ ID NO: 392

KKKRK-[LINKER]-KTKKK-[LINKER]-AK-[LINKER]-KALKKK-[LINKER]-
KKGKKKKRRRRKAAPKK
(where [LINKER] could be any amino acid sequence described in Table 12 but not
limited to it)

SEQ ID NO: 393

CKKKKKKKKKKKKKKKKKKKKKKKKKKKKKKK

CBA-F8 plasmid

SEQ ID NO: 460

TCGCGCGTTTCGGTGATCGAGGTGAGCCCCACGTTCTGCTTCACTCTCCCCATCTCCC

CCCCCTCCCCACCCCCAATTTTGTATTTATTTATTTTTTAATTATTTTGTGCAGCGATG

GGGGCGGGGGGGGGGGGGGGGGCGCGCGCCAGGCGGGGCGGGGCGGGGCGAGGGG

CGGGGCGGGGCGAGGCGGAGAGGTGCGGCGGCAGCCAATCAGAGCGGCGCGCTCC

GAAAGTTTCCTTTTATGGCGAGGCGGCGGCGGCGGCGGCCCTATAAAAAGCGAAGC

GCGCGGCGGGCGGGAGTCGCTGCGACGCTGCCTTCGCCCCGTGCCCCGCTCCGCCGC

CGCCTCGCGCCGCCCGCCCCGGCTCTGACTGACCGCGTTACTCCCACAGGTGAGCGG

GCGGGACGGCCCTTCTCCTCCGGGCTGTAATTAGCGCTTGGTTTAATGACGGCTTGT

TTCTTTTCTGTGGCTGCGTGAAAGCCTTGAGGGGCTCCGGGAGGGCCCTTTGTGCGG

GGGGGAGCGGCTCGGGGGGTGCGTGCGTGTGTGTGTGCGTGGGGAGCGCCGCGTGC

GGCCCGCGCTGCCCGGCGGCTGTGAGCGCTGCGGGCGCGGCGCGGGGCTTTGTGCG

CTCCGCAGTGTGCGCGAGGGGAGCGCGGCCGGGGGCGGTGCCCCGCGGTGCGGGGG

GGGCTGCGAGGGGAACAAAGGCTGCGTGCGGGGTGTGTGCGTGGGGGGGTGAGCA

GGGGGTGTGGGCGCGGCGGTCGGGCTGTAACCCCCCCCTGCACCCCCCTCCCCGAGT

TGCTGAGCACGGCCCGGCTTCGGGTGCGGGGCTCCGTACGGGGCGTGGCGCGGGGC

TCGCCGTGCCGGGCGGGGGGTGGCGGCAGGTGGGGGTGCCGGGCGGGGCGGGGCC

GCCTCGGGCCGGGGAGGGCTCGGGGGAGGGGCGCGGCGGCCCCCGGAGCGCCGGC

GGCTGTCGAGGCGCGGCGAGCCGCAGCCATTGCCTTTTATGGTAATCGTGCGAGAG

GGCGCAGGGACTTCCTTTGTCCCAAATCTGTGCGGAGCCGAAATCTGGGAGGCGCC

GCCGCACCCCCTCTAGCGGGCGCGGGGCGAAGCGGTGCGGCGCCGGCAGGAAGGA

AATGGGCGGGGAGGGCCTTCGTGCGTCGCCGCGCCGCCGTCCCCTTCTCCCTCTCCA

GCCTCGGGGCTGTCCGCGGGGGGACGGCTGCCTTCGGGGGGGGACGGGGCAGGGCGG

GGTTCGGCTTCTGGCGTGTGACCGGCGGCTCTAGAGCCTCTGCTAACCATGTTCATG

CCTTCTTCTTTTTCCTACAGCTCCTGGGCAACGTGCTGGTTATTGTGCTGTCTCATCAT

TTTGGCAAAACCGGTCTCGAAGGCCTGCAGGCGGCCGCCGCCACCGCCACCATGCA

AATAGCACTCTTCGCTTGCTTCTTTCTGAGCCTTTTCAATTTCTGCTCTAGTGCCATCA

GAAGATACTACCTTGGTGCAGTGGAATTGTCCTGGAACTATATTCAGAGTGATCTGC

TCAGTGTGCTGCATACAGACTCAAGATTTCTTCCTAGAATGTCAACATCTTTTCCATT

CAACACCTCCATCATGTATAAAAAGACTGTGTTTGTAGAGTACAAGGACCAGCTTTT

```
CAACATTGCCAAGCCCAGGCCACCCTGGATGGGTTTGCTAGGTCCTACCATTTGGAC

TGAGGTTCATGACACAGTGGTCATTACACTTAAAAACATGGCTTCTCATCCTGTCAG

TCTTCATGCTGTTGGTGTGTCCTACTGGAAAGCTTCTGAGGGAGATGAATATGAAGA

TCAGACAAGCCAAATGGAGAAGGAAGATGATAAAGTTTTCCCTGGTGAAAGTCATA

CTTATGTTTGGCAAGTCCTGAAAGAGAATGGTCCAATGGCCTCTGACCCTCCATGTC

TCACTTACTCATATATGTCTCATGTGGATCTGGTGAAAGATTTGAATTCAGGCCTCAT

TGGAGCTCTGCTAGTATGTAAAGAAGGCAGTCTCTCCAAAGAAAGAACACAGATGT

TGTACCAATTTGTACTGCTTTTTGCTGTATTTGATGAAGGGAAGAGCTGGCACTCAG

AAACAAACGACTCTTATACACAGTCTATGGATTCTGCATCTGCTAGAGACTGGCCTA

AAATGCACACAGTCAATGGCTATGTAAACAGGTCTCTTCCAGGTCTGATTGGATGCC

ATAGGAAATCAGTCTACTGGCACGTGATTGGAATGGGCACCACTCCTGAAATACACT

CAATATTCCTCGAAGGTCACACATTTTTTGTGAGGAACCACCGTCAAGCTTCATTGG

AGATATCACCAATAACTTTCCTTACTGCTCAAACACTCTTGATAGATCTTGGGCAGTT

CCTACTATTTTGTCATATCTCTTCCCATAAACATGATGGCATGGAAGCTTATGTCAAA

GTAGATAGCTGCCCTGAGGAATCCCAATGGCAAAGAAAAATAATAATGAGGAAAT

GGAAGATTATGATGATGATCTTTATTCAGAAATGGATATGTTCACATTGGATTATGA

CAGCTCTCCTTTTATCCAAATTCGCTCGGTTGCTAAAAAGTACCCTAAAACTTGGAT

ACATTATATTTCTGCTGAGGAGGAAGACTGGGACTATGCACCTTCAGTTCCTACCTC

GGATAATGGAAGTTATAAAAGCCAGTATCTGAGCAATGGTCCTCATCGGATTGGTA

GGAAATATAAAAAAGTCAGATTTATAGCATACACAGATGAAACCTTTAAGACTCGT

GAAACTATTCAGCATGAATCAGGACTCTTGGGACCTTTACTTTATGGAGAAGTTGGA

GACACACTGTTGATTATTTTTAAGAATCAAGCAAGCCGACCATATAACATTTACCCT

CATGGAATCACTGATGTCAGTCCTCTACATGCAAGGAGATTGCCAAGAGGTATAAA

GCACGTGAAGGATTTGCCAATTCATCCAGGAGAGATATTCAAGTACAAGTGGACAG

TTACAGTAGAAGATGGACCAACTAAATCAGATCCACGGTGCCTGACCCGCTATTATT

CAAGTTTCATTAACCCTGAGAGAGATCTAGCTTCAGGACTGATTGGCCCTCTTCTCA

TCTGCTACAAAGAATCTGTAGATCAAAGGGGAAACCAGATGATGTCAGACAAAAGA

AATGTCATCCTGTTTTCTATATTTGATGAGAACCAAAGCTGGTACATCACAGAGAAC

ATGCAACGCTTCCTCCCCAATGCAGCTAAAACACAGCCCCAGGACCCTGGGTTCCAG

GCCTCCAACATCATGCACAGCATCAATGGCTATGTTTTTGATAGCTTGGAGTTGACA

GTTTGTTTGCATGAGGTGGCATACTGGCACATTCTCAGTGTTGGAGCACAGACAGAC

TTCTTATCTATCTTCTTCTCTGGATATACTTTCAAACACAAAATGGTCTATGAAGATA

CACTTACCCTGTTCCCATTCTCAGGAGAAACTGTCTTTATGTCGATGGAAAACCCAG

GTCTATGGGTCTTGGGGTGTCATAATTCAGACTTTCGGAAGAGAGGTATGACAGCAT

TGCTGAAAGTTTCTAGTTGTGACAAGAGCACTAGTGATTATTATGAAGAAATATATG

AAGATATTCCAACACAGTTGGTGAATGAGAACAATGTCATTGATCCCAGAAGCTTCT

TCCAGAATACAAATCATCCTAATACTAGGAAAAAGAAATTCAAAGATTCCACAATT

CCAAAAAATGATATGGAGAAGATTGAGCCTCAGTTTGAAGAGATAGCAGAGATGCT

TAAAGTACAGAGTGTCTCAGTTAGTGACATGTTGATGCTCTTGGGACAGAGTCATCC

TACTCCACATGGCTTATTTTTTATCAGATGGCCAAGAAGCCATCTATGAGGCTATTCA
```

-continued

```
TGATGATCATTCACCAAATGCAATAGACAGCAATGAAGGCCCATCTAAAGTGACCC

AACTCAGGCCAGAATCCCATCACAGTGAGAAAATAGTATTTACTCCTCAGCCCGGCC

TCCAGTTAAGATCCAATAAAAGTTTGGAGACAACTATAGAAGTAAAGTGGAAGAAA

CTTGGTTTGCAAGTTTCTAGTTTGCCAAGTAATCTAATGACTACAACAATTCTGTCAG

ACAATTTGAAAGCAACTTTTGAAAAGACAGATTCTTCAGGATTTCCAGATATGCCAG

TTCACTCTAGTAGTAAATTAAGTACTACTGCATTTGGTAAGAAAGCATATTCCCTTGT

TGGGTCTCATGTACCTTTAAACGTGAGTGAAGAAAATAGTGATTCCAACATATTGGA

TTCAACTTTAATGTATAGTCAAGAAAGTTTACCAAGAGATAATATATTATCAATGGA

GAATGATAGATTACTCAGAGAGAAGAGGTTTCATGGAATTGCTTTATTGACCAAAG

ATAATACTTTATTCAAAGACAATGTCTCCTTAATGAAAACAAACAAAACATATAATC

ATTCAACAACTAATGAAAAACTACACACTGAGAGCCCAACATCAATTGAGAATAGT

ACAACAGACTTGCAAGATGCCATATTAAAGGTCAATAGTGAGATTCAAGAAGTAAC

AGCTTTGATTCATGATGGAACACTTTTAGGCAAAAATTCTACATATTTGAGACTAAA

CCATATGCTAAATAGAACTACCTCAACAAAAAATAAAGACATATTTCATAGAAAAG

ATGAAGATCCTATTCCACAAGATGAAGAGAATACAATCATGCCATTTTCCAAGATGT

TGTTCTTGTCAGAATCTTCAAATTGGTTTAAAAAGACCAATGGAAATAATTCCTTGA

ACTCTGAGCAAGAACATAGTCCAAAGCAATTAGTATATTTAATGTTTAAAAAATATG

TAAAAAATCAAAGTTTCTTGTCAGAGAAAAATAAAGTCACAGTAGAACAGGATGGA

TTTACAAAGAACATAGGACTTAAAGACATGGCTTTTCCACATAATATGAGCATATTT

CTTACCACTTTGTCTAACGTACATGAAAATGGTAGGCACAATCAAGAAAAAAATATT

CAGGAAGAGATAGAGAAGGAAGCACTAATTGAAGAGAAAGTAGTTTTGCCCCAGGT

GCACGAAGCAACTGGCTCTAAGAATTTCTTGAAAGACATATTGATACTAGGCACTAG

GCAAAATATAAGTTTATATGAAGTACATGTACCAGTACTTCAAAACATCACATCAAT

AAACAATTCAACAAATACAGTACAGATTCACATGGAGCATTTCTTTAAAAGAAGGA

AGGACAAGGAAACAAATTCAGAAGGCTTGGTAAATAAAACCAGAGAAATGGTAAA

AAACTATCCAAGCCAGAAGAATATTACTACTCAACGTAGTAAACGGGCTTTGGGAC

AATTCAGACTGTCAACTCAATGGCTTAAAACCATAAACTGTTCAACACAGTGTATCA

TTAAACAGATAGACCACAGCAAGGAAATGAAAAAGTTCATTACTAAATCTTCCTTAT

CAGATTCTTCTGTGATTAAAAGCACCACTCAGACAAATAGTTCTGACTCACACATTG

TAAAAACATCAGCATTTCCACCAATAGATCTCAAAAGGAGTCCATTCCAAAACAAA

TTTTCTCATGTTCAAGCATCATCCTACATTTATGACTTTAAGACAAAAAGTTCAAGA

ATTCAAGAAAGCAATAATTTCTTAAAAGAAACCAAAATAAATAACCCTTCTTTAGCC

ATTCTACCATGGAATATGTTCATAGATCAAGGAAAATTTACCTCCCCAGGGAAAAGT

AACACAAACTCAGTCACATATAAGAAACGTGAGAACATTATTTTCTTGAAACCAACT

TTGCCTGAAGAATCTGGCAAAATTGAATTGCTTCCTCAAGTTTCCATTCAAGAGGAA

GAAATTTTACCTACAGAAACTAGCCATGGATCTCCTGGACACTTGAATCTCATGAAA

GAGGTCTTTCTTCAGAAAATACAGGGGCCTACTAAATGGAATAAAGCAAAGAGGCA

TGGAGAAAGTATAAAAGGTAAAACAGAGAGCTCTAAAAATACTCGCTCAAAACTGC

TAAATCATCATGCTTGGGATTATCATTATGCTGCACAGATACCAAAAGATATGTGGA

AATCCAAAGAGAAGTCACCAGAAATTATATCCATTAAGCAAGAGGACACCATTTTG

TCTCTGAGGCCTCATGGAAACAGTCATTCAATAGGGGCAAATGAGAAACAAAATTG
```

-continued

```
GCCTCAAAGAGAAACCACTTGGGTAAAGCAAGGCCAAACTCAAAGGACATGCTCTC

AAATCCCACCAGTGTTGAAACGACATCAAAGGGAACTTAGTGCTTTTCAATCAGAAC

AAGAAGCAACTGACTATGATGATGCCATCACCATTGAAACAATCGAGGATTTTGAC

ATTTACAGTGAGGACATAAAGCAAGGTCCCCGCAGCTTTCAACAGAAAACAAGGCA

CTATTTTATTGCAGCTGTGGAACGACTCTGGGACTATGGGATGAGTACATCTCATGT

TCTACGAAATAGGTATCAAAGTGACAATGTACCTCAGTTCAAGAAAGTAGTTTTCCA

GGAATTTACTGATGGCTCCTTTAGTCAGCCCTTATATCGTGGAGAATTAAATGAACA

CCTGGGGTTGTTGGGCCCATATATAAGAGCAGAAGTTGAAGACAACATTATGGTAA

CTTTCAAAAACCAGGCCTCCCGTCCCTACTCCTTCTATTCTAGCCTCATTTCTTATAA

AGAAGATCAGAGAGGAGAAGAACCTAGAAGAAACTTTGTCAAGCCTAATGAAACC

AAAATTTATTTTTGGAAAGTACAACATCATATGGCACCCACAGAAGATGAGTTTGAC

TGCAAGGCCTGGGCTTATTTCTCTGATGTTGATCTTGAAAGAGATATGCACTCGGGA

TTAATTGGACCCCTTCTGATTTGCCACGCGAACACACTGAATCCTGCTCATGGGAGA

CAAGTGTCAGTACAGGAATTTGCTCTGCTTTTCACTATCTTTGATGAGACCAAGAGC

TGGTACTTCACTGAAAACGTGAAAAGGAACTGCAAGACACCCTGCAATTTCCAGAT

GGAAGACCCCACTTTGAAAGAGAATTATCGCTTCCATGCAATCAATGGTTATGTAAT

GGATACCCTACCAGGCTTAGTAATGGCTCAAGATCAAAGGATTCGATGGTATCTTCT

CAGCATGGGCAACAATGAGAACATCCAATCTATTCATTTCAGTGGACATGTTTTCAC

TGTACGGAAAAAAGAGGAGTATAAAAATGGCAGTGTACAACCTCTACCCAGGTGTTT

TTGAGACTCTGGAAATGATACCATCCAGAGCTGGAATATGGCGAGTAGAATGCCTT

ATTGGCGAGCACTTACAGGCTGGGATGAGCACTCTTTTTCTGGTGTACAGCAAGCAG

TGTCAGATTCCTCTTGGAATGGCTTCTGGAAGCATCCGTGATTTCCAGATTACAGCTT

CAGGACATTATGGACAGTGGGCCCCAAACCTGGCAAGACTTCATTATTCCGGATCAA

TCAATGCCTGGAGTACCAAGGAGCCCTTTTCTTGGATCAAGGTAGATCTGTTGGCAC

CAATGATTGTTCATGGCATCAAGACTCAGGGTGCTCGTCAGAAATTTTCCAGCCTTT

ATATCTCTCAATTTATCATCATGTATAGCCTGGATGGGAAGAAGTGGCTGAGTTATC

AAGGAAATTCCACTGGAACCTTAATGGTTTTCTTTGGCAATGTGGACTCATCTGGGA

TTAAGCATAATAGTTTTAATCCTCCAATTATTGCTCGATATATCCGTTTGCACCCCAC

TCATTCTAGCATCCGTAGTACTCTTCGCATGGAGTTGATGGGCTGTGATTTAAACAG

TTGCAGCATACCATTGGGAATGGAAAGTAAAGTAATATCAGATACACAAATCACTG

CCTCATCCTACTTCACCAACATGTTTGCTACTTGGTCTCCTTCACAAGCTCGACTTCA

CCTCCAGGGAAGGACTAATGCCTGGCGACCTCAGGTGAATGATCCAAAACAATGGT

TGCAAGTGGACTTACAAAAGACAATGAAAGTCACTGGAATAATAACCCAGGGAGTG

AAATCTCTCTTTACCAGCATGTTTGTGAAAGAGTTCCTTATTTCCAGCAGTCAAGATG

GCCATCACTGGACTCAAATTTTATACAATGGCAAGGTAAAGGTTTTTCAGGGGAATC

AGGACTCATCCACACCTATGATGAATTCTCTAGACCCACCATTACTCACTCGCTATC

TTCGAATTCACCCCCAGATCTGGGAGCACCAAATTGCTCTGAGGCTTGAGATTCTAG

GATGTGAGGCCCAGCAGCAATACTGACCATGGCCCAACTTGTTTATTGCAGCTTATA

ATGGTTACAAATAAAGCAATAGCATCACAAATTTCACAAATAAAGCATTTTTTTCAC

TGCATTCTAGTTGTGGTTTGTCCAAACTCATCAATGTATCTTATCATGTCTGGATCTC
```

-continued

GTTAACTCGAGGGATCCATCGATGTCGACTGCAGAGGCCTGCATGCAAGCTTGGTGT

AATCATGGTCATAGCTGTTTCCTGTGTGAAATTGTTATCCGCTCACAATTCCACACAA

CATACGAGCCGGAAGCATAAAGTGTAAAGCCTGGGGTGCCTAATGAGTGAGCTAAC

TCACATTAATTGCGTTGCGCTCACTGCCCGCTTTCCAGTCGGGAAACCTGTCGTGCC

AGCTGCATTAATGAATCGGCCAACGCGCGGGGAGAGGCGGTTTGCGTATTGGGCGC

TCTTCCGCTTCCTCGCTCACTGACTCGCTGCGCTCGGTCGTTCGGCTGCGGCGAGCG

GTATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGGCC

GCGTTGCTGGCGTTTTTCCATAGGCTCCGCCCCCCTGACGAGCATCACAAAAATCGA

CGCTCAAGTCAGAGGTGGCGAAACCCGACAGGACTATAAAGATACCAGGCGTTTCC

CCCTGGAAGCTCCCTCGTGCGCTCTCCTGTTCCGACCCTGCCGCTTACCGGATACCTG

TCCGCCTTTCTCCCTTCGGGAAGCGTGGCGCTTTCTCATAGCTCACGCTGTAGGTATC

TCAGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAGAC

ACGACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAGAAG

AACAGTATTTGGTATCTGCGCTCTGCTGAAGCCAGTTACCTTCGGAAAAAGAGTTGG

TAGCTCTTGATCCGGCAAACAAACCACCGCTGGTAGCGGTGGTTTTTTTGTTTGCAA

GCAGCAGATTACGCGCAGAAAAAAAGGATCTCAAGAAGATCCTTTGATCTTTTCTAC

GGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAAG

CCCAATCTGAATAATGTTACAACCAATTAACCAATTCTGATTAGAAAAACTCATCGA

GCATCAAATGAAACTGCAATTTATTCATATCAGGATTATCAATACCATATTTTTGAA

AAAGCCGTTTCTGTAATGAAGGAGAAAACTCACCGAGGCAGTTCCATAGGATGGCA

AGATCCTGGTATCGGTCTGCGATTCCGACTCGTCCAACATCAATACAACCTATTAAT

TTCCCCTCGTCAAAAATAAGGTTATCAAGTGAGAAATCACCATGAGTGACGACTGA

ATCCGGTGAGAATGGCAAAAGTTTATGCATTTCTTTCCAGACTTGTTCAACAGGCCA

GCCATTACGCTCGTCATCAAAATCACTCGCATCAACCAAACCGTTATTCATTCGTGA

TTGCGCCTGAGCGAGACGAAATACGCGATCGCTGTTAAAAGGACAATTACAAACAG

GAATCGAATGCAACCGGCGCAGGAACACTGCCAGCGCATCAACAATATTTTCACCT

GAATCAGGATATTCTTCTAATACCTGGAATGCTGTTTTTCCGGGGATCGCAGTGGTG

AGTAACCATGCATCATCAGGAGTACGGATAAAATGCTTGATGGTCGGAAGAGGCAT

AAATTCCGTCAGCCAGTTTAGTCTGACCATCTCATCTGTAACATCATTGGCAACGCT

ACCTTTGCCATGTTTCAGAAACAACTCTGGCGCATCGGGCTTCCCATACAAGCGATA

GATTGTCGCACCTGATTGCCCGACATTATCGCGAGCCCATTTATACCCATATAAATC

AGCATCCATGTTGGAATTTAATCGCGGCCTCGACGTTTCCCGTTGAATATGGCTCAT

AACACCCCTTGTATTACTGTTTATGTAAGCAGACAGTTTTATTGTTCATGATGATATA

TTTTTATCTTGTGCAATGTAACATCAGAGATTTTGAGACACGGGCCAGAGCTGCA

CBA-GFP plasmid

SEQ ID NO: 395

TCGCGCGTTTCGGTGATGACGGTCGAGGTGAGCCCCACGTTCTGCTTCACTCTCCCC

ATCTCCCCCCCCTCCCCACCCCCAATTTTGTATTTATTTATTTTTTAATTATTTTGTGC

-continued

```
AGCGATGGGGGCGGGGGGGGGGGGGGGGGCGCGCGCCAGGCGGGGCGGGGCGGGG

CGAGGGGGGGGCGGGGCGAGGCGGAGAGGTGCGGCGGCAGCCAATCAGAGCGGC

GCGCTCCGAAAGTTTCCTTTTATGGCGAGGCGGCGGCGGCGGCGGCCCTATAAAAA

GCGAAGCGCGCGGCGGGCGGGAGTCGCTGCGACGCTGCCTTCGCCCCGTGCCCCGC

TCCGCCGCCGCCTCGCGCCGCCCGCCCCGGCTCTGACTGACCGCGTTACTCCCACAG

GTGAGCGGGCGGGACGGCCCTTCTCCTCCGGGCTGTAATTAGCGCTTGGTTTAATGA

CGGCTTGTTTCTTTTCTGTGGCTGCGTGAAAGCCTTGAGGGGCTCCGGGAGGGCCCT

TTGTGCGGGGGGGAGCGGCTCGGGGGGTGCGTGCGTGTGTGTGCGTGGGGAGCG

CCGCGTGCGGCCCGCGCTGCCCGGCGGCTGTGAGCGCTGCGGGCGCGGCGCGGGGC

TTTGTGCGCTCCGCAGTGTGCGCGAGGGGAGCGCGGCCGGGGGCGGTGCCCCGCGG

TGCGGGGGGGGCTGCGAGGGGAACAAAGGCTGCGTGCGGGGTGTGTGCGTGGGGG

GGTGAGCAGGGGGTGTGGGCGCGGCGGTCGGGCTGTAACCCCCCCCTGCACCCCCC

TCCCCGAGTTGCTGAGCACGGCCCGGCTTCGGGTGCGGGGCTCCGTACGGGGCGTG

GCGCGGGGCTCGCCGTGCCGGGCGGGGGGTGGCGGCAGGTGGGGGTGCCGGGCGG

GGCGGGGCCGCCTCGGGCCGGGGAGGGCTCGGGGGAGGGGCGCGGCGGCCCCCGG

AGCGCCGGCGGCTGTCGAGGCGCGGCGAGCCGCAGCCATTGCCTTTTATGGTAATC

GTGCGAGAGGGCGCAGGGACTTCCTTTGTCCCAAATCTGTGCGGAGCCGAAATCTG

GGAGGCGCCGCCGCACCCCCTCTAGCGGGCGCGGGGCGAAGCGGTGCGGCGCCGGC

AGGAAGGAAATGGGCGGGGAGGGCCTTCGTGCGTCGCCGCGCCGCCGTCCCCTTCT

CCCTCTCCAGCCTCGGGGCTGTCCGCGGGGGGACGGCTGCCTTCGGGGGGGACGGG

GCAGGGCGGGGTTCGGCTTCTGGCGTGTGACCGGCGGCTCTAGAGCCTCTGCTAACC

ATGTTCATGCCTTCTTCTTTTTCCTACAGCTCCTGGGCAACGTGCTGGTTATTGTGCT

GTCTCATCATTTTGGCAAAACCGGTCTCGAAGGCCTGCAGGCGGCCGCCGCCACCGC

CACCATGGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGCGAGGGC

GATGCCACCTACGGCAAGCTGACCCTGAAGTTCATCTGCACCACCGGCAAGCTGCCC

GTGCCCTGGCCCACCCTCGTGACCACCCTGACCTACGGCGTGCAGTGCTTCAGCCGC

TACCCCGACCACATGAAGCAGCACGACTTCTTCAAGTCCGCCATGCCCGAAGGCTAC

GTCCAGGAGCGCACCATCTTCTTCAAGGACGACGGCAACTACAAGACCCGCGCCGA

GGTGAAGTTCGAGGGCGACACCCTGGTGAACCGCATCGAGCTGAAGGGCATCGACT

TCAAGGAGGACGGCAACATCCTGGGGCACAAGCTGGAGTACAACTACAACAGCCAC

AACGTCTATATCATGGCCGACAAGCAGAAGAACGGCATCAAGGTGAACTTCAAGAT

CCGCCACAACATCGAGGACGGCAGCGTGCAGCTCGCCGACCACTACCAGCAGAACA

CCCCCATCGGCGACGGCCCCGTGCTGCTGCCCGACAACCACTACCTGAGCACCCAGT

CCGCCCTGAGCAAAGACCCCAACGAGAAGCGCGATCACATGGTCCTGCTGGAGTTC

GTGACCGCCGCCGGGATCACTCTCGGCATGGACGAGCTGTACAAGTAATCCATGGC

CCAACTTGTTTATTGCAGCTTATAATGGTTACAAATAAAGCAATAGCATCACAAATT

TCACAAATAAAGCATTTTTTTCACTGCATTCTAGTTGTGGTTTGTCCAAACTCATCAA

TGTATCTTATCATGTCTGGATCTCGTTAACTCGAGGGATCCATCGATGTCGACTGCA

GAGGCCTGCATGCAAGCTTGGTGTAATCATGGTCATAGCTGTTTCCTGTGTGAAATT
```

-continued

GTTATCCGCTCACAATTCCACACAACATACGAGCCGGAAGCATAAAGTGTAAAGCC

TGGGGTGCCTAATGAGTGAGCTAACTCACATTAATTGCGTTGCGCTCACTGCCCGCT

TTCCAGTCGGGAAACCTGTCGTGCCAGCTGCATTAATGAATCGGCCAACGCGCGGG

GAGAGGCGGTTTGCGTATTGGGCGCTCTTCCGCTTCCTCGCTCACTGACTCGCTGCG

CTCGGTCGTTCGGCTGCGGCGAGCGGTATCAGCTCACTCAAAGGCGGTAATACGGTT

ATCCACAGAATCAGGGGATAACGCAGGAAAGAACATGTGAGCAAAAGGCCAGCAA

AAGGCCAGGAACCGTAAAAAGGCCGCGTTGCTGGCGTTTTTCCATAGGCTCCGCCCC

CCTGACGAGCATCACAAAAATCGACGCTCAAGTCAGAGGTGGCGAAACCCGACAGG

ACTATAAAGATACCAGGCGTTTCCCCCTGGAAGCTCCCTCGTGCGCTCTCCTGTTCC

GACCCTGCCGCTTACCGGATACCTGTCCGCCTTTCTCCCTTCGGGAAGCGTGGCGCT

TTCTCATAGCTCACGCTGTAGGTATCTCAGTTCGGTGTAGGTCGTTCGCTCCAAGCTG

GGCTGTGTGCACGAACCCCCCGTTCAGCCCGACCGCTGCGCCTTATCCGGTAACTAT

CGTCTTGAGTCCAACCCGGTAAGACACGACTTATCGCCACTGGCAGCAGCCACTGGT

AACAGGATTAGCAGAGCGAGGTATGTAGGCGGTGCTACAGAGTTCTTGAAGTGGTG

GCCTAACTACGGCTACACTAGAAGAACAGTATTTGGTATCTGCGCTCTGCTGAAGCC

AGTTACCTTCGGAAAAAGAGTTGGTAGCTCTTGATCCGGCAAACAAACCACCGCTG

GTAGCGGTGGTTTTTTTGTTTGCAAGCAGCAGATTACGCGCAGAAAAAAAGGATCTC

AAGAAGATCCTTTGATCTTTTCTACGGGGTCTGACGCTCAGTGGAACGAAAACTCAC

GTTAAGGGATTTTGGTCATGAGATTATCAAAAAGGATCTTCACCTAGATCCTTTTAA

ATTAAAAATGAAGTTTTAAATCAAGCCCAATCTGAATAATGTTACAACCAATTAACC

AATTCTGATTAGAAAAACTCATCGAGCATCAAATGAAACTGCAATTTATTCATATCA

GGATTATCAATACCATATTTTTGAAAAAGCCGTTTCTGTAATGAAGGAGAAAACTCA

CCGAGGCAGTTCCATAGGATGGCAAGATCCTGGTATCGGTCTGCGATTCCGACTCGT

CCAACATCAATACAACCTATTAATTTCCCCTCGTCAAAAATAAGGTTATCAAGTGAG

AAATCACCATGAGTGACGACTGAATCCGGTGAGAATGGCAAAAGTTTATGCATTTCT

TTCCAGACTTGTTCAACAGGCCAGCCATTACGCTCGTCATCAAAATCACTCGCATCA

ACCAAACCGTTATTCATTCGTGATTGCGCCTGAGCGAGACGAAATACGCGATCGCTG

TTAAAAGGACAATTACAAACAGGAATCGAATGCAACCGGCGCAGGAACACTGCCAG

CGCATCAACAATATTTTCACCTGAATCAGGATATTCTTCTAATACCTGGAATGCTGTT

TTTCCGGGGATCGCAGTGGTGAGTAACCATGCATCATCAGGAGTACGGATAAAATG

CTTGATGGTCGGAAGAGGCATAAATTCCGTCAGCCAGTTTAGTCTGACCATCTCATC

TGTAACATCATTGGCAACGCTACCTTTGCCATGTTTCAGAAACAACTCTGGCGCATC

GGGCTTCCCATACAAGCGATAGATTGTCGCACCTGATTGCCCGACATTATCGCGAGC

CCATTTATACCCATATAAATCAGCATCCATGTTGGAATTTAATCGCGGCCTCGACGT

TTCCCGTTGAATATGGCTCATAACACCCCTTGTATTACTGTTTATGTAAGCAGACAGT

TTTATTGTTCATGATGATATATTTTTATCTTGTGCAATGTAACATCAGAGATTTTGAG

ACACGGGCCAGAGCTGCA

CBA-Luciferase plasmid

TCGCGCGTTTCGGTGATGACGGTCGAGGTGAGCCCCACGTTCTGCTTCACTCTCCCC

ATCTCCCCCCCCTCCCCACCCCCAATTTTGTATTTATTTATTTTTTAATTATTTTGTGC

AGCGATGGGGGCGGGGGGGGGGGGGGGGCGCGCGCCAGGCGGGGGGGGCGGGG

SEQ ID NO: 396

-continued

```
CGAGGGGCGGGGCGGGGCGAGGCGGAGAGGTGCGGCGGCAGCCAATCAGAGCGGC

GCGCTCCGAAAGTTTCCTTTTATGGCGAGGCGGCGGCGGCGGCGGCCCTATAAAAA

GCGAAGCGCGCGGCGGGCGGGAGTCGCTGCGACGCTGCCTTCGCCCCGTGCCCCGC

TCCGCCGCCGCCTCGCGCCGCCCGCCCCGGCTCTGACTGACCGCGTTACTCCCACAG

GTGAGCGGGCGGGACGGCCCTTCTCCTCCGGGCTGTAATTAGCGCTTGGTTTAATGA

CGGCTTGTTTCTTTTCTGTGGCTGCGTGAAAGCCTTGAGGGGCTCCGGGAGGGCCCT

TTGTGCGGGGGGGAGCGGCTCGGGGGGTGCGTGCGTGTGTGTGCGTGGGGAGCG

CCGCGTGCGGCCCGCGCTGCCCGGCGGCTGTGAGCGCTGCGGGCGCGGCGCGGGGC

TTTGTGCGCTCCGCAGTGTGCGCGAGGGGAGCGCGGCCGGGGGCGGTGCCCCGCGG

TGCGGGGGGGGCTGCGAGGGGAACAAAGGCTGCGTGCGGGGTGTGTGCGTGGGGG

GGTGAGCAGGGGGTGTGGGCGCGGCGGTCGGGCTGTAACCCCCCCCTGCACCCCCC

TCCCCGAGTTGCTGAGCACGGCCCGGCTTCGGGTGCGGGGCTCCGTACGGGGCGTG

GCGCGGGGCTCGCCGTGCCGGGCGGGGGGTGGCGGCAGGTGGGGGTGCCGGGCGG

GGCGGGGCCGCCTCGGGCCGGGGAGGGGCTCGGGGGAGGGGCGCGGCGGCCCCCGG

AGCGCCGGCGGCTGTCGAGGCGCGGCGAGCCGCAGCCATTGCCTTTTATGGTAATC

GTGCGAGAGGGCGCAGGGACTTCCTTTGTCCCAAATCTGTGCGGAGCCGAAATCTG

GGAGGCGCCGCCGCACCCCCTCTAGCGGGCGCGGGGCGAAGCGGTGCGGCGCCGGC

AGGAAGGAAATGGGCGGGGAGGGCCTTCGTGCGTCGCCGCGCCGCCGTCCCCTTCT

CCCTCTCCAGCCTCGGGGCTGTCCGCGGGGGGACGGCTGCCTTCGGGGGGGACGGG

GCAGGGCGGGGTTCGGCTTCTGGCGTGTGACCGGCGGCTCTAGAGCCTCTGCTAACC

ATGTTCATGCCTTCTTCTTTTTCCTACAGCTCCTGGGCAACGTGCTGGTTATTGTGCT

GTCTCATCATTTTGGCAAAACCGGTCTCGAAGGCCTGCAGGCGGCCGCCGCCACCGC

CACCATGGAAGACGCCAAAAACATAAAGAAAGGCCCGGCGCCATTCTATCCGCTGG

AAGATGGAACCGCTGGAGAGCAACTGCATAAGGCTATGAAGAGATACGCCCTGGTT

CCTGGAACAATTGCTTTTACAGATGCACATATCGAGGTGGACATCACTTACGCTGAG

TACTTCGAAATGTCCGTTCGGTTGGCAGAAGCTATGAAACGATATGGGCTGAATACA

AATCACAGAATCGTCGTATGCAGTGAAAACTCTCTTCAATTCTTTATGCCGGTGTTG

GGCGCGTTATTTATCGGAGTTGCAGTTGCGCCCGCGAACGACATTTATAATGAACGT

GAATTGCTCAACAGTATGGGCATTTCGCAGCCTACCGTGGTGTTCGTTTCCAAAAAG

GGGTTGCAAAAAATTTTGAACGTGCAAAAAAAGCTCCCAATCATCCAAAAAATTAT

TATCATGGATTCTAAAACGGATTACCAGGGATTTCAGTCGATGTACACGTTCGTCAC

ATCTCATCTACCTCCCGGTTTTAATGAATACGATTTTGTGCCAGAGTCCTTCGATAGG

GACAAGACAATTGCACTGATCATGAACTCCTCTGGATCTACTGGTCTGCCTAAAGGT

GTCGCTCTGCCTCATAGAACTGCCTGCGTGAGATTCTCGCATGCCAGAGATCCTATT

TTTGGCAATCAAATCATTCCGGATACTGCGATTTTAAGTGTTGTTCCATTCCATCACG

GTTTTGGAATGTTTACTACACTCGGATATTTGATATGTGGATTTCGAGTCGTCTTAAT

GTATAGATTTGAAGAAGAGCTGTTTCTGAGGAGCCTTCAGGATTACAAGATTCAAAG

TGCGCTGCTGGTGCCAACCCTATTCTCCTTCTTCGCCAAAAGCACTCTGATTGACAA

ATACGATTTATCTAATTTACACGAAATTGCTTCTGGTGGCGCTCCCCTCTCTAAGGAA

GTCGGGGAAGCGGTTGCCAAGAGGTTCCATCTGCCAGGTATCAGGCAAGGATATGG
```

-continued

```
GCTCACTGAGACTACATCAGCTATTCTGATTACACCCGAGGGGGATGATAAACCGG

GCGCGGTCGGTAAAGTTGTTCCATTTTTTGAAGCGAAGGTTGTGGATCTGGATACCG

GGAAAACGCTGGGCGTTAATCAAAGAGGCGAACTGTGTGTGAGAGGTCCTATGATT

ATGTCCGGTTATGTAAACAATCCGGAAGCGACCAACGCCTTGATTGACAAGGATGG

ATGGCTACATTCTGGAGACATAGCTTACTGGGACGAAGACGAACACTTCTTCATCGT

TGACCGCCTGAAGTCTCTGATTAAGTACAAAGGCTATCAGGTGGCTCCCGCTGAATT

GGAATCCATCTTGCTCCAACACCCCAACATCTTCGACGCAGGTGTCGCAGGTCTTCC

CGACGATGACGCCGGTGAACTTCCCGCCGCCGTTGTTGTTTTGGAGCACGGAAAGAC

GATGACGGAAAAAGAGATCGTGGATTACGTCGCCAGTCAAGTAACAACCGCGAAAA

AGTTGCGCGGAGGAGTTGTGTTTGTGGACGAAGTACCGAAAGGTCTTACCGGAAAA

CTCGACGCAAGAAAAATCAGAGAGATCCTCATAAAGGCCAAGAAGGGCGGAAAGA

TCGCCGTGTAATCCATGGCCCAACTTGTTTATTGCAGCTTATAATGGTTACAAATAA

AGCAATAGCATCACAAATTTCACAAATAAAGCATTTTTTTCACTGCATTCTAGTTGT

GGTTTGTCCAAACTCATCAATGTATCTTATCATGTCTGGATCTCGTTAACTCGAGGGA

TCCATCGATGTCGACTGCAGAGGCCTGCATGCAAGCTTGGTGTAATCATGGTCATAG

CTGTTTCCTGTGTGAAATTGTTATCCGCTCACAATTCCACACAACATACGAGCCGGA

AGCATAAAGTGTAAAGCCTGGGGTGCCTAATGAGTGAGCTAACTCACATTAATTGC

GTTGCGCTCACTGCCCGCTTTCCAGTCGGGAAACCTGTCGTGCCAGCTGCATTAATG

AATCGGCCAACGCGCGGGGAGAGGCGGTTTGCGTATTGGGCGCTCTTCCGCTTCCTC

GCTCACTGACTCGCTGCGCTCGGTCGTTCGGCTGCGGCGAGCGGTATCAGCTCACTC

AAAGGCGGTAATACGGTTATCCACAGAATCAGGGGATAACGCAGGAAAGAACATGT

GAGCAAAAGGCCAGCAAAAGGCCAGGAACCGTAAAAAGGCCGCGTTGCTGGCGTTT

TTCCATAGGCTCCGCCCCCCTGACGAGCATCACAAAAATCGACGCTCAAGTCAGAG

GTGGCGAAACCCGACAGGACTATAAAGATACCAGGCGTTTCCCCCTGGAAGCTCCC

TCGTGCGCTCTCCTGTTCCGACCCTGCCGCTTACCGGATACCTGTCCGCCTTTCTCCC

TTCGGGAAGCGTGGCGCTTTCTCATAGCTCACGCTGTAGGTATCTCAGTTCGGTGTA

GGTCGTTCGCTCCAAGCTGGGCTGTGTGCACGAACCCCCCGTTCAGCCCGACCGCTG

CGCCTTATCCGGTAACTATCGTCTTGAGTCCAACCCGGTAAGACACGACTTATCGCC

ACTGGCAGCAGCCACTGGTAACAGGATTAGCAGAGCGAGGTATGTAGGCGGTGCTA

CAGAGTTCTTGAAGTGGTGGCCTAACTACGGCTACACTAGAAGAACAGTATTTGGTA

TCTGCGCTCTGCTGAAGCCAGTTACCTTCGGAAAAAGAGTTGGTAGCTCTTGATCCG

GCAAACAAACCACCGCTGGTAGCGGTGGTTTTTTTGTTTGCAAGCAGCAGATTACGC

GCAGAAAAAAAGGATCTCAAGAAGATCCTTTGATCTTTTCTACGGGGTCTGACGCTC

AGTGGAACGAAAACTCACGTTAAGGGATTTTGGTCATGAGATTATCAAAAAGGATC

TTCACCTAGATCCTTTTAAATTAAAAATGAAGTTTTAAATCAAGCCCAATCTGAATA

ATGTTACAACCAATTAACCAATTCTGATTAGAAAAACTCATCGAGCATCAAATGAAA

CTGCAATTTATTCATATCAGGATTATCAATACCATATTTTTGAAAAAGCCGTTTCTGT

AATGAAGGAGAAAACTCACCGAGGCAGTTCCATAGGATGGCAAGATCCTGGTATCG

GTCTGCGATTCCGACTCGTCCAACATCAATACAACCTATTAATTTCCCCTCGTCAAA

AATAAGGTTATCAAGTGAGAAATCACCATGAGTGACGACTGAATCCGGTGAGAATG

GCAAAAGTTTATGCATTTCTTTCCAGACTTGTTCAACAGGCCAGCCATTACGCTCGTC
```

-continued

```
ATCAAAATCACTCGCATCAACCAAACCGTTATTCATTCGTGATTGCGCCTGAGCGAG

ACGAAATACGCGATCGCTGTTAAAAGGACAATTACAAACAGGAATCGAATGCAACC

GGCGCAGGAACACTGCCAGCGCATCAACAATATTTTCACCTGAATCAGGATATTCTT

CTAATACCTGGAATGCTGTTTTTCCGGGGATCGCAGTGGTGAGTAACCATGCATCAT

CAGGAGTACGGATAAAATGCTTGATGGTCGGAAGAGGCATAAATTCCGTCAGCCAG

TTTAGTCTGACCATCTCATCTGTAACATCATTGGCAACGCTACCTTTGCCATGTTTCA

GAAACAACTCTGGCGCATCGGGCTTCCCATACAAGCGATAGATTGTCGCACCTGATT

GCCCGACATTATCGCGAGCCCATTTATACCCATATAAATCAGCATCCATGTTGGAAT

TTAATCGCGGCCTCGACGTTTCCCGTTGAATATGGCTCATAACACCCCTTGTATTACT

GTTTATGTAAGCAGACAGTTTTATTGTTCATGATGATATATTTTTATCTTGTGCAATG

TAACATCAGAGATTTTGAGACACGGGCCAGAGCTGCA
```

INCORPORATION BY REFERENCE

The publications and patents referenced in this application have been incorporated in their entirety.

Non-Patent Literature

1. Lai, Y, Yue, Y and Duan, D Evidence for the failure of adeno-associated virus serotype 5 to package a viral genome ≥8.2 kb. (2010). Mol Ther 18:75-79.
2. Smith R.H. Adeno-associated virus integration: virus versus vector. Gene Ther. 2008; 15:817-822.
3. Fitzpatrick Z., Leborgne C, Barbon E., et al. Influence of Pre-existing Anti-capsid Neutralizing and Binding Antibodies on AAV Vector Transduction. Mol Ther Methods Clin Dev. 2018 Jun. 15; 9:119-129.
4. Guerra-Crespo M, Charli JL, Rosales-Garcia VH, Pedraza-Alva G, Perez-Martinez L. Polyethylenimine improves the transfection efficiency of primary cultures of post-mitotic rat fetal hypothalamic neurons. J Neurosci Methods. 2003; 127 (2): 179-92.
5. Sutapa Barua and Samir Mitragotri. Challenges associated with Penetration of Nanoparticles across Cell and Tissue Barriers: A Review of Current Status and Future Prospects. Nano today. 2014. 9 (2): 223-243.
6. Zabner, J., Fasbender, A.J., Moninger, T., Poellinger, D. A., and Welsh, M.J. Cellular and molecular barriers to gene transfer by a cationic lipid. J. Biol. Chem. (1995) 270:18997-19007.
7. Templeton NS, Senzer N (2011) Optimization of Non-Viral Gene Therapeutics Using Bilamellar Invaginated Vesicles. J Genet Syndr Gene Ther S5: 002
8. Wilke, M., Fortunati, E., van den Broek, M., Hoogeveen, A. T., and Scholte, B.J. Efficacy of a peptide-based gene delivery system depends on mitotic activity. Gene Ther. (1996) 3:1133-1142.
9. Ge Liu, DeShan Li, Murali K Pasumarthy, et al. 2003. Nanoparticles of Compacted DNA Transfect Postmitotic Cells. The Journal of Biological Chemistry. Vol. 278, No. 35, Issue of August 29, pp. 32578-32586
10. Michael W. Konstan, Pamela B. D., Jefferey S. W., Kathleen A. H., Robert C. S., Laura J. H. M., Tomasz H. K., Susannah L. H., Tamara L. F., Christopher R. G., Sharon M. O., Jennifer M. P., Osman M., Assem G. Z., Robert C. M., and Mark J. C. Compacted DNA Nanoparticles Administered to the Nasal Mucosa of Cystic Fibrosis Subjects Are Safe and Demonstrate Partial to Complete Cystic Fibrosis Transmembrane Regulator Reconstitution. 2004. Human Gene Therapy. 15:1255-1269
11. D'Souza SE, Ginsberg MH, Plow $\mu$F. Arginyl-glycyl-aspartic acid (RGD): a cell adhesion motif. Trends Biochem Sci. 1991 July; 16 (7): 246-50.
12. Christian Hinderer, Nathan Katz, Elizabeth L. Buza, Cecilia Dyer, Tamara Goode, Peter Bell, Laura K. Richman, and James M. Wilson. Severe Toxicity in Nonhuman Primates and Piglets Following High-Dose Intravenous Administration of an Adeno-Associated Virus Vector Expressing Human SMN. 2018. Human Gene Therapy. Vol 29. No 3.
13. Wodrich H, Henaff D, Jammart B, Segura-Morales C, Seelmeir S, et al. (2010) A Capsid-Encoded PPxY-Motif Facilitates Adenovirus Entry. PLOS Pathog 6 (3): e1000808.
14. Kailash N. Pandey. Functional roles of short sequence motifs in the endocytosis of membrane receptors. Frontiers in Bioscience 14, 5339-5360 Jun. 1, 2009
15. Claire Sunyach, Angela Jen, Juelin Deng, Kathleen T. Fitzgerald, Yveline Frobert, Jacques Grassi, Mary W. McCaffrey, Roger Morris. The mechanism of internalization of glycosylphosphatidylinositol-anchored prion protein. The EMBO Journal Vol. 22 No. 14. pp. 3591+3601, 2003
16. Modesto Redrejo-Rodríguez, Daniel Muñoz-Espín, Isabel Holguera, Mario Mencía, and Margarita Salas. Functional eukaryotic nuclear localization signals are widespread in terminal proteins of bacteriophages. PNAS. 2012. Vol 109. No 45. 18482-18487.
17. Chee Kai Chan and David A Jans. Enhancement of Polylysine-Mediated Transferrinfection by Nuclear Localization Sequences: Polylysine Does Not Function as a Nuclear Localization Sequence. Human Gene Therapy. Vol 10. No 10. 1999.
18. Jans DA, Moll T, Nasmyth K, Jans P. Cyclin-dependent kinase site-regulated signal-dependent nuclear localization of the SW15 yeast transcription factor in mammalian cells. J Biol Chem. 1995 Jul. 21; 270 (29): 17064-7.
19. Kirchhausen T, 1999. Adaptors for clathrin-mediated traffic. Annu Rev Cell Dev. 1999; 15:705-32.
20. Stephanie VandeVondele Janos Voros, Jeffrey A. Hubbell. RGD-Grafted Poly-L-lysine-graft (polyethylene glycol) Copolymers Block Non-specific Protein Adsorption While Promoting Cell Adhesion. Biotechnology and Bioengineering, Vol. 82, No. 7, 2003

21. L. Feuz et al.: Small-angle neutron scattering of PLL grafted PEG molecular brushes. Eur. Phys. J. E 23, 237-245 (2007).

22. Sun Tian, Qingsheng Huang, Ying Fang, Jianhua Wu. (2011) FurinDB: a database of 20-residue furin cleavage site motifs, substrates and their associated drugs. International Journal of Molecular Sciences., 12, 1060-1065.

23. Najjar K, Erazo-Oliveras A, Pellois J. Delivery of proteins, peptides or cell-impermeable small molecules into live cells by incubation with the endosomolytic reagent of TAT. J Vis Exp. 2015; 103

24. Tashiro K, Sephel G. C., Weeks B., Sasaki, M., Martin, G. R., Kleinman, H. K. et al. 1989. A synthetic peptide containing the IKVAVA sequence form the A chain of Laminin mediates cell attachment, migration and neurite growth. J. Biol Chem. 264, 16174-16182.

25. Graf, J., Iwamoto, Y., Sasaki, M., Martin, G. R., Kleinman, H. K., Robey, F. A., et al. 1987. Identification of the major epithelial-cell attachment site (yigsr) in the b1-chain of Laminin. J. Invest. Dermatol., 88, 491.

26. Mishra, A., Gordon, V., Yang, L., Coridan, R. and Wong, G. (2008) HIV TAT forms pores in membranes by inducing saddle-splay curvature: potential role of bidentate hydrogen bonding. Angew. Chem., Int. Ed. 47, 2986-2989.

27. Rothbard, J.B., Jessop, T. C. and Wender, P.A. (2005) Adaptive translocation: the 28. role of hydrogen bonding and membrane potential in the uptake of guanidinium-rich transporters into cells. Adv. Drug Deliv. Rev. 57, 495-504.

29. Yuxin Chen, Michael T. Guarnieri Adriana I. Vasil, Michael L. Vasil, Colin T. Mant, and Robert S. Hodges. Role of Peptide Hydrophobicity in the Mechanism of Action of-Helical Antimicrobial Peptides. 2007. Antimicrobial Agents and Chemotherapy, April 2007, p. 1398-1406

30. Wu Z, Simister N E. Tryptophan- and dileucine-based endocytosis signals in the neonatal Fc receptor. J Biol Chem. 2001. eb 16; 276 (7): 5240-7. Epub 2000 Nov. 28.

31. John P. H. Th'ng, Rohyun Sung, Ming Ye Michael J. Hendzel. H₁ family histones in the nucleus control of binding and localization by the C-terminal domain. J. Biol. Chem. 2005; 280:27809-27814

32. Cardin AD, Weintraub HJ (1989) Molecular modeling of protein-glycosamino-glycan interactions. Arteriosclerosis 9:21-32.

33. Torrent M, Nogue s MV, Andreu D, Boix E (2012) The "CPC Clip Motif": A Conserved Structural Signature for Heparin-Binding Proteins. PLOS ONE 7 (8): e42692. doi: 10.1371/journal.pone.0042692

34. Nelson C. Di Paolo, Oleksandr Kalyuzhniy, and Dmitry M. Shayakhmetov. Fiber Shaft-Chimeric Adenovirus Vectors Lacking the KKTK Motif Efficiently Infect Liver Cells In Vivo. Journal of Virology, November 2007, p. 12249-12259

35. Laetitia Jean, Charlotte Mizon, William J. Larsen, Jacques Mizon and Jean-Philippe Salier. Unmasking a hyaluronan-binding site of the BX7B type in the H₃ heavy chain of the inter-α-inhibitor family. Eur. J. Biochem. 268, 544+553 (2001)

36. Kokona Kouzi-Koliakos, George G. Koliakos, EffieC. Tsilibary, Leo T. Furcht S, and Aristidis S. Charonis. Mapping of Three Major Heparin-binding Sites on Laminin and Identification of a Novel Heparin-binding Site on theB1 Chain. The Journal of Biological Chemistry. 1989. Vol 264. No 30.

37. Joji lida, Alexandra M. L. Meijne, Theodore R. Oegema, Jr., Ted A. Yednock, Nicholas L. Kovach, Leo T. Furcht, and James B. McCarthy. A Role of Chondroitin Sulfate Glycosaminoglycan Binding Site in a4ß 1 Integrin-mediated Melanoma Cell Adhesion. The Journal of Biological Chemistry273, 5955-5962.

38. Melissa S. Maginnis, J. Craig Forrest, Sarah A. Kopecky-Bromberg, S. Kent Dickeson, Samuel A. Santoro, Mary M. Zutter, Glen R. Nemerow, Jeffrey M. Bergelson, and Terence S. Dermody. Beta1 Integrin Mediates Internalization of Mammalian Reovirus. Journal of Virology, March 2006, p. 2760-277

39. Alfred A. Reszka, Yokichi Hayashi, and Alan E Horwitz. Identification of Amino Acid Sequences in the Integrin/31 Cytoplasmic Domain Implicated in Cytoskeletal Association. The Journal of CeU Biology, Volume 117, Number 6, June 1992 1321-1330

40. Kusakawa T, Simakami T, Kaneko S, Yoshioka K, Murakami S. Functional interaction of hepatitis C Virus NS5B with Nucleolin GAR domain. J Biochemistry. 2007. Jun 141 (6) 917-27

41. C. Graham Knight, Laurence F. Morton, Anthony R. Peachey, Danny S. Tuckwell, Richard W. Farndale, and Michael J. Barnes. The Collagen-binding A-domains of Integrins alß1 and a2B1Recognize the Same Specific Amino Acid Sequence, GFOGER, in Native (Triple-helical) Collagens. The Journal of Biological Chemistry. 2000. Vol 275. No. 1

42. Kalthoff C, Alves J, Urbanke C, Knorr R, Ungewickell EJ. (2002). Unusual structural organization of the endocytic proteins AP180 and epsin 1. J Biol Chem 277:8209-8216

43. Igor Beitia Ortiz de Zarate, Lilia Cantero-Aguilar, Magalie Longo, Clarisse Berlioz-Torrent, and Flore Rozenberg. Contribution of Endocytic Motifs in the Cytoplasmic Tail of Herpes Simplex Virus Type 1 Glycoprotein B to Virus Replication and Cell-Cell Fusion. Journal of Virology, December 2007, p. 13889-13903

44. Shaynoor Dramsi, Sophie Magnet, Sophie Davison, Michel Arthur. Covalent attachment of proteins to peptidoglycan. FEMS Microbiol Rev32 (2008) 307-320

45. Olli Pentikainen, Anna-Marja Hoffren, Johanna Ivaska, Jarmo Kapyla, Tommi Nyronen, Jyrki Heino, and Mark S. Johnson. "RKKH" Peptides from the Snake Venom Metalloproteinase of Bothrops jararaca Bind Near the Metal Ion-dependent Adhesion Site of the Human Integrin a2 I-domain. The Journal of Biological Chemistry. 274, 31493-31505.

46. Thomas Brand. The Popeye Domain Containing Genes and Their Function as CAMP Effector Proteins in Striated Muscle. J.Cardiovasc.Dev.Dis. 2018,5,18

47. Asch AS, Silbiger S, Heimer E, Nachman RL. Thrombospondin sequence motif (CSVTCG) is responsible for CD36 binding. Biochemical and biophysical research communications. Feb. 14 1992; 182 (3): 1208-1217.

48. Nora B Caberoy, Yixiong Zhoul and Wei Li. Tubby and tubby-like protein 1 are new MerTK ligands for phagocytosis. The EMBO Journal (2010) 29, 3898-3910

49. Chi-Yi Yu, Zhenhua Yuan, Zhongren Cao, Bing Wang, Chunping Qiao, Juan Li, Xiao Xiao. A muscle-targeting peptide displayed on AAV2 improves muscle tropism upon systemic delivery. Gene Ther. 2009 August; 16 (8): 953-962

50. H Buning, M U Ried, L Perabo, F M Gerner, NA Huttner, J Enssle and M Hallekn. Receptor targeting of adeno-associated virus vectors. Gene Therapy (2003) 10, 1142-1151.

51. Wischnjow A, Sarko D, Janzer M, Kaufman C, Beijer B, Brings S, Haberkorn U, Larbig G, Kubelbeck A, Mier W. Bioconjugate Chem. 2016; 27:1050-1057.

52. Lorraine M. Work, Hildegard Buning, Ela Hunt, Stuart A. Nicklin, Laura Denby, Nicola Britton, Kristen Leike, Margarete Odenthal, Uta Drebber, Michael Hallek, and Andrew H. Baker. Vascular Bed-Targeted in Vivo Gene Delivery Using Tropism-Modified Adeno-associated Viruses. Molecular Therapy. Vol. 13, No. 4, April 2006

53. Lorraine M. Work, Stuart A. Nicklin, Nick J. R. Brain, Kate L Dishart, Dan J. Von Seggern, Michael Hallek, Hildegard Buning and Andrew H. Baker. Development of Efficient Viral Vectors Selective for Vascular Smooth Muscle Cells. Molecular Therapy Vol. 9, No. 2, February 2004

54. Wadih Arap, Renata Pasqualini, Erkki Ruoslahti. Cancer Treatment by Targeted Drug Delivery to Tumor Vasculature in a Mouse Model. Science. 16 Jan. 1998: Vol. 279, Issue 5349, pp. 377-380

55. Dale D. Hunter, Brenda E. Porter, Joseph W. Mock, Steven R Adams, John R Merlie, and Joshua R. Sanes. Primary Sequence of a Motor Neuron-Selective Adhesive Site in the Synaptic Basal Lamina Protein S-Laminin. Cell, Vol. 59, 905-913, Dec. 1, 1989, 56. Eric Anderson, Sandra Maday, Jeff Sfakianos, Michael Hull, Bettina Winckler, David Sheff, Heike Fölsch, and Ira Mellman. Transcytosis of NgCAM in epithelial cells reflects differential signal recognition on the endocytic and secretory pathways. The Journal of Cell Biology, Vol. 170, No. 4, Aug. 15, 2005 595-605

57. Matthew J. Bottomley. Structures of protein domains that create or recognize histone modifications., EMBO reports 5, 464-469 (2004).

58. Dahlin-Huppe K, Berglund EO., Ranscht B, Stallcup WB. Mutational analysis of the L1 neuronal cell adhesion molecule identifies membrane-proximal amino acids of the cytoplasmic domain that are required for cytoskeletal anchorage. Mol Cell Neurosci. 1997; 9 (2): 144-56.

59. P Zheng, J Eastman, S V Pol, and S W. Pimplikar. PAT1, a microtubule-interacting protein, recognizes the basolateral sorting signal of amyloid precursor protein Proc. Natl. Acad. Sci. USA. Vol. 95, pp. 14745-14750, December 1998

60. Daniel J.-F. Chinnapen, Himani Chinnapen, David Saslowsky, and Wayne I. Lencer. Rafting with cholera toxin: endocytosis and tra/cking from plasma membrane to ER. FEMS Microbiol Lett. 2007 January; 266 (2): 129-137.

61. D. Gowanlock R. Tervo, Bum-Yeol Hwang, Sarada Viswanathan, Loren L. Looger, David V. Schaffer, Alla Y. Karpova. A Designer AAV Variant Permits Efficient Retrograde Access to Projection Neurons. 2016, Neuron 92, 372-382

62. K Inabe, M Nishizawa, S Tajima, K Ikuta, and Y Aida. The YXXL sequences of a transmembrane protein of bovine leukemia virus are required for viral entry and incorporation of viral envelope protein into virions. J. Virol. 1999 February; 73 (2): 1293-301.

63. Ton-That, H., and O. Schneewind. 2003. Assembly of pili on the surface of C. diphtheriae. Mol. Microbiol.50: 1429-1438.

64. Aravind Asokan, Julie B. Hamra, Lakshmanan Govindasamy, Mavis Agbandje-McKenna, and Richard J. Samulski. Adeno-Associated Virus Type 2 Contains an Integrin alpha 5 betal Binding Domain Essential for Viral Cell Entry. Journal of Virology, September 2006, p. 8961-8969

65. Ji-Seon Park, Dong-Hou Kim, Seung-Yong Yoon. Regulation of amyloid precursor protein processing by its KFERQ motif. BMB Rep. 2016; 49 (6): 337-342

66. Kobayashi M, Shimomura A, Hagiwara M, Kawakami K. Phosphorylation of ATF-1 enhancesits DNA binding and transcription of the Na,K-ATPase alpha 1 subunit gene promoter. Nucleic Acids Res. 1997; 25 (4): 877-882. doi: 10.1093/nar/25.4.877

67. Marie-Anne Robin, Subbuswamy K. Prabu, Haider Raza, Hindupur K. Anandatheerthavarada, and Narayan G. Avadhani. Phosphorylation Enhances Mitochondrial Targeting of GSTA4-4 through Increased Affinity for Binding to Cytoplasmic Hsp70. THE JOURNAL OF BIOLOGICAL CHEMISTRY. Vol. 278, No. 21, Issue of May 23, pp. 18960-18970, 2003.

68. Rossetto D, Avvakumov N, Côté J. Histone phosphorylation: a chromatin modification involved in diverse nuclear events. Epigenetics. 2012; 7 (10): 1098-1108. doi: 10.4161/epi.21975

69. Ojida, A., Mito-Oka, Y., Inoue, M. A., & Hamachi, I. (2002). First artificial receptors and chemosensors toward phosphorylated peptide in aqueous solution. Journal of the American Chemical Society, 124 (22), 6256-6258.

70. Anai, T., Nakata, E., Koshi, Y., Ojida, A., & Hamachi, I. (2007). Design of a hybrid biosensor for enhanced phosphopeptide recognition based on a phosphoprotein binding domain coupled with a fluorescent chemosensor. Journal of the American Chemical Society, 129 (19), 6232-6239.

71. Somers WS1, Tang J, Shaw GD, Camphausen RT. Insights into the molecular basis of leukocyte tethering and rolling revealed by structures of P- and E-selectin bound to SLe (X) and PSGL-1. Cell. 2000 Oct. 27; 103 (3): 467-79.

72. Farzan M., Mirzabekov T., Kolchinsky P., Wyatt R., Cayabyab M., Gerard N.P., Gerard C., Sodroski J., Choe H. Tyrosine sulfation of the amino terminus of CCR5 facilitates HIV-1 entry." Cell 96:667-676 (1999)

73. Gelb, M. H., Scholten, J. D., & Sebolt-Leopold, J. S. (1998). Protein prenylation: from discovery to prospects for cancer treatment. Current opinion in chemical biology, 2 (1), 40-48.

74. Xie, F., Li, P., Gong, J., Zhang, J., & Ma, J. (2015). The bisphosphonate zoledronic acid effectively targets lung cancer cells by inhibition of protein prenylation. Biochemical and biophysical research communications, 467 (4), 664-669.

75. Ochocki JD, Mullen DG, Wattenberg EV, Distefano MD. Evaluation of a cell penetrating prenylated peptide lacking an intrinsic fluorophore via in situ click reaction. Bioorg Med Chem Lett. 2011; 21 (17): 4998-5001. doi: 10.1016/j.bmcl.2011.04.138

76. Hosseini V, Dani C, Geranmayeh MH, Mohammadzadeh F, Nazari Soltan Ahmad S, Darabi M. Wnt lipidation: Roles in trafficking, modulation, and function. J Cell Physiol. 2019; 234 (6): 8040-8054. doi: 10.1002/jcp.27570

77. Walsh, C. T., Garneau-Tsodikova, S., & Gatto Jr, G. J. (2005). Protein posttranslational modifications: the chemistry of proteome diversifications. Angewandte Chemie International Edition, 44 (45), 7342-7372.

78. Shi, S. P., Chen, X., Xu, H. D., & Qiu, J. D. (2015). PredHydroxy: computational prediction of protein hydroxylation site locations based on the primary structure. Molecular BioSystems, 11 (3), 819-825.

79. Bartels MF, Winterhalter P R, Yu J, Liu Y, Lommel M, Möhrlen F, et al. (2016) Protein OMannosylation in the Murine Brain: Occurrence of Mono-O-Mannosyl Glycans and Identification of New Substrates. PLOS ONE 11 (11): e0166119.

| Publication number | Publication date | Author | Assignee | Title |
|---|---|---|---|---|
| U S. Pat. No. 6,506,890 B1 | Jan. 14, 2003 | Mark J. C et al | Mark J Cooper et al | Method of nucleic acid compaction |
| US20100203627 A1 | Aug. 12, 2010 | Mark J. C et al | Copernicus Therapeutics | Long term in vivo transgene expression |
| US20110035819 A1 | Feb. 10, 2011 | Mark J. C et al | Copernicus Therapeutics | Codon optimized CFTR |
| WO2011017313 A1 | Feb. 10, 2011 | Mark J Cooper | Copernicus Therapeutics | Method of administering non-viral nucleic acid vectors to the eye |
| U.S. Pat. No. 9,486,540 (B2) 2016 Nov. 8 | Nov. 8, 2016 | Harmon Bredan, and Waszczak Barbara | Copernicus Therapeutics | Methods for delivery to the central nervous system of nucleic acid nanoparticles to treat central nervous system disorders |
| WO2008137066 (A1) | Nov. 13, 2008 | Naash Muna I, and Mark J. C | Univ Oklahoma, Copernicus Therapeutics | Use of compacted nucleic acids nanoparticles in non-viral treatments of ocular diseases. |
| WO1997030731A2 | Aug. 28, 1997 | Lollo Charles P. et. al. | Immune Response Corp Inc. | Method of preparing polynucleotide-carrier complexes for delivery to cells |
| WO1998046274A2 | Oct. 22, 1998 | Burgess Stephen W et. al. | Avanti Polar Lipids Inc, UAB Research Foundation | Cationic polymers for nucleic Lipids, Inc. acid transfection |
| EP1031626A1 | Aug. 30, 2000 | Erbacher Christoph et al. | Qiagen GmbH | Method for stabilising and/or isolating nucleic acids |
| US2014134232 (A1) | May 15, 2014 | Boulikas Teni | Regulon Inc. | Encapsulation of Plasmid DNA (Lipogenes(TM)) and Therapeutic Agents with Nuclear Localization Signal/Fusogenic Peptide Conjugates into Targeted Liposome Complexes |
| U.S. Pat. No. 5,844,107 | Dec. 1, 1998 | Richard, WH. et. al. | Case Western Reserve Uni | Compacted nucleic acids and their delivery to cells |
| U.S. Pat. No. 5,166,320 | Nov. 24, 1992 | Wu G. Y and Wu C. H. | Univ Connecticut | Carrier system and method for the introduction of genes into mammalian cells |
| US2017258933 (A1) | Sep. 14, 2017 | Jean-Phillipe P. | Texas A & M Univ Sys | Compositions and methods for the delivery of molecules into live cells |
| US2017057997 (A1) | Mar. 2, 2017 | Je-Min C. et al. | IUCF-HYU | 1. Cell penetrating peptide and method for delivering biologically active substance using same |

The invention claimed is:

1. An engineered polypeptide comprising: A modified amino acid, wherein the amino acid modification comprises mannosylation; and wherein the engineered polypeptide comprises an amino acid sequence having at least 90% sequence identity over the full length of SEQ ID NO: 447.

2. A polynucleotide that encodes the amino acid sequence of an engineered polypeptide of claim 1.

3. A composition comprising:
(i) at least one polynucleotide, and
(ii) at least one engineered polypeptide of claim 1.

4. The engineered polypeptide of claim 1, wherein the engineered polypeptide comprises SEQ ID NO: 447.

\* \* \* \* \*